(12) United States Patent
Meehl et al.

(10) Patent No.: US 11,111,297 B2
(45) Date of Patent: Sep. 7, 2021

(54) ANTIBODIES SPECIFIC FOR IMMUNOGLOBULIN-LIKE TRANSCRIPT 3 (ILT3) AND USES THEREOF

(71) Applicant: Merck Sharp & Dohme Corp., Rahway, NJ (US)

(72) Inventors: Michael A. Meehl, Northborough, MA (US); Philip E. Brandish, Needham, MA (US); Laurence Fayadat-Dilman, Sunnyvale, CA (US); Veronica Juan, Redwood City, CA (US); Carl Mieczkowski, Mountain View, CA (US); Latika Singh, Belmont, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 62 days.

(21) Appl. No.: 16/191,485

(22) Filed: Nov. 15, 2018

(65) Prior Publication Data

US 2019/0153093 A1 May 23, 2019

Related U.S. Application Data

(60) Provisional application No. 62/587,604, filed on Nov. 17, 2017.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *C07K 16/2818* (2013.01); *A61K 2039/505* (2013.01); *A61K 2039/507* (2013.01); *C07K 2317/24* (2013.01); *C07K 2317/32* (2013.01); *C07K 2317/33* (2013.01); *C07K 2317/34* (2013.01); *C07K 2317/76* (2013.01); *C07K 2317/92* (2013.01)

(58) Field of Classification Search
CPC ............ C07K 2317/33; C07K 2317/24; C07K 2317/565; C07K 16/2803; A61K 2039/507
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,487,603 A | 12/1984 | Harris | |
| 4,596,556 A | 6/1986 | Morrow et al. | |
| 4,741,900 A | 5/1988 | Alvarez | |
| 4,790,824 A | 12/1988 | Morrow et al. | |
| 4,816,567 A | 3/1989 | Cabilly et al. | |
| 4,941,880 A | 7/1990 | Burns | |
| 5,064,413 A | 11/1991 | McKinnon et al. | |
| 5,312,335 A | 5/1994 | McKinnon et al. | |
| 5,383,851 A | 1/1995 | McKinnon, Jr. et al. | |
| 5,399,163 A | 3/1995 | Peterson et al. | |
| 5,591,828 A | 1/1997 | Bosslet et al. | |
| 6,096,002 A | 8/2000 | Landau | |
| 6,329,511 B1 | 12/2001 | Vasquez et al. | |
| 6,620,135 B1 | 9/2003 | Weston et al. | |
| 7,777,008 B2 | 8/2010 | Ponath | |
| 7,943,743 B2 | 5/2011 | Korman et al. | |
| 8,008,449 B2 | 8/2011 | Korman et al. | |
| 8,354,509 B2 | 1/2013 | Carven et al. | |
| 8,609,089 B2 | 12/2013 | Langermann | |
| 8,691,730 B2 | 4/2014 | Vasquez | |
| 8,877,688 B2 | 11/2014 | Vasquez | |
| 8,901,281 B2 | 12/2014 | Ponath | |
| 8,969,526 B2 | 3/2015 | Baehner | |
| 9,296,815 B2 | 3/2016 | D'angelo | |
| 9,708,406 B2 | 7/2017 | Zhang | |
| 2009/0202544 A1 | 8/2009 | Suciu-foca | |
| 2010/0028330 A1 | 2/2010 | Collins et al. | |
| 2012/0039906 A1 | 2/2012 | Olive | |
| 2012/0114649 A1 | 5/2012 | Langermann | |
| 2013/0071403 A1 | 3/2013 | Rolland et al. | |
| 2015/0110714 A1 | 4/2015 | Suciu Foca et al. | |
| 2015/0139986 A1 | 5/2015 | Ponath et al. | |
| 2017/0267759 A1 | 9/2017 | Liang | |

FOREIGN PATENT DOCUMENTS

| | | |
|---|---|---|
| EP | 404097 B1 | 12/1990 |
| EP | 1964852 A1 | 9/2008 |
| WO | WO199311161 A1 | 6/1993 |
| WO | WO199428027 A1 | 12/1994 |
| WO | 2003093474 A1 | 11/2003 |
| WO | 2004099249 A2 | 11/2004 |
| WO | 2006121168 A1 | 11/2006 |
| WO | 2006138739 A2 | 12/2006 |
| WO | 2007005874 A2 | 1/2007 |
| WO | 2008117049 A1 | 10/2008 |

(Continued)

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Dufner (Trends Biotechnol. 24(11):523-29 (2006)).*
Rudikoff et al (Proc Natl Acad Sci USA 1982 vol. 79 p. 1979).*
MacCallum et al. (J. Mol. Biol. (1996) 262:732-745).*
De Pascalis et al. (The Journal of Immunology (2002) 169, 3076-3084).*

(Continued)

*Primary Examiner* — Lynn A Bristol
(74) *Attorney, Agent, or Firm* — Andrew W. Custer; Anna L. Cocuzzo

(57) ABSTRACT

Humanized, non-promiscuous monoclonal antibodies specific for immunoglobulin-like transcript 3 (ILT3), also known as Leukocyte immunoglobulin-like receptor subfamily B member 4 (LILRB4), are described.

21 Claims, 33 Drawing Sheets

Specification includes a Sequence Listing.

(56) References Cited

FOREIGN PATENT DOCUMENTS

| WO | WO2009101611 A1 | 8/2009 |
|---|---|---|
| WO | 2009114335 A2 | 9/2009 |
| WO | 2010027827 A3 | 3/2010 |
| WO | 2010077634 A1 | 7/2010 |
| WO | 2011066342 A3 | 6/2011 |
| WO | 2011127543 A1 | 10/2011 |
| WO | 2013033734 A1 | 3/2013 |
| WO | WO2013043569 A1 | 3/2013 |
| WO | WO2013181438 A2 | 12/2013 |
| WO | WO2014116846 A3 | 10/2014 |
| WO | WO2016049641 A1 | 3/2016 |
| WO | WO2016127427 A1 | 8/2016 |
| WO | WO2017015227 A1 | 1/2017 |
| WO | 2018089300 A1 | 5/2018 |
| WO | WO2018148494 A1 | 8/2018 |

OTHER PUBLICATIONS

Gasset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. (J. Mol. Bio. (1999) 293, 865-881).*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
USPTO, TC1600, BCPM Kolker "Antibodies and the written description requirement of 35 U.S.C.112(a)" pp. 1-36 (Sep. 17, 2020).*
Agata et al., Expression of the PD-1 antigen on the surface of stimulated mouse T and B lymphocytes, International Immunology, 1996, pp. 765-772, vol. 8, No. 5.
Armour et al., Recombinant Human IgG Molecules Lacking Fcy receptor I Binding and Monocyte Triggering Activities, Eur. J. Immunol., 1999, pp. 2613-2624, vol. 29.
Baca et al., Antibody Humanization Using Monovalent Phage Display, J. Biol. Chem., 1997, pp. 10678-10684, vol. 272.
Baert et al., Influence of Immunogenicity on the long term efficacy of Infliximab in Crohns disease, New England Journal Med., 2003, pp. 601-608, vol. 348.
Barbas et al., Synthetic Human Antibodies, Nature Medicine, 1995, pp. 837-839, vol. 1.
Beiboer, Sigrid H. W. et al., Guided Selection of a Pan Carcinoma Specific Antibody Reveals Similar Binding Characteristics yet Structural Divergence Between the Original Murine Antibody and its Human Equivalent, J. Mol. Biol., 2000, pp. 833-849, vol. 296.
Beniaminovitz et al., Prevention of rejection in cardiac transplantation by blockade of the interleukin 2 receptor with a monoclonal antibody, New England Journal of Medicine, 2000, pp. 613-619, vol. 342.
Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses, The Journal of Immunology, 2003, pp. 711-718, vol. vol. 170.
Blank et al., Contribution of the PD-L1/PD-1 pathway to T-cell exhaustion: an update on implications for chronic infections, Cancer Immunol. Immunother., 2007, pp. 739-745, vol. 56(5).
Blank, Interaction of PD-L1 on tumor cells with PD-1 on tumor-specific T cells as a mechanism of immune evasion: implications for tumor immunotherapy, Cancer Immunol. Immunother., 2005, pp. 307-314, vol. 54.
Brown, Blockade of Programmed Death-1 Ligands on Dendritic Cells Enhances T Cell Activation and Cytokine Production, J. Immunol., 2003, pp. 1257-1266, vol. vol. 170.
Carpenter et al., Non-Fc Receptor-Binding Humanized Anti-CD3 Antibodies Induce Apoptosis of Activated Human T Cells, J. Ummunol., 2000, pp. 6205-6213, vol. 165.
Carter et al., PD-1:PD-L Inhibitory Pathway Affects Both CD4 Plus and CD8 Plus and CD8 Plus T Cells and is overcome by IL-2, Eur. J. Immunol., 2002, pp. 634-643, vol. 32.
Cella et al., A Novel Inhibitory Receptor (ILT3) Expressed on Monocytes, Macrophages, and Dendritic Cells Involved in Antigen Processing, J. Exp. Med., 1997, Issue 10, pp. 1743-1751, vol. 185.
Cheung et al., Epitope-specific antibody response to the surface antigen of duck hepatitis B virus in infected ducks, Virology, 1990, pp. 546-552, vol. 176.
Chothia et al, Canonical Structures for the Hypervariable Regions of Imrnunoglobins, J. Mol. Biol., 1987, pp. 901-917, vol. 196.
Chothia et al., Conformations of immunoglobin hypervariable regions, Nature, 1989, pp. 877-883, vol. 342.
Clackson et al., Making Antibody Fragments Using Phage Display Libraries, Nature, 1991, pp. 624-628, vol. 352.
Cunningham et al., High resolution Epitope mapping of hgH-receptor interactions by alanine-scanning mutagenesis, Science, 1985, pp. 1081-1085, vol. 244.
Dong et al., B7-H1 pathway and its role in the evasion of tumor immunity, J. Mol. Med., 2003, pp. 281-287, vol. 81.
Everts et al., Selective Intracellular Delivery ofDexamethasone into Activated Endothelial Cells Using an E-Selectin-Directed Immunoconjugate, J. Immunol., 2002, pp. 883-889, vol. 168.
Foote et al., Antibody Framework Residues Affecting the Conformation of the Hypervariable Loops, J. Mol. Biol., 1992, pp. 487-499, vol. 224.
Freeman et al., Engagement of the PD-1 Immunoinhibitory Receptor by a Novel B7 Family Member Leads to Negative Regulation of Lymphocyte Activation, J. Exp. Med., 2000, pp. 1027-1034, vol. 192.
Ghosh et al., Natalizumab for active Crohns disease, New England J. Med., 2003, pp. 24-32, vol. 348.
Gibellini et al., Extracellular HIV-1 Tat Protein Induces the Rapid Ser 133 Phosphorylation and Activation of CREB Transcription Factor in Both Jurkat Lymphoblastoid T Cells and Primary Peripheral Blood Mononuclear Cells, J. Immunol., 1998, pp. 3891-3898, vol. 160.
Hamid et al., Safety and Tumor Responses with Lambrolizumab (Anti-PD-1) in Melanoma, New Eng. J. Med., 2013, pp. 134-144, vol. 369(2).
He et al., Humanization and Pharmacokinetics of a Monoclonal Antibody with Specificity for both E- and P-Selectin, J. Immunol. 1998, pp. 1029-1035, vol. 160.
Herold, New England Journal of Medicine, New England Journal of Medicine, 2002, pp. 1692-1698, vol. 346.
Holliger et al., Diabodies, Proc. Natl. Acad. Sci. USA, 1993, No. 14, pp. 6444-6448, vol. 90.
Holliger et al., Engineered antibody fragments and the rise of single domains, Nat. Biotechnol., 2005, pp. 1126-1136, vol. 23.
Hoogenboom et al., Natural and designer binding sites made by phage display technology, Immunol. Today, 2000, pp. 371-377, vol. 21.
Hsing et al., Requirement for Nuclear Factor-κBActivation by a Distinct Subset of CD40-Mediated Effector Functions in B Lymphocytes, J. Immunol., 1999, pp. 2804-2811, vol. 162.
Ishida et al., Induced expression of PD-1, a novel member of the immunoglobulin gene superfamily, upon programmed cell death, The EMBO Journal, 1992, pp. 3887-3895, vol. 11(11).
Iwai, Involvement of PD-L1 on tumor cells in the escape from host immune system and tumor immunotherapy by PD-L1 blockade, Proc. Natl. Acad. Sci. USA, 2002, pp. 12293-12297, vol. 99.
Kabat, The Structural Basis of Antibody Complementarity, Adv. Prot. Chem., 1978, pp. 1-75, vol. 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, pp. 6609-6616, vol. 252.
Kirkland et al., Analysis of the fine specificity and cross-reactivity of monoclonal anti-lipid A antibodies, J. Immunol., 1986, pp. 3614-3619, vol. 137.
Klimka, A. et al., Human anti-CD30 recombinant antibodies by guided phage antibody selection using cell panning, British Journal of Cancer, 2000, pp. 252-260, vol. 83(2).

(56) References Cited

OTHER PUBLICATIONS

Kohler et al., Continuous Cultures of Fused Cells Secreting Antibody of Predefined Specificity, Nature, 1975, pp. 495-497, vol. 256.
Konishi et al., B7-H1 Expression on Non-Small Cell Lung Cancer Cells and Its Relationship with Tumor-Infiltrating Lymphocytes and Their PD-1 Expression, Clin. Cancer Res., 2004, pp. 5094-5100, vol. 10.
Kostelny et al., Formation of a bispecific antibody by the use of leucine zippers, J. Immunol., 1992, pp. 1547-1553, vol. 148.
Le Doussal et al., Enhanced in vivo targeting of an asymmetric bivalent hapten to double-antigen-positive mouse B cells with monoclonal antibody conjugate cocktails, J. Immunol., 1991, pp. 169-175, vol. 146.
Lipsky et al., Infliximab and methotrexate in the treatment of rheumatoid arthritis, New England Journal of Medicine, 2000, pp. 1594-1602, vol. 343.
Liu et al., J. Neurol. Neurosurg. Psych., N. Neurol. Neurosurg. Psych., 1999, pp. 451-456, vol. 67.
Marks et al., By passing Immunization, J. Mol. Biol., 1991, pp. 581-597, vol. 222.
Meene et al., A comparison of signal sequence prediction methods using a test set of signal peptides, Bioinformatics, 2000, pp. 741-742, vol. 16.
Mendez et al., Functional Transplant of Megabase Human Immunoglobulin loc Recapitulates Human Antibody Response in Mice, Nature Genetics, 1997, pp. 146-156, vol. 15.
Milgrom et al., Treatment of allergic asthma with monoclonal anti IgE antibody, New England Journal Med., 1999, pp. 1966-1973, vol. 341.
Moldenhauer et al., Identity of HML-1 Antigen on Intestinal Intra Epithelial T Cells and of B-ly7 Antigen on Hairy Cell Leukemia, Scan. J. Immunol., 1990, pp. 77-82, vol. 32.
Morel et al., Monoclonal Antibodies to Bovine Serum Albumin: Affinity and Specificity Determinations, Mol. Immunol., 1988, Issue No. 1, pp. 7-15, vol. 25.
Morrison, Sherie L. et al., Chimeric human antibody molecules: Mouse antigen-binding domains with human constant region domains, Proc. Natl. Acad. Sci. USA, 1984, pp. 6851-6855, vol. 81.
Okazaki et al., New regulatory co-receptors: inducible co-stimulator and PD1, Curr. Opin. Immunol., 2002, pp. 779-782, vol. 14.
Portielje, IL-12: a promising adjuvant for cancer vaccination, Cancer Immunol Immunother, 2003, pp. 133-144, vol. 52.
Presta, Leonard G. et al., Selection, design, and engineering of therapeutic antibodies, J. Allergy Clin. Immunol., 2005, pp. 731-736, vol. 116(4).
Rader et al., A phage display approach for rapid antibody humanization: Designed combinatorial V gene libraries, Proc. Natl. Acad. Sci. USA, 1998, pp. 8910-8915, vol. 95.
Samaridis et al., Cloning of novel immunoglobulin superfamily receptors expressed on human myeloid and lymphoid cells: structural evidence for new stimulatory and inhibitory pathways, Eur. J. Immunol., 1997, Issue 3, pp. 660-665, vol. 27.
Shields, High Resolution Mapping of the Binding Site on Human IgG1 for FcyRI, FcyRII, FcyRIII, and FcRn and Design of IgG1 Variants with Improved Binding to the FeyR, J. of Biol. Chem., 2001, pp. 6591-6604, vol. 276, No. 9.
Slamon et al., Use of chemotherapy plus a monoclonal antibody against HER2 for metastatic breast cancer that overexpresses HER2, New England J. Med., 2001, pp. 783-792, vol. 344.
Sondermann et al., The 3.2-Angstrom Crystal Structure of the Human IgG1 Fc Fragment-Fc gamma RIII Complex, Nature, 2000, pp. 267-273, vol. 406.
Songsivilai et al., Bispecific antibody: a tool for diagnosis and treatment of disease, Clin. Exp. Immunol, 1990, pp. 315-321, vol. 79.
Stahli et al., Distinction of Epitopes by monoclonal antibodies, Methods in Enzymology, 1983, pp. 242-253, vol. 9.
Tang et al., Use of a Peptide Mimotope to Guide the Humanization of MRK-16, an Anti-P-glycoprotein Monoclonal Antibody, J. Biol. Chem., 1999, pp. 27371-27378, vol. 274.
Traunecker et al., Bispecific single chain molecules (Janusins) target cytotoxic lymphocytes on HIV infected cells, EMBO J., 1991, pp. 3655-3659, vol. 10.
Traunecker et al., Janusin: New Molecular Design for Bispecific Reagents, Int. J. Cancer Suppl., 1992, pp. 51-52, vol. 7.
Vaughan et al., Human Antibodies with Sub-nanomolar affinities isolated from a large non-immunized phage display library, Nature Biotechnology, 1996, pp. 309-314, vol. vol. 14.
Von Heijne et al., A new method for predkting signal sequence cleavage sites, Nucleic Acids Res., 1986, pp. 4683-4690, vol. 14.
Von Heijne, Patterns of Amino Acids near Signal-Sequence Cleavage Sites, Eur. J. Biochem., 1983, pp. 17-21, vol. 133.
Watson et al., The fine structure of bacterial and phage genes, Molecular biology of the gene, 1987, pp. 224-238, vol. 4.
Wren et al., SIGNAL-Sequence Information and GeNomic AnaLysis, Comput. Methods Programs Biomed., 2002, pp. 177-181, vol. 68.
Xu, JL et al., Diversity in the CDR3 region of Vh is sufficient for most antibody specificities, Immunity, 2000, pp. 37-45, vol. 13.
Yang et al., Identification of the ebola virus glycoprotein as the main viral determinant of vascular cell cytotoxicity and injury, Natl. Med., 2000, pp. 886-889, vol. 6.
Yang et al., New England J. Med., New England Journal of Medicine, 2003, pp. 427-434, vol. 349.
Columbia University in the City of New York, Recombinant ILT3 protein for the treatment of cancer, Columbia Technology Ventures, 2015, 1-2, N/A.
Kang, Xunlei et al., Inhibitory leukocyte immunoglobulin-like receptors: Immune checkpoint proteins and tumor sustaining factors, Cell Cycle, 2015, 25-40, 15(1).
Xu, Zheng et al., ILT3.Fc-CD166 Interaction Induces Inactivation of p70 S6 Kinase and Inhibits Tumor Cell Growth, The Journal of Immunology, 2017, 1207-1219, 200.

* cited by examiner

| mAb No. | Description | huILT3 KD (nM) | rhILT3 KD (nM) | rhILT3/huILT3 ratio | pI measured | Purity by SEC (% main) | Tm (Fab) onset | Tm (Fab) | Tagg |
|---|---|---|---|---|---|---|---|---|---|
| 10 | Humanized anti-ILT3 mAb (52B8 VH1 M64V / VL2) IgG4 S228P / Kappa | 0.72 | 8.77 | 12.2 | 6.33 | 95.5% | 55.8°C | 63.7°C | 62.7°C |
| 25 | Humanized anti-ILT3 mAb ((52B8 VH1 M64V / VL2) IgG1 L234A L235A D265S) /Kappa | 0.74 | 8.66 | 11.8 | 7.76 | 94.9% | 60.4°C | 65.8°C | 64.2°C |
| 26 | Humanized anti-ILT3 mAb ((52B8 VH1 M64V / VL5) IgG1 L234A L235A D265S) /Kappa | 0.61 | 4.9 | 8.1 | 8.62 | 96.1% | 62.1°C | 67.6°C | 66.1°C |
| 27 | Humanized anti-ILT3 mAb ((52B8 VH1 M64V / VL6) IgG1 L234A L235A D265S) /Kappa | 0.92 | 10.35 | 11.3 | 8.84 | 90.2% | 55.6°C | 61.9°C | 57.2°C |
| 28 | Humanized anti-ILT3 mAb ((52B8 VH1 M64V / VL7) IgG1 L234A L235A D265S) /Kappa | 0.57 | 5.56 | 9.8 | 8.8 | 94.4% | 59.6°C | 65.3°C | 63.9°C |
| 29 | Humanized anti-ILT3 mAb ((52B8 VH1 M64V / VL8) IgG1 L234A L235A D265S) /Kappa | 0.56 | 5.74 | 10.2 | 8.85 | 94.1% | 59.1°C | 65.2°C | 65.2°C |
| 30 | Humanized anti-ILT3 mAb (52B8 VH1 M64V / VL5) IgG4 S228P / Kappa | 0.6 | 4.8 | 8 | 7.21 | 98.2% | 57.9°C | 65.7°C | 64.1°C |
| 31 | Humanized anti-ILT3 mAb (52B8 VH1 M64V / VL6) IgG4 S228P / Kappa | 0.88 | 10.3 | 11.7 | 7.45 | 91.7% | 54.9°C | 61.1°C | 58.4°C |
| 32 | Humanized anti-ILT3 mAb (52B8 VH1 M64V / VL7) IgG4 S228P / Kappa | 0.53 | 5.61 | 10.5 | 7.45 | 97.8% | 57.9°C | 64.2°C | 61.7°C |
| 33 | Humanized anti-ILT3 mAb (52B8 VH1 M64V / VL8) IgG4 S228P / Kappa | 0.54 | 5.59 | 10.4 | 7.45 | 97.3% | 58.1°C | 64.1°C | 59.8°C |

FIG. 2A

Protected residues on surface structure model of the extracellular domain of hILT3

|  | huIgG4 20 mpk | 52B8 2 mpk | 52B8 20 mpk |
|---|---|---|---|
| infiltration score (mean ± SEM) | 1.25 ± 0.25 | 1.5 ± 0.29 | 1.75 ± 0.25 |
| comments | T cells in the core of 2/4 tumors |  | T cells in the core of 4/4 tumors |

IHC score scale: 0-Negative; 1-rare; 2-low; 3-moderate; 4-high; 5-very high

FIG.8D

SEQUENCE LISTING

```
<160> NUMBER OF SEQ ID NOS: 227

<210> SEQ ID NO 1
<211> LENGTH: 246
<212> TYPE: PRT
<213> ORGANISM: Artificial Sequence
<220> FEATURE:
<223> OTHER INFORMATION: Human ILT3 (LILRB4) extracellular domain with
      C-terminal His Tag

<400> SEQUENCE: 1

Gln Ala Gly Pro Leu Pro Lys Pro Thr Leu Trp Ala Glu Pro Gly Ser
1               5                   10                  15

Val Ile Ser Trp Gly Asn Ser Val Thr Ile Trp Cys Gln Gly Thr Leu
            20                  25                  30

Glu Ala Arg Glu Tyr Arg Leu Asp Lys Glu Glu Ser Pro Ala Pro Trp
        35                  40                  45

Asp Arg Gln Asn Pro Leu Glu Pro Lys Asn Lys Ala Arg Phe Ser Ile
    50                  55                  60

Pro Ser Met Thr Glu Asp Tyr Ala Gly Arg Tyr Arg Cys Tyr Tyr Arg
65                  70                  75                  80

Ser Pro Val Gly Trp Ser Gln Pro Ser Asp Pro Leu Glu Leu Val Met
                85                  90                  95

Thr Gly Ala Tyr Ser Lys Pro Thr Leu Ser Ala Leu Pro Ser Pro Leu
            100                 105                 110

Val Thr Ser Gly Lys Ser Val Thr Leu Leu Cys Gln Ser Arg Ser Pro
        115                 120                 125

Met Asp Thr Phe Leu Leu Ile Lys Glu Arg Ala Ala His Pro Leu Leu
    130                 135                 140

His Leu Arg Ser Glu His Gly Ala Gln Gln His Gln Ala Glu Phe Pro
145                 150                 155                 160
```

Met Ser Pro Val Thr Ser Val His Gly Gly Thr Tyr Arg Cys Phe Ser
            165                 170                 175

Ser His Gly Phe Ser His Tyr Leu Leu Ser His Pro Ser Asp Pro Leu
            180                 185                 190

Glu Leu Ile Val Ser Gly Ser Leu Glu Asp Pro Arg Pro Ser Pro Thr
            195                 200                 205

Arg Ser Val Ser Thr Ala Ala Gly Pro Glu Asp Gln Pro Leu Met Pro
        210                 215                 220

Thr Gly Ser Val Pro His Ser Gly Leu Arg Arg His Trp Glu His His
225                 230                 235                 240

His His His His His His
            245

<210> SEQ ID NO 2
<211> LENGTH: 237
<212> TYPE: PRT
<213> ORGANISM: Artificial Sequence
<220> FEATURE:
<223> OTHER INFORMATION: Macaca mulatta (Rhesus) ILT3 (LILRB4)
      extracellular domain (sequence obtained from GenBank NP_001035766)

<400> SEQUENCE: 2

Gln Ala Gly Pro Leu Pro Lys Pro Thr Ile Trp Ala Glu Pro Gly Ser
1               5                   10                  15

Val Ile Ser Trp Gly Ser Pro Val Thr Ile Trp Cys Gln Gly Thr Leu
            20                  25                  30

Asp Ala Gln Glu Tyr Tyr Leu Asp Lys Glu Gly Ser Pro Ala Pro Trp
        35                  40                  45

Asp Thr Gln Asn Pro Leu Glu Pro Arg Asn Lys Ala Lys Phe Ser Ile
    50                  55                  60

Pro Ser Met Thr Gln His Tyr Ala Gly Arg Tyr Arg Cys Tyr Tyr His
65                  70                  75                  80

Ser His Pro Asp Trp Ser Glu Asp Ser Asp Pro Leu Asp Leu Val Met
                85                  90                  95

Thr Gly Ala Tyr Ser Lys Pro Ile Leu Ser Val Leu Pro Ser Pro Leu
            100                 105                 110

Val Thr Ser Gly Glu Ser Val Thr Leu Leu Cys Gln Ser Gln Ser Pro
        115                 120                 125

Met Asp Thr Phe Leu Leu Phe Lys Glu Gly Ala Ala His Pro Leu Pro
    130                 135                 140

Arg Leu Arg Ser Gln His Gly Ala Gln Leu His Trp Ala Glu Phe Pro
145                 150                 155                 160

Met Gly Pro Val Thr Ser Val His Gly Gly Thr Tyr Arg Cys Ile Ser
                165                 170                 175

Ser Arg Ser Phe Ser His Tyr Leu Leu Ser Arg Pro Ser Asp Pro Val
            180                 185                 190

Glu Leu Thr Val Leu Gly Ser Leu Glu Ser Pro Ser Pro Ser Pro Thr
        195                 200                 205

Arg Ser Ile Ser Ala Ala Gly Pro Glu Asp Gln Ser Leu Met Pro Thr
    210                 215                 220

Gly Ser Asp Pro Gln Ser Gly Leu Arg Arg His Trp Glu
225                 230                 235

<210> SEQ ID NO 3
<211> LENGTH: 6
<212> TYPE: PRT

```
<213> ORGANISM: Artificial Sequence
<220> FEATURE:
<223> OTHER INFORMATION: Human ILT3 peptide A

<400> SEQUENCE: 3

Ile Ser Trp Gly Asn Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Human ILT3 peptide B

<400> SEQUENCE: 4

Ile Pro Ser Met Thr Glu
1               5

<210> SEQ ID NO 5
<211> LENGTH: 6
<212> TYPE: PRT
<213> ORGANISM: Artificial Sequence
<220> FEATURE:
<223> OTHER INFORMATION: Human ILT3 peptide C

<400> SEQUENCE: 5

Met Thr Gly Ala Tyr Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Human ILT3 peptide D

<400> SEQUENCE: 6

Gln Ser Arg Ser Pro Met Asp Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Human ILT3 peptide E

<400> SEQUENCE: 7

Ala Gln Gln His Gln Ala Glu Phe
1               5

<210> SEQ ID NO 8
<211> LENGTH: 4
<212> TYPE: PRT
<213> ORGANISM: Artificial Sequence
<220> FEATURE:
<223> OTHER INFORMATION: Human ILT3 peptide F

<400> SEQUENCE: 8

Leu Leu Ser His
1

<210> SEQ ID NO 9
<211> LENGTH: 327
<212> TYPE: PRT
<213> ORGANISM: Artificial Sequence
```

<220> FEATURE:
<223> OTHER INFORMATION: Human IgG4 HC Constant domain (S228P)

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 10
<211> LENGTH: 326
<212> TYPE: PRT
<213> ORGANISM: Artificial Sequence
<220> FEATURE:
<223> OTHER INFORMATION: Human IgG4 HC Constant domain (S228P)(K-)

<400> SEQUENCE: 10

```
Ala Ser Thr Lys Gly Pro Ser Val Phe Pro Leu Ala Pro Cys Ser Arg
```

```
            1               5                  10                 15
          Ser Thr Ser Glu Ser Thr Ala Ala Leu Gly Cys Leu Val Lys Asp Tyr
                       20                  25                 30

Phe Pro Glu Pro Val Thr Val Ser Trp Asn Ser Gly Ala Leu Thr Ser
                       35                  40                 45

Gly Val His Thr Phe Pro Ala Val Leu Gln Ser Ser Gly Leu Tyr Ser
                       50                  55                 60

Leu Ser Ser Val Val Thr Val Pro Ser Ser Leu Gly Thr Lys Thr
           65                  70                  75                 80

Tyr Thr Cys Asn Val Asp His Lys Pro Ser Asn Thr Lys Val Asp Lys
                           85                  90                 95

Arg Val Glu Ser Lys Tyr Gly Pro Pro Cys Pro Pro Cys Pro Ala Pro
                          100                 105                110

Glu Phe Leu Gly Gly Pro Ser Val Phe Leu Phe Pro Pro Lys Pro Lys
                          115                 120                125

Asp Thr Leu Met Ile Ser Arg Thr Pro Glu Val Thr Cys Val Val Val
                          130                 135                140

Asp Val Ser Gln Glu Asp Pro Glu Val Gln Phe Asn Trp Tyr Val Asp
          145                 150                 155                160

Gly Val Glu Val His Asn Ala Lys Thr Lys Pro Arg Glu Glu Gln Phe
                              165                 170                175

Asn Ser Thr Tyr Arg Val Val Ser Val Leu Thr Val Leu His Gln Asp
                          180                 185                190

Trp Leu Asn Gly Lys Glu Tyr Lys Cys Lys Val Ser Asn Lys Gly Leu
                          195                 200                205

Pro Ser Ser Ile Glu Lys Thr Ile Ser Lys Ala Lys Gly Gln Pro Arg
                          210                 215                220

Glu Pro Gln Val Tyr Thr Leu Pro Pro Ser Gln Glu Glu Met Thr Lys
          225                 230                 235                240

Asn Gln Val Ser Leu Thr Cys Leu Val Lys Gly Phe Tyr Pro Ser Asp
                          245                 250                255

Ile Ala Val Glu Trp Glu Ser Asn Gly Gln Pro Glu Asn Asn Tyr Lys
                          260                 265                270

Thr Thr Pro Pro Val Leu Asp Ser Asp Gly Ser Phe Phe Leu Tyr Ser
                          275                 280                285

Arg Leu Thr Val Asp Lys Ser Arg Trp Gln Glu Gly Asn Val Phe Ser
                          290                 295                300

Cys Ser Val Met His Glu Ala Leu His Asn His Tyr Thr Gln Lys Ser
          305                 310                 315                320

Leu Ser Leu Ser Leu Gly
                          325

<210> SEQ ID NO 11
<211> LENGTH: 330
<212> TYPE: PRT
<213> ORGANISM: Artificial Sequence
<220> FEATURE:
<223> OTHER INFORMATION: Human IgG1 HC constant domain

<400> SEQUENCE: 11

Ala Ser Thr Lys Gly Pro Ser Val Phe Pro Leu Ala Pro Ser Ser Lys
          1                   5                  10                 15

Ser Thr Ser Gly Gly Thr Ala Ala Leu Gly Cys Leu Val Lys Asp Tyr
                       20                  25                 30

Phe Pro Glu Pro Val Thr Val Ser Trp Asn Ser Gly Ala Leu Thr Ser
```

```
              35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 12
<211> LENGTH: 330
<212> TYPE: PRT
<213> ORGANISM: Artificial Sequence
<220> FEATURE:
<223> OTHER INFORMATION: Human IgG1 HC Constant domain (L234A L235A
      D265S)

<400> SEQUENCE: 12

Ala Ser Thr Lys Gly Pro Ser Val Phe Pro Leu Ala Pro Ser Ser Lys
1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 329
<212> TYPE: PRT
<213> ORGANISM: Artificial Sequence
<220> FEATURE:
<223> OTHER INFORMATION: Human IgG1 HC Constant domain (K-) (L234A L235A
      D265S)

<400> SEQUENCE: 13

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95
```

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 14
<211> LENGTH: 107
<212> TYPE: PRT
<213> ORGANISM: Artificial Sequence
<220> FEATURE:
<223> OTHER INFORMATION: Human LC Kappa Constant domain

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 15

```
<211> LENGTH: 122
<212> TYPE: PRT
<213> ORGANISM: Artificial Sequence
<220> FEATURE:
<223> OTHER INFORMATION: Anti-ILT3 52B8 parental HC variable domain

<400> SEQUENCE: 15

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Arg Arg Leu Glu Trp Val
        35                  40                  45

Ala Thr Ile Ser Gly Gly Asp Tyr Thr Asn Tyr Pro Asp Ser Met
    50                  55                  60

Arg Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Ser Val Thr Val Ser Ser
        115                 120

<210> SEQ ID NO 16
<211> LENGTH: 111
<212> TYPE: PRT
<213> ORGANISM: Artificial Sequence
<220> FEATURE:
<223> OTHER INFORMATION: Anti-ILT3 52B8 parental LC variable domain

<400> SEQUENCE: 16

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Lys Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Ala
    50                  55                  60

Arg Phe Ser Gly Ser Gly Ser Arg Thr Asp Phe Ala Leu Thr Ile Asp
65                  70                  75                  80

Pro Val Glu Ala Asp Asp Ala Thr Tyr Tyr Cys Gln Gln Asn Asn
                85                  90                  95

Glu Asp Pro Tyr Thr Phe Gly Gly Thr Lys Leu Glu Ile Lys
            100                 105                 110

<210> SEQ ID NO 17
<211> LENGTH: 5
<212> TYPE: PRT
<213> ORGANISM: Artificial Sequence
<220> FEATURE:
<223> OTHER INFORMATION: 52B8 HC-CDR1

<400> SEQUENCE: 17

Asn Tyr Gly Met Ser
1               5

<210> SEQ ID NO 18
<211> LENGTH: 17
```

```
<212> TYPE: PRT
<213> ORGANISM: Artificial Sequence
<220> FEATURE:
<223> OTHER INFORMATION: 52B8 HC-CDR2
<220> FEATURE:
<221> NAME/KEY: VARIANT
<222> LOCATION: (15)..(15)
<223> OTHER INFORMATION: Xaa is M, V, or L

<400> SEQUENCE: 18

Thr Ile Ser Gly Gly Gly Asp Tyr Thr Asn Tyr Pro Asp Ser Xaa Arg
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: 52B8 HC-CDR2 M

<400> SEQUENCE: 19

Thr Ile Ser Gly Gly Gly Asp Tyr Thr Asn Tyr Pro Asp Ser Met Arg
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: 52B8 HC-CDR2 V

<400> SEQUENCE: 20

Thr Ile Ser Gly Gly Gly Asp Tyr Thr Asn Tyr Pro Asp Ser Val Arg
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: 52B8 HC-CDR2 L

<400> SEQUENCE: 21

Thr Ile Ser Gly Gly Gly Asp Tyr Thr Asn Tyr Pro Asp Ser Leu Arg
1               5                   10                  15

Gly

<210> SEQ ID NO 22
<211> LENGTH: 13
<212> TYPE: PRT
<213> ORGANISM: Artificial Sequence
<220> FEATURE:
<223> OTHER INFORMATION: 52B8 HC-CDR3
<220> FEATURE:
<221> NAME/KEY: VARIANT
<222> LOCATION: (3)..(3)
<223> OTHER INFORMATION: Xaa3 is W, Y, Q, or F

<400> SEQUENCE: 22

Arg Leu Xaa Phe Arg Ser Leu Tyr Tyr Ala Met Asp Tyr
1               5                   10
```

```
<210> SEQ ID NO 23
<211> LENGTH: 13
<212> TYPE: PRT
<213> ORGANISM: Artificial Sequence
<220> FEATURE:
<223> OTHER INFORMATION: 52B8 HC-CDR3

<400> SEQUENCE: 23

Arg Leu Trp Phe Arg Ser Leu Tyr Tyr Ala Met Asp Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: 52B8 HC-CDR3

<400> SEQUENCE: 24

Arg Leu Tyr Phe Arg Ser Leu Tyr Tyr Ala Met Asp Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: 52B8 HC-CDR3

<400> SEQUENCE: 25

Arg Leu Gln Phe Arg Ser Leu Tyr Tyr Ala Met Asp Tyr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: 52B8 HC-CDR3

<400> SEQUENCE: 26

Arg Leu Phe Phe Arg Ser Leu Tyr Tyr Ala Met Asp Tyr
1               5                   10

<210> SEQ ID NO 27
<211> LENGTH: 15
<212> TYPE: PRT
<213> ORGANISM: Artificial Sequence
<220> FEATURE:
<223> OTHER INFORMATION: 52B8 LC-CDR1
<220> FEATURE:
<221> NAME/KEY: VARIANT
<222> LOCATION: (11)..(11)
<223> OTHER INFORMATION: Xaa is N, D, or Q
<220> FEATURE:
<221> NAME/KEY: VARIANT
<222> LOCATION: (12)..(12)
<223> OTHER INFORMATION: Xaa is S, N, or A

<400> SEQUENCE: 27

Arg Ala Ser Glu Lys Val Asp Ser Phe Gly Xaa Xaa Phe Met His
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: 52B8 LC-CDR1 N
```

```
<220> FEATURE:
<221> NAME/KEY: VARIANT
<222> LOCATION: (12)..(12)
<223> OTHER INFORMATION: Xaa is S, N, or A

<400> SEQUENCE: 28

Arg Ala Ser Glu Lys Val Asp Ser Phe Gly Asn Xaa Phe Met His
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: 52B8 LC-CDR1 D
<220> FEATURE:
<221> NAME/KEY: VARIANT
<222> LOCATION: (12)..(12)
<223> OTHER INFORMATION: Xaa is S, N, or A

<400> SEQUENCE: 29

Arg Ala Ser Glu Lys Val Asp Ser Phe Gly Asp Xaa Phe Met His
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: 52B8 LC-CDR1 Q
<220> FEATURE:
<221> NAME/KEY: VARIANT
<222> LOCATION: (12)..(12)
<223> OTHER INFORMATION: Xaa is S, N, or A

<400> SEQUENCE: 30

Arg Ala Ser Glu Lys Val Asp Ser Phe Gly Gln Xaa Phe Met His
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: 52B8 LC-CDR1 S
<220> FEATURE:
<221> NAME/KEY: VARIANT
<222> LOCATION: (11)..(11)
<223> OTHER INFORMATION: Xaa is N, D, or Q

<400> SEQUENCE: 31

Arg Ala Ser Glu Lys Val Asp Ser Phe Gly Xaa Ser Phe Met His
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: 52B8 LC-CDR1 N
<220> FEATURE:
<221> NAME/KEY: VARIANT
<222> LOCATION: (11)..(11)
<223> OTHER INFORMATION: Xaa is N, D, or Q

<400> SEQUENCE: 32

Arg Ala Ser Glu Lys Val Asp Ser Phe Gly Xaa Asn Phe Met His
1               5                   10                  15
```

```
<210> SEQ ID NO 33
<211> LENGTH: 15
<212> TYPE: PRT
<213> ORGANISM: Artificial Sequence
<220> FEATURE:
<223> OTHER INFORMATION: 52B8 LC-CDR1 A
<220> FEATURE:
<221> NAME/KEY: VARIANT
<222> LOCATION: (11)..(11)
<223> OTHER INFORMATION: Xaa is N, D, or Q

<400> SEQUENCE: 33

Arg Ala Ser Glu Lys Val Asp Ser Phe Gly Xaa Ala Phe Met His
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: 52B8 LC-CDR1 NN

<400> SEQUENCE: 34

Arg Ala Ser Glu Lys Val Asp Ser Phe Gly Asn Asn Phe Met His
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: 52B8 LC-CDR1 DN

<400> SEQUENCE: 35

Arg Ala Ser Glu Lys Val Asp Ser Phe Gly Asp Asn Phe Met His
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: 52B8 LC-CDR1 QN

<400> SEQUENCE: 36

Arg Ala Ser Glu Lys Val Asp Ser Phe Gly Gln Asn Phe Met His
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: 52B8 LC-CDR1 NS

<400> SEQUENCE: 37

Arg Ala Ser Glu Lys Val Asp Ser Phe Gly Asn Ser Phe Met His
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: 52B8 LC-CDR1 DS

<400> SEQUENCE: 38

Arg Ala Ser Glu Lys Val Asp Ser Phe Gly Asp Ser Phe Met His
```

```
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: 52B8 LC-CDR1 NA

<400> SEQUENCE: 39

Arg Ala Ser Glu Lys Val Asp Ser Phe Gly Asn Ala Phe Met His
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: 52B8 LC-CDR1 DA

<400> SEQUENCE: 40

Arg Ala Ser Glu Lys Val Asp Ser Phe Gly Asp Ala Phe Met His
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: 52B8 LC-CDR1 QS

<400> SEQUENCE: 41

Arg Ala Ser Glu Lys Val Asp Ser Phe Gly Gln Ser Phe Met His
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: 52B8 LC-CDR1 AF

<400> SEQUENCE: 42

Arg Ala Ser Glu Lys Val Asp Ser Phe Gly Gln Ala Phe Met His
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: 52B8 LC-CDR2

<400> SEQUENCE: 43

Leu Thr Ser Asn Leu Asp Ser
1               5

<210> SEQ ID NO 44
<211> LENGTH: 9
<212> TYPE: PRT
<213> ORGANISM: Artificial Sequence
<220> FEATURE:
<223> OTHER INFORMATION: 52B8 LC-CDR3

<400> SEQUENCE: 44

Gln Gln Asn Asn Glu Asp Pro Tyr Thr
1               5
```

```
<210> SEQ ID NO 45
<211> LENGTH: 121
<212> TYPE: PRT
<213> ORGANISM: Artificial Sequence
<220> FEATURE:
<223> OTHER INFORMATION: Anti-ILT3 40A6 parental HC variable domain

<400> SEQUENCE: 45

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Ile Asn Trp Val Arg Gln Ser Ser Gly Lys Gly Pro Glu Trp Met
        35                  40                  45

Gly Arg Phe Trp Tyr Asp Glu Gly Ile Ala Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Ser Leu Arg Thr Gly Asp Thr Gly Thr Tyr Tyr Cys Thr
                85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: Anti-ILT3 40A6 parental LC variable domain

<400> SEQUENCE: 46

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Val Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60

Ser Gly Phe Gly Ser Asp Phe Thr Leu Thr Ile Ser Asp Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Ala Gly Thr Lys Leu Glu Leu Lys
            100                 105

<210> SEQ ID NO 47
<211> LENGTH: 5
<212> TYPE: PRT
<213> ORGANISM: Artificial Sequence
<220> FEATURE:
<223> OTHER INFORMATION: 40A6  HC-CDR1

<400> SEQUENCE: 47

Ser Tyr Ser Ile Asn
1               5
```

<210> SEQ ID NO 48
<211> LENGTH: 16
<212> TYPE: PRT
<213> ORGANISM: Artificial Sequence
<220> FEATURE:
<223> OTHER INFORMATION: 40A6 HC-CDR2

<400> SEQUENCE: 48

Arg Phe Trp Tyr Asp Glu Gly Ile Ala Tyr Asn Leu Thr Leu Glu Ser
1               5                   10                  15

<210> SEQ ID NO 49
<211> LENGTH: 13
<212> TYPE: PRT
<213> ORGANISM: Artificial Sequence
<220> FEATURE:
<223> OTHER INFORMATION: 40A6 HC-CDR3

<400> SEQUENCE: 49

Asp Arg Asp Thr Val Gly Ile Thr Gly Trp Phe Ala Tyr
1               5                   10

<210> SEQ ID NO 50
<211> LENGTH: 11
<212> TYPE: PRT
<213> ORGANISM: Artificial Sequence
<220> FEATURE:
<223> OTHER INFORMATION: 40A6 LC-CDR1

<400> SEQUENCE: 50

Lys Ala Ser Gln Ser Val Gly Val Asn Val Asp
1               5                   10

<210> SEQ ID NO 51
<211> LENGTH: 7
<212> TYPE: PRT
<213> ORGANISM: Artificial Sequence
<220> FEATURE:
<223> OTHER INFORMATION: 40A6 LC-CDR2

<400> SEQUENCE: 51

Gly Ser Ala Asn Arg His Thr
1               5

<210> SEQ ID NO 52
<211> LENGTH: 9
<212> TYPE: PRT
<213> ORGANISM: Artificial Sequence
<220> FEATURE:
<223> OTHER INFORMATION: 40A6 LC-CDR3

<400> SEQUENCE: 52

Leu Gln Tyr Gly Ser Val Pro Tyr Thr
1               5

<210> SEQ ID NO 53
<211> LENGTH: 121
<212> TYPE: PRT
<213> ORGANISM: Artificial Sequence
<220> FEATURE:
<223> OTHER INFORMATION: Anti-ILT3 16B1 parental HC variable domain

<400> SEQUENCE: 53

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Asn Tyr

```
                      20                  25                  30
Cys Val Asn Trp Val Arg Gln Pro Ser Gly Lys Gly Pro Glu Trp Leu
            35                  40                  45

Gly Arg Phe Trp Phe Asp Glu Gly Lys Ala Tyr Asn Leu Thr Leu Glu
        50                  55                  60

Ser Arg Leu Ser Ile Ser Gly Asp Thr Ser Lys Asn Gln Val Phe Leu
65                  70                  75                  80

Arg Met Asn Ser Leu Arg Ala Asp Asp Thr Gly Thr Tyr Tyr Cys Thr
                85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser
        115                 120

<210> SEQ ID NO 54
<211> LENGTH: 107
<212> TYPE: PRT
<213> ORGANISM: Artificial Sequence
<220> FEATURE:
<223> OTHER INFORMATION: Anti-ILT3 16B1 parental LC variable domain

<400> SEQUENCE: 54

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Ile Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60

Ser Gly Phe Gly Ser Asp Phe Thr Leu Thr Ile Ser Asn Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Pro Gly Thr Lys Leu Glu Leu Lys
            100                 105

<210> SEQ ID NO 55
<211> LENGTH: 5
<212> TYPE: PRT
<213> ORGANISM: Artificial Sequence
<220> FEATURE:
<223> OTHER INFORMATION: 16B1 HC-CDR1

<400> SEQUENCE: 55

Asn Tyr Cys Val Asn
1               5

<210> SEQ ID NO 56
<211> LENGTH: 16
<212> TYPE: PRT
<213> ORGANISM: Artificial Sequence
<220> FEATURE:
<223> OTHER INFORMATION: 16B1 HC-CDR2

<400> SEQUENCE: 56

Arg Phe Trp Phe Asp Glu Gly Lys Ala Tyr Asn Leu Thr Leu Glu Ser
1               5                   10                  15

<210> SEQ ID NO 57
```

```
<211> LENGTH: 13
<212> TYPE: PRT
<213> ORGANISM: Artificial Sequence
<220> FEATURE:
<223> OTHER INFORMATION: 16B1 HC-CDR3

<400> SEQUENCE: 57

Asp Arg Asp Thr Val Gly Ile Thr Gly Trp Phe Ala Tyr
1               5                   10

<210> SEQ ID NO 58
<211> LENGTH: 11
<212> TYPE: PRT
<213> ORGANISM: Artificial Sequence
<220> FEATURE:
<223> OTHER INFORMATION: 16B1 LC-CDR1

<400> SEQUENCE: 58

Lys Ala Ser Gln Ser Val Gly Ile Asn Val Asp
1               5                   10

<210> SEQ ID NO 59
<211> LENGTH: 7
<212> TYPE: PRT
<213> ORGANISM: Artificial Sequence
<220> FEATURE:
<223> OTHER INFORMATION: 16B1 LC-CDR2

<400> SEQUENCE: 59

Gly Ser Ala Asn Arg His Thr
1               5

<210> SEQ ID NO 60
<211> LENGTH: 9
<212> TYPE: PRT
<213> ORGANISM: Artificial Sequence
<220> FEATURE:
<223> OTHER INFORMATION: 16B1 LC-CDR3

<400> SEQUENCE: 60

Leu Gln Tyr Gly Ser Val Pro Tyr Thr
1               5

<210> SEQ ID NO 61
<211> LENGTH: 118
<212> TYPE: PRT
<213> ORGANISM: Artificial Sequence
<220> FEATURE:
<223> OTHER INFORMATION: Anti-ILT3 11D1 parental HC variable domain

<400> SEQUENCE: 61

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Arg Thr Tyr
            20                  25                  30

Trp Ile Glu Trp Val Lys Gln Arg Pro Gly His Gly Leu Glu Trp Ile
        35                  40                  45

Gly Glu Ile Leu Pro Gly Asn Gly Asn Thr His Phe Asn Glu Asn Phe
    50                  55                  60

Lys Asp Lys Ala Thr Phe Thr Ala Asp Thr Ser Asn Ala Ala Tyr
65                  70                  75                  80

Met Gln Leu Ser Ser Leu Thr Ser Glu Asp Ser Ala Val Tyr Tyr Cys
                85                  90                  95

Val Arg Arg Leu Gly Arg Gly Pro Phe Asp Phe Trp Gly Gln Gly Thr
```

Thr Leu Thr Val Ser Ser
            115

<210> SEQ ID NO 62
<211> LENGTH: 107
<212> TYPE: PRT
<213> ORGANISM: Artificial Sequence
<220> FEATURE:
<223> OTHER INFORMATION: Anti-ILT3 11D1 parental LC variable domain

<400> SEQUENCE: 62

Asp Ile Gln Met Thr Gln Ser Pro Ser Ser Leu Ser Val Ser Leu Gly
1               5                   10                  15

Gly Lys Val Thr Ile Thr Cys Lys Ala Ser Gln Asp Ile Asn Glu Tyr
            20                  25                  30

Ile Gly Trp Tyr Gln Arg Lys Pro Gly Lys Pro Arg Leu Leu Ile
        35                  40                  45

His Tyr Thr Ser Thr Leu Gln Ser Gly Ile Pro Ser Arg Phe Ser Gly
    50                  55                  60

Ser Gly Ser Gly Arg Asp Tyr Ser Leu Ser Ile Ser Asn Leu Glu Pro
65                  70                  75                  80

Glu Asp Ile Ala Thr Tyr Tyr Cys Leu Gln Tyr Ala Asn Pro Leu Pro
                85                  90                  95

Thr Phe Gly Gly Gly Thr Lys Leu Glu Ile Lys
            100                 105

<210> SEQ ID NO 63
<211> LENGTH: 5
<212> TYPE: PRT
<213> ORGANISM: Artificial Sequence
<220> FEATURE:
<223> OTHER INFORMATION: 11D1 HC-CDR1

<400> SEQUENCE: 63

Thr Tyr Trp Ile Glu
1               5

<210> SEQ ID NO 64
<211> LENGTH: 17
<212> TYPE: PRT
<213> ORGANISM: Artificial Sequence
<220> FEATURE:
<223> OTHER INFORMATION: 11D1 HC-CDR2

<400> SEQUENCE: 64

Glu Ile Leu Pro Gly Asn Gly Asn Thr His Phe Asn Glu Asn Phe Lys
1               5                   10                  15

Asp

<210> SEQ ID NO 65
<211> LENGTH: 10
<212> TYPE: PRT
<213> ORGANISM: Artificial Sequence
<220> FEATURE:
<223> OTHER INFORMATION: 11D1 HC-CDR3

<400> SEQUENCE: 65

Arg Arg Leu Gly Arg Gly Pro Phe Asp Phe
1               5                   10

<210> SEQ ID NO 66

```
<211> LENGTH: 11
<212> TYPE: PRT
<213> ORGANISM: Artificial Sequence
<220> FEATURE:
<223> OTHER INFORMATION: 11D1 LC-CDR1

<400> SEQUENCE: 66

Lys Ala Ser Gln Asp Ile Asn Glu Tyr Ile Gly
1               5                   10

<210> SEQ ID NO 67
<211> LENGTH: 7
<212> TYPE: PRT
<213> ORGANISM: Artificial Sequence
<220> FEATURE:
<223> OTHER INFORMATION: 11D1 LC-CDR2

<400> SEQUENCE: 67

Tyr Thr Ser Thr Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: 11D1 LC-CDR3

<400> SEQUENCE: 68

Leu Gln Tyr Ala Asn Pro Leu Pro Thr
1               5

<210> SEQ ID NO 69
<211> LENGTH: 122
<212> TYPE: PRT
<213> ORGANISM: Artificial Sequence
<220> FEATURE:
<223> OTHER INFORMATION: Anti-ILT3 17H12 parental HC variable domain

<400> SEQUENCE: 69

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Asn Phe
            20                  25                  30

Asp Met Ala Trp Val Arg Gln Ala Pro Thr Arg Gly Leu Glu Trp Val
        35                  40                  45

Ser Ser Ile Thr Tyr Asp Gly Gly Ser Thr Ser Tyr Arg Asp Ser Val
    50                  55                  60

Lys Gly Arg Phe Thr Ile Ser Arg Asp Asn Ala Lys Gly Thr Leu Tyr
65                  70                  75                  80

Leu Gln Met Asp Ser Leu Arg Ser Glu Asp Thr Ala Thr Tyr Tyr Cys
                85                  90                  95

Thr Thr Val Glu Ser Ile Ala Thr Ile Ser Thr Tyr Phe Asp Tyr Trp
            100                 105                 110

Gly Gln Gly Val Met Val Thr Val Ser Ser
        115                 120

<210> SEQ ID NO 70
<211> LENGTH: 110
<212> TYPE: PRT
<213> ORGANISM: Artificial Sequence
<220> FEATURE:
<223> OTHER INFORMATION: Anti-ILT3 17H12 parental LC variable domain
```

```
<400> SEQUENCE: 70

Asp Ile Val Leu Thr Gln Ser Pro Ala Leu Ala Val Ser Leu Gly Gln
1               5                   10                  15

Arg Ala Thr Ile Ser Cys Arg Ala Ser Gln Ser Val Ser Met Ser Arg
                20                  25                  30

Tyr Asp Leu Ile His Trp Tyr Gln Gln Lys Pro Gly Gln Gln Pro Lys
            35                  40                  45

Leu Leu Ile Phe Arg Ala Ser Asp Leu Ala Ser Gly Ile Pro Ala Arg
    50                  55                  60

Phe Ser Gly Ser Gly Ser Gly Thr Asp Phe Thr Leu Thr Ile Asn Pro
65                  70                  75                  80

Val Gln Ala Asp Asp Ile Ala Thr Tyr Tyr Cys Gln Gln Thr Arg Lys
                85                  90                  95

Ser Pro Pro Thr Phe Gly Gly Gly Thr Arg Leu Glu Leu Lys
            100                 105                 110

<210> SEQ ID NO 71
<211> LENGTH: 5
<212> TYPE: PRT
<213> ORGANISM: Artificial Sequence
<220> FEATURE:
<223> OTHER INFORMATION: 17H12 HC-CDR1

<400> SEQUENCE: 71

Asn Phe Asp Met Ala
1               5

<210> SEQ ID NO 72
<211> LENGTH: 17
<212> TYPE: PRT
<213> ORGANISM: Artificial Sequence
<220> FEATURE:
<223> OTHER INFORMATION: 17H12 HC-CDR2

<400> SEQUENCE: 72

Ser Ile Thr Tyr Asp Gly Gly Ser Thr Ser Tyr Arg Asp Ser Val Lys
1               5                   10                  15

Gly

<210> SEQ ID NO 73
<211> LENGTH: 13
<212> TYPE: PRT
<213> ORGANISM: Artificial Sequence
<220> FEATURE:
<223> OTHER INFORMATION: 17H12 HC-CDR3

<400> SEQUENCE: 73

Val Glu Ser Ile Ala Thr Ile Ser Thr Tyr Phe Asp Tyr
1               5                   10

<210> SEQ ID NO 74
<211> LENGTH: 15
<212> TYPE: PRT
<213> ORGANISM: Artificial Sequence
<220> FEATURE:
<223> OTHER INFORMATION: 17H12 LC-CDR1

<400> SEQUENCE: 74

Arg Ala Ser Gln Ser Val Ser Met Ser Arg Tyr Asp Leu Ile His
1               5                   10                  15

<210> SEQ ID NO 75
```

```
<211> LENGTH: 7
<212> TYPE: PRT
<213> ORGANISM: Artificial Sequence
<220> FEATURE:
<223> OTHER INFORMATION: 17H12 LC-CDR2

<400> SEQUENCE: 75

Arg Ala Ser Asp Leu Ala Ser
1               5

<210> SEQ ID NO 76
<211> LENGTH: 9
<212> TYPE: PRT
<213> ORGANISM: Artificial Sequence
<220> FEATURE:
<223> OTHER INFORMATION: 17H12 LC-CDR3

<400> SEQUENCE: 76

Gln Gln Thr Arg Lys Ser Pro Pro Thr
1               5

<210> SEQ ID NO 77
<211> LENGTH: 121
<212> TYPE: PRT
<213> ORGANISM: Artificial Sequence
<220> FEATURE:
<223> OTHER INFORMATION: Anti-ILT3 37C8 parental HC variable domain

<400> SEQUENCE: 77

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Cys Val Asn Trp Val Arg Gln Pro Ser Gly Lys Gly Pro Glu Trp Leu
        35                  40                  45

Gly Arg Phe Trp Tyr Asp Glu Gly Lys Val Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Arg Leu Arg Thr Asp Asp Thr Gly Thr Tyr Tyr Cys Thr
                85                  90                  95

Arg Asp Arg Asp Thr Met Gly Ile Thr Gly Trp Phe Ala Tyr Trp Gly
            100                 105                 110

Gln Gly Thr Leu Val Thr Val Ser Ser
        115                 120

<210> SEQ ID NO 78
<211> LENGTH: 107
<212> TYPE: PRT
<213> ORGANISM: Artificial Sequence
<220> FEATURE:
<223> OTHER INFORMATION: Anti-ILT3 37C8 parental LC variable domain

<400> SEQUENCE: 78

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Ile Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60
```

```
Ser Gly Phe Gly Ser Gly Phe Thr Leu Thr Ile Ser Asn Val Glu Pro
 65                  70                  75                  80

Glu Asp Leu Gly Val Tyr Tyr Cys Leu Gln Tyr Gly Ser Val Pro Tyr
                 85                  90                  95

Thr Phe Gly Pro Gly Thr Lys Leu Glu Leu Lys
            100                 105
```

```
<210> SEQ ID NO 79
<211> LENGTH: 5
<212> TYPE: PRT
<213> ORGANISM: Artificial Sequence
<220> FEATURE:
<223> OTHER INFORMATION: 37C8 HC-CDR1

<400> SEQUENCE: 79

Ser Tyr Cys Val Asn
1               5
```

```
<210> SEQ ID NO 80
<211> LENGTH: 16
<212> TYPE: PRT
<213> ORGANISM: Artificial Sequence
<220> FEATURE:
<223> OTHER INFORMATION: 37C8 HC-CDR2

<400> SEQUENCE: 80

Arg Phe Trp Tyr Asp Glu Gly Lys Val Tyr Asn Leu Thr Leu Glu Ser
1               5                   10                  15
```

```
<210> SEQ ID NO 81
<211> LENGTH: 13
<212> TYPE: PRT
<213> ORGANISM: Artificial Sequence
<220> FEATURE:
<223> OTHER INFORMATION: 37C8 HC-CDR3

<400> SEQUENCE: 81

Asp Arg Asp Thr Met Gly Ile Thr Gly Trp Phe Ala Tyr
1               5                   10
```

```
<210> SEQ ID NO 82
<211> LENGTH: 11
<212> TYPE: PRT
<213> ORGANISM: Artificial Sequence
<220> FEATURE:
<223> OTHER INFORMATION: 37C8 LC-CDR1

<400> SEQUENCE: 82

Lys Ala Ser Gln Ser Val Gly Ile Asn Val Asp
1               5                   10
```

```
<210> SEQ ID NO 83
<211> LENGTH: 7
<212> TYPE: PRT
<213> ORGANISM: Artificial Sequence
<220> FEATURE:
<223> OTHER INFORMATION: 37C8 LC-CDR2

<400> SEQUENCE: 83

Gly Ser Ala Asn Arg His Thr
1               5
```

```
<210> SEQ ID NO 84
<211> LENGTH: 9
<212> TYPE: PRT
```

<213> ORGANISM: Artificial Sequence
<220> FEATURE:
<223> OTHER INFORMATION: 37C8 LC-CDR3

<400> SEQUENCE: 84

Leu Gln Tyr Gly Ser Val Pro Tyr Thr
1               5

<210> SEQ ID NO 85
<211> LENGTH: 118
<212> TYPE: PRT
<213> ORGANISM: Artificial Sequence
<220> FEATURE:
<223> OTHER INFORMATION: Anti-ILT3 1G12 parental HC variable domain

<400> SEQUENCE: 85

Gln Val Gln Met Gln Gln Ser Gly Thr Glu Leu Met Lys Pro Gly Ala
1               5                   10                  15

Ser Met Lys Ile Ser Cys Lys Ala Thr Gly Tyr Thr Phe Ser Thr Tyr
            20                  25                  30

Trp Ile Gln Trp Ile Lys Gln Arg Pro Gly His Gly Leu Glu Trp Ile
        35                  40                  45

Gly Glu Ile Leu Pro Gly Ser Gly Thr Thr Asn Tyr Asn Glu Asn Phe
    50                  55                  60

Lys Gly Lys Ala Thr Phe Ser Ala Asp Thr Ser Ser Asn Thr Ala Tyr
65                  70                  75                  80

Ile His Leu Ser Ser Leu Thr Ser Glu Asp Ser Ala Val Phe Tyr Cys
                85                  90                  95

Ala Arg Arg Leu Gly Arg Gly Pro Phe Asp Tyr Trp Gly Gln Gly Thr
            100                 105                 110

Thr Leu Thr Val Ser Ser
        115

<210> SEQ ID NO 86
<211> LENGTH: 107
<212> TYPE: PRT
<213> ORGANISM: Artificial Sequence
<220> FEATURE:
<223> OTHER INFORMATION: Anti-ILT3 1G12 parental LC variable domain

<400> SEQUENCE: 86

Asp Ile Gln Met Thr Gln Ser Pro Ser Ser Leu Ser Ala Ser Leu Gly
1               5                   10                  15

Gly Lys Val Thr Ile Thr Cys Glu Ala Ser Gln Asp Ile Asn Lys His
            20                  25                  30

Ile Asp Trp Tyr Gln His Gln Pro Gly Arg Gly Pro Ser Leu Leu Ile
        35                  40                  45

His Tyr Ala Ser Ile Leu Gln Pro Gly Ile Pro Ser Arg Phe Ser Gly
    50                  55                  60

Ser Gly Ser Gly Arg Asp Tyr Ser Phe Ser Ile Thr Ser Leu Glu Pro
65                  70                  75                  80

Glu Asp Ile Ala Thr Tyr Tyr Cys Leu Gln Tyr Asp Asn Leu Leu Pro
                85                  90                  95

Thr Phe Gly Gly Gly Thr Lys Leu Glu Ile Lys
            100                 105

<210> SEQ ID NO 87
<211> LENGTH: 5
<212> TYPE: PRT
<213> ORGANISM: Artificial Sequence

```
<220> FEATURE:
<223> OTHER INFORMATION: 1G12 HC-CDR1

<400> SEQUENCE: 87

Thr Tyr Trp Ile Gln
1               5

<210> SEQ ID NO 88
<211> LENGTH: 17
<212> TYPE: PRT
<213> ORGANISM: Artificial Sequence
<220> FEATURE:
<223> OTHER INFORMATION: 1G12 HC-CDR2

<400> SEQUENCE: 88

Glu Ile Leu Pro Gly Ser Gly Thr Thr Asn Tyr Asn Glu Asn Phe Lys
1               5                   10                  15
Gly

<210> SEQ ID NO 89
<211> LENGTH: 9
<212> TYPE: PRT
<213> ORGANISM: Artificial Sequence
<220> FEATURE:
<223> OTHER INFORMATION: 1G12 HC-CDR3

<400> SEQUENCE: 89

Arg Leu Gly Arg Gly Pro Phe Asp Tyr
1               5

<210> SEQ ID NO 90
<211> LENGTH: 11
<212> TYPE: PRT
<213> ORGANISM: Artificial Sequence
<220> FEATURE:
<223> OTHER INFORMATION: 1G12 LC-CDR1

<400> SEQUENCE: 90

Glu Ala Ser Gln Asp Ile Asn Lys His Ile Asp
1               5                   10

<210> SEQ ID NO 91
<211> LENGTH: 7
<212> TYPE: PRT
<213> ORGANISM: Artificial Sequence
<220> FEATURE:
<223> OTHER INFORMATION: 1G12 LC-CDR2

<400> SEQUENCE: 91

Tyr Ala Ser Ile Leu Gln Pro
1               5

<210> SEQ ID NO 92
<211> LENGTH: 9
<212> TYPE: PRT
<213> ORGANISM: Artificial Sequence
<220> FEATURE:
<223> OTHER INFORMATION: 1G12 LC-CDR3

<400> SEQUENCE: 92

Leu Gln Tyr Asp Asn Leu Leu Pro Thr
1               5

<210> SEQ ID NO 93
<211> LENGTH: 121
<212> TYPE: PRT
```

```
<213> ORGANISM: Artificial Sequence
<220> FEATURE:
<223> OTHER INFORMATION: Anti-ILT3 20E4 parental HC variable domain

<400> SEQUENCE: 93

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Val Asn Trp Val Arg Gln Pro Ser Gly Lys Gly Leu Glu Trp Met
        35                  40                  45

Gly Arg Phe Trp Tyr Asp Gly Gly Thr Ala Tyr Asn Ser Thr Leu Glu
50                  55                  60

Ser Arg Leu Ser Ile Ser Gly Asp Thr Ser Lys Asn Gln Val Phe Leu
65                  70                  75                  80

Lys Met Asn Ser Leu Gln Thr Asp Asp Thr Gly Thr Tyr Tyr Cys Thr
                85                  90                  95

Arg Asp Arg Asp Thr Met Gly Ile Thr Gly Trp Phe Ala Tyr Trp Gly
            100                 105                 110

Gln Gly Thr Leu Val Thr Val Ser Pro
        115                 120

<210> SEQ ID NO 94
<211> LENGTH: 107
<212> TYPE: PRT
<213> ORGANISM: Artificial Sequence
<220> FEATURE:
<223> OTHER INFORMATION: Anti-ILT3 20E4 parental LC variable domain

<400> SEQUENCE: 94

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Val Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
50                  55                  60

Ser Gly Phe Gly Ser Asp Phe Thr Leu Thr Ile Ser Asn Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Ala Gly Thr Lys Leu Glu Leu Lys
            100                 105

<210> SEQ ID NO 95
<211> LENGTH: 5
<212> TYPE: PRT
<213> ORGANISM: Artificial Sequence
<220> FEATURE:
<223> OTHER INFORMATION: 20E4

<400> SEQUENCE: 95

Ser Tyr Ser Val Asn
1               5

<210> SEQ ID NO 96
<211> LENGTH: 16
<212> TYPE: PRT
<213> ORGANISM: Artificial Sequence
```

```
<220> FEATURE:
<223> OTHER INFORMATION: 20E4

<400> SEQUENCE: 96

Arg Phe Trp Tyr Asp Gly Gly Thr Ala Tyr Asn Ser Thr Leu Glu Ser
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: 20E4

<400> SEQUENCE: 97

Asp Arg Asp Thr Met Gly Ile Thr Gly Trp Phe Ala Tyr
1               5                   10

<210> SEQ ID NO 98
<211> LENGTH: 11
<212> TYPE: PRT
<213> ORGANISM: Artificial Sequence
<220> FEATURE:
<223> OTHER INFORMATION: 20E4

<400> SEQUENCE: 98

Lys Ala Ser Gln Ser Val Gly Val Asn Val Asp
1               5                   10

<210> SEQ ID NO 99
<211> LENGTH: 7
<212> TYPE: PRT
<213> ORGANISM: Artificial Sequence
<220> FEATURE:
<223> OTHER INFORMATION: 20E4

<400> SEQUENCE: 99

Gly Ser Ala Asn Arg His Thr
1               5

<210> SEQ ID NO 100
<211> LENGTH: 9
<212> TYPE: PRT
<213> ORGANISM: Artificial Sequence
<220> FEATURE:
<223> OTHER INFORMATION: 20E4

<400> SEQUENCE: 100

Leu Gln Tyr Gly Ser Val Pro Tyr Thr
1               5

<210> SEQ ID NO 101
<211> LENGTH: 121
<212> TYPE: PRT
<213> ORGANISM: Artificial Sequence
<220> FEATURE:
<223> OTHER INFORMATION: Anti-ILT3 24A4 parental HC variable domain

<400> SEQUENCE: 101

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
                20                  25                  30

Cys Val Asn Trp Val Arg Gln Pro Ser Gly Lys Gly Pro Glu Trp Leu
            35                  40                  45
```

Gly Arg Phe Trp Tyr Asp Glu Gly Lys Val Tyr Asn Leu Thr Leu Glu
        50                  55                  60

Ser Arg Leu Ser Ile Ser Gly Asp Thr Ser Lys Asn Gln Val Phe Leu
 65                  70                  75                  80

Lys Met Asn Arg Leu Arg Thr Asp Asp Thr Gly Thr Tyr Tyr Cys Thr
                 85                  90                  95

Arg Asp Arg Asp Thr Leu Gly Ile Thr Gly Trp Phe Ala Tyr Trp Gly
            100                 105                 110

Gln Gly Thr Leu Val Thr Val Ser Ser
        115                 120

<210> SEQ ID NO 102
<211> LENGTH: 107
<212> TYPE: PRT
<213> ORGANISM: Artificial Sequence
<220> FEATURE:
<223> OTHER INFORMATION: Anti-ILT3 24A4 parental LC variable domain

<400> SEQUENCE: 102

Glu Thr Val Met Thr Gln Ser Pro Thr Ser Leu Ser Ala Ser Ile Gly
 1               5                  10                  15

Glu Arg Val Thr Leu Asn Cys Lys Ala Ser Gln Ser Val Gly Ile Asn
                20                  25                  30

Val Asp Trp Tyr Gln Gln Thr Pro Gly Gln Ser Pro Lys Leu Leu Ile
            35                  40                  45

Tyr Gly Ser Ala Asn Arg His Thr Gly Val Pro Asp Arg Phe Thr Gly
        50                  55                  60

Ser Gly Phe Gly Ser Gly Phe Thr Leu Thr Ile Ser Asn Val Glu Pro
 65                  70                  75                  80

Glu Asp Leu Gly Val Tyr Tyr Cys Leu Gln Tyr Gly Ser Val Pro Tyr
                 85                  90                  95

Thr Phe Gly Pro Gly Thr Lys Leu Glu Leu Lys
            100                 105

<210> SEQ ID NO 103
<211> LENGTH: 5
<212> TYPE: PRT
<213> ORGANISM: Artificial Sequence
<220> FEATURE:
<223> OTHER INFORMATION: 24A4 HC-CDR1

<400> SEQUENCE: 103

Ser Tyr Cys Val Asn
 1               5

<210> SEQ ID NO 104
<211> LENGTH: 16
<212> TYPE: PRT
<213> ORGANISM: Artificial Sequence
<220> FEATURE:
<223> OTHER INFORMATION: 24A4 HC-CDR2

<400> SEQUENCE: 104

Arg Phe Trp Tyr Asp Glu Gly Lys Val Tyr Asn Leu Thr Leu Glu Ser
 1               5                  10                  15

<210> SEQ ID NO 105
<211> LENGTH: 13
<212> TYPE: PRT
<213> ORGANISM: Artificial Sequence
<220> FEATURE:
<223> OTHER INFORMATION: 24A4 HC-CDR3

```
<400> SEQUENCE: 105

Asp Arg Asp Thr Leu Gly Ile Thr Gly Trp Phe Ala Tyr
1               5                   10

<210> SEQ ID NO 106
<211> LENGTH: 11
<212> TYPE: PRT
<213> ORGANISM: Artificial Sequence
<220> FEATURE:
<223> OTHER INFORMATION: 24A4 LC-CDR1

<400> SEQUENCE: 106

Lys Ala Ser Gln Ser Val Gly Ile Asn Val Asp
1               5                   10

<210> SEQ ID NO 107
<211> LENGTH: 7
<212> TYPE: PRT
<213> ORGANISM: Artificial Sequence
<220> FEATURE:
<223> OTHER INFORMATION: 24A4 LC-CDR2

<400> SEQUENCE: 107

Gly Ser Ala Asn Arg His Thr
1               5

<210> SEQ ID NO 108
<211> LENGTH: 9
<212> TYPE: PRT
<213> ORGANISM: Artificial Sequence
<220> FEATURE:
<223> OTHER INFORMATION: 24A4 LC-CDR3

<400> SEQUENCE: 108

Leu Gln Tyr Gly Ser Val Pro Tyr Thr
1               5

<210> SEQ ID NO 109
<211> LENGTH: 19
<212> TYPE: PRT
<213> ORGANISM: Artificial Sequence
<220> FEATURE:
<223> OTHER INFORMATION: Leader sequence A

<400> SEQUENCE: 109

Met Glu Trp Ser Trp Val Phe Leu Phe Phe Leu Ser Val Thr Thr Gly
1               5                   10                  15

Val His Ser

<210> SEQ ID NO 110
<211> LENGTH: 20
<212> TYPE: PRT
<213> ORGANISM: Artificial Sequence
<220> FEATURE:
<223> OTHER INFORMATION: Leader sequence B

<400> SEQUENCE: 110

Met Ser Val Pro Thr Gln Val Leu Gly Leu Leu Leu Leu Trp Leu Thr
1               5                   10                  15

Asp Ala Arg Cys
            20

<210> SEQ ID NO 111
<211> LENGTH: 452
```

<212> TYPE: PRT
<213> ORGANISM: Artificial Sequence
<220> FEATURE:
<223> OTHER INFORMATION: Mouse Anti-ILT3 p52B8 parental HC: Murine IgG2a heavy chain

<400> SEQUENCE: 111

| Glu | Val | Gln | Leu | Val | Glu | Ser | Gly | Gly | Asp | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Lys | Leu | Ser | Cys | Ala | Ala | Ser | Gly | Phe | Thr | Phe | Ser | Asn | Tyr |
| | | | 20 | | | | | 25 | | | | | 30 | | |

| Gly | Met | Ser | Trp | Val | Arg | Gln | Thr | Pro | Asp | Arg | Arg | Leu | Glu | Trp | Val |
| | | 35 | | | | | 40 | | | | | 45 | | | |

| Ala | Thr | Ile | Ser | Gly | Gly | Asp | Tyr | Thr | Asn | Tyr | Pro | Asp | Ser | Met |
| 50 | | | | | 55 | | | | | 60 | | | | |

Arg Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg Arg Leu Trp Phe Arg Ser Leu Tyr Tyr Ala Met Asp Tyr Trp
                100                 105                 110

Gly Gln Gly Thr Ser Val Thr Val Ser Ser Ala Lys Thr Thr Ala Pro
                115                 120                 125

Ser Val Tyr Pro Leu Ala Pro Val Cys Gly Asp Thr Thr Gly Ser Ser
130                 135                 140

Val Thr Leu Gly Cys Leu Val Lys Gly Tyr Phe Pro Glu Pro Val Thr
145                 150                 155                 160

Leu Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Thr Ser Ser Thr Trp Pro Ser Gln Ser Ile Thr Cys Asn Val Ala His
                195                 200                 205

Pro Ala Ser Ser Thr Lys Val Asp Lys Lys Ile Glu Pro Arg Gly Pro
210                 215                 220

Thr Ile Lys Pro Cys Pro Pro Cys Lys Cys Pro Ala Pro Asn Leu Leu
225                 230                 235                 240

Gly Gly Pro Ser Val Phe Ile Phe Pro Pro Lys Ile Lys Asp Val Leu
                245                 250                 255

Met Ile Ser Leu Ser Pro Ile Val Thr Cys Val Val Val Asp Val Ser
                260                 265                 270

Glu Asp Asp Pro Asp Val Gln Ile Ser Trp Phe Val Asn Asn Val Glu
275                 280                 285

Val His Thr Ala Gln Thr Gln Thr His Arg Glu Asp Tyr Asn Ser Thr
                290                 295                 300

Leu Arg Val Val Ser Ala Leu Pro Ile Gln His Gln Asp Trp Met Ser
305                 310                 315                 320

Gly Lys Glu Phe Lys Cys Lys Val Asn Asn Lys Asp Leu Pro Ala Pro
                325                 330                 335

Ile Glu Arg Thr Ile Ser Lys Pro Lys Gly Ser Val Arg Ala Pro Gln
                340                 345                 350

Val Tyr Val Leu Pro Pro Pro Glu Glu Glu Met Thr Lys Lys Gln Val
                355                 360                 365

Thr Leu Thr Cys Met Val Thr Asp Phe Met Pro Glu Asp Ile Tyr Val
                370                 375                 380

```
Glu Trp Thr Asn Asn Gly Lys Thr Glu Leu Asn Tyr Lys Asn Thr Glu
385                 390                 395                 400

Pro Val Leu Asp Ser Asp Gly Ser Tyr Phe Met Tyr Ser Lys Leu Arg
                405                 410                 415

Val Glu Lys Lys Asn Trp Val Glu Arg Asn Ser Tyr Ser Cys Ser Val
            420                 425                 430

Val His Glu Gly Leu His Asn His His Thr Thr Lys Ser Phe Ser Arg
        435                 440                 445

Thr Pro Gly Lys
    450

<210> SEQ ID NO 112
<211> LENGTH: 218
<212> TYPE: PRT
<213> ORGANISM: Artificial Sequence
<220> FEATURE:
<223> OTHER INFORMATION: Mouse Anti-ILT3 p52B8 parental LC: murine Kappa
      light chain

<400> SEQUENCE: 112

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Lys Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Ala
    50                  55                  60

Arg Phe Ser Gly Ser Gly Ser Arg Thr Asp Phe Ala Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Thr Lys Leu Glu Ile Lys Arg
            100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
        130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 113
<211> LENGTH: 449
<212> TYPE: PRT
<213> ORGANISM: Artificial Sequence
<220> FEATURE:
<223> OTHER INFORMATION: Chimeric Anti-ILT3 mouse 52B8 VH parental/human
      IgG4 (S228P)

<400> SEQUENCE: 113
```

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Arg Arg Leu Glu Trp Val
        35                  40                  45

Ala Thr Ile Ser Gly Gly Asp Tyr Thr Asn Tyr Pro Asp Ser Met
    50                  55                  60

Arg Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415
```

```
Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 114
<211> LENGTH: 449
<212> TYPE: PRT
<213> ORGANISM: Artificial Sequence
<220> FEATURE:
<223> OTHER INFORMATION: Chimeric Anti-ILT3 mouse 52B8 VH M64V/human
      IgG4 (S228P)

<400> SEQUENCE: 114

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Arg Arg Leu Glu Trp Val
            35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 115
<211> LENGTH: 449
<212> TYPE: PRT
<213> ORGANISM: Artificial Sequence
<220> FEATURE:
<223> OTHER INFORMATION: Mouse Anti-ILT3 52B8 VH M64L/human IgG4 (S228P)

<400> SEQUENCE: 115

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Arg Arg Leu Glu Trp Val
        35                  40                  45

Ala Thr Ile Ser Gly Gly Gly Asp Tyr Thr Asn Tyr Pro Asp Ser Leu
    50                  55                  60

Arg Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
```

```
            225                 230                 235                 240
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
        435                 440                 445

Lys

<210> SEQ ID NO 116
<211> LENGTH: 218
<212> TYPE: PRT
<213> ORGANISM: Artificial Sequence
<220> FEATURE:
<223> OTHER INFORMATION: Chimeric Anti-ILT3 mouse 52B8 parental VL /
      human Kappa

<400> SEQUENCE: 116

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Lys Val Asp Ser Phe
                20                  25                  30

Gly Asn Ser Phe Met His Trp Tyr Gln Gln Lys Pro Gly Gln Pro Pro
            35                  40                  45

Lys Leu Leu Ile Tyr Leu Thr Ser Asn Leu Asp Ser Gly Val Pro Ala
        50                  55                  60

Arg Phe Ser Gly Ser Gly Ser Arg Thr Asp Phe Ala Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
```

```
            130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 117
<211> LENGTH: 122
<212> TYPE: PRT
<213> ORGANISM: Artificial Sequence
<220> FEATURE:
<223> OTHER INFORMATION: Humanized 52B8 HC variable domain  VH1

<400> SEQUENCE: 117

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 118
<211> LENGTH: 122
<212> TYPE: PRT
<213> ORGANISM: Artificial Sequence
<220> FEATURE:
<223> OTHER INFORMATION: Humanized 52B8 HC variable domain  VH1 M64V

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Gly Arg Arg Leu Trp Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 119
<211> LENGTH: 122
<212> TYPE: PRT
<213> ORGANISM: Artificial Sequence
<220> FEATURE:
<223> OTHER INFORMATION: Humanized 52B8 HC variable domain VH1 M64L

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Leu
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 120
<211> LENGTH: 122
<212> TYPE: PRT
<213> ORGANISM: Artificial Sequence
<220> FEATURE:
<223> OTHER INFORMATION: Humanized 52B8 HC variable domain VH1 M64V
    W101F

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Phe Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 121
<211> LENGTH: 122
<212> TYPE: PRT

<213> ORGANISM: Artificial Sequence
<220> FEATURE:
<223> OTHER INFORMATION: Humanized 52B8 HC variable domain   VH1 M64V
    W101Y

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Tyr Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 122
<211> LENGTH: 122
<212> TYPE: PRT
<213> ORGANISM: Artificial Sequence
<220> FEATURE:
<223> OTHER INFORMATION: Humanized 52B8 HC variable domain   VH1 M64V
    W101Q

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Gln Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 123
<211> LENGTH: 122
<212> TYPE: PRT
<213> ORGANISM: Artificial Sequence
<220> FEATURE:
<223> OTHER INFORMATION: Humanized 52B8 HC variable domain   VH2

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Met
50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 124
<211> LENGTH: 122
<212> TYPE: PRT
<213> ORGANISM: Artificial Sequence
<220> FEATURE:
<223> OTHER INFORMATION: Humanized 52B8 HC variable domain VH2 M64V

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 125
<211> LENGTH: 122
<212> TYPE: PRT
<213> ORGANISM: Artificial Sequence
<220> FEATURE:
<223> OTHER INFORMATION: Humanized 52B8 HC variable domain VH2 M64L

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Leu
50                  55                  60

Arg Gly Arg Phe Thr Ile Ser Arg Asp Asn Ala Lys Asn Ser Leu Tyr
65                  70                  75                  80

```
Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser
        115                 120

<210> SEQ ID NO 126
<211> LENGTH: 111
<212> TYPE: PRT
<213> ORGANISM: Artificial Sequence
<220> FEATURE:
<223> OTHER INFORMATION: Humanized 52B8 LC  variable domain VL1

<400> SEQUENCE: 126

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 127
<211> LENGTH: 111
<212> TYPE: PRT
<213> ORGANISM: Artificial Sequence
<220> FEATURE:
<223> OTHER INFORMATION: Humanized 52B8 LC  variable domain VL2

<400> SEQUENCE: 127

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 128
<211> LENGTH: 111
<212> TYPE: PRT
<213> ORGANISM: Artificial Sequence
<220> FEATURE:
<223> OTHER INFORMATION: Humanized 52B8 LC  variable domain VL3
```

<400> SEQUENCE: 128

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Lys Val Asp Ser Phe
            20                  25                  30

Gly Asn Ser Phe Met His Trp Tyr Gln Gln Lys Pro Gly Gln Ala Pro
        35                  40                  45

Arg Leu Leu Ile Tyr Leu Thr Ser Asn Leu Asp Ser Gly Val Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 129
<211> LENGTH: 111
<212> TYPE: PRT
<213> ORGANISM: Artificial Sequence
<220> FEATURE:
<223> OTHER INFORMATION: Humanized 52B8 LC  variable domain VL4

<400> SEQUENCE: 129

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Lys Val Asp Ser Phe
            20                  25                  30

Gly Asn Ser Phe Met His Trp Tyr Gln Gln Lys Pro Gly Gln Ala Pro
        35                  40                  45

Arg Leu Leu Ile Tyr Leu Thr Ser Asn Leu Asp Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 130
<211> LENGTH: 111
<212> TYPE: PRT
<213> ORGANISM: Artificial Sequence
<220> FEATURE:
<223> OTHER INFORMATION: Humanized 52B8 LC  variable domain VL5

<400> SEQUENCE: 130

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
            85                  90                  95

Glu Asp Pro Tyr Thr Phe Gly Gln Gly Thr Lys Leu Glu Ile Lys
        100                 105                 110

<210> SEQ ID NO 131
<211> LENGTH: 111
<212> TYPE: PRT
<213> ORGANISM: Artificial Sequence
<220> FEATURE:
<223> OTHER INFORMATION: Humanized 52B8 LC  variable domain VL6

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
            85                  90                  95

Glu Asp Pro Tyr Thr Phe Gly Gln Gly Thr Lys Leu Glu Ile Lys
        100                 105                 110

<210> SEQ ID NO 132
<211> LENGTH: 111
<212> TYPE: PRT
<213> ORGANISM: Artificial Sequence
<220> FEATURE:
<223> OTHER INFORMATION: Humanized 52B8 LC  variable domain VL7

<400> SEQUENCE: 132

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
            85                  90                  95

Glu Asp Pro Tyr Thr Phe Gly Gln Gly Thr Lys Leu Glu Ile Lys
        100                 105                 110

<210> SEQ ID NO 133
<211> LENGTH: 111
<212> TYPE: PRT
<213> ORGANISM: Artificial Sequence
<220> FEATURE:
<223> OTHER INFORMATION: Humanized 52B8 LC  variable domain VL8

<400> SEQUENCE: 133

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
            35                  40                  45

Lys Leu Leu Ile Tyr Leu Thr Ser Asn Leu Asp Ser Gly Val Pro Ala
        50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 134
<211> LENGTH: 111
<212> TYPE: PRT
<213> ORGANISM: Artificial Sequence
<220> FEATURE:
<223> OTHER INFORMATION: Humanized 52B8 LC  variable domain VL2 S35A

<400> SEQUENCE: 134

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Ala Phe Met His Trp Tyr Gln Gln Lys Pro Gly Gln Pro Pro
            35                  40                  45

Lys Leu Leu Ile Tyr Leu Thr Ser Asn Leu Asp Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 135
<211> LENGTH: 111
<212> TYPE: PRT
<213> ORGANISM: Artificial Sequence
<220> FEATURE:
<223> OTHER INFORMATION: Humanized 52B8 LC  variable domain VL2 S35N

<400> SEQUENCE: 135

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Asn Phe Met His Trp Tyr Gln Gln Lys Pro Gly Gln Pro Pro
            35                  40                  45

Lys Leu Leu Ile Tyr Leu Thr Ser Asn Leu Asp Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95
```

Glu Asp Pro Tyr Thr Phe Gly Gln Gly Thr Lys Leu Glu Ile Lys
            100                 105                 110

<210> SEQ ID NO 136
<211> LENGTH: 111
<212> TYPE: PRT
<213> ORGANISM: Artificial Sequence
<220> FEATURE:
<223> OTHER INFORMATION: Humanized 52B8 LC variable domain VL2 N34Q

<400> SEQUENCE: 136

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Gln Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 137
<211> LENGTH: 111
<212> TYPE: PRT
<213> ORGANISM: Artificial Sequence
<220> FEATURE:
<223> OTHER INFORMATION: Humanized 52B8 LC variable domain VL2 N34D

<400> SEQUENCE: 137

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asp Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 138
<211> LENGTH: 111
<212> TYPE: PRT
<213> ORGANISM: Artificial Sequence
<220> FEATURE:
<223> OTHER INFORMATION: Humanized 52B8 LC variable domain VL5 S35A

<400> SEQUENCE: 138

Asp Ile Gln Leu Thr Gln Ser Pro Ser Ser Leu Ser Ala Ser Val Gly
1               5                   10                  15

```
Asp Arg Val Thr Ile Thr Cys Arg Ala Ser Glu Lys Val Asp Ser Phe
            20                  25                  30

Gly Asn Ala Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 139
<211> LENGTH: 111
<212> TYPE: PRT
<213> ORGANISM: Artificial Sequence
<220> FEATURE:
<223> OTHER INFORMATION: Humanized 52B8 LC  variable domain VL5 S35N

<400> SEQUENCE: 139

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Lys Val Asp Ser Phe
            20                  25                  30

Gly Asn Asn Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110

<210> SEQ ID NO 140
<211> LENGTH: 111
<212> TYPE: PRT
<213> ORGANISM: Artificial Sequence
<220> FEATURE:
<223> OTHER INFORMATION: Humanized 52B8 LC  variable domain VL5 N34Q

<400> SEQUENCE: 140

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Glu Lys Val Asp Ser Phe
            20                  25                  30

Gly Gln Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110
```

```
<210> SEQ ID NO 141
<211> LENGTH: 111
<212> TYPE: PRT
<213> ORGANISM: Artificial Sequence
<220> FEATURE:
<223> OTHER INFORMATION: Humanized 52B8 LC  variable domain VL5 N34D

<400> SEQUENCE: 141
```

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asp Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys
            100                 105                 110

```
<210> SEQ ID NO 142
<211> LENGTH: 449
<212> TYPE: PRT
<213> ORGANISM: Artificial Sequence
<220> FEATURE:
<223> OTHER INFORMATION: Humanized 52B8 HC variable domain  VH1/Human
      IgG4 (S228P)
      constant domain

<400> SEQUENCE: 142
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

```
Val Pro Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 143
<211> LENGTH: 449
<212> TYPE: PRT
<213> ORGANISM: Artificial Sequence
<220> FEATURE:
<223> OTHER INFORMATION: Humanized 52B8 HC variable domain  VH1
      M64V/Human IgG4 (S228P) constant domain

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 144
<211> LENGTH: 449
<212> TYPE: PRT
<213> ORGANISM: Artificial Sequence
<220> FEATURE:
<223> OTHER INFORMATION: Humanized 52B8 HC variable domain  VH1
      M64L/Human IgG4 (S228P) constant domain

<400> SEQUENCE: 144

-continued

```
Glu Val Gln Leu Val Glu Ser Gly Gly Leu Val Gln Pro Gly Gly
  1               5                  10                 15

Ser Leu Arg Leu Ser Cys Ala Ala Ser Gly Phe Thr Phe Ser Asn Tyr
             20                  25                  30

Gly Met Ser Trp Val Arg Gln Ala Pro Gly Lys Gly Leu Glu Trp Val
         35                  40                  45

Ala Thr Ile Ser Gly Gly Asp Tyr Thr Asn Tyr Pro Asp Ser Leu
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Gly Arg Arg Leu Trp Phe Arg Ser Leu Tyr Tyr Ala Met Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 145
<211> LENGTH: 449
<212> TYPE: PRT
<213> ORGANISM: Artificial Sequence
<220> FEATURE:
<223> OTHER INFORMATION: Humanized 52B8 HC variable domain VH1 M64V
      W101F/Human IgG4 (S228P) constant domain

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Gly Arg Arg Leu Phe Phe Arg Ser Leu Tyr Tyr Ala Met Asp Tyr Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Lys Thr Tyr Thr Cys Asn Val Asp
    195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

-continued

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 146
<211> LENGTH: 449
<212> TYPE: PRT
<213> ORGANISM: Artificial Sequence
<220> FEATURE:
<223> OTHER INFORMATION: Humanized 52B8 HC variable domain  VH1 M64V
      W101Y/Human IgG4 (S228P) constant domain

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Tyr Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220
```

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser Gln Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Gln Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
        420                 425                 430

Ala Leu His Asn His Tyr Thr Gln Lys Ser Leu Ser Leu Ser Leu Gly
    435                 440                 445

Lys

<210> SEQ ID NO 147
<211> LENGTH: 449
<212> TYPE: PRT
<213> ORGANISM: Artificial Sequence
<220> FEATURE:
<223> OTHER INFORMATION: Humanized 52B8 HC variable domain  VH1 M64V
      W101Q/Human IgG4 (S228P) constant domain

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Gln Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

```
Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
        435                 440                 445

Lys

<210> SEQ ID NO 148
<211> LENGTH: 449
<212> TYPE: PRT
<213> ORGANISM: Artificial Sequence
<220> FEATURE:
<223> OTHER INFORMATION: Humanized 52B8 HC variable domain  VH2/Human
      IgG4 (S228P) constant domain

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met Ser Trp Val Arg Gln Ala Pro Gly Lys Gly Leu Glu Trp Val
        35                  40                  45

Ala Thr Ile Ser Gly Gly Asp Tyr Thr Asn Tyr Pro Asp Ser Met
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
               100                 105                 110

Gly Gln Gly Thr Leu Val Thr Val Ser Ser Ala Ser Thr Lys Gly Pro
               115                 120                 125

Ser Val Phe Pro Leu Ala Pro Cys Ser Arg Ser Thr Ser Glu Ser Thr
       130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
               165                 170                 175

Ala Val Leu Gln Ser Ser Gly Leu Tyr Ser Leu Ser Ser Val Val Thr
               180                 185                 190

Val Pro Ser Ser Ser Leu Gly Thr Lys Thr Tyr Thr Cys Asn Val Asp
               195                 200                 205

His Lys Pro Ser Asn Thr Lys Val Asp Lys Arg Val Glu Ser Lys Tyr
       210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
               245                 250                 255

Arg Thr Pro Glu Val Thr Cys Val Val Val Asp Val Ser Gln Glu Asp
               260                 265                 270

Pro Glu Val Gln Phe Asn Trp Tyr Val Asp Gly Val Glu Val His Asn
               275                 280                 285

Ala Lys Thr Lys Pro Arg Glu Glu Gln Phe Asn Ser Thr Tyr Arg Val
       290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
               325                 330                 335

Thr Ile Ser Lys Ala Lys Gly Gln Pro Arg Glu Pro Gln Val Tyr Thr
               340                 345                 350

Leu Pro Pro Ser Gln Glu Glu Met Thr Lys Asn Gln Val Ser Leu Thr
       355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
               405                 410                 415

Ser Arg Trp Gln Glu Gly Asn Val Phe Ser Cys Ser Val Met His Glu
       420                 425                 430

Ala Leu His Asn His Tyr Thr Gln Lys Ser Leu Ser Leu Ser Leu Gly
       435                 440                 445

Lys
```

<210> SEQ ID NO 149
<211> LENGTH: 449
<212> TYPE: PRT
<213> ORGANISM: Artificial Sequence
<220> FEATURE:
<223> OTHER INFORMATION: Humanized 52B8 HC variable domain VH2 M64V/Human IgG4 (S228P) constant domain

<400> SEQUENCE: 149

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

Lys

<210> SEQ ID NO 150
<211> LENGTH: 449
<212> TYPE: PRT
<213> ORGANISM: Artificial Sequence
<220> FEATURE:
<223> OTHER INFORMATION: Humanized 52B8 HC variable domain  VH2
      M64L/Human IgG4 (S228P) constant domain

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
                35                  40                  45

Ala Thr Ile Ser Gly Gly Gly Asp Tyr Thr Asn Tyr Pro Asp Ser Leu
                50                  55                  60

Arg Gly Arg Phe Thr Ile Ser Arg Asp Asn Ala Lys Asn Ser Leu Tyr
65              70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Cys Ser Arg Ser Thr Ser Glu Ser Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
```

```
            260                 265                 270
Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

Lys

<210> SEQ ID NO 151
<211> LENGTH: 218
<212> TYPE: PRT
<213> ORGANISM: Artificial Sequence
<220> FEATURE:
<223> OTHER INFORMATION: Humanized 52B8 LC  variable domain VL1/kappa
      constant domain

<400> SEQUENCE: 151

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
                    165                 170                 175
Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 152
<211> LENGTH: 218
<212> TYPE: PRT
<213> ORGANISM: Artificial Sequence
<220> FEATURE:
<223> OTHER INFORMATION: Humanized 52B8 LC  variable domain VL2/kappa
      constant domain

<400> SEQUENCE: 152

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 153
<211> LENGTH: 218
<212> TYPE: PRT
<213> ORGANISM: Artificial Sequence
<220> FEATURE:
<223> OTHER INFORMATION: Humanized 52B8 LC  variable domain VL3/kappa
      constant domain

<400> SEQUENCE: 153

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Lys Val Asp Ser Phe
```

```
                20                  25                  30
Gly Asn Ser Phe Met His Trp Tyr Gln Gln Lys Pro Gly Gln Ala Pro
            35                  40                  45
Arg Leu Leu Ile Tyr Leu Thr Ser Asn Leu Asp Ser Gly Val Pro Ala
 50                  55                  60
Arg Phe Ser Gly Ser Gly Ser Arg Thr Asp Phe Thr Leu Thr Ile Ser
 65                  70                  75                  80
Ser Leu Glu Pro Glu Asp Phe Ala Val Tyr Tyr Cys Gln Gln Asn Asn
                85                  90                  95
Glu Asp Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215

<210> SEQ ID NO 154
<211> LENGTH: 218
<212> TYPE: PRT
<213> ORGANISM: Artificial Sequence
<220> FEATURE:
<223> OTHER INFORMATION: Humanized 52B8 LC  variable domain VL4/kappa
      constant domain

<400> SEQUENCE: 154

Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Glu Lys Val Asp Ser Phe
            20                  25                  30
Gly Asn Ser Phe Met His Trp Tyr Gln Gln Lys Pro Gly Gln Ala Pro
        35                  40                  45
Arg Leu Leu Ile Tyr Leu Thr Ser Asn Leu Asp Ser Gly Ile Pro Ala
 50                  55                  60
Arg Phe Ser Gly Ser Gly Ser Gly Thr Asp Phe Thr Leu Thr Ile Ser
 65                  70                  75                  80
Ser Leu Glu Pro Glu Asp Phe Ala Val Tyr Tyr Cys Gln Gln Asn Asn
                85                  90                  95
Glu Asp Pro Tyr Thr Phe Gly Gln Gly Thr Lys Leu Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
```

-continued

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 155
<211> LENGTH: 218
<212> TYPE: PRT
<213> ORGANISM: Artificial Sequence
<220> FEATURE:
<223> OTHER INFORMATION: Humanized 52B8 LC  variable domain VL5/kappa
      constant domain

<400> SEQUENCE: 155

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 156
<211> LENGTH: 218
<212> TYPE: PRT
<213> ORGANISM: Artificial Sequence
<220> FEATURE:
<223> OTHER INFORMATION: Humanized 52B8 LC  variable domain VL6/kappa
      constant domain

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 157
<211> LENGTH: 218
<212> TYPE: PRT
<213> ORGANISM: Artificial Sequence
<220> FEATURE:
<223> OTHER INFORMATION: Humanized 52B8 LC  variable domain VL7/kappa
      constant domain

<400> SEQUENCE: 157

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 158
<211> LENGTH: 218
<212> TYPE: PRT
<213> ORGANISM: Artificial Sequence
<220> FEATURE:
<223> OTHER INFORMATION: Humanized 52B8 LC  variable domain VL8/kappa
      constant domain

<400> SEQUENCE: 158

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ala
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 159
<211> LENGTH: 218
<212> TYPE: PRT
<213> ORGANISM: Artificial Sequence
<220> FEATURE:
<223> OTHER INFORMATION: Humanized 52B8 LC  variable domain VL2
      S35A/kappa constant domain

<400> SEQUENCE: 159

Asp Ile Val Leu Thr Gln Ser Pro Asp Ser Leu Ala Val Ser Leu Gly
1               5                   10                  15

```
Glu Arg Ala Thr Ile Asn Cys Arg Ala Ser Glu Lys Val Asp Ser Phe
            20                  25                  30

Gly Asn Ala Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
 50                      55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 160
<211> LENGTH: 218
<212> TYPE: PRT
<213> ORGANISM: Artificial Sequence
<220> FEATURE:
<223> OTHER INFORMATION: Humanized 52B8 LC  variable domain VL2
      S35N/kappa constant domain

<400> SEQUENCE: 160

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Lys Val Asp Ser Phe
            20                  25                  30

Gly Asn Asn Phe Met His Trp Tyr Gln Gln Lys Pro Gly Gln Pro Pro
        35                  40                  45

Lys Leu Leu Ile Tyr Leu Thr Ser Asn Leu Asp Ser Gly Val Pro Asp
 50                      55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
```

```
                145                 150                 155                 160
Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                    180                 185                 190

His Lys Val Tyr Ala Cys Glu Val Thr His Gln Gly Leu Ser Ser Pro
                    195                 200                 205

Val Thr Lys Ser Phe Asn Arg Gly Glu Cys
                    210                 215

<210> SEQ ID NO 161
<211> LENGTH: 218
<212> TYPE: PRT
<213> ORGANISM: Artificial Sequence
<220> FEATURE:
<223> OTHER INFORMATION: Humanized 52B8 LC  variable domain VL2
      N34Q/kappa constant domain

<400> SEQUENCE: 161

Asp Ile Val Leu Thr Gln Ser Pro Asp Ser Leu Ala Val Ser Leu Gly
1               5                   10                  15

Glu Arg Ala Thr Ile Asn Cys Arg Ala Ser Lys Val Asp Ser Phe
                20                  25                  30

Gly Gln Ser Phe Met His Trp Tyr Gln Gln Lys Pro Gly Gln Pro Pro
                35                  40                  45

Lys Leu Leu Ile Tyr Leu Thr Ser Asn Leu Asp Ser Gly Val Pro Asp
            50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                    180                 185                 190

His Lys Val Tyr Ala Cys Glu Val Thr His Gln Gly Leu Ser Ser Pro
                    195                 200                 205

Val Thr Lys Ser Phe Asn Arg Gly Glu Cys
                    210                 215

<210> SEQ ID NO 162
<211> LENGTH: 218
<212> TYPE: PRT
<213> ORGANISM: Artificial Sequence
<220> FEATURE:
<223> OTHER INFORMATION: Humanized 52B8 LC  variable domain VL2
      N34D/kappa constant domain

<400> SEQUENCE: 162

Asp Ile Val Leu Thr Gln Ser Pro Asp Ser Leu Ala Val Ser Leu Gly
```

```
              1               5              10              15
            Glu Arg Ala Thr Ile Asn Cys Arg Ala Ser Glu Lys Val Asp Ser Phe
                            20                  25                  30
            Gly Asp Ser Phe Met His Trp Tyr Gln Gln Lys Pro Gly Gln Pro Pro
                        35                  40                  45
            Lys Leu Leu Ile Tyr Leu Thr Ser Asn Leu Asp Ser Gly Val Pro Asp
                    50                  55                  60
            Arg Phe Ser Gly Ser Gly Ser Gly Thr Asp Phe Thr Leu Thr Ile Ser
            65                  70                  75                  80
            Ser Leu Gln Ala Glu Asp Val Ala Val Tyr Tyr Cys Gln Gln Asn Asn
                            85                  90                  95
            Glu Asp Pro Tyr Thr Phe Gly Gln Gly Thr Lys Leu Glu Ile Lys Arg
                        100                 105                 110
            Thr Val Ala Ala Pro Ser Val Phe Ile Phe Pro Pro Ser Asp Glu Gln
                        115                 120                 125
            Leu Lys Ser Gly Thr Ala Ser Val Val Cys Leu Leu Asn Asn Phe Tyr
                    130                 135                 140
            Pro Arg Glu Ala Lys Val Gln Trp Lys Val Asp Asn Ala Leu Gln Ser
            145                 150                 155                 160
            Gly Asn Ser Gln Glu Ser Val Thr Glu Gln Asp Ser Lys Asp Ser Thr
                            165                 170                 175
            Tyr Ser Leu Ser Ser Thr Leu Thr Leu Ser Lys Ala Asp Tyr Glu Lys
                        180                 185                 190
            His Lys Val Tyr Ala Cys Glu Val Thr His Gln Gly Leu Ser Ser Pro
                    195                 200                 205
            Val Thr Lys Ser Phe Asn Arg Gly Glu Cys
                    210                 215

<210> SEQ ID NO 163
<211> LENGTH: 218
<212> TYPE: PRT
<213> ORGANISM: Artificial Sequence
<220> FEATURE:
<223> OTHER INFORMATION: Humanized 52B8 LC  variable domain VL5
      S35A/kappa constant domain

<400> SEQUENCE: 163

Asp Ile Gln Leu Thr Gln Ser Pro Ser Ser Leu Ser Ala Ser Val Gly
            1               5                  10                  15
            Asp Arg Val Thr Ile Thr Cys Arg Ala Ser Glu Lys Val Asp Ser Phe
                        20                  25                  30
            Gly Asn Ala Phe Met His Trp Tyr Gln Gln Lys Pro Gly Lys Ala Pro
                    35                  40                  45
            Lys Leu Leu Ile Tyr Leu Thr Ser Asn Leu Asp Ser Gly Val Pro Ser
                50                  55                  60
            Arg Phe Ser Gly Ser Gly Ser Gly Thr Asp Phe Thr Leu Thr Ile Ser
            65                  70                  75                  80
            Ser Leu Gln Pro Glu Asp Phe Ala Thr Tyr Tyr Cys Gln Gln Asn Asn
                            85                  90                  95
            Glu Asp Pro Tyr Thr Phe Gly Gln Gly Thr Lys Leu Glu Ile Lys Arg
                        100                 105                 110
            Thr Val Ala Ala Pro Ser Val Phe Ile Phe Pro Pro Ser Asp Glu Gln
                        115                 120                 125
            Leu Lys Ser Gly Thr Ala Ser Val Val Cys Leu Leu Asn Asn Phe Tyr
                    130                 135                 140
```

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 164
<211> LENGTH: 218
<212> TYPE: PRT
<213> ORGANISM: Artificial Sequence
<220> FEATURE:
<223> OTHER INFORMATION: Humanized 52B8 LC  variable domain VL5
    S35N/kappa constant domain

<400> SEQUENCE: 164

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asn Asn Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 165
<211> LENGTH: 218
<212> TYPE: PRT
<213> ORGANISM: Artificial Sequence
<220> FEATURE:
<223> OTHER INFORMATION: Humanized 52B8 LC  variable domain VL5
    N34Q/kappa constant domain

<400> SEQUENCE: 165

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Gln Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
            85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 166
<211> LENGTH: 218
<212> TYPE: PRT
<213> ORGANISM: Artificial Sequence
<220> FEATURE:
<223> OTHER INFORMATION: Humanized 52B8 LC  variable domain VL5
      N34D/kappa constant domain

<400> SEQUENCE: 166

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Lys Val Asp Ser Phe
            20                  25                  30

Gly Asp Ser Phe Met His Trp Tyr Gln Gln Lys Pro Gly Lys Ala Pro
        35                  40                  45

Lys Leu Leu Ile Tyr Leu Thr Ser Asn Leu Asp Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Asn Asn
            85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

```
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 167
<211> LENGTH: 452
<212> TYPE: PRT
<213> ORGANISM: Artificial Sequence
<220> FEATURE:
<223> OTHER INFORMATION: Humanized 52B8 HC variable domain  VH1/ Human
      IgG1 HC (L234A L235A D265S) constant domain

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Ser Val Ser
        260                 265                 270

His Glu Asp Pro Glu Val Lys Phe Asn Trp Tyr Val Asp Gly Val Glu
```

```
                275                 280                 285
Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly Lys
    450

<210> SEQ ID NO 168
<211> LENGTH: 452
<212> TYPE: PRT
<213> ORGANISM: Artificial Sequence
<220> FEATURE:
<223> OTHER INFORMATION: Humanized 52B8 HC variable domain  VH1 M64V/
      Human IgG1 HC (L234A L235A D265S) constant domain

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 169
<211> LENGTH: 452
<212> TYPE: PRT
<213> ORGANISM: Artificial Sequence
<220> FEATURE:
<223> OTHER INFORMATION: Humanized 52B8 HC variable domain  VH1 M64L/
      Human IgG1 HC (L234A L235A D265S) constant domain

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Leu
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 170
<211> LENGTH: 452
<212> TYPE: PRT
<213> ORGANISM: Artificial Sequence
<220> FEATURE:

<223> OTHER INFORMATION: Humanized 52B8 HC variable domain VH1 M64V
W101F/ Human IgG1 HC (L234A L235A D265S) constant domain

<400> SEQUENCE: 170

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Phe Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
            450

<210> SEQ ID NO 171
<211> LENGTH: 452
<212> TYPE: PRT
<213> ORGANISM: Artificial Sequence
<220> FEATURE:
<223> OTHER INFORMATION: Humanized 52B8 HC variable domain  VH1 M64V
      W101Y/ Human IgG1 HC (L234A L235A D265S) constant domain

<400> SEQUENCE: 171

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Thr Ile Ser Gly Gly Gly Asp Tyr Thr Asn Tyr Pro Asp Ser Val
50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Gly Arg Arg Leu Tyr Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
```

```
            290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 172
<211> LENGTH: 452
<212> TYPE: PRT
<213> ORGANISM: Artificial Sequence
<220> FEATURE:
<223> OTHER INFORMATION: Humanized 52B8 HC variable domain VH1 M64V
      W101Q/ Human IgG1 HC (L234A L235A D265S) constant domain

<400> SEQUENCE: 172

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Gln Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

```
Val Pro Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 173
<211> LENGTH: 452
<212> TYPE: PRT
<213> ORGANISM: Artificial Sequence
<220> FEATURE:
<223> OTHER INFORMATION: Humanized 52B8 HC variable domain  VH2/ Human
      IgG1 HC (L234A L235A D265S) constant domain

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95
```

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 174
<211> LENGTH: 452
<212> TYPE: PRT
<213> ORGANISM: Artificial Sequence
<220> FEATURE:
<223> OTHER INFORMATION: Humanized 52B8 HC variable domain  VH2 M64V/
      Human IgG1 HC (L234A L235A D265S) constant domain

<400> SEQUENCE: 174

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

```
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 175
<211> LENGTH: 452
<212> TYPE: PRT
<213> ORGANISM: Artificial Sequence
<220> FEATURE:
<223> OTHER INFORMATION: Humanized 52B8 HC variable domain  VH2 M64L/
      Human IgG1 HC (L234A L235A D265S) constant domain

<400> SEQUENCE: 175

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Thr Ile Ser Gly Gly Gly Asp Tyr Thr Asn Tyr Pro Asp Ser Leu
        50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
        210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
```

```
                    305                 310                 315                 320
        Gly Lys Glu Tyr Lys Cys Lys Val Ser Asn Lys Ala Leu Pro Ala Pro
                        325                 330                 335
        Ile Glu Lys Thr Ile Ser Lys Ala Lys Gly Gln Pro Arg Glu Pro Gln
                        340                 345                 350
        Val Tyr Thr Leu Pro Pro Ser Arg Asp Glu Leu Thr Lys Asn Gln Val
                        355                 360                 365
        Ser Leu Thr Cys Leu Val Lys Gly Phe Tyr Pro Ser Asp Ile Ala Val
                        370                 375                 380
        Glu Trp Glu Ser Asn Gly Gln Pro Glu Asn Asn Tyr Lys Thr Thr Pro
        385                 390                 395                 400
        Pro Val Leu Asp Ser Asp Gly Ser Phe Phe Leu Tyr Ser Lys Leu Thr
                        405                 410                 415
        Val Asp Lys Ser Arg Trp Gln Gln Gly Asn Val Phe Ser Cys Ser Val
                        420                 425                 430
        Met His Glu Ala Leu His Asn His Tyr Thr Gln Lys Ser Leu Ser Leu
                        435                 440                 445
        Ser Pro Gly Lys
                450

<210> SEQ ID NO 176
<211> LENGTH: 448
<212> TYPE: PRT
<213> ORGANISM: Artificial Sequence
<220> FEATURE:
<223> OTHER INFORMATION: Humanized 52B8 HC variable domain  VH1/Human
      IgG4 (S228P) (K-) constant domain

<400> SEQUENCE: 176

Glu Val Gln Leu Val Glu Ser Gly Gly Gly Leu Val Gln Pro Gly Gly
        1               5                   10                  15
        Ser Leu Arg Leu Ser Cys Ala Ala Ser Gly Phe Thr Phe Ser Asn Tyr
                        20                  25                  30
        Gly Met Ser Trp Val Arg Gln Ala Pro Gly Lys Gly Leu Glu Trp Val
                        35                  40                  45
        Ala Thr Ile Ser Gly Gly Gly Asp Tyr Thr Asn Tyr Pro Asp Ser Met
                        50                  55                  60
        Arg Gly Arg Phe Thr Ile Ser Arg Asp Asn Ala Lys Asn Ser Leu Tyr
        65                  70                  75                  80
        Leu Gln Met Asn Ser Leu Arg Ala Glu Asp Thr Ala Val Tyr Tyr Cys
                        85                  90                  95
        Gly Arg Arg Leu Trp Phe Arg Ser Leu Tyr Tyr Ala Met Asp Tyr Trp
                        100                 105                 110
        Gly Gln Gly Thr Leu Val Thr Val Ser Ser Ala Ser Thr Lys Gly Pro
                        115                 120                 125
        Ser Val Phe Pro Leu Ala Pro Cys Ser Arg Ser Thr Ser Glu Ser Thr
                        130                 135                 140
        Ala Ala Leu Gly Cys Leu Val Lys Asp Tyr Phe Pro Glu Pro Val Thr
        145                 150                 155                 160
        Val Ser Trp Asn Ser Gly Ala Leu Thr Ser Gly Val His Thr Phe Pro
                        165                 170                 175
        Ala Val Leu Gln Ser Ser Gly Leu Tyr Ser Leu Ser Ser Val Val Thr
                        180                 185                 190
        Val Pro Ser Ser Ser Leu Gly Thr Lys Thr Tyr Thr Cys Asn Val Asp
                        195                 200                 205
```

His Lys Pro Ser Asn Thr Lys Val Asp Lys Arg Val Glu Ser Lys Tyr
            210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 177
<211> LENGTH: 448
<212> TYPE: PRT
<213> ORGANISM: Artificial Sequence
<220> FEATURE:
<223> OTHER INFORMATION: Humanized 52B8 HC variable domain  VH1
      M64V/Human IgG4 (S228P) (K-) constant domain

<400> SEQUENCE: 177

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 178
<211> LENGTH: 448
<212> TYPE: PRT
<213> ORGANISM: Artificial Sequence
<220> FEATURE:
<223> OTHER INFORMATION: Humanized 52B8 HC variable domain  VH1
      M64L/Human IgG4 (S228P) (K-) constant domain

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val

```
                35                  40                  45
Ala Thr Ile Ser Gly Gly Asp Tyr Thr Asn Tyr Pro Asp Ser Leu
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Gly Arg Arg Leu Trp Phe Arg Ser Leu Tyr Tyr Ala Met Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Cys Ser Arg Ser Thr Ser Glu Ser Thr
                130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
                210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
                435                 440                 445

<210> SEQ ID NO 179
```

```
<211> LENGTH: 448
<212> TYPE: PRT
<213> ORGANISM: Artificial Sequence
<220> FEATURE:
<223> OTHER INFORMATION: Humanized 52B8 HC variable domain  VH1 M64V
      W101F/Human IgG4 (S228P) (K-) constant domain

<400> SEQUENCE: 179
```

| | | | | | | | | | | | | | | |
|---|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly|
|1| | | |5| | | | |10| | | | |15|

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Thr Ile Ser Gly Gly Gly Asp Tyr Thr Asn Tyr Pro Asp Ser Val
 50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Gly Arg Arg Leu Phe Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu

```
                    370               375               380
Ser Asn Gly Gln Pro Glu Asn Tyr Lys Thr Thr Pro Pro Val Leu
385                 390               395               400

Asp Ser Asp Gly Ser Phe Phe Leu Tyr Ser Arg Leu Thr Val Asp Lys
            405               410               415

Ser Arg Trp Gln Glu Gly Asn Val Phe Ser Cys Ser Val Met His Glu
            420               425               430

Ala Leu His Asn His Tyr Thr Gln Lys Ser Leu Ser Leu Ser Leu Gly
            435               440               445

<210> SEQ ID NO 180
<211> LENGTH: 448
<212> TYPE: PRT
<213> ORGANISM: Artificial Sequence
<220> FEATURE:
<223> OTHER INFORMATION: Humanized 52B8 HC variable domain  VH1 M64V
      W101Y/Human IgG4 (S228P) (K-) constant domain

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Tyr Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285
```

```
Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 181
<211> LENGTH: 448
<212> TYPE: PRT
<213> ORGANISM: Artificial Sequence
<220> FEATURE:
<223> OTHER INFORMATION: Humanized 52B8 HC variable domain  VH1 M64V
      W101Q/Human IgG4 (S228P) (K-) constant domain

<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Gln Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205
```

-continued

```
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445

<210> SEQ ID NO 182
<211> LENGTH: 448
<212> TYPE: PRT
<213> ORGANISM: Artificial Sequence
<220> FEATURE:
<223> OTHER INFORMATION: Humanized 52B8 HC variable domain  VH2/Human
      IgG4 (S228P) (K-) constant domain

<400> SEQUENCE: 182

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Met Ser Trp Val Arg Gln Ala Pro Gly Lys Gly Leu Glu Trp Val
        35                  40                  45
Ala Thr Ile Ser Gly Gly Gly Asp Tyr Thr Asn Tyr Pro Asp Ser Met
    50                  55                  60
Arg Gly Arg Phe Thr Ile Ser Arg Asp Asn Ala Lys Asn Ser Leu Tyr
65                  70                  75                  80
Leu Gln Met Asn Ser Leu Lys Ala Glu Asp Thr Ala Val Tyr Tyr Cys
                85                  90                  95
Gly Arg Arg Leu Trp Phe Arg Ser Leu Tyr Tyr Ala Met Asp Tyr Trp
            100                 105                 110
Gly Gln Gly Thr Leu Val Thr Val Ser Ser Ala Ser Thr Lys Gly Pro
```

```
                115                 120                 125
Ser Val Phe Pro Leu Ala Pro Cys Ser Arg Ser Thr Ser Glu Ser Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Lys Thr Tyr Thr Cys Asn Val Asp
                195                 200                 205
His Lys Pro Ser Asn Thr Lys Val Asp Lys Arg Val Glu Ser Lys Tyr
                210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
                260                 265                 270
Pro Glu Val Gln Phe Asn Trp Tyr Val Asp Gly Val Glu Val His Asn
                275                 280                 285
Ala Lys Thr Lys Pro Arg Glu Glu Gln Phe Asn Ser Thr Tyr Arg Val
                290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
                355                 360                 365
Cys Leu Val Lys Gly Phe Tyr Pro Ser Asp Ile Ala Val Glu Trp Glu
                370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
                420                 425                 430
Ala Leu His Asn His Tyr Thr Gln Lys Ser Leu Ser Leu Ser Leu Gly
                435                 440                 445

<210> SEQ ID NO 183
<211> LENGTH: 448
<212> TYPE: PRT
<213> ORGANISM: Artificial Sequence
<220> FEATURE:
<223> OTHER INFORMATION: Humanized 52B8 HC variable domain  VH2
      M64V/Human IgG4 (S228P) (K-) constant domain

<400> SEQUENCE: 183

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
                20                  25                  30
```

-continued

```
Gly Met Ser Trp Val Arg Gln Ala Pro Gly Lys Gly Leu Glu Trp Val
         35                  40                  45
Ala Thr Ile Ser Gly Gly Asp Tyr Thr Asn Tyr Pro Asp Ser Val
 50                  55                  60
Arg Gly Arg Phe Thr Ile Ser Arg Asp Asn Ala Lys Asn Ser Leu Tyr
 65                  70                  75                  80
Leu Gln Met Asn Ser Leu Lys Ala Glu Asp Thr Ala Val Tyr Tyr Cys
                 85                  90                  95
Gly Arg Arg Leu Trp Phe Arg Ser Leu Tyr Tyr Ala Met Asp Tyr Trp
            100                 105                 110
Gly Gln Gly Thr Leu Val Thr Val Ser Ser Ala Ser Thr Lys Gly Pro
            115                 120                 125
Ser Val Phe Pro Leu Ala Pro Cys Ser Arg Ser Thr Ser Glu Ser Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Lys Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Phe Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
```

-continued

```
<210> SEQ ID NO 184
<211> LENGTH: 448
<212> TYPE: PRT
<213> ORGANISM: Artificial Sequence
<220> FEATURE:
<223> OTHER INFORMATION: Humanized 52B8 HC variable domain  VH2
      M64L/Human IgG4 (S228P) (K-) constant domain

<400> SEQUENCE: 184
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Leu
    50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
            405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

<210> SEQ ID NO 185
<211> LENGTH: 451
<212> TYPE: PRT
<213> ORGANISM: Artificial Sequence
<220> FEATURE:
<223> OTHER INFORMATION: Humanized 52B8 HC variable domain  VH1/ Human
      IgG1 HC (L234A L235A D265S) (K-) constant domain

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Met
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 186
<211> LENGTH: 451
<212> TYPE: PRT
<213> ORGANISM: Artificial Sequence
<220> FEATURE:
<223> OTHER INFORMATION: Humanized 52B8 HC variable domain  VH1 M64V/
      Human IgG1 HC (L234A L235A D265S) (K-) constant domain

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Gly Arg Arg Leu Trp Phe Arg Ser Leu Tyr Tyr Ala Met Asp Tyr Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr

```
                180             185               190
Val Pro Ser Ser Leu Gly Thr Gln Thr Tyr Ile Cys Asn Val Asn
            195                 200             205
His Lys Pro Ser Asn Thr Lys Val Asp Lys Lys Val Glu Pro Lys Ser
        210                 215                 220
Cys Asp Lys Thr His Thr Cys Pro Pro Cys Pro Ala Pro Glu Ala Ala
225             230                 235                 240
Gly Gly Pro Ser Val Phe Leu Phe Pro Pro Lys Pro Lys Asp Thr Leu
            245                 250                 255
Met Ile Ser Arg Thr Pro Glu Val Thr Cys Val Val Val Ser Val Ser
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305             310                 315                 320
Gly Lys Glu Tyr Lys Cys Lys Val Ser Asn Lys Ala Leu Pro Ala Pro
            325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
        370                 375                 380
Glu Trp Glu Ser Asn Gly Gln Pro Glu Asn Asn Tyr Lys Thr Thr Pro
385             390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly
    450

<210> SEQ ID NO 187
<211> LENGTH: 451
<212> TYPE: PRT
<213> ORGANISM: Artificial Sequence
<220> FEATURE:
<223> OTHER INFORMATION: Humanized 52B8 HC variable domain  VH1 M64L/
      Human IgG1 HC (L234A L235A D265S) (K-) constant domain

<400> SEQUENCE: 187

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Met Ser Trp Val Arg Gln Ala Pro Gly Lys Gly Leu Glu Trp Val
        35                  40                  45
Ala Thr Ile Ser Gly Gly Gly Asp Tyr Thr Asn Tyr Pro Asp Ser Leu
    50                  55                  60
Arg Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 188
<211> LENGTH: 451
<212> TYPE: PRT
<213> ORGANISM: Artificial Sequence
<220> FEATURE:
<223> OTHER INFORMATION: Humanized 52B8 HC variable domain  VH1 M64V
```

W101F/ Human IgG1 HC (L234A L235A D265S) (K-) constant domain

<400> SEQUENCE: 188

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly |
| 1 | | | | 5 | | | | | 10 | | | | | 15 |
| Ser | Leu | Arg | Leu | Ser | Cys | Ala | Ala | Ser | Gly | Phe | Thr | Phe | Ser | Asn | Tyr |
| | | | 20 | | | | | 25 | | | | | 30 | | |
| Gly | Met | Ser | Trp | Val | Arg | Gln | Ala | Pro | Gly | Lys | Gly | Leu | Glu | Trp | Val |
| | | 35 | | | | | 40 | | | | | 45 | | | |
| Ala | Thr | Ile | Ser | Gly | Gly | Asp | Tyr | Thr | Asn | Tyr | Pro | Asp | Ser | Val |
| | 50 | | | | | 55 | | | | | 60 | | | |
| Arg | Gly | Arg | Phe | Thr | Ile | Ser | Arg | Asp | Asn | Ala | Lys | Asn | Ser | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Gly | Arg | Arg | Leu | Phe | Phe | Arg | Ser | Leu | Tyr | Tyr | Ala | Met | Asp | Tyr | Trp |
| | | | 100 | | | | | 105 | | | | | 110 | | |
| Gly | Gln | Gly | Thr | Leu | Val | Thr | Val | Ser | Ser | Ala | Ser | Thr | Lys | Gly | Pro |
| | | 115 | | | | | 120 | | | | | 125 | | | |
| Ser | Val | Phe | Pro | Leu | Ala | Pro | Ser | Ser | Lys | Ser | Thr | Ser | Gly | Gly | Thr |
| | 130 | | | | | 135 | | | | | 140 | | | | |
| Ala | Ala | Leu | Gly | Cys | Leu | Val | Lys | Asp | Tyr | Phe | Pro | Glu | Pro | Val | Thr |
| 145 | | | | | 150 | | | | | 155 | | | | | 160 |
| Val | Ser | Trp | Asn | Ser | Gly | Ala | Leu | Thr | Ser | Gly | Val | His | Thr | Phe | Pro |
| | | | | 165 | | | | | 170 | | | | | 175 | |
| Ala | Val | Leu | Gln | Ser | Ser | Gly | Leu | Tyr | Ser | Leu | Ser | Ser | Val | Val | Thr |
| | | | 180 | | | | | 185 | | | | | 190 | | |
| Val | Pro | Ser | Ser | Ser | Leu | Gly | Thr | Gln | Thr | Tyr | Ile | Cys | Asn | Val | Asn |
| | | 195 | | | | | 200 | | | | | 205 | | | |
| His | Lys | Pro | Ser | Asn | Thr | Lys | Val | Asp | Lys | Lys | Val | Glu | Pro | Lys | Ser |
| | 210 | | | | | 215 | | | | | 220 | | | | |
| Cys | Asp | Lys | Thr | His | Thr | Cys | Pro | Pro | Cys | Pro | Ala | Pro | Glu | Ala | Ala |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Ser | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Tyr | Thr | Leu | Pro | Pro | Ser | Arg | Asp | Glu | Leu | Thr | Lys | Asn | Gln | Val |
| | | 355 | | | | | 360 | | | | | 365 | | | |
| Ser | Leu | Thr | Cys | Leu | Val | Lys | Gly | Phe | Tyr | Pro | Ser | Asp | Ile | Ala | Val |
| | 370 | | | | | 375 | | | | | 380 | | | | |
| Glu | Trp | Glu | Ser | Asn | Gly | Gln | Pro | Glu | Asn | Asn | Tyr | Lys | Thr | Thr | Pro |
| 385 | | | | | 390 | | | | | 395 | | | | | 400 |

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 189
<211> LENGTH: 451
<212> TYPE: PRT
<213> ORGANISM: Artificial Sequence
<220> FEATURE:
<223> OTHER INFORMATION: Humanized 52B8 HC variable domain   VH1 M64V
      W101Y/ Human IgG1 HC (L234A L235A D265S) (K-) constant domain

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Gly Arg Arg Leu Tyr Phe Arg Ser Leu Tyr Tyr Ala Met Asp Tyr Trp
        100                 105                 110

Gly Gln Gly Thr Leu Val Thr Val Ser Ser Ala Ser Thr Lys Gly Pro
    115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Ser Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

```
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
435                 440                 445

Ser Pro Gly
    450

<210> SEQ ID NO 190
<211> LENGTH: 451
<212> TYPE: PRT
<213> ORGANISM: Artificial Sequence
<220> FEATURE:
<223> OTHER INFORMATION: Humanized 52B8 HC variable domain  VH1 M64V
      W101Q/ Human IgG1 HC (L234A L235A D265S) (K-) constant domain

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Gly Arg Arg Leu Gln Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
```

```
                195                 200                 205
    His Lys Pro Ser Asn Thr Lys Val Asp Lys Val Glu Pro Lys Ser
        210                 215                 220

Cys Asp Lys Thr His Thr Cys Pro Pro Cys Pro Ala Pro Glu Ala Ala
    225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Ser Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
    305                 310                 315                 320

Gly Lys Glu Tyr Lys Cys Lys Val Ser Asn Lys Ala Leu Pro Ala Pro
                    325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
    385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly
        450

<210> SEQ ID NO 191
<211> LENGTH: 451
<212> TYPE: PRT
<213> ORGANISM: Artificial Sequence
<220> FEATURE:
<223> OTHER INFORMATION: Humanized 52B8 HC variable domain  VH2/ Human
      IgG1 HC (L234A L235A D265S) (K-)  constant domain

<400> SEQUENCE: 191

Glu Val Gln Leu Val Glu Ser Gly Gly Gly Leu Val Gln Pro Gly Gly
    1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Thr Ile Ser Gly Gly Gly Asp Tyr Thr Asn Tyr Pro Asp Ser Met
        50                  55                  60

Arg Gly Arg Phe Thr Ile Ser Arg Asp Asn Ala Lys Asn Ser Leu Tyr
    65                  70                  75                  80

Leu Gln Met Asn Ser Leu Lys Ala Glu Asp Thr Ala Val Tyr Tyr Cys
                    85                  90                  95
```

Gly Arg Arg Leu Trp Phe Arg Ser Leu Tyr Tyr Ala Met Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 192
<211> LENGTH: 451
<212> TYPE: PRT
<213> ORGANISM: Artificial Sequence
<220> FEATURE:
<223> OTHER INFORMATION: Humanized 52B8 HC variable domain  VH2 M64V/
      Human IgG1 HC (L234A L235A D265S) (K-) constant domain

<400> SEQUENCE: 192

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Asp Tyr Thr Asn Tyr Pro Asp Ser Val
50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415
```

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 193
<211> LENGTH: 451
<212> TYPE: PRT
<213> ORGANISM: Artificial Sequence
<220> FEATURE:
<223> OTHER INFORMATION: Humanized 52B8 HC variable domain  VH2 M64L/
      Human IgG1 HC (L234A L235A D265S) (K-) constant domain

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Gly Gly Gly Asp Tyr Thr Asn Tyr Pro Asp Ser Leu
    50                  55                  60

Arg Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Gly Arg Arg Leu Trp Phe Arg Ser Leu Tyr Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

```
Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly
    450

<210> SEQ ID NO 194
<211> LENGTH: 451
<212> TYPE: PRT
<213> ORGANISM: Artificial Sequence
<220> FEATURE:
<223> OTHER INFORMATION: Chimeric Anti-ILT3 rat 40A6 parental HC
      variable domain/human IgG4 (S228P) constant domain

<400> SEQUENCE: 194

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Ile Asn Trp Val Arg Gln Ser Ser Gly Lys Gly Pro Glu Trp Met
        35                  40                  45

Gly Arg Phe Trp Tyr Asp Glu Gly Ile Ala Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Ser Leu Arg Thr Gly Asp Thr Gly Thr Tyr Tyr Cys Thr
                85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
```

```
                210                 215                 220
Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 195
<211> LENGTH: 214
<212> TYPE: PRT
<213> ORGANISM: Artificial Sequence
<220> FEATURE:
<223> OTHER INFORMATION: Chimeric Anti-ILT3 rat 40A6 parental LC
      variable domain/human kappa

<400> SEQUENCE: 195

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Val Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60

Ser Gly Phe Gly Ser Asp Phe Thr Leu Thr Ile Ser Asp Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Ala Gly Thr Lys Leu Glu Leu Lys Arg Thr Val Ala Ala
            100                 105                 110
```

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 196
<211> LENGTH: 451
<212> TYPE: PRT
<213> ORGANISM: Artificial Sequence
<220> FEATURE:
<223> OTHER INFORMATION: Chimeric Anti-ILT3 rat 16B1 parental HC
      variable domain/human IgG4 (S228P) constant domain

<400> SEQUENCE: 196

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Asn Tyr
            20                  25                  30

Cys Val Asn Trp Val Arg Gln Pro Ser Gly Lys Gly Pro Glu Trp Leu
        35                  40                  45

Gly Arg Phe Trp Phe Asp Glu Gly Lys Ala Tyr Asn Leu Thr Leu Glu
    50                  55                  60

Ser Arg Leu Ser Ile Ser Gly Asp Thr Ser Lys Asn Gln Val Phe Leu
65                  70                  75                  80

Arg Met Asn Ser Leu Arg Ala Asp Asp Thr Gly Thr Tyr Tyr Cys Thr
                85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

```
Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 197
<211> LENGTH: 214
<212> TYPE: PRT
<213> ORGANISM: Artificial Sequence
<220> FEATURE:
<223> OTHER INFORMATION: Chimeric Anti-ILT3 rat 16B1 parental LC
      variable domain/human kappa

<400> SEQUENCE: 197

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Ile Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60

Ser Gly Phe Gly Ser Asp Phe Thr Leu Thr Ile Ser Asn Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Pro Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

145                 150                 155                 160
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 198
<211> LENGTH: 448
<212> TYPE: PRT
<213> ORGANISM: Artificial Sequence
<220> FEATURE:
<223> OTHER INFORMATION: Chimeric Anti-ILT3 mouse 11D1 parental HC
      variable domain/human IgG4 (S228P) constant domain

<400> SEQUENCE: 198

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Arg Thr Tyr
            20                  25                  30

Trp Ile Glu Trp Val Lys Gln Arg Pro Gly His Gly Leu Glu Trp Ile
        35                  40                  45

Gly Glu Ile Leu Pro Gly Asn Gly Asn Thr His Phe Asn Glu Asn Phe
    50                  55                  60

Lys Asp Lys Ala Thr Phe Thr Ala Asp Thr Ser Ser Asn Ala Ala Tyr
65                  70                  75                  80

Met Gln Leu Ser Ser Leu Thr Ser Glu Asp Ser Ala Val Tyr Tyr Cys
                85                  90                  95

Val Arg Arg Leu Gly Arg Gly Pro Phe Asp Phe Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ser Val Ser His Glu Asp Pro
            260                 265                 270

Glu Val Lys Phe Asn Trp Tyr Val Asp Gly Val Glu Val His Asn Ala
        275                 280                 285

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 199
<211> LENGTH: 214
<212> TYPE: PRT
<213> ORGANISM: Artificial Sequence
<220> FEATURE:
<223> OTHER INFORMATION: Chimeric Anti-ILT3 mouse 11D1 parental LC
      variable domain/human kappa

<400> SEQUENCE: 199

Asp Ile Gln Met Thr Gln Ser Pro Ser Ser Leu Ser Val Ser Leu Gly
1               5                   10                  15

Gly Lys Val Thr Ile Thr Cys Lys Ala Ser Gln Asp Ile Asn Glu Tyr
            20                  25                  30

Ile Gly Trp Tyr Gln Arg Lys Pro Gly Lys Gly Pro Arg Leu Leu Ile
        35                  40                  45

His Tyr Thr Ser Thr Leu Gln Ser Gly Ile Pro Ser Arg Phe Ser Gly
    50                  55                  60

Ser Gly Ser Gly Arg Asp Tyr Ser Leu Ser Ile Ser Asn Leu Glu Pro
65                  70                  75                  80

Glu Asp Ile Ala Thr Tyr Tyr Cys Leu Gln Tyr Ala Asn Pro Leu Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 200
<211> LENGTH: 452
<212> TYPE: PRT
<213> ORGANISM: Artificial Sequence
<220> FEATURE:
<223> OTHER INFORMATION: Chimeric Anti-ILT3 rat 17H12 parental HC
      variable domain/human IgG4 (S228P) constant domain

<400> SEQUENCE: 200

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Asn Phe
            20                  25                  30

Asp Met Ala Trp Val Arg Gln Ala Pro Thr Arg Gly Leu Glu Trp Val
        35                  40                  45

Ser Ser Ile Thr Tyr Asp Gly Ser Thr Ser Tyr Arg Asp Ser Val
50                  55                  60

Lys Gly Arg Phe Thr Ile Ser Arg Asp Asn Ala Lys Gly Thr Leu Tyr
65              70                  75                  80

Leu Gln Met Asp Ser Leu Arg Ser Glu Asp Thr Ala Thr Tyr Tyr Cys
                85                  90                  95

Thr Thr Val Glu Ser Ile Ala Thr Ile Ser Thr Tyr Phe Asp Tyr Trp
                100                 105                 110

Gly Gln Gly Val Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Ser Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
```

```
                340               345               350
Val Tyr Thr Leu Pro Pro Ser Arg Asp Glu Leu Thr Lys Asn Gln Val
            355               360               365

Ser Leu Thr Cys Leu Val Lys Gly Phe Tyr Pro Ser Asp Ile Ala Val
        370               375               380

Glu Trp Glu Ser Asn Gly Gln Pro Glu Asn Asn Tyr Lys Thr Thr Pro
385               390               395               400

Pro Val Leu Asp Ser Asp Gly Ser Phe Phe Leu Tyr Ser Lys Leu Thr
                405               410               415

Val Asp Lys Ser Arg Trp Gln Gln Gly Asn Val Phe Ser Cys Ser Val
            420               425               430

Met His Glu Ala Leu His Asn His Tyr Thr Gln Lys Ser Leu Ser Leu
        435               440               445

Ser Pro Gly Lys
    450
```

```
<210> SEQ ID NO 201
<211> LENGTH: 217
<212> TYPE: PRT
<213> ORGANISM: Artificial Sequence
<220> FEATURE:
<223> OTHER INFORMATION: Chimeric Anti-ILT3 rat 17H12 parental LC
      variable domain/human kappa

<400> SEQUENCE: 201

Asp Ile Val Leu Thr Gln Ser Pro Ala Leu Ala Val Ser Leu Gly Gln
1               5                   10                  15

Arg Ala Thr Ile Ser Cys Arg Ala Ser Gln Ser Val Ser Met Ser Arg
            20                  25                  30

Tyr Asp Leu Ile His Trp Tyr Gln Gln Lys Pro Gly Gln Gln Pro Lys
        35                  40                  45

Leu Leu Ile Phe Arg Ala Ser Asp Leu Ala Ser Gly Ile Pro Ala Arg
    50                  55                  60

Phe Ser Gly Ser Gly Ser Gly Thr Asp Phe Thr Leu Thr Ile Asn Pro
65                  70                  75                  80

Val Gln Ala Asp Asp Ile Ala Thr Tyr Tyr Cys Gln Gln Thr Arg Lys
                85                  90                  95

Ser Pro Pro Thr Phe Gly Gly Gly Thr Arg Leu Glu Leu Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 202
<211> LENGTH: 451
```

```
<212> TYPE: PRT
<213> ORGANISM: Artificial Sequence
<220> FEATURE:
<223> OTHER INFORMATION: Chimeric Anti-ILT3 rat 37C8 parental HC
      variable domain/human IgG4 (S228P) constant domain

<400> SEQUENCE: 202

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Cys Val Asn Trp Val Arg Gln Pro Ser Gly Lys Gly Pro Glu Trp Leu
        35                  40                  45

Gly Arg Phe Trp Tyr Asp Glu Gly Lys Val Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Arg Leu Arg Thr Asp Asp Thr Gly Thr Tyr Tyr Cys Thr
                85                  90                  95

Arg Asp Arg Asp Thr Met Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 203
<211> LENGTH: 214
<212> TYPE: PRT
<213> ORGANISM: Artificial Sequence
<220> FEATURE:
<223> OTHER INFORMATION: Chimeric Anti-ILT3 rat 37C8 parental LC
      variable domain/human kappa

<400> SEQUENCE: 203

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Ile Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60

Ser Gly Phe Gly Ser Gly Phe Thr Leu Thr Ile Ser Asn Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Pro Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 204
<211> LENGTH: 448
<212> TYPE: PRT
<213> ORGANISM: Artificial Sequence
<220> FEATURE:
<223> OTHER INFORMATION: Chimeric Anti-ILT3 mouse 1G12 parental HC
      variable domain/human IgG4 (S228P) constant domain

<400> SEQUENCE: 204

-continued

```
Gln Val Gln Met Gln Gln Ser Gly Thr Glu Leu Met Lys Pro Gly Ala
1               5                   10                  15

Ser Met Lys Ile Ser Cys Lys Ala Thr Gly Tyr Thr Phe Thr Tyr
            20                  25                  30

Trp Ile Gln Trp Ile Lys Gln Arg Pro Gly His Gly Leu Glu Trp Ile
            35                  40                  45

Gly Glu Ile Leu Pro Gly Ser Gly Thr Asn Tyr Asn Glu Asn Phe
        50                  55                  60

Lys Gly Lys Ala Thr Phe Ser Ala Asp Thr Ser Ser Asn Thr Ala Tyr
65                  70                  75                  80

Ile His Leu Ser Ser Leu Thr Ser Glu Asp Ser Ala Val Phe Tyr Cys
                85                  90                  95

Ala Arg Arg Leu Gly Arg Gly Pro Phe Asp Tyr Trp Gly Gln Gly Thr
                100                 105                 110

Thr Leu Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Ser Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 205
<211> LENGTH: 214
<212> TYPE: PRT
<213> ORGANISM: Artificial Sequence
<220> FEATURE:
<223> OTHER INFORMATION: Chimeric Anti-ILT3 mouse 1G12 parental LC
      variable domain/human kappa

<400> SEQUENCE: 205

Asp Ile Gln Met Thr Gln Ser Pro Ser Ser Leu Ser Ala Ser Leu Gly
1               5                   10                  15

Gly Lys Val Thr Ile Thr Cys Glu Ala Ser Gln Asp Ile Asn Lys His
            20                  25                  30

Ile Asp Trp Tyr Gln His Gln Pro Gly Arg Gly Pro Ser Leu Leu Ile
        35                  40                  45

His Tyr Ala Ser Ile Leu Gln Pro Gly Ile Pro Ser Arg Phe Ser Gly
    50                  55                  60

Ser Gly Ser Gly Arg Asp Tyr Ser Phe Ser Ile Thr Ser Leu Glu Pro
65                  70                  75                  80

Glu Asp Ile Ala Thr Tyr Tyr Cys Leu Gln Tyr Asp Asn Leu Leu Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 206
<211> LENGTH: 451
<212> TYPE: PRT
<213> ORGANISM: Artificial Sequence
<220> FEATURE:
<223> OTHER INFORMATION: Chimeric Anti-ILT3 rat 20E4 parental HC
      variable domain/human IgG4 (S228P) constant domain

<400> SEQUENCE: 206

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Val Asn Trp Val Arg Gln Pro Ser Gly Lys Gly Leu Glu Trp Met
        35                  40                  45

```
Gly Arg Phe Trp Tyr Asp Gly Gly Thr Ala Tyr Asn Ser Thr Leu Glu
     50                  55                  60

Ser Arg Leu Ser Ile Ser Gly Asp Thr Ser Lys Asn Gln Val Phe Leu
 65                  70                  75                  80

Lys Met Asn Ser Leu Gln Thr Asp Asp Thr Gly Thr Tyr Tyr Cys Thr
                 85                  90                  95

Arg Asp Arg Asp Thr Met Gly Ile Thr Gly Trp Phe Ala Tyr Trp Gly
                100                 105                 110

Gln Gly Thr Leu Val Thr Val Ser Pro Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
         210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
450
```

-continued

<210> SEQ ID NO 207
<211> LENGTH: 214
<212> TYPE: PRT
<213> ORGANISM: Artificial Sequence
<220> FEATURE:
<223> OTHER INFORMATION: Chimeric Anti-ILT3 rat 20E4 parental LC
      variable domain/human kappa

<400> SEQUENCE: 207

Glu Thr Val Met Thr Gln Ser Pro Thr Ser Leu Ser Ala Ser Ile Gly
1               5                   10                  15

Glu Arg Val Thr Leu Asn Cys Lys Ala Ser Gln Ser Val Gly Val Asn
            20                  25                  30

Val Asp Trp Tyr Gln Gln Thr Pro Gly Gln Ser Pro Lys Leu Leu Ile
        35                  40                  45

Tyr Gly Ser Ala Asn Arg His Thr Gly Val Pro Asp Arg Phe Thr Gly
    50                  55                  60

Ser Gly Phe Gly Ser Asp Phe Thr Leu Thr Ile Ser Asn Val Glu Pro
65                  70                  75                  80

Glu Asp Leu Gly Val Tyr Tyr Cys Leu Gln Tyr Gly Ser Val Pro Tyr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 208
<211> LENGTH: 451
<212> TYPE: PRT
<213> ORGANISM: Artificial Sequence
<220> FEATURE:
<223> OTHER INFORMATION: Chimeric Anti-ILT3 rat 24A4 parental HC
      variable domain/human IgG4 (S228P) constant domain

<400> SEQUENCE: 208

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Cys Val Asn Trp Val Arg Gln Pro Ser Gly Lys Gly Pro Glu Trp Leu
        35                  40                  45

Gly Arg Phe Trp Tyr Asp Glu Gly Lys Val Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Arg Leu Arg Thr Asp Asp Thr Gly Thr Tyr Tyr Cys Thr

```
                85                  90                  95
Arg Asp Arg Asp Thr Leu Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 209
<211> LENGTH: 214
<212> TYPE: PRT
<213> ORGANISM: Artificial Sequence
<220> FEATURE:
<223> OTHER INFORMATION: Chimeric Anti-ILT3 rat 24A4 parental LC
      variable domain/human kappa
```

<400> SEQUENCE: 209

```
Glu Thr Val Met Thr Gln Ser Pro Thr Ser Leu Ser Ala Ser Ile Gly
1               5                   10                  15
Glu Arg Val Thr Leu Asn Cys Lys Ala Ser Gln Ser Val Gly Ile Asn
            20                  25                  30
Val Asp Trp Tyr Gln Gln Thr Pro Gly Gln Ser Pro Lys Leu Leu Ile
        35                  40                  45
Tyr Gly Ser Ala Asn Arg His Thr Gly Val Pro Asp Arg Phe Thr Gly
    50                  55                  60
Ser Gly Phe Gly Ser Gly Phe Thr Leu Thr Ile Ser Asn Val Glu Pro
65                  70                  75                  80
Glu Asp Leu Gly Val Tyr Tyr Cys Leu Gln Tyr Gly Ser Val Pro Tyr
                85                  90                  95
Thr Phe Gly Pro Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 210
<211> LENGTH: 452
<212> TYPE: PRT
<213> ORGANISM: Artificial Sequence
<220> FEATURE:
<223> OTHER INFORMATION: Humanized 52B8 HC variable domain VH1 M64V/
      Human IgG1 HC (N297A) constant domain

<400> SEQUENCE: 210

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Met Ser Trp Val Arg Gln Ala Pro Gly Lys Gly Leu Glu Trp Val
        35                  40                  45
Ala Thr Ile Ser Gly Gly Gly Asp Tyr Thr Asn Tyr Pro Asp Ser Val
    50                  55                  60
Arg Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Gly Arg Arg Leu Trp Phe Arg Ser Leu Tyr Tyr Ala Met Asp Tyr Trp
            100                 105                 110
Gly Gln Gly Thr Leu Val Thr Val Ser Ser Ala Ser Thr Lys Gly Pro
        115                 120                 125
```

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 211
<211> LENGTH: 330
<212> TYPE: PRT
<213> ORGANISM: Artificial Sequence
<220> FEATURE:
<223> OTHER INFORMATION: Human IgG1 HC constant domain (N297A)

<400> SEQUENCE: 211

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 212
<211> LENGTH: 451
<212> TYPE: PRT
<213> ORGANISM: Artificial Sequence
<220> FEATURE:
<223> OTHER INFORMATION: Chimeric anti-ILT3 40A6 rat VH /human IgG1
      (N297A)

<400> SEQUENCE: 212

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Ile Asn Trp Val Arg Gln Ser Ser Gly Lys Gly Pro Glu Trp Met
        35                  40                  45

Gly Arg Phe Trp Tyr Asp Glu Gly Ile Ala Tyr Asn Leu Thr Leu Glu

```
            50                  55                  60
Ser Arg Leu Ser Ile Ser Gly Asp Thr Ser Lys Asn Gln Val Phe Leu
 65                  70                  75                  80

Lys Met Asn Ser Leu Arg Thr Gly Asp Thr Gly Thr Tyr Tyr Cys Thr
                 85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 213
```

```
<211> LENGTH: 451
<212> TYPE: PRT
<213> ORGANISM: Artificial Sequence
<220> FEATURE:
<223> OTHER INFORMATION: Chimeric anti-ILT3 16B1 rat VH /human IgG1
      (N297A)

<400> SEQUENCE: 213
```

Gln Val Gln Leu Lys Glu Ser Gly Pro Gly Leu Val Gln Ala Ser Glu
1               5                   10                  15

Thr Leu Ser Leu Thr Cys Thr Val Gly Phe Ser Leu Thr Asn Tyr
            20                  25                  30

Cys Val Asn Trp Val Arg Gln Pro Ser Gly Lys Gly Pro Glu Trp Leu
        35                  40                  45

Gly Arg Phe Trp Phe Asp Glu Gly Lys Ala Tyr Asn Leu Thr Leu Glu
    50                  55                  60

Ser Arg Leu Ser Ile Ser Gly Asp Thr Ser Lys Asn Gln Val Phe Leu
65                  70                  75                  80

Arg Met Asn Ser Leu Arg Ala Asp Asp Thr Gly Thr Tyr Tyr Cys Thr
                85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu

```
                    370                 375                 380
Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 214
<211> LENGTH: 448
<212> TYPE: PRT
<213> ORGANISM: Artificial Sequence
<220> FEATURE:
<223> OTHER INFORMATION: Chimeric anti-ILT3 11D1 mouse VH /human IgG1
      (N297A)

<400> SEQUENCE: 214

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Arg Thr Tyr
                20                  25                  30

Trp Ile Glu Trp Val Lys Gln Arg Pro Gly His Gly Leu Glu Trp Ile
            35                  40                  45

Gly Glu Ile Leu Pro Gly Asn Gly Asn Thr His Phe Asn Glu Asn Phe
    50                  55                  60

Lys Asp Lys Ala Thr Phe Thr Ala Asp Thr Ser Ser Asn Ala Ala Tyr
65                  70                  75                  80

Met Gln Leu Ser Ser Leu Thr Ser Glu Asp Ser Ala Val Tyr Tyr Cys
                85                  90                  95

Val Arg Arg Leu Gly Arg Gly Pro Phe Asp Phe Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 215
<211> LENGTH: 452
<212> TYPE: PRT
<213> ORGANISM: Artificial Sequence
<220> FEATURE:
<223> OTHER INFORMATION: Chimeric anti-ILT3 17H12 rat VH /human IgG1
      (N297A)

<400> SEQUENCE: 215

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Asn Phe
            20                  25                  30

Asp Met Ala Trp Val Arg Gln Ala Pro Thr Arg Gly Leu Glu Trp Val
            35                  40                  45

Ser Ser Ile Thr Tyr Asp Gly Gly Ser Thr Ser Tyr Arg Asp Ser Val
        50                  55                  60

Lys Gly Arg Phe Thr Ile Ser Arg Asp Asn Ala Lys Gly Thr Leu Tyr
65                  70                  75                  80

Leu Gln Met Asp Ser Leu Arg Ser Glu Asp Thr Ala Thr Tyr Tyr Cys
                85                  90                  95

Thr Thr Val Glu Ser Ile Ala Thr Ile Ser Thr Tyr Phe Asp Tyr Trp
            100                 105                 110

Gly Gln Gly Val Met Val Thr Val Ser Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190
```

Val Pro Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 216
<211> LENGTH: 451
<212> TYPE: PRT
<213> ORGANISM: Artificial Sequence
<220> FEATURE:
<223> OTHER INFORMATION: Chimeric anti-ILT3 37C8 rat VH /human IgG1
      (N297A)

<400> SEQUENCE: 216

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Cys Val Asn Trp Val Arg Gln Pro Ser Gly Lys Gly Pro Glu Trp Leu
        35                  40                  45

Gly Arg Phe Trp Tyr Asp Glu Gly Lys Val Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Arg Leu Arg Thr Asp Asp Thr Gly Thr Tyr Tyr Cys Thr

```
                        85                  90                  95
Arg Asp Arg Asp Thr Met Gly Ile Thr Gly Trp Phe Ala Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 217
<211> LENGTH: 448
<212> TYPE: PRT
<213> ORGANISM: Artificial Sequence
<220> FEATURE:
<223> OTHER INFORMATION: Chimeric anti-ILT3 1G12 mouse VH /human IgG1
      (N297A)
```

<400> SEQUENCE: 217

```
Gln Val Gln Met Gln Gln Ser Gly Thr Glu Leu Met Lys Pro Gly Ala
1               5                   10                  15

Ser Met Lys Ile Ser Cys Lys Ala Thr Gly Tyr Thr Phe Ser Thr Tyr
            20                  25                  30

Trp Ile Gln Trp Ile Lys Gln Arg Pro Gly His Gly Leu Glu Trp Ile
        35                  40                  45

Gly Glu Ile Leu Pro Gly Ser Gly Thr Thr Asn Tyr Asn Glu Asn Phe
    50                  55                  60

Lys Gly Lys Ala Thr Phe Ser Ala Asp Thr Ser Ser Asn Thr Ala Tyr
65                  70                  75                  80

Ile His Leu Ser Ser Leu Thr Ser Glu Asp Ser Ala Val Phe Tyr Cys
                85                  90                  95

Ala Arg Arg Leu Gly Arg Gly Pro Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
```

```
                    405                 410                 415
Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 218
<211> LENGTH: 451
<212> TYPE: PRT
<213> ORGANISM: Artificial Sequence
<220> FEATURE:
<223> OTHER INFORMATION: Chimeric anti-ILT3 20E4 rat VH /human IgG1
      (N297A)

<400> SEQUENCE: 218

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Val Asn Trp Val Arg Gln Pro Ser Gly Lys Gly Leu Glu Trp Met
        35                  40                  45

Gly Arg Phe Trp Tyr Asp Gly Gly Thr Ala Tyr Asn Ser Thr Leu Glu
    50                  55                  60

Ser Arg Leu Ser Ile Ser Gly Asp Thr Ser Lys Asn Gln Val Phe Leu
65                  70                  75                  80

Lys Met Asn Ser Leu Gln Thr Asp Asp Thr Gly Thr Tyr Tyr Cys Thr
                85                  90                  95

Arg Asp Arg Asp Thr Met Gly Ile Thr Gly Trp Phe Ala Tyr Trp Gly
            100                 105                 110

Gln Gly Thr Leu Val Thr Val Ser Pro Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 219
<211> LENGTH: 451
<212> TYPE: PRT
<213> ORGANISM: Artificial Sequence
<220> FEATURE:
<223> OTHER INFORMATION: Chimeric anti-ILT3 24A4 rat VH /human IgG1
      (N297A)

<400> SEQUENCE: 219

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Cys Val Asn Trp Val Arg Gln Pro Ser Gly Lys Gly Pro Glu Trp Leu
        35                  40                  45

Gly Arg Phe Trp Tyr Asp Glu Gly Lys Val Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Arg Leu Arg Thr Asp Asp Thr Gly Thr Tyr Tyr Cys Thr
                85                  90                  95

Arg Asp Arg Asp Thr Leu Gly Ile Thr Gly Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Ala Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
   450

<210> SEQ ID NO 220
<211> LENGTH: 451
<212> TYPE: PRT
<213> ORGANISM: Artificial Sequence
<220> FEATURE:
<223> OTHER INFORMATION: Chimeric anti-ILT3 40A6 rat VH /human IgG1
      (N297A)

<400> SEQUENCE: 220

Gln Val Gln Leu Lys Glu Ser Gly Pro Gly Leu Val Gln Ala Ser Glu
1               5                   10                  15

Thr Leu Ser Leu Thr Cys Thr Val Ser Gly Phe Ser Leu Thr Ser Tyr
            20                  25                  30

Ser Ile Asn Trp Val Arg Gln Ser Ser Gly Lys Gly Pro Glu Trp Met
            35                  40                  45

Gly Arg Phe Trp Tyr Asp Glu Gly Ile Ala Tyr Asn Leu Thr Leu Glu
    50                  55                  60

Ser Arg Leu Ser Ile Ser Gly Asp Thr Ser Lys Asn Gln Val Phe Leu
65                  70                  75                  80

Lys Met Asn Ser Leu Arg Thr Gly Asp Thr Gly Thr Tyr Tyr Cys Thr
                85                  90                  95

Arg Asp Arg Asp Thr Val Gly Ile Thr Gly Trp Phe Ala Tyr Trp Gly
            100                 105                 110

Gln Gly Thr Leu Val Thr Val Ser Ser Ala Ser Thr Lys Gly Pro Ser
```

```
            115                 120                 125
Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 221
<211> LENGTH: 4
<212> TYPE: PRT
<213> ORGANISM: Artificial Sequence
<220> FEATURE:
<223> OTHER INFORMATION: Residues after LC-CDR3
<220> FEATURE:
<221> NAME/KEY: VARIANT
<222> LOCATION: (3)..(3)
<223> OTHER INFORMATION: X is any amino acid

<400> SEQUENCE: 221
```

```
Phe Gly Xaa Gly
1

<210> SEQ ID NO 222
<211> LENGTH: 4
<212> TYPE: PRT
<213> ORGANISM: Artificial Sequence
<220> FEATURE:
<223> OTHER INFORMATION: Residues before HC-CDR1
<220> FEATURE:
<221> NAME/KEY: VARIANT
<222> LOCATION: (2)..(4)
<223> OTHER INFORMATION: X is any amino acid

<400> SEQUENCE: 222

Cys Xaa Xaa Xaa
1

<210> SEQ ID NO 223
<211> LENGTH: 5
<212> TYPE: PRT
<213> ORGANISM: Artificial Sequence
<220> FEATURE:
<223> OTHER INFORMATION: Residues before HC-CDR2

<400> SEQUENCE: 223

Leu Glu Trp Ile Gly
1               5

<210> SEQ ID NO 224
<211> LENGTH: 4
<212> TYPE: PRT
<213> ORGANISM: Artificial Sequence
<220> FEATURE:
<223> OTHER INFORMATION: Residues after HC-CDR2
<220> FEATURE:
<221> NAME/KEY: VARIANT
<222> LOCATION: (3)..(3)
<223> OTHER INFORMATION: X is any amino acid

<400> SEQUENCE: 224

Trp Gly Xaa Gly
1

<210> SEQ ID NO 225
<211> LENGTH: 447
<212> TYPE: PRT
<213> ORGANISM: Artificial Sequence
<220> FEATURE:
<223> OTHER INFORMATION: Pembrolizumab Heavy Chain

<400> SEQUENCE: 225

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
```

```
                100             105             110
Gly Thr Thr Val Thr Val Ser Ser Ala Ser Thr Lys Gly Pro Ser Val
            115             120             125

Phe Pro Leu Ala Pro Cys Ser Arg Ser Thr Ser Glu Ser Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
        180             185             190

Ser Ser Ser Leu Gly Thr Lys Thr Tyr Thr Cys Asn Val Asp His Lys
        195             200             205

Pro Ser Asn Thr Lys Val Asp Lys Arg Val Glu Ser Lys Tyr Gly Pro
    210             215             220

Pro Cys Pro Pro Cys Pro Ala Pro Glu Phe Leu Gly Gly Pro Ser Val
225             230             235             240

Phe Leu Phe Pro Pro Lys Pro Lys Asp Thr Leu Met Ile Ser Arg Thr
            245             250             255

Pro Glu Val Thr Cys Val Val Val Asp Val Ser Gln Glu Asp Pro Glu
        260             265             270

Val Gln Phe Asn Trp Tyr Val Asp Gly Val Glu Val His Asn Ala Lys
        275             280             285

Thr Lys Pro Arg Glu Glu Gln Phe Asn Ser Thr Tyr Arg Val Val Ser
    290             295             300

Val Leu Thr Val Leu His Gln Asp Trp Leu Asn Gly Lys Glu Tyr Lys
305             310             315             320

Cys Lys Val Ser Asn Lys Gly Leu Pro Ser Ser Ile Glu Lys Thr Ile
            325             330             335

Ser Lys Ala Lys Gly Gln Pro Arg Glu Pro Gln Val Tyr Thr Leu Pro
        340             345             350

Pro Ser Gln Glu Glu Met Thr Lys Asn Gln Val Ser Leu Thr Cys Leu
        355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
            405             410             415

Trp Gln Glu Gly Asn Val Phe Ser Cys Ser Val Met His Glu Ala Leu
        420             425             430

His Asn His Tyr Thr Gln Lys Ser Leu Ser Leu Ser Leu Gly Lys
        435             440             445

<210> SEQ ID NO 226
<211> LENGTH: 218
<212> TYPE: PRT
<213> ORGANISM: Artificial Sequence
<220> FEATURE:
<223> OTHER INFORMATION: Pembrolizumab Light Chain

<400> SEQUENCE: 226

Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Gly Val Ser Thr Ser
```

```
                    20                  25                  30
Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 227
<211> LENGTH: 330
<212> TYPE: PRT
<213> ORGANISM: Artificial sequence
<220> FEATURE:
<223> OTHER INFORMATION: Human IgG1 HC constant domain (N297A; D265A)

<400> SEQUENCE: 227

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Ala Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

-continued

```
                165                 170                 175
Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

ANTIBODIES SPECIFIC FOR IMMUNOGLOBULIN-LIKE TRANSCRIPT 3 (ILT3) AND USES THEREOF

CROSS REFERENCE TO RELATED APPLICATIONS

The present application claims benefit of U.S. Provisional Patent Application No. 62/587,604 filed Nov. 17, 2017, and which is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "24530US_NP_SEQTXT_05NOVEMBER2018.txt", creation date of Nov. 5, 2018, and a size of 376 Kb. This sequence listing submitted via EFS-Web is part of the specification and is herein incorporated by reference in its entirety.

BACKGROUND OF THE INVENTION

(1) Field of the Invention

The present invention provides non-promiscuous monoclonal antibodies specific for immunoglobulin-like transcript 3 (ILT3), an inhibitory receptor expressed on the surface of myeloid immune cells.

(2) Description of Related Art

Immunoglobulin-like transcript 3 (ILT3), designated CD85 k and also known as Leukocyte Immunoglobulin-Like Receptor subfamily B member 4 (LILRB4) and Leukocyte Immunoglobulin-like Receptor 5 (LIR-5), is a type I membrane protein that contains cytoplasmic immunoreceptor tyrosine-based inhibition motif (ITIM) motifs and is involved in the down-regulation of immune responses (Cella et al., J Exp Med. 185 (10): 1743-51 (1997); Samaridis et Eur J Immunol. 27 (3): 660-665 (1997). Expression of ILT3 is up-regulated on tolerogenic dendritic cells. This gene is a member of the leukocyte immunoglobulin-like receptor (LIR) family, which is found in a gene cluster at chromosomal region 19q13.4. The encoded protein belongs to the subfamily B class of LIR receptors, which contain two or four extracellular immunoglobulin domains, a transmembrane domain, and two to four ITIMs. ILT3 is selectively expressed by myeloid antigen presenting cells (APCs) such as monocytes, macrophages, and dendritic cells, e.g., monocyte-derived dendritic cells differentiated in the presence of IL-10 or vitamin $D_3$. ILT3 consists of 447 amino acids with a predicted molecular mass of about 47 kD. The amino terminal portion of ILT3 begins with a hydrophobic signal peptide of 23 amino acids followed by an extracellular domain composed of two $C_2$ type immunoglobulin superfamily domains and having the amino acid sequence set forth in SEQ ID NO: 1 less the C-terminal His Tag. (The Rhesus monkey ILT3 extracellular domain has the amino acid sequence set forth in SEQ ID NO: 2). The putative transmembrane domain of ILT3 consists of 21 amino acids, followed by a long cytoplasmic region of 167 amino acids, which is characterized by the presence of motifs spaced by 26 amino acid residues and are reminiscent of the ITIM motifs identified in KIRs (natural-killer cell Ig receptors) as binding sites for protein tyrosine phosphatase SHP-1. ILT3 is expressed on immune cells where it binds to MHC class I molecules on antigen-presenting cells and transduces a negative signal that inhibits stimulation of an immune response. The receptor can also function in antigen capture and presentation. ILT3 is thought to control inflammatory responses and cytotoxicity to help focus the immune response and to limit auto-reactivity. Multiple transcript variants encoding different isoforms of ILT3 have been identified.

Patent publications that disclose use of an antibody for modulating ILT3 activity with applications for inhibiting transplant rejection or for use in treatments for cancer or infectious diseases include U.S. Pub. Nos. 20090202544, 20150110714, 20150139986, and 20170267759; and, Intl. Pub. Nos. WO2013043569, WO2013181438, WO2014116846, WO2016049641, WO2016127427, WO2018089300, and WO2018148494. Of interest is Intl. Pub. No. WO2017015227, which discloses CD166, also known as lymphocyte cell adhesion molecule (ALCAM), as a ligand for ILT3 and provides methods for treating cancer comprising in some embodiments an antibody against CD166 or ALCAM. Also of interest are U.S. Pat. Nos. 7,777,008 and 8,901,281, which disclose monoclonal antibody 9B11 for use in various treatments where it is desirable to upregulate the immune system for anti-cancer treatments and to downregulate the immune system for inhibiting transplant rejection.

While the patent publications disclose anti-ILT3 antibodies, in some instances no specific antibody is disclosed or specific antibodies are disclosed, which in some cases are shown to be promiscuous and cross-react with one or more ILT3-related receptors such as LILRA6 and ILT8. Promiscuous anti-ILT3 antibodies may have off-target effects, which may have undesirable effects that contraindicate its use for therapeutic applications. Therefore there is a need for antibodies and antigen binding fragments that specifically bind ILT3 and have no measurable promiscuity towards other related receptors.

BRIEF SUMMARY OF THE INVENTION

The present invention provides monoclonal antibodies and antigen binding fragments that bind specifically to immunoglobulin-like transcript 3 (ILT3) with no measurable binding to closely related proteins (e.g., ILT5, ILT7, ILT8, or ILT11) as determined by (i) a cell ELISA using 10 μg/mL antibody or antigen binding fragment or (ii) Biacore using 10 μg/mL antibody or antigen binding fragment. In particular embodiments, the antibodies and antigen binding fragments specifically bind to both human ILT3 and Rhesus monkey ILT3. These antibodies and antigen binding fragments are capable of antagonizing ILT3 activity thereby enhancing dendritic cell activation and T cell priming. Tolerized dendritic cells and myeloid-derived suppressor cells (MDSCs) are also responsive to these antibodies. Furthermore, in vivo studies of these antibodies in humanized NSG™ mouse model systems (The Jackson Laboratories, Bar Harbor, Me.) show that these antibodies may have the ability to reduce tumor burden and shift cellular phenotypes to a more activated state.

In clinical trial samples, ILT3 expression, like PD-L1, LAG3, and the GEP signature, was found to be associated with responsiveness to the anti-PD-1 antibody, pembrolizumab. Soluble ILT3 in circulation is also increased in certain cancer types. Taken together, the anti-ILT3 antibodies of the present invention may be useful for treating particular cancers either as a monotherapy treatment or in combination with an anti-PD-1 and/or anti-PD-L1 antibody to enhance responsiveness to the anti-PD-1 or anti-PD-L1 antibody, particularly in cancer treatments in which the cancer is non-responsive to anti-PD-1 or anti-PD-L1 monotherapies. In particular embodiments, the present invention provides chimeric or humanized anti-ILT3 antibodies. In certain embodiments, the antibodies may be fully human antibodies that compete with the antibodies disclosed herein for binding to the ILT3 epitope disclosed herein.

The present invention provides an antibody or antigen binding fragment comprising one, two, or three complementarity determining regions (CDRs) of a heavy chain variable $V_H$ domain having heavy chain complementarity determining region (HC-CDR) 1, 2, and 3 and one, two, or three CDRs of a light chain variable domain $V_L$ having LC-CDR1, 2, and 3, wherein the antibody or antigen binding fragment is capable of specifically binding human ILT3 wherein the the binding of the antibody or antigen binding fragment may be determined by cell ELISA or Biacore.

In a further embodiment, the antibody or antigen binding fragment binds to an epitope on the human ILT3 or competes with an antibody disclosed for binding to an epitope on the human ILT3, wherein the epitope comprises at least one amino acid within one or more of the amino acid sequences set forth in the group consisting of SEQ ID NOs:3, 4, 5, 6, 7, and 8. In further embodiments, the antibody or antigen binding fragment binds to an epitope on the human ILT3 or competes with an antibody disclosed for binding to an epitope on the human ILT3, wherein the epitope comprises one or more of the amino acid sequences set forth in the group consisting of SEQ ID NOs:3, 4, 5, 6, 7, and 8. In further embodiments, the antibody or antigen binding fragment binds to an epitope on the human ILT3 or competes with an antibody disclosed for binding to an epitope on the human ILT3, wherein the epitope comprises the amino acid sequences set forth in the group consisting of SEQ ID NOs:3, 4, 5, 6, 7, and 8. In particular embodiments, the epitope is determined by hydrogen deuterium exchange mass spectrometry (HDX-MS) analysis.

The present invention further provides an antibody or antigen binding fragment that binds human ILT3 comprising a heavy chain (HC) wherein the heavy chain variable domain ($V_H$) comprises a heavy chain complementarity determining region (HC-CDR) 3 having an amino acid sequence selected from the group consisting of SEQ ID NO: 22, 49, 57, 65, 73, 81, 89, 97, and 105, or having an amino acid sequence that has 3, 2, or 1 differences with an amino acid sequence selected from the group consisting of SEQ ID NO: 22, 49, 57, 65, 73, 81, 89, 97, and 105. In some embodiments the amino acid sequence differences are conservative changes/substitutions. In particular embodiments, the antibody or antigen binding fragment that binds human ILT3 comprises a heavy chain (HC) wherein the heavy chain variable domain ($V_H$) comprises a heavy chain complementarity determining region (HC-CDR) 3 having an amino acid sequence selected from the group consisting of SEQ ID NO: 23, 49, 57, 65, 73, 81, 89, 97, and 105, or having an amino acid sequence that has 3, 2, or 1 differences with an amino acid sequence selected from the group consisting of SEQ ID NO: 23, 49, 57, 65, 73, 81, 89, 97, and 105. In particular embodiments the amino acid sequence differences are conservative changes/substitutions.

In a further embodiment, the antibody or antigen binding fragment binds to an epitope on the human ILT3 or competes with an antibody disclosed for binding to an epitope on the human ILT3, wherein the epitope comprises at least one amino acid from one or more of the amino acid sequences set forth in in the group consisting of SEQ ID NO: 3, 4, 5, 6, 7, and 8. In further embodiments, the antibody or antigen binding fragment binds to an epitope on the human ILT3 or competes with an antibody disclosed for binding to an epitope on the human ILT3, wherein the epitope comprises one or more of the amino acid sequences set forth in SEQ ID NOs:3, 4, 5, 6, 7, and 8. In further embodiments, the antibody or antigen binding fragment binds to an epitope on the human ILT3 or competes with an antibody disclosed for binding to an epitope on the human ILT3, wherein the epitope comprises the amino acid sequences set forth in SEQ ID NOs:3, 4, 5, 6, 7, and 8. In particular embodiments, the epitope is determined by hydrogen deuterium exchange mass spectrometry (HDX-MS) analysis.

The present invention further provides an antibody or antigen binding fragment that binds human ILT3 comprising (a) an HC having a variable domain ($V_H$) comprising a variable domain complementarity determining region (HC-CDR) 1 having the amino acid sequence set forth in SEQ ID NO: 17, 47, 55, 63, 71, 79, 87, 95, or 103; an HC-CDR2 having the amino acid sequence set forth in SEQ ID NO: 18, 48, 56, 64, 72, 80, 88, 96, or 104; and an HC-CDR3 having the amino acid sequence set forth in SEQ ID NO: 23, 49, 57, 65, 73, 81, 89, 97, or 105; and, variants thereof wherein one or more of the HC-CDRs has one, two, or three amino acid substitutions, additions, deletions, or combinations thereof; and (b) a light chain (LC) having variable domain ($V_L$) comprising a variable domain complementarity determining region (LC-CDR) 1 having the amino acid sequence set forth in SEQ ID NO: 27, 50, 58, 66, 74, 82, 90, 98, or 106; an LC-CDR2 having the amino acid sequence set forth in SEQ ID NO: 43, 51, 59, 67, 75, 83, 91, 99, or 107; and an LC-CDR3 having the amino acid sequence set forth in SEQ ID NO: 44, 60, 68, 76, 84, 92, 100, or 108; and, variants thereof wherein one or more of the LC-CDRs has one, two, or three amino acid substitutions, additions, deletions, or combinations thereof. In particular embodiments the amino acid sequence differences are conservative changes/substitutions.

In a further embodiment of the antibody or antigen binding fragment, HC-CDR1 has the amino acid sequence set forth in SEQ ID NO:17; HC-CDR2 has the amino acid sequence set forth in SEQ ID NO: 19, 20, or 21; HC-CDR3 has the amino acid sequence set forth in SEQ ID NO: 23; and LC-CDR1 has the amino acid sequence set forth in SEQ ID NO: 34, 35, 36, 37, 38, 39, 40, 41, or 42; LC-CDR2 has the amino acid sequence set forth in SEQ ID NO: 43; and, LC-CDR3 has the amino acid sequence set forth in SEQ ID NO:44; and, variants thereof wherein one or more of the HC-CDRs and LC-CDRs has one, two, or three amino acid substitutions, additions, deletions, or combinations thereof. In particular embodiments the amino acid sequence differences are conservative changes/substitutions.

In a further embodiment of the antibody or antigen binding fragment, HC-CDR1 has the amino acid sequence set forth in SEQ ID NO: 17; HC-CDR2 has the amino acid sequence set forth in SEQ ID NO: 20; and HC-CDR3 has the amino acid sequence set forth in SEQ ID NO: 23; and LC-CDR1 having the amino acid sequence set forth in SEQ ID NO: 41; LC-CDR2 having the amino acid sequence set forth in SEQ ID NO: 43; and, LC-CDR3 having the amino acid sequence set forth in SEQ ID NO: 44; and, variants thereof wherein one or more of the HC-CDRs and LC-CDRs has one, two, or three amino acid substitutions, additions, deletions, or combinations thereof. In particular embodiments the amino acid sequence differences are conservative changes/substitutions.

In a further embodiment of the antibody or antigen binding fragment, the antibody or antigen binding fragment comprises (a) a $V_H$ having a framework selected from the group consisting of human $V_H1$, $V_H2$, $V_H3$, $V_H4$, $V_H5$, and $V_H6$ family and variants thereof having 1, 2, 3, 4, 5, 6, 7, 8, 9, or 10 amino acid substitutions, additions, deletions, or combinations thereof; and, (b) a $V_L$ having a framework selected from the group consisting of human $V_\kappa1$, $V_\kappa2$, $V_\kappa3$, $V_\kappa4$, $V_\kappa5$, $V_\kappa6$, $V_\lambda2$, $V_\lambda3$, $V_\lambda4$, $V_\lambda5$, $V_\lambda6$, $V_\lambda7$, $V_\lambda8$, $V_\lambda9$, and $V_\lambda10$ family and variants thereof having 1, 2, 3, 4, 5, 6, 7, 8, 9, or 10 amino acid substitutions, additions, deletions, or combinations thereof. In particular embodiments the amino acid sequence differences are conservative changes/substitutions.

In particular embodiments, the antibody or antigen binding fragment comprises (a) a $V_H$ having a human $V_H1$ family framework or variant thereof having 1, 2, 3, 4, 5, 6, 7, 8, 9, or 10 amino acid substitutions, additions, deletions, or combinations thereof; and, (b) a $V_L$ having a human $V_\kappa5$ family framework or variant thereof having 1, 2, 3, 4, 5, 6, 7, 8, 9, or 10 amino acid substitutions, additions, deletions, or combinations thereof. In particular embodiments the amino acid sequence differences are conservative changes/substitutions.

In a further embodiment of the antibody, the antibody comprises a human IgG1, IgG2, IgG3, or IgG4 HC constant domain or variant thereof having 1, 2, 3, 4, 5, 6, 7, 8, 9, or 10 amino acid substitutions, additions, deletions, or combinations thereof compared to the amino acid sequence of the native human IgG1, IgG2, IgG3, or IgG4 isotype HC constant domain. In particular aspects, the constant domain may comprise a C-terminal lysine or may lack a C-terminal lysine or a C-terminal glycine-lysine dipeptide.

In particular embodiments, the heavy chain constant domain is of the human IgG1 isotype, which has been modified to have reduced or minimal effector function. In further aspects, the minimal effector function results from an effector-less Fc mutation, which may comprise or consist of the mutation N297A or D265A/N297A as identified using Kabat numbering in which case the minimal effector function results from aglycosylation (see for example, the amino acid sequence shown in SEQ ID NO: 211 wherein the N297A mutation corresponds to amino acid position 180; a D265A mutation, if present, would correspond to amino acid position 148). In particular aspects, the IgG1 has been modified to comprise or consist of an L234A, an L235A, and a D265S mutation as identified using Kabat numbering to render the Fc effector-less (see for example the amino acid sequence shown in SEQ ID NO: 12 or 13 wherein the L234A, L235A, and D265S mutations correspond to amino acid positions 117, 118, and 148, respectively).

In a further aspect, the HC constant domain is of the human IgG4 isotype and which isotype further includes a substitution of the serine residue at position 228 (EU numbering) with proline, which corresponds to position 108 of SEQ ID NO: 9 or 10 (Serine at position 108).

In a further embodiment of the antibody or antigen binding fragment, the antibody comprises a human kappa or lambda LC constant domain or variant thereof comprising 1, 2, 3, 4, 5, 6, 7, 8, 9, or 10 amino acid substitutions, additions, deletions, or combinations thereof compared to the amino acid sequence of the native human kappa or lambda LC constant domain.

In particular embodiments the amino acid sequence differences are conservative changes/substitutions.

In a further embodiment of the antibody or antigen binding fragment, the antibody comprises (i) a $V_H$ having a framework selected from the human $V_H1$, $V_H2$, $V_H3$, $V_H4$, $V_H5$, and $V_H6$ family and a human IgG1 or IgG4 HC constant domain or variant thereof comprising 1, 2, 3, 4, 5, 6, 7, 8, 9, or 10 amino acid substitutions, additions, deletions, or combinations thereof compared to the amino acid sequence of the native human IgG1 or IgG4 isotype HC constant domain; and, (ii) and a $V_L$ having a framework selected from the human $V_\kappa1$, $V_\kappa2$, $V_\kappa3$, $V_\kappa4$, $V_\kappa5$, $V_\kappa6$, $V_\lambda1$, $V_\lambda2$, $V_\lambda3$, $V_\lambda4$, $V_\lambda5$, $V_\lambda6$, $V_\lambda7$, $V_\lambda8$, $V_\lambda2$, and $V_\lambda10$ family and a human kappa or lambda LC constant domain or variant thereof comprising 1, 2, 3, 4, 5, 6, 7, 8, 9, or 10 amino acid substitutions, additions, deletions, or combinations thereof compared to the amino acid sequence of the native human kappa or lambda LC constant domain. In particular embodiments the amino acid sequence differences are conservative changes/substitutions.

In a further embodiment of the antibody or antigen binding fragment, the antibody comprises (i) a $V_H$ having a human $V_H2$ family framework and a $V_L$ having a human $V_\kappa5$ family framework; (ii) a human IgG1 or IgG4 HC constant domain or variant thereof comprising 1, 2, 3, 4, 5, 6, 7, 8, 9, or 10 amino acid substitutions, additions, deletions, or combinations thereof compared to the amino acid sequence of the native human IgG1 or IgG4 isotype HC constant domain; and, (iii) a human kappa LC constant domain or variant thereof comprising 1, 2, 3, 4, 5, 6, 7, 8, 9, or 10 amino acid substitutions, additions, deletions, or combinations thereof compared to the amino acid sequence of the native human kappa LC constant domain. In particular embodiments the amino acid sequence differences are conservative changes/substitutions.

In a further embodiment of the antibody or antigen binding fragment, the antibody comprises (i) a $V_H$ having a human $V_H1$ family framework and a human $V_L$ having a human $V_\kappa5$ family framework; (ii) a human IgG4 HC constant domain or variant thereof comprising 1, 2, 3, 4, 5, 6, 7, 8, 9, or 10 amino acid substitutions, additions, deletions, or combinations thereof compared to the amino acid sequence of the native human IgG4 isotype HC constant domain; and, (iii) a human kappa LC constant domain or variant thereof comprising 1, 2, 3, 4, 5, 6, 7, 8, 9, or 10 amino acid substitutions, additions, deletions, or combinations thereof compared to the amino acid sequence of the native human kappa LC constant domain. In particular embodiments the amino acid sequence differences are conservative changes/substitutions.

In a further embodiment of the antibody or antigen binding fragment, the antibody or antigen binding fragment comprises a $V_H$ and a $V_L$ having the amino acid sequences set forth in SEQ ID NO: 15 and SEQ ID NO: 16, respectively; SEQ ID NO: 45 and SEQ ID NO: 46, respectively; SEQ ID NO: 53 and SEQ ID NO: 54, respectively; SEQ ID NO: 61 and SEQ ID NO: 62, respectively; SEQ ID NO: 69 and SEQ ID NO: 70, respectively; SEQ ID NO: 77 and SEQ ID NO: 78, respectively; SEQ ID NO: 85 and SEQ ID NO: 86, respectively; SEQ ID NO: 93 and SEQ ID NO: 94, respectively; or SEQ ID NO: 101 and SEQ ID NO: 102, respectively.

In a further embodiment of the antibody or antigen binding fragment, the antibody or antigen binding fragment comprises a $V_H$ having the amino acid sequence set forth in SEQ ID NO: 117, 118, 119, 123, 124, or 125 and a $V_L$ having the amino acid sequence set forth in SEQ ID NO: 126, 127, 128, 129, 130, 131, 132, 133, 134, 135, 136, 137, 138, 139, 140, or 141.

In a further embodiment of the antibody or antigen binding fragment, the antibody or antigen binding fragment comprises a $V_H$ having the amino acid sequence set forth in SEQ ID NO: 118 and a $V_L$ having the amino acid sequence set forth in SEQ ID NO: 140.

In a further embodiment of the antibody, the antibody comprises an HC constant domain comprising the amino acid sequence set forth in SEQ ID NO: 9, 10, 11, 12, or 13. In particular aspects, the HC constant domain comprising the amino acid sequence set forth in SEQ ID NOs: 9, 11, 12, or 13 may lack a C-terminal lysine or a C-terminal glycine-lysine dipeptide. In particular embodiments, the HC constant domain comprises the amino acid sequence set forth in SEQ ID NO: 10.

In a further embodiment of the antibody, the antibody comprises an LC constant domain comprising the amino acid sequence set forth in SEQ ID NO: 14.

In a further embodiment of the antibody, the antibody comprises an HC comprising the amino acid sequence of SEQ ID NO: 142, 143, 144, 148, 149, 150, 167, 168, 169, 170, 174, 175, 176, 177, 178, 182, 183, 184, 185, 186, 187, 191, 192, or 193. In particular aspects, the HC comprising the amino acid sequence set forth in SEQ ID NOs: 142, 143, 144, 148, 149, 150, 167, 168, 169, 170, 174, or 175, may lack a C-terminal lysine or a C-terminal glycine-lysine dipeptide. In particular embodiments, the HC comprises the amino acid sequence set forth in SEQ ID NO: 143 or 177. In particular embodiments, the HC set forth in SEQ ID NO: 177 further lacks a C-terminal glycine.

In a further embodiment of the antibody, the antibody comprises an LC comprising the amino acid sequence set forth in SEQ ID NO: 151, 152, 153, 154, 155, 156, 157, 158, 159, 160, 161, 162, 163, 164, 165, or 166. In particular embodiments, the LC comprises the amino acid set forth in SEQ ID NO: 165.

In a further embodiment of the antibody, the antibody comprises an HC having the amino acid sequence set forth in SEQ ID NO:143 and an LC comprising the amino acid sequence set forth in SEQ ID NO:165. In particular aspects, the HC comprising the amino acid sequence set forth in SEQ ID NO: 143 lacks a C-terminal lysine or a C-terminal glycine-lysine dipeptide.

The present invention further provides a chimeric, humanized, or recombinant human antibody or antigen binding fragment that binds to an epitope on a human ILT3, wherein the epitope comprises at least one amino acid within the amino acid sequences set forth in the group consisting of SEQ ID NOs:3, 4, 5, 6, 7, and 8. In a further embodiment, the chimeric, humanized, or recombinant human antibody or antigen binding fragment binds to an epitope on a human ILT3 comprising the amino acid sequences set forth in SEQ ID NOs: 3, 4, 5, 6, 7, and 8. In these embodiments, the epitope is determined by hydrogen deuterium exchange mass spectrometry (HDX-MS) analysis.

The present invention further provides a chimeric, humanized, or recombinant human antibody or antigen binding fragment that binds ILT3 wherein the binding cross-blocks or competes with the binding of an antibody comprising a heavy chain having the amino acid sequence set forth in SEQ ID NO: 15 and a light chain having the amino acid sequence shown in SEQ ID NO: 16. In a further embodiment, the chimeric, humanized, or recombinant human antibody or antigen binding fragment that cross-blocks or competes with an antibody comprising a heavy chain having the amino acid sequence set forth in SEQ ID NO: 15 and a light chain having the amino acid sequence shown in SEQ ID NO: 16 binds an epitope on ILT3 that comprises the amino acid sequences set forth in SEQ ID NOS: 3, 4, 5, 6, 7, and 8.

The present invention further provides a composition comprising one or more of any one of the antibody or antigen binding fragment disclosed or claimed herein and a pharmaceutically acceptable carrier.

The present invention further provides a method for treating a cancer in a subject comprising administering to the subject an effective amount of an antibody or antigen binding fragment disclosed or claimed herein sufficient to treat the cancer in the subject.

In a further embodiment, the cancer is pancreatic cancer, melanomas, breast cancer, lung cancer, head and neck cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The present invention further provides a method for treatment of a cancer in a subject comprising administering to the subject concurrently or consecutively an antibody or antigen binding fragment disclosed herein in combination with one or more inhibitors or antagonists of PD-1, PD-L1 and/or PD-L2. In one embodiment, the antagonist of PD-1 is an antibody or antigen binding fragment thereof that binds to human PD-1 and blocks the binding of PD1 to human PD-L1 and PD-L2. In one embodiment, the antagonist of PD-L1 or PD-L2 is an antibody or antigen binding fragment thereof that binds to human PD-L1 or PD-L2 and blocks the binding of human PD-L1 or PD-L2 PD1.

In a further embodiment, the anti PD1 antagonist is an anti-PD-1 antibody is nivolumab, pembrolizumab, cemiplimab, or pidilizumab and the PD-L1 inhibitor is durvalumab, atezolizumab, avelumab, YW243.55.S70, MPDL3280A, MEDI-4736, MSB-0010718C, or MDX-1105.

The present invention further provides an antibody or antigen binding fragment disclosed or claimed herein for treatment of cancer in a subject.

In a further embodiment, the cancer is pancreatic cancer, melanomas, breast cancer, lung cancer, head and neck cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The present invention further provides an antibody or antigen binding fragment disclosed or claimed herein for treatment of a cancer in a subject wherein the treatment further comprises one or more inhibitors or antagonists of PD-1, PD-L1 and/or PD-L2.

In one embodiment, the antagonist of PD-1 is an antibody or antigen binding fragment thereof that binds to human PD-1 and blocks the binding of PD1 to PD-L1 and PD-L2.

In one embodiment, the antagonist of PD-L1 or PD-L2 is an antibody or antigen binding fragment thereof that binds to human PD-L1 or PD-L2 and blocks the binding of human PD-L1 or PD-L2 PD1.

In a further embodiment, the anti-PD-1 antibody is nivolumab, pembrolizumab, cemiplimab, or pidilizumab and the PD-L1 inhibitor is durvalumab, atezolizumab, avelumab, YW243.55.S70, MPDL3280A, MEDI-4736, MSB-0010718C, or MDX-1105.

The present invention further provides for use of an antibody or antigen binding fragment disclosed or claimed herein for the treatment of a cancer.

The present invention further provides for use of an antibody or antigen binding fragment disclosed or claimed herein for the manufacture of a medicament for the treatment of a cancer.

In a further embodiment, the cancer is pancreatic cancer, melanomas, breast cancer, lung cancer, head and neck cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The present invention further provides a composition comprising any one of the aforementioned antibodies or antigen binding fragments and a pharmaceutically acceptable carrier. In particular embodiments, the composition comprises a mixture of antibodies comprising a heavy chain having a C-terminal lysine and antibodies comprising a heavy chain lacking a C-terminal lysine. In particular embodiments, the composition comprises an antibody disclosed herein wherein the predominant antibody form comprises a heavy chain having a C-terminal lysine. In particular embodiments, the composition comprises an antibody disclosed herein wherein the predominant antibody form comprises a heavy chain lacking a C-terminal lysine. In particular embodiments, the composition comprises an antibody disclosed herein wherein about 100% of the antibodies in the composition comprise a heavy chain lacking a C-terminal lysine.

BRIEF DESCRIPTION OF THE DRAWINGS

FIG. 2A shows data characteristics on binding affinity, isoelectric point, purity of monomer species, and thermal stability measurements for variants of mAb 10. Terms: "huILT3" refers to human ILT3; "rhILT3" refers to Rhesus monkey ILT3; "pI" refers to isoelectric point; "Tm" refers to temperature mid-point of a thermal unfolding curve; "Tagg" refers to mid-point of a thermal aggregation curve; "SEC" refers size-exclusion ultra-high performance liquid chromatography).

FIG. 8A, FIG. 8B, FIG. 8C, and FIG. 8D show the effect of c52B8 in tumor growth and immune activation in SK-MEL-5 hu-NSG model. FIG. 8A shows a tumor growth curve; FIG. 8B shows CyTOF quantification of TILs collected 7 days after the $2^{nd}$ dose: % $CD4^+$ T regulatory cells and CD69 expression levels on $CD4^+$ T cells; FIG. 8C shows sHLA-G levels in blood plasma harvested at the end of the study; FIG. 8D shows IHC analysis of human $CD3^+$ T cells infiltration in the tumor, 4 tumors in each group.

FIG. 9A shows a tumor growth curve; FIG. 9B shows CyTOF quantification of % Tregs and CD69 expression levels on CD4+ T cells from tumors harvested at the end of the study; FIG. 9C shows plasma sHLA-G levels in terminal blood samples; FIG. 9D shows plasma $IFN_\gamma$ and IL-8 levels in terminal blood samples quantitated using 10 plex MSD (Meso Scale Discovery).

FIG. 10 shows that humanized anti-ILT3 antibody 52B8 (mAb 46) reduces the suppressive capacity of MDSCs to an extent comparable to chimeric anti-ILT3 antibody c52B8 (mAb 73) in an MDSC/T cell suppression assay at a 4:1 ratio of T cell to MDSC.

DETAILED DESCRIPTION OF THE INVENTION

Figure 1A:
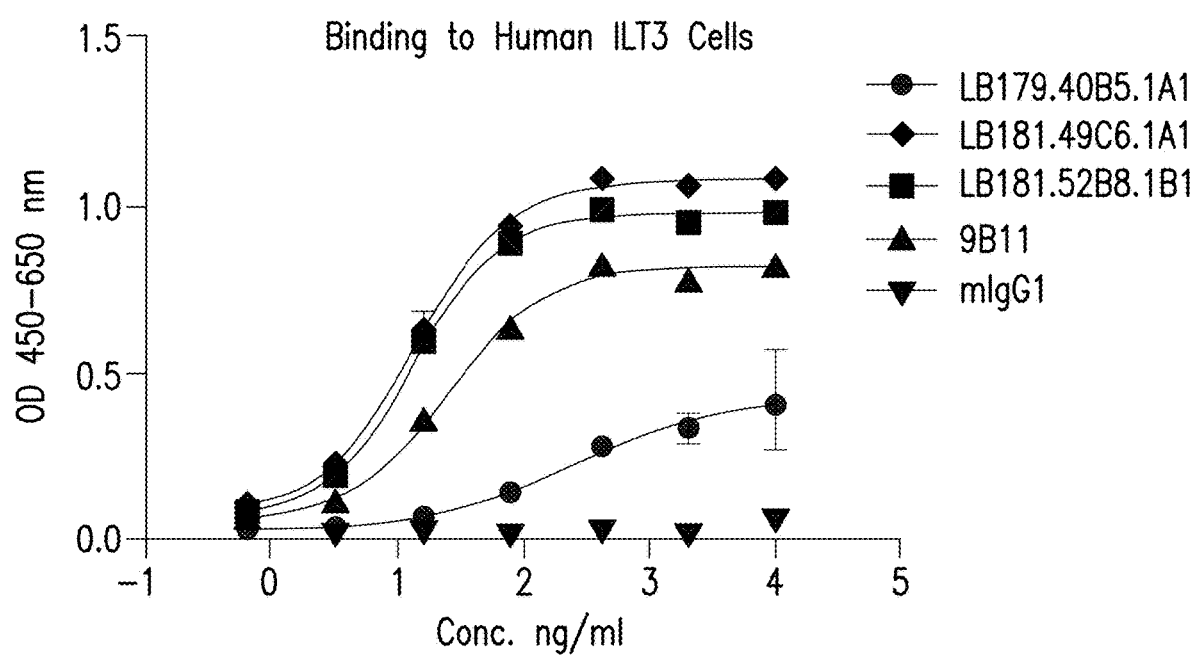
FIG. 1A, FIG. 1B, FIG. 1C, FIG. 10, FIG. 1E, and FIG. 1F show a comparison of the selectivity of several of the anti-ILT3 antibodies disclosed herein to monoclonal antibody 9B11 and mouse IgG1 (mIgG1) using a cell-based ELISA format. CHO-K1 cells expressing human ILT3 (FIG. 1A), Rhesus monkey ILT3 (FIG. 1B), human ILT5 (FIG. 1C), human ILT7 (FIG. 10), human ILT8 (FIG. 1E), or human ILT11 (FIG. 1F) were each tested with monoclonal antibody p40B5 (LB179.40B5.1A1), p49C6 (LB181.49C6.1A1), and p52B8 lb181.52B8.1B1); antibody 9B11 (U.S. Pat. No. 7,777,008 as having the amino acid sequences of SEQ ID NO: 33 (light chain) and SEQ ID NO: 34 (heavy chain)), and mouse IgG1.
Figure 1B:
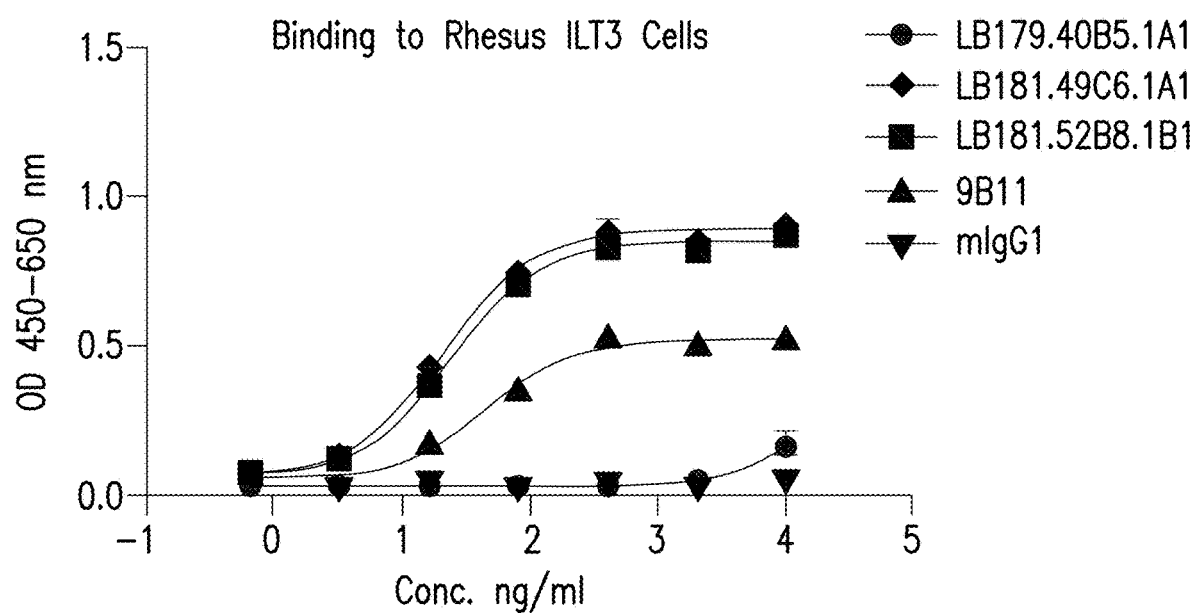
Figure 1C:
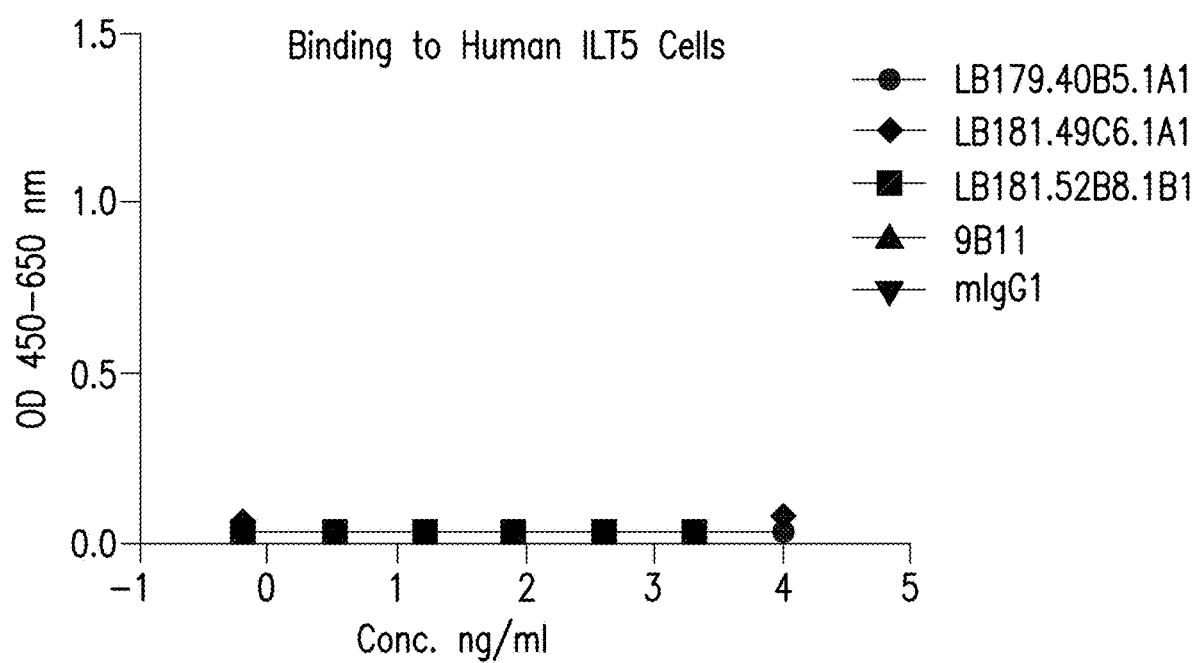
Figure 1D:
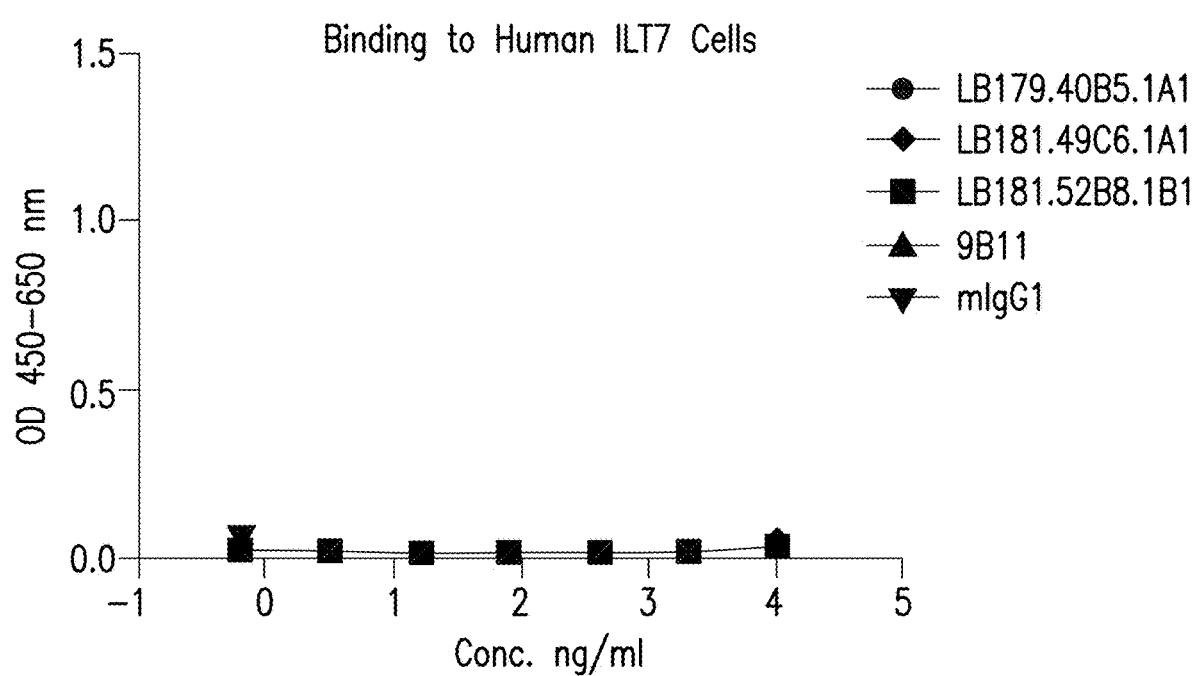
Figure 1E:
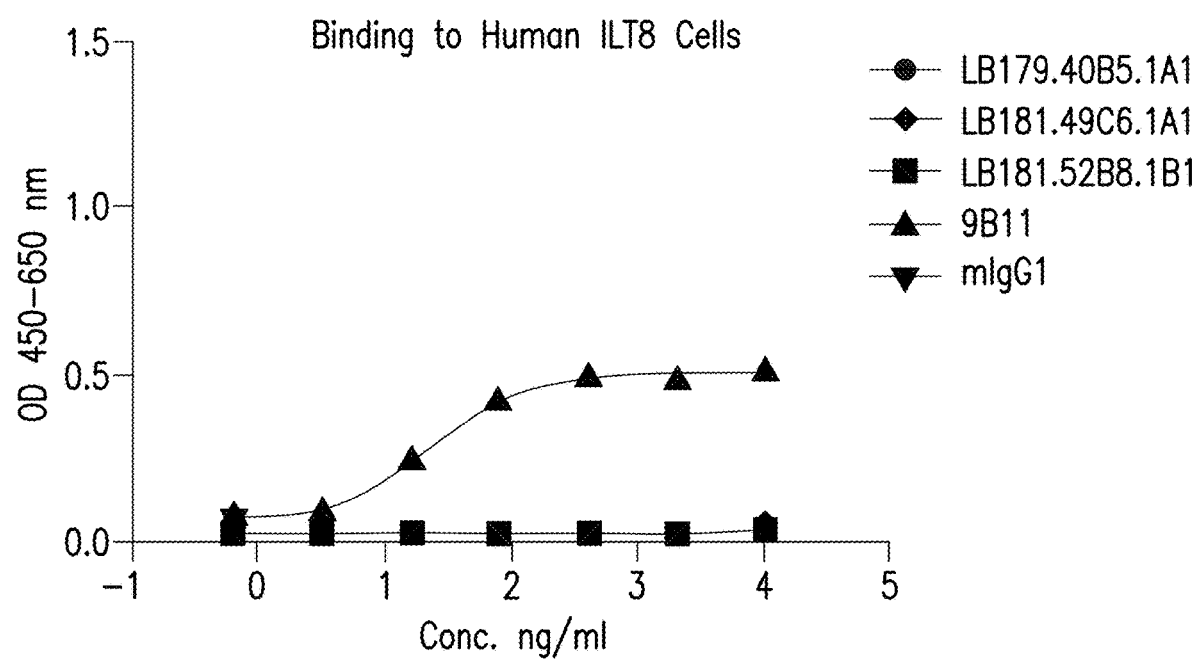
Figure 1F:
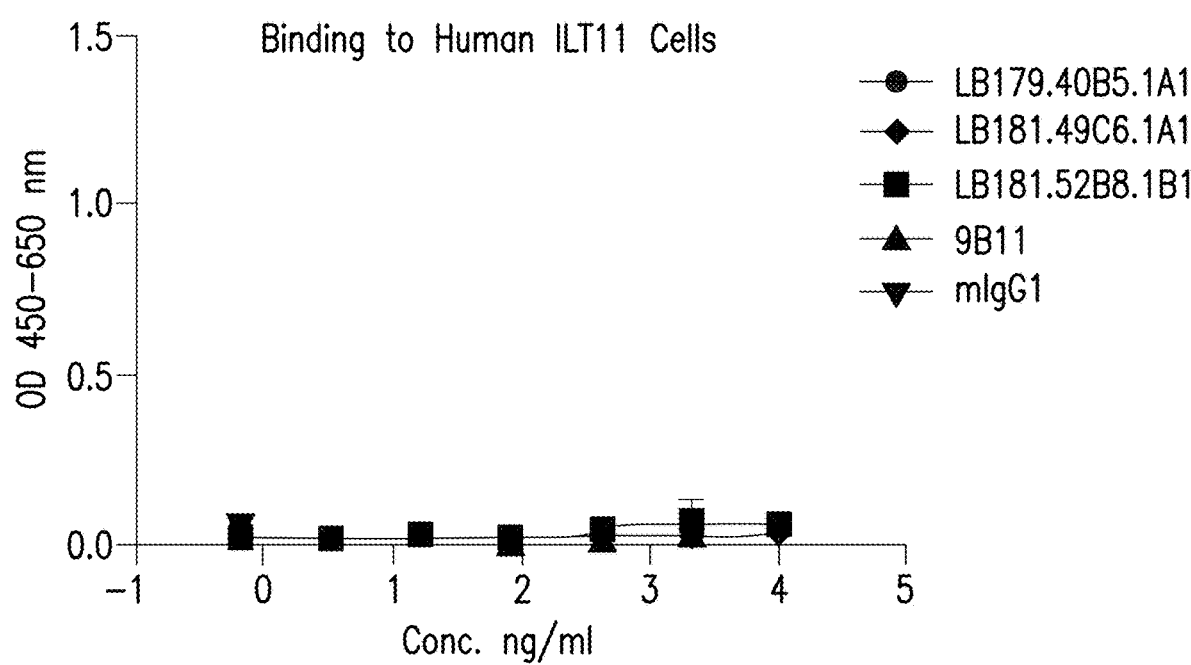

The present invention provides non-promiscuous monoclonal antibodies specific for human immunoglobulin-like transcript 3 (ILT3), an inhibitory receptor expressed on the surface of myeloid immune cells.

Definitions

The term "immunoglobulin-like transcript 3" (abbreviated herein as "ILT3", and also known as LIR-5, LILRB4, or CD85 k), as used herein and unless otherwise indicated, refers to the human member of the ILT3 family, which is selectively expressed by myeloid antigen presenting cells (APCs) such as monocytes, macrophages, and dendritic cells, e.g., monocyte-derived dendritic cells differentiated in the presence of IL-10 or vitamin $D_3$.

As used herein, "antibody" refers to an entire immunoglobulin, including recombinantly produced forms and includes any form of antibody that exhibits the desired biological activity. Thus, it is used in the broadest sense and specifically covers, but is not limited to, monoclonal antibodies (including full length monoclonal antibodies), polyclonal antibodies, multi specific antibodies (e.g., bispecific antibodies), humanized antibodies, fully human antibodies, biparatopic antibodies, humanized camelid heavy chain antibodies, and non-human/human chimeric antibodies. "Parental antibodies" are antibodies obtained by exposure of an immune system to an antigen prior to modification of the antibodies for an intended use, such as humanization of a non-human antibody for use as a human therapeutic antibody.

An "antibody" refers, in one embodiment, to a glycoprotein comprising at least two heavy chains (HCs) and two light chains (LCs) inter-connected by disulfide bonds, or an antigen binding portion thereof. Each heavy chain is comprised of a heavy chain variable region or domain (abbreviated herein as $V_H$) and a heavy chain constant region or domain. In certain naturally occurring IgG, IgD and IgA antibodies, the heavy chain constant region is comprised of three domains, $C_H1$, $C_H2$ and $C_H3$. In certain naturally occurring antibodies, each light chain is comprised of a light chain variable region or domain (abbreviated herein as $V_L$) and a light chain constant region or domain. The light chain constant region is comprised of one domain, CL. The human $V_H$ includes six family members: $V_H1$, $V_H2$, $V_H3$, $V_H4$, $V_H5$, and $V_H6$ and the human $V_L$ family includes 16 family members: $V_\kappa1$, $V_\kappa2$, $V_\kappa3$, $V_\kappa4$, $V_\kappa5$, $V_\kappa6$, $V_\lambda1$, $V_\lambda2$, $V_\lambda3$, $V_\lambda4$, $V_\lambda5$, $V_\lambda6$, $V_\lambda7$, $V_\lambda8$, $V_\lambda9$, and $V_\lambda10$. Each of these family members can be further divided into particular subtypes.

The $V_H$ and $V_L$ regions can be further subdivided into regions of hypervariability, termed complementarity determining regions (CDR), interspersed with regions that are more conserved, termed framework regions (FR). Each $V_H$ and V$_L$ is composed of three CDR regions and four FR regions, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

In general, while an antibody comprises six CDRs, three on the V$_H$ and three on the V$_L$, the state of the art recognizes that in most cases, the CDR3 region of the heavy chain is the primary determinant of antibody specificity, and examples of specific antibody generation based on CDR3 of the heavy chain alone are known in the art (e.g., Beiboer et al., J. Mol. Biol. 296: 833-849 (2000); Klimka et al., British J. Cancer 83: 252-260 (2000); Rader et al., Proc. Natl. Acad. Sci. USA 95: 8910-8915 (1998); Xu et al., Immunity 13: 37-45 (2000). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) J. Mol. Biol. 196: 901-917 (defining the CDR regions of an antibody by structure).

The following general rules shown in Table 1 may be used to identify the CDRs in an antibody sequence. There are rare examples where these virtually constant features do not occur; however, the Cys residues are the most conserved feature.

TABLE 1

| | |
|---|---|
| Light chain CDR1 | |
| Start | About amino acid residue 24 |
| Residue before | Usually a Cys |
| Residue after | Usually a Trp. Typically Trp-Tyr-Gln, but also, Trp-Leu-Gln, Trp-Phe-Gln, or Trp-Tyr-Leu |
| Length | 10 to 17 amino acid residues |
| Light chain CDR2 | |
| Start | Usually 16 amino acid residues after the end of CDR1 |
| Residues before | Generally Ile-Tyr, but also, Val-Tyr, Ile-Lys, or Ile-Phe |
| Length | Usually seven amino acid residues |
| Light chain CDR3 | |
| Start | Usually 33 amino acid residues after end of CDR2 |
| Residue before | Usually Cys |
| Residues after | Usually Phe-Gly-Xaa-Gly (SEQ ID NO: 221) |
| Length | Seven to 11 amino acid residues |
| Heavy chain CDR1 | |
| Start | About amino acid residue 26 (usually four amino acid residues after a Cys) [Chothia/AbM defintion]; Kabat definition starts five amino acid residues later |
| Residues before | Usually Cys-Xaa-Xaa-Xaa (SEQ ID NO: 222) |
| Residues after | Usually a Trp. Typically Trp-Val, but also, Trp-Ile or Trp-Ala |
| Length | 10 to 12 amino acid residues [AbM definition]; Chothia definition excludes the last four amino acid residues |
| Heavy chain CDR2 | |
| Start | Usually 15 amino acid residues after the end of Kabat/AbM definition) of heavy chain CDR1 |
| Residues before | Typically Leu-Glu-Trp-Ile-Gly (SEQ ID NO: 223), but a number of variations |
| Residues after | Lys/Arg-Leu/Ile/Val/Phe/Thr/Ala-Thr/Ser/Ile/Ala |
| Length | Kabat definition 16 to 19 amino acid residues; AbM (and recent Chothia) definition ends seven amino acid residues earlier |
| Heavy chain CDR3 | |
| Start | Usually 33 amino acid residues after end of heavy chain CDR2 (usually two amino acid residues after a Cys) |
| Residues before | Usually Cys-Xaa-Xaa (typically Cys-Ala-Arg) |
| Residues after | Usually Trp-Gly-Xaa-Gly (SEQ ID NO: 224) |
| Length | Three to 25 amino acid residues |

In general, the basic antibody structural unit comprises a tetramer. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function of the antibody. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989).

The heavy chain of an antibody may or may not contain a terminal lysine (K) residue, or terminal glycine and lysine (GK) residues. Thus, in particular embodiments of the anti-ILT3 antibodies herein comprising a heavy chain constant region amino acid sequence shown herein lacking a terminal lysine but terminating with a glycine residue further include embodiments in which the terminal glycine residue is also lacking. This is because the terminal lysine and sometimes glycine and lysine together may be cleaved during expression of the antibody or cleaved off when introduced into the human body with no apparent adverse effect on antibody efficacy, stability, or immunogenicity. In some cases cases, the nucleic acid molecule encoding the heavy chain may purposely omit the codons encoding the terminal lysine or the codons for the terminal lysine and glycine.

As used herein, "antigen binding fragment" refers to fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; single-chain antibody molecules, e.g., scFv; nanobodies and multispecific antibodies formed from antibody fragments.

As used herein, a "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

As used herein, a "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

As used herein, a "F(ab')$_2$ fragment" contains two light chains and two heavy chains containing the $V_H$ domain and a portion of the constant region between the $C_H1$ and $C_H2$ domains, such that an interchain disulfide bond is formed between the two heavy chains. An F(ab')$_2$ fragment thus is composed of two Fab' fragments that are held together by a disulfide bond between the two heavy chains. An "F(ab')$_2$ fragment" can be the product of pepsin cleavage of an antibody.

As used herein, an "Fv region" comprises the variable regions from both the heavy and light chains, but lacks the constant regions.

These and other potential constructs are described in Chan & Carter (2010) Nat. Rev. Immunol. 10:301. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

As used herein, an "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

As used herein, a "diabody" refers to a small antibody fragment with two antigen-binding sites, which fragments comprise a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementarity domains of another chain and create two antigen-binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

As used herein, a "bispecific antibody" is an artificial hybrid antibody having two different heavy/light chain pairs and thus two different binding sites. For example, a bispecific antibody may comprise a first heavy/light chain pair comprising one heavy and one light chain of a first antibody comprising at least the six CDRs of an anti-ILT3 antibody disclosed herein or embodiments wherein one or more of the six CDRs has one, two, or three amino acid substitutions, additions, deletions, or combinations thereof along with a second heavy/light chain pair comprising one heavy and one light chain of a second antibody having specificity for an antigen of interest other than ILT3. Bispecific antibodies can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antibodies may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

As used herein, "isolated" antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

As used herein, a "monoclonal antibody" refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al (1991) *Nature* 352: 624-628 and Marks et al. (1991) *J. Mot Biol.* 222: 581-597, for example. See also Presta (2005) *J. Allergy Clin. Immunol.* 116:731.

As used herein, a "chimeric antibody" is an antibody having the variable domain from a first antibody and the constant domain from a second antibody wherein (i) the first and second antibodies are from different species (U.S. Pat. No. 4,816,567; and Morrison et al., (1984) *Proc. Natl. Acad. Sci. USA* 81: 6851-6855) or (ii) the first and second antibodies are from different isotypes, e.g., variable domain from an IgG1 antibody and the constant domains from an IgG4 antibody). In one aspect, the variable domains are obtained from a non-human antibody such as a mouse antibody (the "parental antibody"), and the constant domain sequences are obtained from a human antibody. In a further aspect, the variable domains are humanized variable domains from a mouse antibody and the constant domains of a human antibody.

As used herein, a "humanized antibody" refers to forms of antibodies that contain sequences from both human and non-human (e.g., murine, rat) antibodies. In general, the humanized antibody will comprise all of at least one, and typically two, variable domains, in which the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

"Humanization" (also called Reshaping or CDR-grafting) is now a well-established technique for reducing the immunogenicity of monoclonal antibodies (mAbs) from xenogeneic sources (commonly rodent) and for improving the effector functions (ADCC, complement activation, C1q binding). The engineered mAb is engineered using the techniques of molecular biology, however simple CDR-grafting of the rodent complementarity-determining regions (CDRs) into human frameworks often results in loss of binding affinity and/or specificity of the original mAb. In order to humanize an antibody, the design of the humanized antibody includes variations such as conservative amino acid substitutions in residues of the CDRs, and back substitution of residues from the rodent mAb into the human framework regions (back mutations). The positions can be discerned or identified by sequence comparison for structural analysis or by analysis of a homology model of the variable regions' 3D structure. The process of affinity maturation has most recently used phage libraries to vary the amino acids at chosen positions. Similarly, many approaches have been used to choose the most appropriate human frameworks in which to graft the rodent CDRs. As the datasets of known parameters for antibody structures increases, so does the sophistication and refinement of these techniques. Consensus or germline sequences from a single antibody or fragments of the framework sequences within each light or heavy chain variable region from several different human mAbs can be used. Another approach to humanization is to modify only surface residues of the rodent sequence with the most common residues found in human mAbs and has been termed "resurfacing" or "veneering." Often, the human or humanized antibody is substantially non-immunogenic in humans.

As used herein, "non-human amino acid sequences" with respect to antibodies or immunoglobulins refers to an amino acid sequence that is characteristic of the amino acid sequence of a non-human mammal. The term does not include amino acid sequences of antibodies or immunoglobulins obtained from a fully human antibody library where diversity in the library is generated in silico (See for example, U.S. Pat. No. 8,877,688 or 8,691,730).

As used herein, "effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

As used herein, "conservatively modified variants" or "conservative substitution" refers to substitutions of amino acids with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson el al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 2.

TABLE 2

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

As used herein, the term "epitope" or "antigenic determinant" refers to a site on an antigen (e.g., ILT3) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. A contiguous linear epitope comprises a peptide domain on an antigen comprising at least 3, 4, 5, 6, 7, 8, 9, 10, 11, 12, 13, 14 or 15 amino acids. A noncontiguous conformational epitope comprises one or more peptide domains or regions on an antigen bound by an antibody interspersed by one or more amino acids or peptide domains not bound by the antibody, each domain independently comprises at least 3, 4, 5, 6, 7, 8, 9, 10, 11, 12, 13, 14 or 15 amino acids. Methods for determining what epitopes are bound by a given antibody (i.e., epitope mapping) are well known in the art and include, for example, immunoblotting and immunoprecipitation assays, wherein overlapping or contiguous peptides (e.g., from ILT3) are tested for reactivity with a given antibody (e.g., anti-ILT3 antibody). Methods of determining spatial conformation of epitopes include techniques in the art and those described herein, for example, x-ray crystallography, two-dimensional nuclear magnetic resonance, and HDX-MS (see, e.g., Epitope Mapping Protocols in Methods in Molecular Biology, Vol. 66, G. E. Morris, Ed. (1996)).

The term "epitope mapping" refers to the process of identifying the molecular determinants on the antigen involved in antibody-antigen recognition using techniques in the art and those described herein, for example, x-ray crystallography, two-dimensional nuclear magnetic resonance, and Hydrogen-Deuterium-Exchange-with-Mass-Spectroscopy (HDX-MS).

The term "binds to the same epitope" with reference to two or more antibodies means that the antibodies bind to the same segment of amino acid residues or combinations of segments of amino acids, as determined by a given method. Techniques for determining whether antibodies bind to the "same epitope on ILT3" with the antibodies described herein include, for example, epitope mapping methods, such as, x-ray analyses of crystals of antigen:antibody complexes, which provides atomic resolution of the epitope, and HDX-MS. Other methods that monitor the binding of the antibody to antigen fragments (e.g. proteolytic fragments) or to mutated variations of the antigen where loss of binding due to a modification of an amino acid residue within the antigen sequence is often considered an indication of an epitope component (e.g. alanine scanning mutagenesis—Cunningham & Wells (1985) Science 244:1081). In addition, computational combinatorial methods for epitope mapping can also be used. These methods rely on the ability of the antibody of interest to affinity isolate specific short peptides from combinatorial phage display peptide libraries.

Antibodies that "compete with another antibody for binding to a target such as ILT3" refer to antibodies that inhibit (partially or completely) the binding of the other antibody to the target, i.e., ILT3. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)).

As used herein, "specifically binds" refers, with respect to an antigen or molecule such as human ILT3, to the preferential association of an antibody or other ligand, in whole or part, with human ILT3 and not to other molecules, particularly molecules found in human blood or serum. Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "specifically binds" or "binds specifically" to human ILT3 refers to an antibody that binds to the human ILT3 with high affinity, which means having a $K_D$ of $10^{-7}$ M or less, in particular embodiments a $K_D$ of $10^{-8}$ M or less, or $5 \times 10^{-9}$ M or less, or between $10^{-8}$ M and $10^{-11}$ M or less, but does not bind with measurable binding to closely related proteins such as human ILT5, human ILT7, human ILT8, and human ILT11 as determined in a cell ELISA or Biacore assay using 10 µg/mL antibody.

As used herein, an antigen is "substantially identical" to a given antigen if it exhibits a high degree of amino acid sequence identity to the given antigen, for example, if it exhibits at least 80%, at least 90%, at least 95%, at least 97%, or at least 99% or greater amino acid sequence identity to the amino acid sequence of the given antigen. By way of example, an antibody that binds specifically to human ILT3 may also cross-react with ILT3 from certain non-human primate species (e.g., rhesus monkey or cynomolgus monkey).

As used herein, "isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

As used herein, "treat" or "treating" means to administer a therapeutic agent, such as a composition containing any of the antibodies or antigen binding fragments thereof of the present invention, internally or externally to a subject or patient having one or more disease symptoms, or being suspected of having a disease, for which the agent has therapeutic activity or prophylactic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a human or animal subject with a disorder, disease or symptom, or with the potential to develop such a disorder, disease or symptom.

As used herein, "treatment," as it applies to a human or veterinary subject, refers to therapeutic treatment, as well as diagnostic applications. "Treatment" as it applies to a human or veterinary subject, encompasses contact of the antibodies or antigen binding fragments of the present invention to a human or animal subject.

As used herein, "therapeutically effective amount" refers to a quantity of a specific substance sufficient to achieve a desired effect in a subject being treated. For instance, this may be the amount necessary to inhibit activation of ILT3 or the amount necessary for enhanced pembrolizumab responsiveness when co-administered with pembrolizumab.

As used herein the term "PD-1" refers to the programmed Death 1 (PD-1) protein, an inhibitory member of the extended CD28/CTLA-4 family of T cell regulators (Okazaki et al. (2002) Curr Opin Immunol 14: 391779-82; Bennett et al. (2003) J. Immunol. 170:711-8). Other members of the CD28 family include CD28, CTLA-4, ICOS and BTLA. The PD-1 gene encodes a 55 kDa type I transmembrane protein (Agata et al. (1996) Int Immunol. 8:765-72). Two ligands for PD-1 have been identified, PD-L1 (B7-H1) and PD-L2 (B7-DC), that have been shown to downregulate T cell activation upon binding to PD-1 (Freeman et al. (2000) J. Exp. Med. 192:1027-34; Carter et al. (2002) Eur. J. Immunol. 32:634-43). PD-1 is known as an immunoinhibitory protein that negatively regulates TCR signals (Ishida, Y. et al. (1992) EMBO J. 11:3887-3895; Blank, C. et al. (Epub 2006 Dec. 29) Immunol. Immunother. 56(5): 739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) Proc. Nat'l. Acad. Sci. USA 99:12293-7; Brown et al. (2003) J. Immunol. 170:1257-66).

Antibodies and Antigen Binding Fragments

The present invention provides isolated chimeric, humanized, and human antibodies and antigen binding fragments that specifically bind ILT3 and have no measurable binding to closely related proteins (e.g., ILT5, ILT7, ILT8, and ILT11) as determined in a cell ELISA or Biacore assay using 10 µg/mL antibody. The anti-ILT3 antibodies increase activity of antigen presenting cells and dendritic cells, reduce activity of monocyte repressors, and increase priming of T-cells. Thus, the present invention further includes the use of the anti-ILT3 antibodies in monotherapies for the treatment of cancers and for use in combination with anti-PD-1 or anti-PD-L1 antibodies, for either in a first line, second line, or third line therapy for the treatment of cancer.

An anti-ILT3 antibody includes any antibody disclosed herein by amino acid sequence and includes any antibody that comprises (i) at least one, two, three, four, five, or six CDRs of an antibody disclosed herein by amino acid sequence or (ii) has no CDR amino acid sequence disclosed herein but which binds the same epitope on ILT3 as an antibody disclosed herein by amino acid sequence and which may modulate ILT3 receptor signaling such that the antibody increases activity of antigen presenting cells and dendritic cells, reduces activity of monocyte repressors, and increases priming of T-cells. In particular aspects, the antibody has no measurable binding to human ILT5, human ILT7, human ILT8, and human ILT11 as determined in a cell ELISA or in a Biacore assay using 10 µg/mL of the antibody. The term specifically excludes antibodies comprising at least one CDR of antibody ZM4.1 or antibody 9B11 or any of the other antibodies disclosed in U.S. Pat. Nos. 7,777,008 and 8,901,281 or in U.S. Pub. Nos. 20090202544, 20150110714, 20150139986, and 20170267759; and, Intl. Pub. Nos. WO2013043569, WO2013181438, WO2014116846, WO2016049641, WO2016127427, WO2018089300, and WO2018148494.

An anti-ILT3 antigen binding fragment and the like includes any protein or peptide containing molecule that comprises (i) at least a portion of an anti-ILT3 antibody disclosed herein by amino acid sequence, (ii) at least one, two, three, four, five, or six CDRs of an antibody disclosed herein by sequence, or (iii) has no CDR amino acid sequence disclosed herein but which binds the same epitope on ILT3 as an anti-ILT3 antibody disclosed herein by amino acid sequence, and which may modulate ILT3 receptor signaling such that the antigen binding fragment increases activity of antigen presenting cells and dendritic cells, reduces activity of monocyte repressors, and increases priming of T-cells. In particular aspects, the antigen binding fragment has no measurable binding to human ILT5, human ILT7, human ILT8, and human ILT11 as determined in a cell ELISA or in a Biacore assay using 10 µg/mL of the anti-ILT3 antigen binding fragment. The term specifically excludes antigen binding fragments comprising at least one CDR of antibody ZM4.1 or antibody 9B11 or any of the other antibodies disclosed in U.S. Pat. Nos. 7,777,008 and 8,901,281 or U.S. Pub. Nos. 20090202544, 20150110714, 20150139986, and 20170267759; and, Intl. Pub. Nos. WO2013043569, WO2013181438, WO2014116846, WO2016049641, WO2016127427, WO2018089300, and WO2018148494.

In a further embodiment, an anti-ILT3 antibody includes any antibody that comprises (i) at least HC-CDR3 of an antibody disclosed herein by amino acid sequence or (ii) has no H3-CDR3 amino acid sequence disclosed herein but which binds the same epitope on ILT3 as an antibody disclosed herein by amino acid sequence and which may modulate ILT3 receptor signaling such that the antibody increases activity of antigen presenting cells and dendritic cells, reduces activity of monocyte repressors, and increases priming of T-cells. In particular aspects, the antibody has no measurable binding to human ILT5, human ILT7, human ILT8, and human ILT11 as determined in a cell ELISA or in a Biacore assay using 10 µg/mL of the antibody. The term specifically excludes antibodies comprising at least one CDR of antibody ZM4.1 or antibody 9B11 or any of the other antibodies disclosed in U.S. Pat. Nos. 7,777,008 and 8,901,281 or in U.S. Pub. Nos. 20090202544, 20150110714, 20150139986, and 20170267759; and, Intl. Pub. Nos. WO2013043569, WO2013181438, WO2014116846, WO2016049641, WO2016127427, WO2018089300, and WO2018148494.

An anti-ILT3 antigen binding fragment and the like includes any protein or peptide containing molecule that comprises (i) at least a portion of an anti-ILT3 antibody disclosed herein by amino acid sequence, (ii) at least the HC-CDR3 of an antibody disclosed herein by sequence, or (iii) has no HC-CDR3 amino acid sequence disclosed herein but which binds the same epitope on ILT3 as an anti-ILT3 antibody disclosed herein by amino acid sequence, and which may modulate ILT3 receptor signaling such that the antigen binding fragment increases activity of antigen presenting cells and dendritic cells, reduces activity of monocyte repressors, and increases priming of T-cells. In particular aspects, the antigen binding fragment has no measurable binding to human ILT5, human ILT7, human ILT8, and human ILT11 as determined in a cell ELISA or in a Biacore assay using 10 μg/mL of the anti-ILT3 antigen binding fragment. The term specifically excludes antigen binding fragments comprising at least one CDR of antibody ZM4.1 or antibody 9B11 or any of the other antibodies disclosed in U.S. Pat. Nos. 7,777,008 and 8,901,281 or U.S. Pub. Nos. 20090202544, 20150110714, 20150139986, and 20170267759; and, Intl. Pub. Nos. WO2013043569, WO2013181438, WO2014116846, WO2016049641, WO2016127427, WO2018089300, and WO2018148494.

In particular embodiments, the anti-ILT3 antibody is a human or humanized anti-ILT3 antibody or antigen binding fragment or a chimeric anti-ILT3 antibody or antigen binding fragment that comprises HC-CDR3 of an anti-ILT3 antibody molecule disclosed herein or an H3-CDR3 shown in Table 3.

In particular embodiments, the anti-ILT3 antibody is a human or humanized anti-ILT3 antibody or antigen binding fragment or a chimeric anti-ILT3 antibody or antigen binding fragment that comprises HC-CDR1, HC-CDR2, HC-CDR3, LC-CDR1, LC-CDR2, and LC-CDR3 of an anti-ILT3 antibody molecule disclosed herein or in Table 3.

TABLE 3

| mAb | HC-CDR1 | Seq No. | HC-CDR2 | Seq No. | HC-CDR3 | Seq No. |
|---|---|---|---|---|---|---|
| 52B8 | NYGMS | 17 | TISGGGDYTMYPDSVRG | 20 | RLWFRSLYYAMDY | 23 |
| 40A6 | SYSIN | 47 | RFWYDEGIAYNLTLES | 48 | DRDTVGITGWFAY | 49 |
| 16B1 | NYCVN | 55 | RFWFDEGKAYNLTLES | 56 | DRDTVGITGWFAY | 57 |
| 11D1 | TYWIE | 63 | EILPGNGNTHFNENFKD | 64 | RRLGRGPFDF | 65 |
| 17H12 | NFDMA | 71 | SITYDGGSTSYRDSVKG | 72 | VESIATISTYFDY | 73 |
| 37C8 | SYCVN | 79 | RFWYDEGKVYNLTLES | 80 | DRDTMGITGWFAY | 81 |
| 1G12 | TYWIQ | 87 | EILPGSGTTNYNENFKG | 88 | RLGRGPFDY | 89 |
| 20E4 | SYSVN | 95 | RFWYDGGTAYNSTLES | 96 | DRDTMGITGWFAY | 97 |
| 24A4 | SYCVN | 103 | RFWYDEGKVYNLTLES | 104 | DRDTLGITGWFAY | 105 |

| mAb | LC-CDR1 | | LC-CDR2 | | LC-CDR3 | |
|---|---|---|---|---|---|---|
| 52B8 | RASEKVDSFGQSFMH | 41 | LTSNLDS | 43 | QQNNEDPYT | 44 |
| 40A6 | KASQSVGVNVD | 50 | GSANRHT | 51 | LQYGSVPYT | 52 |
| 16B1 | KASQSVGINVD | 58 | GSANRHT | 59 | LQYGSVPYT | 60 |
| 11D1 | KASQDINEYIG | 66 | YTSTLQS | 67 | LQYANPLPT | 68 |
| 17H12 | RASQSVSMSRYDLIH | 74 | RASDLAS | 75 | QQTRKSPPT | 76 |
| 37C8 | KASQSVGINVD | 82 | GSANRHT | 83 | LQYGSVPYT | 84 |
| 1G12 | EASQDINKHID | 90 | YASILQP | 91 | LQYDNLLPT | 92 |
| 20E4 | KASQSVGVNVD | 98 | GSANRHT | 99 | LQYGSVPYT | 100 |
| 24A4 | KASQSVGINVD | 106 | GSANRHT | 107 | LQYGSVPYT | 108 |

In particular embodiments, the anti-ILT3 antibody is a human or humanized anti-ILT3 antibody or antigen binding fragment or a chimeric anti-ILT3 antibody or antigen binding fragment, in each case comprising a heavy chain variable domain ($V_H$) having a heavy chain complementarity determining region (HC-CDR) 3 comprising an amino acid sequence selected from the group consisting of SEQ ID NO: 22, 49, 57, 65, 73, 81, 89, 97, and 105, or an amino acid sequence that has 3, 2, or 1 differences with an amino acid sequence selected from the group consisting of SEQ ID NO: 22, 49, 57, 65, 73, 81, 89, 97, and 105. In a further embodiment, the antibody or antigen binding fragment binds to an epitope on the human ILT3, wherein the epitope comprises at least one amino acid from one or more of the amino acid sequences set forth in in the group consisting of SEQ ID NO: 3, 4, 5, 6, 7, and 8. In a further embodiment, the antibody or antigen binding fragment binds to an epitope on the human ILT3, wherein the epitope comprises the amino acid sequences set forth in in the group consisting of SEQ ID NO: 3, 4, 5, 6, 7, and 8. In particular embodiments the amino acid sequence differences are conservative changes/substitutions.

In particular embodiments, the anti-ILT3 antibody is a humanized or chimeric anti-ILT3 antibody disclosed herein. In particular embodiments, the anti-ILT3 antibody is a human or humanized anti-ILT3 antibody or antigen binding fragment or a chimeric anti-ILT3 antibody or antigen binding fragment that binds the same epitope bound by an anti-ILT3 antibody disclosed herein or competes with the binding of an anti-ILT3 antibody disclosed herein and the antibody comprises less than three or none of the CDRs of an anti-ILT3 antibody disclosed herein.

The present invention further provides an antibody or antigen binding fragment comprising (i) at least the six complementary determining regions (CDRs) of an anti-immunoglobulin-like transcript 3 (ILT3) antibody or (ii) at least the six CDRs of an anti-ILT3 antibody wherein one or more of the six CDRs has one, two, or three amino acid substitutions, additions, deletions, or combinations; wherein the six CDRs of the anti-ILT3 antibody comprise a heavy chain (HC)-CDR1 having the amino acid sequence set forth in SEQ ID NO: 17, 47, 55, 63, 71, 79, 87, 95, or 103; an HC-CDR2 having the amino acid sequence set forth in SEQ ID NO: 18, 48, 56, 64, 72, 80, 88, 96, or 104; an HC-CDR3 having the amino acid sequence set forth in SEQ ID NO: 22, 49, 57, 65, 73, 81, 89, 97, or 105; a light chain (LC)-CDR1 having the amino acid sequence set forth in SEQ ID NO: 27, 50, 58, 66, 74, 82, 90, 98, or 106; an LC-CDR2 having the amino acid sequence set forth in SEQ ID NO: 43, 51, 59, 67, 75, 83, 91, 99, or 107; and an LC-CDR3 having the amino acid sequence set forth in SEQ ID NO: 44, 60, 68, 76, 84, 92, 100, or 108; and, wherein the antibody or antigen binding fragment specifically binds human or rhesus ILT3 or both human and rhesus ILT3. In particular embodiments the amino acid sequence differences are conservative changes/substitutions.

In particular embodiments, the present invention provides an antibody or antigen binding fragment comprising the six CDRs of the anti-ILT3 antibody comprise a heavy chain (HC)-CDR1 having the amino acid sequence set forth in SEQ ID NO:17; an HC-CDR2 having the amino acid sequence set forth in SEQ ID NO:19, 20, or 21; an HC-CDR3 having the amino acid sequence set forth in SEQ ID NO: 23, 24, 25, or 26; a light chain (LC)-CDR1 having the amino acid sequence set forth in SEQ ID NO: 34, 35, 36, 37, 38, 39, 40, 41, or 42; an LC-CDR2 having the amino acid sequence set forth in SEQ ID NO: 43; and an LC-CDR3 having the amino acid sequence set forth in SEQ ID NO: 44.

In particular embodiments, the present invention provides an antibody or antigen binding fragment comprising the six CDRs of the anti-ILT3 antibody having a heavy chain (HC)-CDR1 having the amino acid sequence set forth in SEQ ID NO: 17; an HC-CDR2 having the amino acid sequence set forth in SEQ ID NO: 20; an HC-CDR3 having the amino acid sequence set forth in SEQ ID NO: 23; a light chain (LC)-CDR1 having the amino acid sequence set forth in SEQ ID NO: 41; an LC-CDR2 having the amino acid sequence set forth in SEQ ID NO: 43; and an LC-CDR3 having the amino acid sequence set forth in SEQ ID NO: 44.

In particular embodiments, the present invention provides the above antibody or antigen binding fragment wherein the antibody or antigen binding fragment comprises a heavy chain variable domain ($V_H$) having a framework selected from the human $V_H1$, $V_H2$, $V_H3$, $V_H4$, $V_H5$, and $V_H6$ family and variants thereof having 1, 2, 3, 4, 5, 6, 7, 8, 9, or 10 amino acid substitutions, additions, deletions, or combinations thereof; and, (b) a light chain variable domain ($V_L$) having a framework selected from the human $V_\kappa1$, $V_\kappa2$, $V_\kappa3$, $V_\kappa4$, $V_\kappa5$, $V_\kappa6$, $V_\lambda1$, $V_\lambda2$, $V_\lambda3$, $V_\lambda4$, $V_\lambda5$, $V_\lambda6$, $V_\lambda7$, $V_\lambda8$, $V_\lambda9$, and $V_\lambda10$ family and variants thereof having 1, 2, 3, 4, 5, 6, 7, 8, 9, or 10 amino acid substitutions, additions, deletions, or combinations thereof.

In particular embodiments, the present invention provides the above antibody or antigen binding fragment wherein the antibody comprises a human IgG1, IgG2, IgG3, or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype.

In particular embodiments, the present invention provides the above antibody or antigen binding fragment wherein the antibody comprises a human kappa or lambda light chain constant domain or variant thereof comprising 1, 2, 3, 4, 5, 6, 7, 8, 9, or 10 amino acid substitutions, additions, deletions, or combinations thereof compared to the amino acid sequence of the native human kappa or lambda light chain domain.

In particular embodiments, the present invention provides the above antibody or antigen binding fragment wherein the antibody comprises (i) a human heavy chain variable domain ($V_H$) having a framework selected from the human $V_H3$ family and a human light chain variable domain ($V_L$) having a framework selected from the human $V_\kappa1$, $V_\kappa3$, and $V_\kappa4$ family; (ii) a human IgG1 or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG1 or IgG4 isotype; and, (iii) a human kappa or lambda light chain constant domain or variant thereof comprising 1, 2, 3, 4, 5, 6, 7, 8, 9, or 10 amino acid substitutions, additions, deletions, or combinations thereof compared to the amino acid sequence of the native human kappa or lambda light chain domain. In particular embodiments the amino acid sequence differences are conservative changes/substitutions.

In particular embodiments, the present invention provides the above antibody or antigen binding fragment wherein the antibody or antigen binding fragment comprises a heavy chain variable domain ($V_H$) and a light chain variable domain ($V_L$) having the amino acid sequences set forth in SEQ ID NO: 15 and SEQ ID NO: 16, respectively; SEQ ID NO: 45 and SEQ ID NO: 46, respectively; SEQ ID NO: 53 and SEQ ID NO: 54, respectively; SEQ ID NO:61 and SEQ ID NO: 62, respectively; SEQ ID NO: 69 and SEQ ID NO: 70, respectively; SEQ ID NO:77 and SEQ ID NO: 78, respectively; SEQ ID NO: 85 and SEQ ID NO: 86, respectively; SEQ ID NO: 93 and SEQ ID NO: 94, respectively; or SEQ ID NO: 101 and SEQ ID NO: 102, respectively.

In particular embodiments, the present invention provides the above antibody or antigen binding fragment wherein the antibody or antigen binding fragment comprises a heavy chain variable domain ($V_H$) having the amino acid sequence set forth in SEQ ID NO: 117, 118, 119, 120, 121, 122, 123, 124, or 125 and a light chain variable domain ($V_L$) having the amino acid sequence set forth in SEQ ID NO: 126, 127, 128, 129, 130, 131, 132, 133, 134, 135, 136, 137, 138, 139, 140, or 141.

In particular embodiments, the present invention provides the above antibody or antigen binding fragment wherein the antibody or antigen binding fragment comprises a heavy chain variable domain (V$_H$) having the amino acid sequence set forth in SEQ ID NO: 118 and a light chain variable domain (V$_L$) having the amino acid sequence set forth in SEQ ID NO: 140.

In particular embodiments, the present invention provides the above antibody or antigen binding fragment wherein, the antibody comprises a heavy chain (HC) constant domain comprising the amino acid sequence set forth in SEQ ID NO: 9, 10, 11, 12, or 13 and variants of SEQ ID NO: 9, 11, 12, or 13 in which the HC lacks a C-terminal Lysine or glycine-lysine.

In particular embodiments, the present invention provides the above antibody or antigen binding fragment wherein, the antibody comprises a light chain (LC) constant domain comprising the amino acid sequence set forth in SEQ ID NO: 14.

In particular embodiments, the present invention provides the above antibody or antigen binding fragment wherein, the antibody comprises a heavy chain (HC) comprising the amino acid sequence of SEQ ID NO: 142, 143, 144, 148, 149, 150, 167, 168, 169, 170, 174, 175, 176, 177, 178, 182, 183, 184, 185, 186, 187, 191, 192, or 193 and variants of an HC comprising the amino acid sequence of SEQ ID NO: 143, 144, 148, 149, 150, 167, 168, 169, 170, 174, or 175 in which the HC lacks a C-terminal Lysine or glycine-lysine.

In particular embodiments, the present invention provides the above antibody or antigen binding fragment wherein, the antibody comprises a light chain (LC) comprising the amino acid sequence set forth in SEQ ID NO: 151, 152, 153, 154, 155, 156, 157, 158, 159, 160, 161, 162, 163, 164, 165, or 166.

In particular embodiments, the present invention provides the above antibody or antigen binding fragment wherein, the antibody comprises a heavy chain (HC) comprising the amino acid sequence of SEQ ID NO: 142, 143, 144, 148, 149, 150, 167, 168, 169, 170, 174, 175, 176, 177, 178, 182, 183, 184, 185, 186, 187, 191, 192, or 193 and a light chain (LC) comprising the amino acid sequence set forth in SEQ ID NO: 151, 152, 153, 154, 155, 156, 157, 158, 159, 160, 161, 162, 163, 164, 165, or 166, and variants of an HC comprising the amino acid sequence of SEQ ID NO: 143, 144, 148, 149, 150, 167, 168, 169, 170, 174, or 175 in which the HC lacks a C-terminal Lysine or glycine-lysine.

In particular embodiments, the present invention provides an antibody selected from the antibodies presented in Table 4.

In particular embodiments, the present invention provides the above antibody or antigen binding fragment wherein, the antibody comprises a heavy chain (HC) having the amino acid sequence set forth in SEQ ID NO: 143 and a light chain (LC) comprising the amino acid sequence set forth in SEQ ID NO: 165 and variants in which the HC lacks a C-terminal Lysine or glycine-lysine.

In particular embodiments, the present invention provides the above antibody or antigen binding fragment wherein the antibody comprises a human IgG1, IgG2, IgG3, or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype, and variants thereof in which the HC lacks a C-terminal Lysine or glycine-lysine.

In some embodiments, different constant domains may be fused to a V$_L$ and V$_H$ regions comprising the CDRs provided herein. In particular embodiments, the V$_H$ regions comprising the CDRs provided herein may be fused to a human IgG1, IgG2, IgG3, or IgG4 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native or wild-type IgG1, IgG2, IgG3, or IgG4 isotype, and variants thereof in which the HC lacks a C-terminal Lysine or glycine-lysine.

In particular embodiments, the anti-ILT3 antibody (or antigen binding fragment) has an altered effector function and may comprise a heavy chain constant domain other than native (wild-type) human IgG1, for example a human IgG1 that has mutations that abrogate or minimize one or more effector functions, including ability to bind complement, human IgG4, or a hybrid human IgG1/human IgG4, and variants thereof in which the HC lacks a C-terminal Lysine or glycine-lysine.

Although native human IgG1 antibodies provide for long half-life and for effector functions, such as complement activation and antibody-dependent cellular cytotoxicity, such activities may not be desirable for all uses of an antibody. Thus, in particular embodiments, it is desirable that the heavy chain constant domain or Fc have minimal or reduced effector function ("effector-less"). In those instances, the anti-ILT3 HC variable domain may be fused to a human IgG4 constant domain, which is generally known to be effector-less, or an IgG1 constant domain that has been mutated to be rendered effecter-less. These effector-less molecules have minimal or reduced binding to human FcγRIIIA, and FcγRIIA, and Fcγ.RI compared to the polypeptide comprising the wildtype IgG Fc region, wherein the affinity to each of human FcγRIIIA, and FcγRIIA, and FcγRI is reduced by 1.15-fold to 100-fold compared to the polypeptide comprising the wildtype IgG constant domain, and wherein the antibody-dependent cell-mediated cytotoxicity (ADCC) induced by said molecule is 0-20% of the ADCC induced by the polypeptide comprising the wild-type human IgG1 constant domain.

Therefore in particular embodiments, the present invention includes chimeric or humanized anti-ILT3 antibodies and antigen-binding fragments thereof that comprise a human IgG4 constant domain. In a further embodiment, the human IgG4 constant domain may be modified to differ from the native (wild-type) human IgG4 constant domain (Swiss-Prot Accession No. P01861.1) at a position corresponding to position 228 in the EU system and position 241 in the Kabat system in which the native serine at position 108 (Ser108) of the HC constant domain is replaced with proline (Pro), see for example SEQ ID NO: 9. This modification prevents formation of a potential inter-chain disulfide bond between the cysteine at position 106 (Cys106) and the cysteine at position 109 (Cys109), which correspond to positions Cys226 and Cys229 in the EU system and positions Cys239 and Cys242 in the Kabat system, which may interfere with proper intra-chain disulfide bond formation. See Angal et al. Mol. Imunol. 30:105 (1993); see also (Schuurman et. al., Mol. Immunol. 38: 1-8, (2001); SEQ ID NOs: 14 and 41). In particular embodiments, the human IgG4 constant domain may further include in addition to the S228P substitution an L235E substitution.

In another embodiment, the chimeric or humanized anti-ILT3 antibody may be fused to a modified human IgG1 constant domain, which has been modified to be effector-less. In one embodiment, the human IgG1 HC may include substitutions of human IgG2 HC residues at positions 233-236 and IgG4 HC residues at positions 327, 330, and 331 to greatly reduce ADCC and CDC (Armour et al., Eur J Immunol. 29(8):2613-24 (1999); Shields et al., J Biol Chem. 276(9):6591-604(2001)). In particular embodiments, the antibody comprises a human IgG1 heavy chain (HC) constant domain or variant thereof comprising 1, 2, 3, 4, 5, 6, 7, 8, 9, or 10 amino acid substitutions, additions, deletions, or combinations thereof compared to the amino acid sequence of the native IgG, which provides an antibody having reduced or minimal effector function. In particular aspects, the IgG1 has been modified to comprise or consist of an L234A, an L235A, and a D265S mutation to render the Fc effector-less. Other mutations that may be used to render an IgG1 Fc effector-less may be found in U.S. Pat. No. 8,969,526.

In another embodiment, the human IgG1 HC is modified to lack N-glycosylation of the asparagine (Asn) residue at around position 297 of the HC. The consensus sequence for N-glycosylation is Asn-Xaa-Ser/Thr (wherein Xaa is any amino acid except Pro); in IgG1 the N-glycosylation consensus sequence is Asn-Ser-Thr. The modification may be achieved by replacing the codon for the Asn at position 297 in the nucleic acid molecule encoding the HC with a codon for another amino acid, for example Gln. Alternatively, the codon for Ser may be replaced with the codon for Pro or the codon for Thr may be replaced with any codon except the codon for Ser, e.g. N297A or N297D Such modified IgG1 molecules have little or no detectable effector function. Alternatively, all three codons are modified.

In another embodiment, the human IgG1 constant domain is modified to include one or more amino acid substitutions selected from E233P, L234A, L235A, L235E, N297A, N297D, D265S, and P331S, wherein the residues are numbered according to the EU index of Kabat, and wherein said polypeptide exhibits a reduced affinity to the human FcγRIIIA and/or FcγRIIA and/or FcγRI compared to a polypeptide comprising the wildtype IgG constant domain region. In particular embodiments, the human IgG constant domain comprises substitutions of L234A, L235A, and D265S as illustrated by SEQ ID NO: 4, for example. In particular embodiments, the human IgG1 constant domain comprises an amino acid substitution at position Pro329 and at least one further amino acid substitution E233P, L234A, L235A, L235E, N297A, N297D, D265S, and P331S. These and other substitutions are disclosed in WO9428027; WO2004099249; WO20121300831, U.S. Pat. Nos. 9,708,406; 8,969,526; 9,296,815; Sondermann et al. Nature 406, 267-273 (20 Jul. 2000)).

In an embodiment of the invention, the anti-ILT3 antibodies or antigen binding fragments thereof include embodiments in which one or more of the six CDRs has one, two, or three amino acid substitutions, additions, deletions, or combinations thereof comprise a full tetrameric structure having two light chains and two heavy chains, including constant regions. The variable regions of each light chain/heavy chain pair form the antibody binding site. Thus, in general, an intact antibody has two binding sites. Except in bispecific antibodies, the two binding sites are, in general, the same.

In specific embodiments, the present invention provides the anti-ILT3 antibodies shown in the Table 4. With the exception of those antibodies comprising a replacement of the tryptophan residue at position 101 of the $V_H$, the antibodies disclosed herein bind the human ILT3.

TABLE 4

| | | SEQ ID NO: | |
| mAb No. | Description | Heavy Chain | Light Chain |
| --- | --- | --- | --- |
| 1 | Humanized anti-ILT3 mAb (52B8 VH1/VL1) IgG4 S228P/Kappa | 142 | 151 |
| 2 | Humanized anti-ILT3 mAb (52B8 VH1/VL2) IgG4 S228P/Kappa | 142 | 152 |
| 3 | Humanized anti-ILT3 mAb (52B8 VH1/VL3) IgG4 S228P/Kappa | 142 | 153 |
| 4 | Humanized anti-ILT3 mAb (52B8 VH1/VL4) IgG4 S228P/Kappa | 142 | 154 |
| 5 | Humanized anti-ILT3 mAb (52B8 VH2/VL1) IgG4 S228P/Kappa | 148 | 151 |
| 6 | Humanized anti-ILT3 mAb (52B8 VH2/VL2) IgG4 S228P/Kappa | 148 | 152 |
| 7 | Humanized anti-ILT3 mAb (52B8 VH2/VL3) IgG4 S228P/Kappa | 148 | 153 |
| 8 | Humanized anti-ILT3 mAb (52B8 VH2/VL4) IgG4 S228P/Kappa | 148 | 154 |
| 9 | Humanized anti-ILT3 mAb (52B8 VH1 M64V/VL1) IgG4 S228P/Kappa | 143 | 151 |
| 10 | Humanized anti-ILT3 mAb (52B8 VH1 M64V/VL2) IgG4 S228P/Kappa | 143 | 152 |
| 11 | Humanized anti-ILT3 mAb (52B8 VH1 M64V/VL3) IgG4 S228P/Kappa | 143 | 153 |
| 12 | Humanized anti-ILT3 mAb (52B8 VH1 M64V/VL4) IgG4 S228P/Kappa | 143 | 154 |
| 13 | Humanized anti-ILT3 mAb (52B8 VH2 M64V/VL1) IgG4 S228P/Kappa | 149 | 151 |
| 14 | Humanized anti-ILT3 mAb (52B8 VH2 M64V/VL2) IgG4 S228P/Kappa | 149 | 152 |
| 15 | Humanized anti-ILT3 mAb (52B8 VH2 M64V/VL3) IgG4 S228P/Kappa | 149 | 153 |
| 16 | Humanized anti-ILT3 mAb (52B8 VH2 M64V/VL4) IgG4 S228P/Kappa | 149 | 154 |
| 17 | Humanized anti-ILT3 mAb (52B8 VH1 M64L/VL1) IgG4 S228P/Kappa | 144 | 151 |
| 18 | Humanized anti-ILT3 mAb (52B8 VH1 M64L/VL2) IgG4 S228P/Kappa | 144 | 152 |

TABLE 4-continued

| mAb No. | Description | SEQ ID NO: Heavy Chain | SEQ ID NO: Light Chain |
|---|---|---|---|
| 19 | Humanized anti-ILT3 mAb (52B8 VH1 M64L/VL3) IgG4 S228P/Kappa | 144 | 153 |
| 20 | Humanized anti-ILT3 mAb (52B8 VH1 M64L/VL4) IgG4 S228P/Kappa | 144 | 155 |
| 21 | Humanized anti-ILT3 mAb (52B8 VH2 M64L/VL1) IgG4 S228P/Kappa | 150 | 151 |
| 22 | Humanized anti-ILT3 mAb (52B8 VH2 M64L/VL2) IgG4 S228P/Kappa | 150 | 152 |
| 23 | Humanized anti-ILT3 mAb (52B8 VH2 M64L/VL3) IgG4 S228P/Kappa | 150 | 153 |
| 24 | Humanized anti-ILT3 mAb (52B8 VH2 M64L/VL4) IgG4 S228P/Kappa | 150 | 154 |
| 25 | Humanized anti-ILT3 mAb ((52B8 VH1 M64V/VL2) L234A L235A D265S) IgG1/Kappa | 169 | 152 |
| 26 | Humanized anti-ILT3 mAb ((52B8 VH1 M64V/VL5) L234A L235A D265S) IgG1/Kappa | 169 | 152 |
| 27 | Humanized anti-ILT3 mAb ((52B8 VH1 M64V/VL6) L234A L235A D265S) IgG1/Kappa | 169 | 156 |
| 28 | Humanized anti-ILT3 mAb ((52B8 VH1 M64V/VL7) L234A L235A D265S) IgG1/Kappa | 169 | 157 |
| 29 | Humanized anti-ILT3 mAb ((52B8 VH1 M64V/VL8) L234A L235A D265S) IgG1/Kappa | 169 | 158 |
| 30 | Humanized anti-ILT3 mAb (52B8 VH1 M64V/VL5) IgG4 S228P/Kappa | 143 | 155 |
| 31 | Humanized anti-ILT3 mAb (52B8 VH1 M64V/VL6) IgG4 S228P/Kappa | 143 | 156 |
| 32 | Humanized anti-ILT3 mAb (52B8 VH1 M64V/VL7) IgG4 S228P/Kappa | 143 | 157 |
| 33 | Humanized anti-ILT3 mAb (52B8 VH1 M64V/VL8) IgG4 S228P/Kappa | 143 | 158 |
| 34 | Humanized anti-ILT3 mAb (52B8 VH1 M64V W101F/VL2) IgG4 S228P/Kappa | 145 | 152 |
| 35 | Humanized anti-ILT3 mAb (52B8 VH1 M64V W101Y/VL2) IgG4 S228P/Kappa | 146 | 152 |
| 36 | Humanized anti-ILT3 mAb (52B8 VH1 M64V W101Q/VL2) IgG4 S228P/Kappa | 147 | 152 |
| 37 | Humanized anti-ILT3 mAb ((52B8 VH1 M64V W101F/VL2) L234A L235A D265S) IgG1/Kappa | 145 | 152 |
| 38 | Humanized anti-ILT3 mAb ((52B8 VH1 M64V W101Y/VL2) L234A L235A D265S) IgG1/Kappa | 146 | 152 |
| 39 | Humanized anti-ILT3 mAb ((52B8 VH1 M64V W101Q/VL2) L234A L235A D265S) IgG1/Kappa | 147 | 152 |
| 40 | Humanized anti-ILT3 mAb (52B8 VH1 M64V/VL2 S35A) IgG4 S228P/Kappa | 143 | 159 |
| 41 | Humanized anti-ILT3 mAb (52B8 VH1 M64V/VL2 S35N) IgG4 S228P/Kappa | 143 | 160 |
| 42 | Humanized anti-ILT3 mAb (52B8 VH1 M64V/VL2 N34Q) IgG4 S228P/Kappa | 143 | 161 |
| 43 | Humanized anti-ILT3 mAb (52B8 VH1 M64V/VL2 N34D) IgG4 S228P/Kappa | 143 | 162 |
| 44 | Humanized anti-ILT3 mAb (52B8 VH1 M64V/VL5 S35A) IgG4 S228P/Kappa | 143 | 163 |
| 45 | Humanized anti-ILT3 mAb (52B8 VH1 M64V/VL5 S35N) IgG4 S228P/Kappa | 143 | 164 |
| 46 | Humanized anti-ILT3 mAb (52B8 VH1 M64V/VL5 N34Q) IgG4 S228P/Kappa | 143 | 165 |
| 47 | Humanized anti-ILT3 mAb (52B8 VH1 M64V/VL5 N34D) IgG4 S228P/Kappa | 143 | 166 |
| 48 | Humanized anti-ILT3 mAb (52B8 VH1 M64V W101F/VL5) IgG4 S228P/Kappa | 145 | 155 |
| 49 | Humanized anti-ILT3 mAb (52B8 VH1 M64V W101Y/VL5) IgG4 S228P/Kappa | 146 | 155 |
| 50 | Humanized anti-ILT3 mAb (52B8 VH1 M64V W101Q/VL5) IgG4 S228P/Kappa | 147 | 155 |
| 51 | Humanized anti-ILT3 mAb (52B8 VH1 M64V W101F/VL5 S35A) IgG4 S228P/Kappa | 145 | 163 |
| 52 | Humanized anti-ILT3 mAb (52B8 VH1 M64V W101F/VL5 S35N) IgG4 S228P/Kappa | 145 | 164 |
| 53 | Humanized anti-ILT3 mAb (52B8 VH1 M64V W101F/VL5 N34Q) IgG4 S228P/Kappa | 145 | 165 |
| 54 | Humanized anti-ILT3 mAb (52B8 VH1 M64V W101F/VL5 N34D) IgG4 S228P/Kappa | 145 | 166 |
| 55 | Humanized anti-ILT3 mAb (52B8 VH1 M64V W101Y/VL5 S35A) IgG4 S228P/Kappa | 146 | 163 |

TABLE 4-continued

| mAb No. | Description | SEQ ID NO: Heavy Chain | SEQ ID NO: Light Chain |
|---|---|---|---|
| 56 | Humanized anti-ILT3 mAb (52B8 VH1 M64V W101Y/VL5 S35N) IgG4 S228P/Kappa | 146 | 164 |
| 57 | Humanized anti-ILT3 mAb (52B8 VH1 M64V W101Y/VL5 N34Q) IgG4 S228P/Kappa | 146 | 165 |
| 58 | Humanized anti-ILT3 mAb (52B8 VH1 M64V W101Y/VL5 N34D) IgG4 S228P/Kappa | 146 | 166 |
| 59 | Humanized anti-ILT3 mAb (52B8 VH1 M64V W101Q/VL5 S35A) IgG4 S228P/Kappa | 147 | 163 |
| 60 | Humanized anti-ILT3 mAb (52B8 VH1 M64V W101Q/VL5 S35N) IgG4 S228P/Kappa | 147 | 164 |
| 61 | Humanized anti-ILT3 mAb (52B8 VH1 M64V W101Q/VL5 N34Q) IgG4 S228P/Kappa | 147 | 165 |
| 62 | Humanized anti-ILT3 mAb (52B8 VH1 M64V W101Q/VL5 N34D) IgG4 S228P/Kappa | 147 | 166 |
| 63 | Humanized anti-ILT3 mAb (52B8 VH1 M64V/VL1 N34Q) IgG1 N297A/Kappa | 210 | 126 |
| 64 | Humanized anti-ILT3 mAb (52B8 VH1 M64V/VL2) IgG1 N297A/Kappa | 210 | 127 |
| 65 | Humanized anti-ILT3 mAb (52B8 VH1 M64V/VL2 N34Q) IgG1 N297A/Kappa | 210 | 161 |
| 66 | Humanized anti-ILT3 mAb (52B8 VH1 M64V/VL3 N34Q) IgG1 N297A/Kappa | 210 | 128 |
| 67 | Humanized anti-ILT3 mAb (52B8 VH1 M64V/VL4 N34Q) IgG1 N297A/Kappa | 210 | 129 |
| 68 | Humanized anti-ILT3 mAb (52B8 VH1 M64V/VL5) IgG1 N297A/Kappa | 210 | 130 |
| 69 | Humanized anti-ILT3 mAb (52B8 VH1 M64V/VL5 N34Q) IgG1 N297A/Kappa | 210 | 165 |
| 70 | Humanized anti-ILT3 mAb (52B8 VH1 M64V/VL6 N34Q) IgG1 N297A/Kappa | 210 | 131 |
| 71 | Humanized anti-ILT3 mAb (52B8 VH1 M64V/VL7 N34Q) IgG1 N297A/Kappa | 210 | 132 |
| 72 | Humanized anti-ILT3 mAb (52B8 VH1 M64V/VL8 N34Q) IgG1 N297A/Kappa | 210 | 133 |
| 73 | Chimeric anti-ILT3 52B8 mouse VH/human IgG4 (S228P):mouse VL/human Kappa | 113 | 116 |
| 74 | Chimeric anti-ILT3 52B8 mouse VH M64V/human IgG4 (S228P):mouse VL/human Kappa | 114 | 116 |
| 75 | Chimeric anti-ILT3 52B8 mouse VH M64L/human IgG4 (S228P):mouse VL/human Kappa | 115 | 116 |
| 76 | Chimeric anti-ILT3 52B8 mouse VH/human IgG1 (N297A):mouse VL/human Kappa | Residues 1-122 of SEQ ID NO: 113 And SEQ ID NO: 211 | 116 |
| 77 | Chimeric anti-ILT3 52B8 mouse VH M64V/human IgG1 (N297A):mouse VL/human Kappa | Residues 1-122 of SEQ ID NO: 114 And SEQ ID NO: 211 | 116 |
| 78 | Chimeric anti-ILT3 52B8 mouse VH/human IgG1:mouse VL/human Kappa | Residues 1-122 of SEQ ID NO: 113 And SEQ ID NO: 11 | 116 |
| 79 | Chimeric anti-ILT3 52B8 mouse VH M64V/human IgG1:mouse VL/human Kappa | Residues 1-122 of SEQ ID NO: 113 And SEQ ID NO: 11 | 116 |
| 80 | Chimeric anti-ILT3 40A6 rat VH/human IgG4 (S228P):rat VL/human Kappa | 194 | 195 |
| 81 | Chimeric anti-ILT3 16B1 rat VH/human IgG4 (S228P):rat VL/human Kappa | 196 | 197 |
| 82 | Chimeric anti-ILT3 11D1 mouse VH/human IgG4 (S228P):mouse VL/human Kappa | 198 | 199 |

TABLE 4-continued

| | | SEQ ID NO: | |
|---|---|---|---|
| mAb No. | Description | Heavy Chain | Light Chain |
| 83 | Chimeric anti-ILT3 17H12 rat VH/human IgG4 (S228P):rat VL/human Kappa | 200 | 201 |
| 84 | Chimeric anti-ILT3 37C8 rat VH/human IgG4 (S228P):rat VL/human Kappa | 202 | 203 |
| 85 | Chimeric anti-ILT3 IG12 mouse VH/human IgG4 (S228P):mouse VL/human Kappa | 203 | 205 |
| 86 | Chimeric anti-ILT3 20E4 rat VH/human IgG4 (S228P):rat VL/human Kappa | 206 | 207 |
| 87 | Chimeric anti-ILT3 24A4 rat VH/human IgG4 (S228P):rat VL/human Kappa | 208 | 209 |
| 88 | Chimeric anti-ILT3 40A6 rat VH/human IgG1 (N297A):rat VL/human Kappa | 212 | 195 |
| 89 | Chimeric anti-ILT3 16B1 rat VH/human IgG1 (N297A):rat VL/human Kappa | 213 | 197 |
| 90 | Chimeric anti-ILT3 11D1 mouse VH/human IgG1 (N297A):mouse VL/human Kappa | 214 | 199 |
| 91 | Chimeric anti-ILT3 17H12 rat VH/human IgG1 (N297A):rat VL/human Kappa | 215 | 201 |
| 92 | Chimeric anti-ILT3 37C8 rat VH/human IgG1 (N297A):rat VL/human Kappa | 216 | 203 |
| 93 | Chimeric anti-ILT3 IG12 mouse VH/human IgG1 (N297A):mouse VL/human Kappa | 217 | 205 |
| 94 | Chimeric anti-ILT3 20E4 rat VH/human IgG1 (N297A):rat VL/human Kappa | 218 | 207 |
| 95 | Chimeric anti-ILT3 24A4 rat VH/human IgG1 (N297A):rat VL/human Kappa | 219 | 209 |
| 96 | Chimeric anti-ILT3 40A6 rat VH/human IgG1 (N297A):rat VL/human Kappa | 220 | 195 |

Epitope mapping by hydrogen-deuterium exchange mass spectrometry (HDX-MS) as described in Example 4 shows that the anti-ILT3 antibodies disclosed herein bind to an epitope on the extracellular domain near the border between the D1 and D2 domains of the extracellular domain of ILT3. The epitope identified using HDX-MS indicates that the epitope bound by the anti-ILT3 antibodies disclosed herein comprises or consists of at least one amino acid within one or more of the peptide domain amino acid sequences selected from the group consisting of SEQ ID NOs: 3, 4, 5, 6, 7, and 8. In a further embodiment, the epitope comprises or consists of one or more of the peptide domain amino acid sequences selected from the group consisting of SEQ ID NOs: 3, 4, 5, 6, 7, and 8. In certain embodiments, the epitope comprises or consists of at least one amino acid in each of the peptide domain amino acid sequences selected from the group consisting of SEQ ID NOs: 3, 4, 5, 6, 7, and 8 and identified in the HDX-MS. In particular embodiments, the epitope comprises or consists of one or more of the peptide domain amino acid sequences selected from the group consisting of SEQ ID NOs: 3, 4, 5, 6, 7, and 8. In particular embodiments, the epitope comprises or consists of the peptide domains shown in SEQ ID Nos: 3, 4, 5, 6, 7, and 8.

Thus, the present invention further provides a chimeric, humanized, or human antibody or antigen binding fragment that binds to an epitope on ILT3 wherein the epitope comprises or consists of at least one amino acid within one or more of the peptide domains comprising amino acid sequences shown by the amino acid sequences set forth in SEQ ID NOs: 3, 4, 5, 6, 7, and 8 as determined by hydrogen deuterium exchange mass spectrometry (HDX-MS) analysis.

In a further embodiment, the present invention further provides a chimeric, humanized, or human antibody or antigen binding fragment that binds to an epitope on ILT3 wherein the epitope comprises or consists of amino acids within the peptide domains shown in one or more of SEQ ID Nos: 3, 4, 5, 6, 7, and 8. In certain embodiments, the epitope comprises or consists of at least one amino acid in each of the peptide domains identified in the heat map determined by HDX-MS and shown in FIG. 3A.

The present invention further provides a chimeric, humanized, or human antibody or antigen binding fragment that cross-blocks the binding of an antibody comprising a heavy chain variable domain having the amino acid sequence set forth in SEQ ID NO: 15 and a light chain variable domain having the amino acid sequence shown in SEQ ID NO: 16 to an epitope on ILT3. In a further embodiment, the epitope comprises or consists of at least one amino acid within one or more of the peptide domains comprising or consisting of amino acid sequences shown by the amino acid sequences set forth in SEQ ID NOs: 3, 4, 5, 6, 7, and 8 as determined by hydrogen deuterium exchange mass spectrometry (HDX-MS) analysis. In a further embodiment, the epitope comprises or consists of amino acids within the peptide domains shown in one or more of SEQ ID NOs: 3, 4, 5, 6, 7, and 8. In certain embodiments, the epitope comprises or consists of at least one amino acid in each of the peptide domains identified in the HDX-MS.

The present invention further provides bispecific antibodies and antigen-binding fragments comprising a first antibody or antigen binding fragment that binds ILT3 and a second antibody or antigen binding fragment that binds a molecule other than ILT3, wherein the first antibody or antigen binding fragment comprises at least the amino acid sequence of an HC-CDR3 having an amino acid sequence selected from the group consisting of SEQ ID NO: 22, 49, 57, 65, 73, 81, 89, 97, and 105, or having an amino acid sequence that has 3, 2, or 1 differences with an amino acid sequence selected from the group consisting of SEQ ID NO: 22, 49, 57, 65, 73, 81, 89, 97, and 105 and wherein the first antibody binds an ILT3 epitope comprising amino acids within the sequences of SEQ ID Nos: 3, 4, 5, 6, 7, and 8 and the second antibody binds a molecule other than ILT3, and methods of use thereof.

The present invention further provides bispecific antibodies and antigen-binding fragments comprising a first antibody or antigen binding fragment that binds ILT3 and a second antibody or antigen binding fragment that binds a molecule other than ILT3, wherein the first antibody or antigen binding fragment comprising at least the six CDRs of an anti-ILT3 antibody or embodiments thereof wherein one or more of the CDRs has one, two, or three amino acid substitutions, additions, deletions, or combinations thereof and wherein the first antibody binds an ILT3 epitope comprising amino acids within the sequences of SEQ ID NOs: 3, 4, 5, 6, 7, and 8 and the second antibody binds a molecule other than ILT3, and methods of use thereof.

The present invention further provides biparatopic antibodies (antibodies having binding specificity for different epitopes on the same antigen) having a first heavy/light chain pair of a first antibody that comprises at least an HC-CDR3 having an amino acid sequence selected from the group consisting of SEQ ID NOs: 22, 49, 57, 65, 73, 81, 89, 97, and 105, or having an amino acid sequence that has 3, 2, or 1 differences with an amino acid sequence selected from the group consisting of SEQ ID NOs: 22, 49, 57, 65, 73, 81, 89, 97, and 105, wherein the first heavy/light chain pair binds an ILT3 epitope comprising amino acids within the sequences of SEQ ID NOs: 3, 4, 5, 6, 7, and 8 and the second antibody binds a molecule other than ILT3 and a second heavy/light chain pair of a second antibody having specificity for an anti-ILT3 epitope that is different from the epitope recognized by the first heavy/light chain pair.

The present invention further provides biparatopic antibodies (antibodies having binding specificity for different epitopes on the same antigen) having first heavy/light chain pair of a first antibody that comprises at least the six CDRs of an anti-ILT3 antibody or embodiments thereof wherein one or more of the CDRs has one, two, or three amino acid substitutions, additions, deletions, or combinations thereof wherein the first antibody binds an ILT3 epitope comprising amino acids within the sequences of SEQ ID NOs: 3, 4, 5, 6, 7, and 8, wherein the first heavy/light chain pair binds an ILT3 epitope comprising amino acids within the sequences of SEQ ID NOs: 3, 4, 5, 6, 7, and 8 and the second antibody binds a molecule other than ILT3 and a second heavy/light chain pair of a second antibody having specificity for an anti-ILT3 epitope that is different from the epitope recognized by the first heavy/light chain pair.

Pharmaceutical Compositions and Administration

To prepare pharmaceutical or sterile compositions of the anti-ILT3 antibodies or antigen binding fragments thereof, the antibody or antigen binding fragments thereof is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984) and continuously updated on the Internet by the U.S. Pharmacopeial Convention (USP) 12601 Twinbrook Parkway, Rockville, Md. 20852-1790, USA.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

In a further embodiment, a composition comprising an antibody or antibody fragment disclosed herein is administered to a subject in accordance with the Physicians' Desk Reference 2017 (Thomson Healthcare; 75st edition (Nov. 1, 2002)). Methods of administering antibody molecules are known in the art and are described below. Suitable dosages of the molecules used will depend on the age and weight of the subject and the particular drug used. Dosages and therapeutic regimens of the anti-ILT3 antibody or antigen binding fragment can be determined by a skilled artisan. In certain embodiments, the anti-ILT3 antibody or antigen binding fragment is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. In some embodiments, the anti-ILT3 antibody or antigen binding fragment is administered at a dose of about 1 mg/kg, about 3 mg/kg, or 10 mg/kg, about 20 mg/kg, about 30 mg/kg, or about 40 mg/kg. In some embodiments, the anti-ILT3 antibody or antigen binding fragment is administered at a dose of about 1-3 mg/kg, or about 3-10 mg/kg. In some embodiments, the anti-ILT3 antibody or antigen binding fragment is administered at a dose of about 0.5-2, 2-4, 2-5, 5-15, or 5-20 mg/kg. The dosing schedule can vary from e.g., once a week to once every 2, 3, or 4 weeks. In one embodiment, the anti-ILT3 antibody or antigen binding fragment is administered at a dose from about 10 to 20 mg/kg every other week.

The mode of administration can vary. Suitable routes of administration is preferably parenteral or subcutaneous. Other routes of administration may include oral, transmucosal, intradermal, direct intraventricular, intravenous, intranasal, inhalation, insufflation, or intra-arterial.

In particular embodiments, the anti-ILT3 antibodies or antigen binding fragments thereof can be administered by an invasive route such as by injection. In further embodiments of the invention, the anti-ILT3 antibodies or antigen binding fragments thereof, or pharmaceutical composition thereof, may be administered intravenously, subcutaneously, intraarterially, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447, 224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engi. J. Med.* 344:783-792; Beniaminovitz et al. (2000) *New Engi. J. Med.* 342:613-619; Ghosh et al. (2003) *New Engl. J. Med.* 348:24-32; Lipsky et al. (2000) *New Engl. J. Med.* 343:1594-1602).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the antibody or antibody binding fragment and the particular therapeutic effect to be achieved, and (b) the limitations inherent in the art of compounding such an active molecules for the treatment of sensitivity in individuals. (see, e.g., Yang, et al. (2003) *New Engl. J. Med.* 349:427-434; Herold, et al. (2002) *New Engl. J. Med.* 346:1692-1698; Liu, et al. (1999) *J. Neural. Neurosurg. Psych.* 67:451-456; Portielji, et al. (20003) *Cancer Immunol. Immunother.* 52:133-144).

Use of the Anti-ILT3 Antibodies or Antigen Binding Fragments Disclosed Herein

The anti-ILT3 antibodies and antigen binding fragments disclosed herein being non-promiscuous for related ILTs may be used to specifically detect human ILT3 (e.g., in a biological sample, such as serum or plasma), using a conventional immunoassay, such as an enzyme linked immunosorbent assays (ELISA), an radioimmunoassay (RIA) or tissue immunohistochemistry. The invention thus provides a method for detecting human ILT3 in a biological sample comprising contacting a biological sample with an anti-ILT3 antibody or antigen binding fragment and detecting either the anti-ILT3 antibody or antigen binding fragment bound to human ILT3 or unbound anti-ILT3 antibody or antigen binding fragment disclosed herein, to thereby detect human ILT3 in the biological sample. The anti-ILT3 antibody or antigen binding fragment is directly or indirectly labeled with a detectable substance to facilitate detection of the bound or unbound anti-ILT3 antibody or antigen binding fragment disclosed herein. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, and $^{3}$H.

Alternative to labeling the anti-ILT3 antibody or antigen binding fragment, human ILT3 can be assayed in biological fluids by a competition immunoassay utilizing ILT3 standards labeled with a detectable substance and an unlabeled anti-human ILT3 anti-ILT3 antibody or antigen binding fragment disclosed herein. In this assay, the biological sample, the labeled ILT3 standards and the anti-ILT3 antibody or antigen binding fragment are combined and the amount of labeled ILT3 standard bound to the unlabeled anti-ILT3 antibody or antigen binding fragment disclosed herein is determined. The amount of human ILT3 in the biological sample is inversely proportional to the amount of labeled ILT3 standard bound to the anti-ILT3 antibody or antigen binding fragment.

An anti-ILT3 antibody or antigen binding fragment disclosed herein may also be used to detect ILT3 from a species other than humans, in particular ILT3 from primates (e.g., cynomolgus monkey or rhesus monkey).

Methods of Upmodulating Immune Responses In Vivo

The anti-ILT3 antibodies or antigen binding fragments disclosed herein may be used as immunostimulatory compositions, e.g., alone or as part of a vaccine or combination therapy, to promote B cell, and/or T cell activation, e.g., either Th1 or Th2 cell activation, in a subject. That is, the anti-ILT3 antibody or antigen binding fragment disclosed herein may serve as adjuvants used in combination with an antigen of interest to enhance an immune response to that antigen of interest in vivo. For example, to stimulate an antibody or cellular immune response to an antigen of interest (e.g., for vaccination purposes), the antigen and anti-ILT3 antibody or antigen binding fragment disclosed herein may be co-administered (e.g., co-administered at the same time in the same or separate compositions, or sequentially in time such that an enhanced immune response occurs). The antigen of interest and the anti-ILT3 antibody or antigen binding fragment disclosed herein may be formulated together into a single pharmaceutical composition or in separate compositions. In one embodiment, the antigen of interest and the anti-ILT3 antibody or antigen binding fragment disclosed herein are administered simultaneously to the subject. Alternatively, in certain situations it may be desirable to administer the antigen first and then the anti-ILT3 antibody or antigen binding fragment disclosed herein or vice versa (for example, in the case of an antigen that naturally evokes a Th1 response, it may be beneficial to first administer the antigen alone to stimulate a Th1 response and then administer an anti-ILT3 antibody or antigen binding fragment disclosed herein, alone or together with a boost of antigen, to shift the immune response to a Th2 response). In preferred embodiments, an anti-ILT3 antibody or antigen binding fragment disclosed herein is administered at the time of priming with antigen, i.e., at the time of the first administration of antigen. For example, day −3, −2, −1, 0, +1, +2, +3. A particularly preferred day of administration of an anti-ILT3 antibody or antigen binding fragment disclosed herein is day −1.

In one embodiment, an anti-ILT3 antibody or antigen binding fragment disclosed herein is administered with an antigen of interest. An antigen of interest is one to which an immune response is desired. For example, an antigen of interest is an antigen capable of stimulating immune protection in a subject against challenge by an infectious agent from which the antigen was derived. Further contemplated is administration of an anti-ILT3 antibody or antigen binding fragment disclosed herein to increase immune responses without having to administer an antigen.

Exemplary antigens of interest therefore include those derived from infectious agents, wherein an immune response directed against the antigen serves to prevent or treat disease caused by the agent. Such antigens include, but are not limited to, viral, bacterial, fungal or parasite proteins and any other proteins, glycoproteins, lipoprotein, glycolipids, and the like. Antigens of interest also include those which provide benefit to a subject which is at risk for acquiring or which is diagnosed as having a tumor. The subject is preferably a mammal and most preferably, is a human.

Typical antigens of interest may be classified as follows: protein antigens, such as ceruloplasmin and serum albumin; bacterial antigens, such as teichoic acids, flagellar antigens, capsular polysaccharides, and extra-cellular bacterial products and toxins; glycoproteins and glycolipids; viruses, such as animal, plant, and bacterial viruses; conjugated and synthetic antigens, such as protein/hapten conjugates, molecules expressed preferentially by tumors, compared to normal tissue; synthetic polypeptides; and nucleic acids, such as ribonucleic acid and deoxyribonucleic acid. The term "infectious agent," as used herein, includes any agent which expresses an antigen, which elicits a host cellular immune response. Non-limiting examples of viral antigens which may be considered useful as include, but are not limited to, the nucleoprotein (NP) of influenza virus and the Gag proteins of HIV. Other heterologous antigens include, but are not limited to, HIV Env protein or its component parts gp120 and gp41, HIV Nef protein, and the HIV Pol proteins, reverse transcriptase and protease. In addition, other viral antigens such as Ebola virus (EBOV) antigens, such as, for example, EBOV NP or glycoprotein (GP), either full-length or GP deleted in the mucin region of the molecule (Yang et al., Nat Med 6:886 (2000), small pox antigens, hepatitis A, B or C virus, human rhinovirus such as type 2 or type 14, herpes simplex virus, poliovirus type 2 or 3, foot-and-mouth disease virus (FMDV), rabies virus, rotavirus, influenza virus, coxsackie virus, human papilloma virus (HPV), for example the type 16 papilloma virus, the E7 protein thereof, and fragments containing the E7 protein or its epitopes; and simian immunodeficiency virus (SIV) may be used. The antigens of interest need not be limited to antigens of viral origin. Parasitic antigens, such as, for example, malarial antigens are included, as are fungal antigens, bacterial antigens and tumor antigens. Examples of antigens derived from bacteria are those derived from *Bordetella pertussis* (e.g., P69 protein and filamentous haemagglutinin (FHA) antigens), *Vibrio cholerae, Bacillus anthracis*, and *E. coli* antigens such as *E. coli* heat labile toxin B subunit (LT-B), *E. coli* K88 antigens, and enterotoxigenic *E.* *coli* antigens. Other examples of antigens include *Schistosoma mansoni* P28 glutathione S-transferase antigens (P28 antigens) and antigens of flukes, mycoplasma, roundworms, tapeworms, *Chlamydia trachomatis*, and malaria parasites, e.g., parasites of the genus *plasmodium* or *babesia*, for example *Plasmodium falciparum*, and peptides encoding immunogenic epitopes from the aforementioned antigens.

By the term "tumor-related antigen," as used herein, is meant an antigen which affects tumor growth or metastasis in a host organism. The tumor-related antigen may be an antigen expressed by a tumor cell, or it may be an antigen that is expressed by a non-tumor cell but when so expressed, promotes the growth or metastasis of tumor cells. The types of tumor antigens and tumor-related antigens include any known or heretofore unknown tumor antigen, including, without limitation, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer.

An infection, disease or disorder which may be treated or prevented by the administration of a composition comprising an anti-ILT3 antibody or antigen binding fragment disclosed herein includes any infection, disease or disorder wherein a host immune response acts to prevent the infection, disease or disorder. Diseases, disorders, or infection which may be treated or prevented by the administration of a composition comprising an anti-ILT3 antibody or antigen binding fragment disclosed herein include, but are not limited to, any infection, disease or disorder caused by or related to a fungus, parasite, virus, or bacteria, diseases, disorders or infections caused by or related to various agents used in bioterrorism, listeriosis, Ebola virus, SARS, small pox, hepatitis A, hepatitis B, hepatitis C, diseases and disorders caused by human rhinovirus, HIV and AIDS, Herpes, polio, foot-and-mouth disease, rabies, diseases or disorders caused by or related to: rotavirus, influenza, coxsackie virus, human papilloma virus, SIV, malaria, cancer, e.g., tumors, and diseases or disorders caused by or related to infection by *Bordetella pertussis, Vibrio cholerae, Bacillus anthracis, E. coli*, flukes, mycoplasma, roundworms, tapeworms, *Chlamydia trachomatis*, and malaria parasites, etc.

Immune Responses to Tumor Cells

Regulatory T cells play an important role in the maintenance of immunological self-tolerance by suppressing immune responses against autoimmune diseases and cancer. Accordingly, in one embodiment, upmodulating an immune response would be beneficial for enhancing an immune response in cancer. Therefore, the anti-ILT3 antibodies or antigen binding fragments disclosed herein may be used in the treatment of malignancies, to inhibit tumor growth or metastasis. The anti-ILT3 antibodies or antigen binding fragments disclosed herein may be administered systemically or locally to the tumor site.

In one embodiment, modulation of human ILT3 function may be useful in the induction of tumor immunity. An ILT3 binding molecule may be administered to a patient having tumor cells (e.g., sarcoma, melanoma, lymphoma, leukemia, neuroblastoma, carcinoma) to overcome tumor-specific tolerance in the subject.

As used herein, the term "neoplastic disease" is characterized by malignant tumor growth or in disease states characterized by benign hyperproliferative and hyperplastic cells. The common medical meaning of the term "neoplasia"

refers to "new cell growth" that results as a loss of responsiveness to normal growth controls, e.g., neoplastic cell growth.

As used herein, the terms "hyperproliferative", "hyperplastic", malignant" and "neoplastic" are used interchangeably, and refer to those cells in an abnormal state or condition characterized by rapid proliferation or neoplasia. The terms are meant to include all types of hyperproliferative growth, hyperplastic growth, cancerous growths or oncogenic processes, metastatic tissues or malignantly transformed cells, tissues, or organs, irrespective of histopathologic type or stage of invasiveness. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be either benign, premalignant or malignant.

The terms "neoplasia," "hyperplasia," and "tumor" are often commonly referred to as "cancer," which is a general name for more than 100 disease that are characterized by uncontrolled, abnormal growth of cells. Examples of cancer include, but are not limited to: breast; colon; non-small cell lung, head and neck; colorectal; lung; prostate; ovary; renal; melanoma; and gastrointestinal (e.g., pancreatic and stomach) cancer; and osteogenic sarcoma.

In one embodiment, the cancer is selected from the group consisting of: pancreatic cancer, melanomas, breast cancer, lung cancer, head and neck cancer, bronchus cancer, colorectal cancer, prostate cancer, pancreatic cancer, stomach cancer, ovarian cancer, urinary bladder cancer, brain or central nervous system cancer (e.g., gliobastoma), peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

Immune Responses to Infectious Agents

Upregulation of immune responses may be in the form of enhancing an existing immune response or eliciting an initial immune response. For example, enhancing an immune response by modulation of ILT3 may be useful in cases of viral infection. As the anti-ILT3 antibodies or antigen binding fragments disclosed herein may act to enhance immune responses, they would be therapeutically useful in situations where more rapid or thorough clearance of pathogenic agents, e.g., bacteria and viruses would be beneficial.

As used herein, the term "viral infection" includes infections with organisms including, but not limited to, HIV (e.g., HIV-1 and HIV-2), human herpes viruses, cytomegalovirus (esp. Human), Rotavirus, Epstein-Barr virus, Varicella Zoster Virus, hepatitis viruses, such as hepatitis B virus, hepatitis A virus, hepatitis C virus and hepatitis E virus, paramyxoviruses: Respiratory Syncytial virus, parainfluenza virus, measles virus, mumps virus, human papilloma viruses (for example HPV6, 11, 16, 18 and the like), flaviviruses (e.g. Yellow Fever Virus, Dengue Virus, Tick-borne encephalitis virus, Japanese Encephalitis Virus) or influenza virus.

As used herein, the term "bacterial infections" include infections with a variety of bacterial organisms, including gram-positive and gram-negative bacteria. Examples include, but are not limited to, *Neisseria* spp, including *N. gonorrhea* and *N. meningitidis*, *Streptococcus* spp, including *S. pneumoniae, S. pyogenes, S. agalactiae, S. matins; Haemophilus* spp, including *H. influenzae* type B, non typeable *H. influenzae, H. ducreyi; Moraxella* spp, including *M. catarrhalis*, also known as *Branhamella catarrhalis; Bordetella* spp, including *B. pertussis, B. parapertussis* and *B. bronchiseptica; Mycobacterium* spp., including *M. tuberculosis, M bovis, M leprae, M avium*, M paratuberculosis, *M. smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae, S. flexnerii; Yersinia* spp, including *Y. enterocolitica, Y. pestis, Y. pseudotuberculosis, Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including *H. pylori; Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic Ehrlichiosis; *Rickettsia* spp, including *R. rickettsii; Chlamydia* spp., including *C. trachomatis, C. neumoniae, C. psittaci; Leptsira* spp., including *L. interrogans; Treponema* spp., including *T. pallidum, T. denticola, T. hyodysenteriae*. Preferred bacteria include, but are not limited to, *Listeria*, mycobacteria, mycobacteria (e.g., tuberculosis), Anthrax, *Salmonella* and *Listeria monocytogenes*.

In another embodiment, T cells can be removed from a patient, and contacted in vitro with an anti-ILT3 antibody or antigen binding fragment disclosed herein, optionally with an activating signal (e.g., antigen plus APCs or a polyclonal antibody) and reintroduced into the patient.

The anti-ILT3 antibodies or antigen binding fragments disclosed herein may also be used prophylactically in vaccines against various pathogens. Immunity against a pathogen, e.g., a virus, could be induced by vaccinating with a viral protein along with an anti-ILT3 antibody or antigen binding fragment disclosed herein. Alternately, an expression vector that encodes genes for both a pathogenic antigen and anti-ILT3 antibody or antigen binding fragment disclosed herein, e.g., a vaccinia virus expression vector engineered to express a nucleic acid encoding a viral protein and a nucleic acid encoding an anti-ILT3 antibody or antigen binding fragment disclosed herein, may be used for vaccination. Pathogens for which vaccines may be useful include, for example, hepatitis B, hepatitis C, Epstein-Barr virus, cytomegalovirus, HIV-1, HIV-2, tuberculosis, malaria and schistosomiasis.

The present invention further encompasses an anti-ILT3 antibody or antigen binding fragment disclosed herein conjugated to a diagnostic or therapeutic agent. The anti-ILT3 antibody or antigen binding fragment disclosed herein can be used diagnostically to, for example, monitor the development or progression of a tumor as part of a clinical testing procedure to, e.g., determine the efficacy of a given treatment regimen. Detection may be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the binding molecule or indirectly, through an intermediate (such as, for example, a linker known in the art) using techniques known in the art. U.S. Pat. No. 4,741,900 discloses metal ions that may be conjugated to binding molecules. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials are $^{125}$I, $^{131}$I, and $^{99}$Tc.

Further, an anti-ILT3 antibody or antigen binding fragment disclosed herein may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, camustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The present invention is further directed to therapies that involve administering an anti-ILT3 antibody or antigen binding fragment disclosed herein to an animal, preferably a mammal, and most preferably a human, patient for treating, detecting, and/or preventing one or more of the diseases, disorders, or conditions disclosed herein. Therapeutic compounds of the invention include, but are not limited to, anti-ILT3 antibody or antigen binding fragment disclosed herein. The anti-ILT3 antibody or antigen binding fragment disclosed herein may be used to treat, diagnose, inhibit or prevent diseases, disorders or conditions associated with aberrant activity of ILT3, including, but not limited to, any one or more of the diseases, disorders, or conditions described herein.

The anti-ILT3 antibody or antigen binding fragment disclosed herein may be advantageously utilized in combination with other monoclonal or chimeric binding molecules, or with lymphokines or hematopoietic growth factors (such as, e.g., IL-2, IL-3 and IL-7), for example, which serve to increase the number or activity of effector cells which interact with the binding molecules.

The anti-ILT3 antibody or antigen binding fragment disclosed herein may be administered alone or in combination with other types of treatments, e.g., immunostimulatory treatments or treatments designed to control the proliferation of a target of activated immune cells (e.g., cancer cells or pathogens). Exemplary therapies include e.g., radiation therapy, chemotherapy, hormonal therapy, immunotherapy and anti-tumor agents, antibiotics, and immunoglobulin.

An anti-ILT3 antibody or antigen binding fragment disclosed herein may be administered to a human subject for therapeutic purposes. Moreover, an anti-ILT3 antibody or antigen binding fragment disclosed herein may be administered to a non-human mammal expressing ILT3 with which the binding molecule cross-reacts (e.g., a primate) for veterinary purposes or as an animal model of human disease.

Combinations

The anti-ILT3 antibodies or antigen binding fragments herein may be used in unconjugated forms or conjugated to a second agent, e.g., a cytotoxic drug, radioisotope, or a protein, e.g., a protein toxin or a viral protein. This method includes: administering the anti-ILT3 antibodies or antigen binding fragments herein, alone or conjugated to a cytotoxic drug, to a subject requiring such treatment. The anti-ILT3 antibodies or antigen binding fragments herein may be used to deliver a variety of therapeutic agents, e.g., a cytotoxic moiety, e.g., a therapeutic drug, a radioisotope, molecules of plant, fungal, or bacterial origin, or biological proteins (e.g., protein toxins) or particles (e.g., a recombinant viral particles, e.g.; via a viral coat protein), or mixtures thereof.

Additional Combination Therapies

The anti-ILT3 antibodies or antigen binding fragments herein may be used in combination with other therapies. For example, the combination therapy may include a composition comprising an anti-ILT3 antibody or antigen binding fragment co-formulated with, and/or co-administered with, one or more additional therapeutic agents, e.g., one or more anti-cancer agents, cytotoxic or cytostatic agents, hormone treatment, vaccines, and/or other immunotherapies. In other embodiments, the anti-ILT3 antibody or antigen binding fragment is administered in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

By "in combination with," it is not intended to imply that the therapy or the therapeutic agents must be administered at the same time and/or formulated for delivery together, although these methods of delivery are within the scope described herein. The anti-ILT3 antibody or antigen binding fragment may be administered concurrently with, prior to, or subsequent to, one or more other additional therapies or therapeutic agents. The anti-ILT3 antibody or antigen binding fragment and the other agent or therapeutic protocol may be administered in any order. In general, each agent will be administered at a dose and/or on a time schedule determined for that agent. In will further be appreciated that the additional therapeutic agent utilized in this combination may be administered together in a single composition or administered separately in different compositions. In general, it is expected that additional therapeutic agents utilized in combination be utilized at levels that do not exceed the levels at which they are utilized individually. In some embodiments, the levels utilized in combination will be lower than those utilized individually.

In certain embodiments, an anti-ILT3 antibody or antigen binding fragment described herein is administered in combination with one or more check point inhibitors or antagonists of programmed death receptor 1 (PD-1) or its ligand PD-L1 and PD-L2. The inhibitor or antagonist may be an antibody, an antigen binding fragment, an immunoadhesin, a fusion protein, or oligopeptide. In some embodiments, the anti-PD-1 antibody is chosen from nivolumab (OPDIVO®, Bristol Myers Squibb, New York, N.Y.), pembrolizumab (KEYTRUDA®, Merck Sharp & Dohme Corp, Kenilworth, N.J. USA), cetiplimab (Regeneron, Tarrytown, N.Y.) or pidilizumab (CT-011). In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence)). In some embodiments, the PD-1 inhibitor is AMP-224. In some embodiments, the PD-L1 inhibitor is anti-PD-L1 antibody such durvalumab (IMFINZI®, Astrazeneca, Wilmingon, Del.), atezolizumab (TECENTRIQ®, Roche, Zurich, CH), or avelumab (BAVENCIO®, EMD Serono, Billerica, Mass.). In some embodiments, the anti-PD-L1 binding antagonist is chosen from YW243.55.S70, MPDL3280A, MEDI-4736, MSB-0010718C, or MDX-1105.

MDX-1105, also known as BMS-936559, is an anti-PD-L1 antibody described in WO2007/005874. Antibody YW243.55.S70 is an anti-PD-L1 described in WO 2010/077634 (heavy and light chain variable region sequences shown in SEQ ID NOs. 20 and 21, respectively).

Nivolumab, also known as OPDIVO®, MDX-1106-04, ONO-4538, or BMS-936558, is a fully human IgG4 anti-PD-1 antibody described in WO2006/121168 and U.S. Pat. No. 8,008,449.

Pembrolizumab, also known as KEYTRUDA®, lambrolizumab, MK-3475 or SCH-900475, is a humanized anti-PD-1 antibody described in U.S. Pat. No. 8,354,509 and WO2009/114335 and disclosed, e.g., in Hamid, et al., New England J. Med. 369 (2): 134-144 (2013). The heavy and light chains for prembrolizumab are shown by the amino acid sequences set forth in SEQ ID Nos: 225 and 226, respectively.

Pidilizumab, also known as CT-011 (Cure Tech) is a humanized IgG1 monoclonal antibody that binds to PD-1. Pidilizumab and other humanized anti-PD-1 monoclonal antibodies are disclosed in WO2009/101611. Other anti-PD-1 antibodies include AMP 514 (Amplimmune), among others, e.g., anti-PD-1 antibodies disclosed in U.S. Pat. No. 8,609,089; U.S Publication No. 2010028330; and U.S Publication No. 20120114649.

AMP-224 (137-DCIg; Amplimmune; e.g., disclosed in WO2010/027827 and WO2011/066342), is a PD-L2 Fc fusion soluble receptor that blocks the interaction between PD-1 and B7-H1.

MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S Publication No. 20120039906.

Other anti-PD-L1 binding agents include YW243.55.570 (heavy and light chain variable regions are shown in SEQ ID NOs 20 and 21 in WO2010/077634) and MDX-1105 (also referred to as BMS-936559). It and other anti-PD-L1 binding agents are disclosed in WO2007/005874).

Kits

Further provided are kits comprising one or more components that include, but are not limited to, the anti-ILT3 antibodies or antigen binding fragments thereof, as discussed herein in association with one or more additional components including, but not limited to, a further therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes the anti-ILT3 antibodies or antigen binding fragments thereof or a pharmaceutical composition thereof in one container (e.g., in a sterile glass or plastic vial) and a further therapeutic agent in another container (e.g., in a sterile glass or plastic vial).

In another embodiment, the kit comprises a combination of the anti-ILT3 antibodies or antigen binding fragments thereof or pharmaceutical composition thereof in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above. Thus, the present invention includes a kit comprising an injection device and t the anti-ILT3 antibodies or antigen binding fragments thereof, e.g., wherein the injection device includes the antibody or fragment or wherein the antibody or fragment is in a separate vessel.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

Methods of Making Antibodies and Antigen Binding Fragments Thereof

The anti-ILT3 antibodies or antigen binding fragments thereof disclosed herein may also be produced recombinantly. In this embodiment, nucleic acid molecules encoding the antibody molecules may be inserted into a vector (plasmid or viral) and transfected or transformed into a host cell where it may be expressed and secreted from the host cell. There are several methods by which to produce recombinant antibodies which are known in the art.

In particular aspects, the present invention provides nucleic acid molecules encoding an HC and an LC wherein the HC comprises at least the HC-CDR3 of an anti-ILT3 antibody disclosed herein or embodiment thereof wherein the HC-CDR3 has one, two, or three amino acid substitutions, additions, deletions, or combinations thereof. In further embodiments, the HC and/or LC variable region framework comprises 0, 1, 2, 3, 4, 5, 6, 7, 8, 9, or 10 amino acid substitutions, additions, deletions, or combinations thereof.

In particular aspects, the present invention provides nucleic acid molecules encoding an HC and an LC wherein the HC comprises the HC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof and wherein the LC comprises the LC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof. In further embodiments, the HC and/or LC variable region framework comprises 0, 1, 2, 3, 4, 5, 6, 7, 8, 9, or 10 amino acid substitutions, additions, deletions, or combinations thereof.

In particular aspects, the present invention provides a first expression vector comprising a nucleic acid molecule encoding an HC comprising at least the HC CDRs of an anti-ILT3 antibody disclosed herein or embodiment thereof wherein one or more of the three HC CDRs has one, two, or three amino acid substitutions, additions, deletions, or combinations thereof and/or wherein the HC variable region framework comprises 0, 1, 2, 3, 4, 5, 6, 7, 8, 9, or 10 amino acid substitutions, additions, deletions, or combinations thereof and a second expression vector comprising a nucleic acid molecule encoding an LC comprising at least the LC CDRs of an anti-ILT3 antibody disclosed herein or embodiment thereof wherein one or more of the three LC CDRs has one, two, or three amino acid substitutions, additions, deletions, or combinations thereof and/or wherein the LC variable region framework comprises 0, 1, 2, 3, 4, 5, 6, 7, 8, 9, or 10 amino acid substitutions, additions, deletions, or combinations thereof.

In particular aspects, the present invention provides nucleic acid molecules encoding a $V_H$ and a $V_L$ wherein the $V_H$ comprises at least the HC-CDR3 of an anti-ILT3 antibody disclosed herein or embodiment thereof wherein the HC-CDR3 has one, two, or three amino acid substitutions, additions, deletions, or combinations thereof. In further embodiments, the $V_H$ and/or $V_L$ variable region framework comprises 0, 1, 2, 3, 4, 5, 6, 7, 8, 9, or 10 amino acid substitutions, additions, deletions, or combinations thereof.

In particular aspects, the present invention provides nucleic acid molecules encoding a $V_H$ and a $V_L$ wherein the HC comprises the HC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof and wherein the $V_L$ comprises the LC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof. In further embodiments, the $V_H$ and/or $V_L$ variable region framework comprises 0, 1, 2, 3, 4, 5, 6, 7, 8, 9, or 10 amino acid substitutions, additions, deletions, or combinations thereof.

In particular aspects, the present invention provides nucleic acid molecules encoding a $V_H$ comprising at least the HC CDRs of an anti-ILT3 disclosed herein or embodiment thereof wherein one or more of the three HC CDRs has one, two, or three amino acid substitutions, additions, deletions, or combinations thereof and/or wherein the $V_H$ and/or $V_L$ variable region framework comprises 0, 1, 2, 3, 4, 5, 6, 7, 8, 9, or 10 amino acid substitutions, additions, deletions, or combinations thereof and nucleic acid molecules encoding a $V_L$ comprising at least the LC CDRs of an anti-ILT3 antibody disclosed herein or embodiment thereof wherein one or more of the three LC CDRs has one, two, or three amino acid substitutions, additions, deletions, or combinations thereof and/or wherein the $V_H$ and/or $V_L$ variable region framework comprises 0, 1, 2, 3, 4, 5, 6, 7, 8, 9, or 10 amino acid substitutions, additions, deletions, or combinations thereof.

Mammalian cell lines available as hosts for expression of the antibodies or fragments disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, human embryo kidney 293 (HEK-293) cells and a number of other cell lines. Cell lines of particular preference are selected through determining which cell lines have high expression levels. Other cell lines that may be used are insect cell lines, such as Sf9 cells, amphibian cells, bacterial cells, plant cells, filamentous fungus cells (e.g. *Trichoderma reesei*), and yeast cells (e.g., *Saccharomyces cerevisiae* or *Pichia pastoris*). In particular aspects, the host cell may be a prokaryote host cell such as *E. coli*.

When recombinant expression vectors comprising a nucleic acid molecule encoding the heavy chain or antigen-binding portion or fragment, the light chain and/or antigen-binding fragment are introduced into host cells, the antibodies are produced by culturing the host cells under conditions and for a period of time sufficient to allow for expression of the antibody in the host cells or, more preferably, secretion of the antibody into the culture medium in which the host cells are grown. The antibodies may be recovered from the culture medium and further purified or processed to produce the antibodies of the invention.

In particular aspects, the host cells are transfected with an expression vector comprising nucleic acid molecules encoding an HC and an LC wherein the HC comprises at least the HC-CDR3 of an anti-ILT3 antibody or embodiment thereof wherein the HC-CDR3 has one, two, or three amino acid substitutions, additions, deletions, or combinations thereof. In further embodiments, the HC and/or LC variable region framework comprises 0, 1, 2, 3, 4, 5, 6, 7, 8, 9, or 10 amino acid substitutions, additions, deletions, or combinations thereof.

In particular aspects, the host cells are transfected with an expression vector comprising nucleic acid molecules encoding an HC and an LC wherein the HC comprises the HC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof and wherein the LC comprises the LC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof. In further embodiments, the HC and/or LC variable region framework comprises 0, 1, 2, 3, 4, 5, 6, 7, 8, 9, or 10 amino acid substitutions, additions, deletions, or combinations thereof.

In particular aspects, the host cells are transfected with a first expression vector comprising a nucleic acid molecule encoding an HC comprising at least the HC CDRs of an anti-ILT3 antibody disclosed herein or embodiment thereof wherein one or more of the three HC CDRs has one, two, or three amino acid substitutions, additions, deletions, or combinations thereof and/or wherein the HC variable region framework comprises 0, 1, 2, 3, 4, 5, 6, 7, 8, 9, or 10 amino acid substitutions, additions, deletions, or combinations thereof and a second expression vector comprising a nucleic acid molecule encoding an LC comprising at least the LC CDRs of an antibody disclosed herein or embodiment thereof wherein one or more of the three LC CDRs has one, two, or three amino acid s substitutions, additions, deletions, or combinations thereof and/or wherein the LC variable region framework comprises 0, 1, 2, 3, 4, 5, 6, 7, 8, 9, or 10 amino acid substitutions, additions, deletions, or combinations thereof.

In particular aspects, the host cells are transfected with an expression vector comprising nucleic acid molecules encoding a $V_H$ and a $V_L$ wherein the $V_H$ comprises at least the HC-CDR3 of an anti-ILT3 antibody disclosed herein or embodiment thereof wherein the HC-CDR3 has one, two, or three amino acid substitutions, additions, deletions, or combinations thereof. In further embodiments, the $V_H$ and/or $V_L$ variable region framework comprises 0, 1, 2, 3, 4, 5, 6, 7, 8, 9, or 10 amino acid substitutions, additions, deletions, or combinations thereof.

In particular aspects, the host cells are transfected with an expression vector comprising nucleic acid molecules encoding a $V_H$ and a $V_L$ wherein the $V_H$ comprises the HC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof and wherein the $V_L$ comprises the LC-CDR1, 2, and 3 of an anti-ILT3 antibody disclosed herein or embodiment thereof wherein one or more of HC-CDR1, 2, and 3 has one, two, or three amino acid substitutions, additions, deletions, or combinations thereof. In further embodiments, the $V_H$ and/or $V_L$ variable region framework comprises 0, 1, 2, 3, 4, 5, 6, 7, 8, 9, or 10 amino acid substitutions, additions, deletions, or combinations thereof.

In particular aspects, the host cells are transfected with a first expression vector comprising a nucleic acid molecule encoding a $V_H$ comprising at least the HC CDRs of an anti-ILT3 antibody disclosed herein or embodiment thereof wherein one or more of the three HC CDRs has one, two, or three amino acid substitutions, additions, deletions, or combinations thereof and/or wherein the $V_H$ variable region framework comprises 0, 1, 2, 3, 4, 5, 6, 7, 8, 9, or 10 amino acid substitutions, additions, deletions, or combinations thereof and a second expression vector comprising a nucleic acid molecule encoding a $V_L$ comprising at least the LC CDRs of an anti-ILT3 antibody disclosed herein or embodiment thereof wherein one or more of the three LC CDRs has one, two, or three amino acid s substitutions, additions, deletions, or combinations thereof and/or wherein the $V_L$ variable region framework comprises 0, 1, 2, 3, 4, 5, 6, 7, 8, 9, or 10 amino acid substitutions, additions, deletions, or combinations thereof.

In particular embodiments, the HC and LC or $V_H$ and $V_L$ are expressed as a fusion protein in which the N-terminus of the HC and the LC are fused to a leader sequence to facilitate the transport of the antibody through the secretory pathway. Examples of leader sequences that may be used include MSVPTQVLGLLLLWLTDARC (SEQ ID NO: 12) or MEWSWVFLFFLSVTTGVHS (SEQ ID NO: 11).

The present invention further provides a plasmid or viral vector comprising a nucleic acid molecule encoding an anti-ILT3 antibody disclosed herein or antigen binding fragment thereof. The present invention further provides a plasmid or viral vector comprising a nucleic acid molecule encoding the HC of an anti-ILT3 antibody disclosed herein or antigen binding fragment thereof or embodiment of the antibody or antigen binding fragment thereof wherein one or more of the three CDRs has one, two, or three amino acid substitutions, additions, deletions, or combinations thereof and/or wherein the HC variable region framework comprises 0, 1, 2, 3, 4, 5, 6, 7, 8, 9, or 10 amino acid substitutions, additions, deletions, or combinations thereof and a nucleic acid molecule encoding the LC of an anti-ILT3 antibody disclosed herein or antigen binding fragment thereof or embodiment of the antibody or antigen binding fragment thereof wherein one or more of the three CDRs has one, two, or three amino acid substitutions, additions, deletions, or combinations thereof and/or wherein the LC variable region framework comprises 0, 1, 2, 3, 4, 5, 6, 7, 8, 9, or 10 amino acid substitutions, additions, deletions, or combinations thereof.

The present invention further provides a plasmid or viral vector comprising a nucleic acid molecule encoding the HC of an anti-ILT3 antibody disclosed herein or antigen binding fragment thereof and a plasmid or viral vector comprising a nucleic acid molecule encoding the LC of an anti-ILT3 antibody disclosed herein or antigen binding fragment thereof.

The present invention further provides a host cell comprising a plasmid or viral vector comprising a nucleic acid molecule encoding the HC of an anti-ILT3 antibody disclosed herein or antigen binding fragment thereof or embodiment of an anti-ILT3 antibody disclosed herein or antigen binding fragment thereof wherein one or more of the three CDRs has one, two, or three amino acid substitutions, additions, deletions, or combinations thereof and/or wherein the HC variable region framework comprises 0, 1, 2, 3, 4, 5, 6, 7, 8, 9, or 10 amino acid substitutions, additions, deletions, or combinations thereof and a plasmid or viral vector comprising a nucleic acid molecule encoding the LC of an anti-ILT3 antibody disclosed herein or antigen binding fragment thereof or embodiment of an anti-ILT3 antibody disclosed herein or antigen binding fragment thereof wherein one or more of the three CDRs has one, two, or three amino acid substitutions, additions, deletions, or combinations thereof and/or wherein the LC variable region framework comprises 0, 1, 2, 3, 4, 5, 6, 7, 8, 9, or 10 amino acid substitutions, additions, deletions, or combinations thereof. In particular embodiments, the host cell is a CHO or HEK-293 host cell.

The present invention further provides a plasmid or viral vector comprising a nucleic acid molecule encoding an anti-ILT3 antibody disclosed herein or antigen binding fragment thereof. The present invention further provides a plasmid or viral vector comprising a nucleic acid molecule encoding the $V_H$ of an anti-ILT3 antibody disclosed herein or antigen binding fragment thereof or embodiment of the antibody or antigen binding fragment thereof wherein one or more of the three CDRs has one, two, or three amino acid substitutions, additions, deletions, or combinations thereof and/or wherein the $V_H$ framework comprises 0, 1, 2, 3, 4, 5, 6, 7, 8, 9, or 10 amino acid substitutions, additions, deletions, or combinations thereof and a nucleic acid molecule encoding the $V_L$ of an anti-ILT3 antibody disclosed herein or antigen binding fragment thereof or embodiment of the antibody or antigen binding fragment thereof wherein one or more of the three CDRs has one, two, or three amino acid substitutions, additions, deletions, or combinations thereof and/or wherein the LC framework comprises 0, 1, 2, 3, 4, 5, 6, 7, 8, 9, or 10 amino acid substitutions, additions, deletions, or combinations thereof.

The present invention further provides a plasmid or viral vector comprising a nucleic acid molecule encoding the $V_H$ of an anti-ILT3 antibody disclosed herein or antigen binding fragment thereof and a plasmid or viral vector comprising a nucleic acid molecule encoding the $V_L$ of an anti-ILT3 antibody disclosed herein or antigen binding fragment thereof.

The present invention further provides a host cell comprising a plasmid or viral vector comprising a nucleic acid molecule encoding the $V_H$ of an anti-ILT3 antibody disclosed herein or antigen binding fragment thereof or embodiment of an anti-ILT3 antibody disclosed herein or antigen binding fragment thereof wherein one or more of the three CDRs has one, two, or three amino acid substitutions, additions, deletions, or combinations thereof and/or wherein the $V_H$ framework comprises 0, 1, 2, 3, 4, 5, 6, 7, 8, 9, or 10 amino acid substitutions, additions, deletions, or combinations thereof and a plasmid or viral vector comprising a nucleic acid molecule encoding the $V_L$ of an anti-ILT3 antibody disclosed herein or antigen binding fragment thereof or embodiment of an anti-ILT3 antibody disclosed herein or antigen binding fragment thereof wherein one or more of the three CDRs has one, two, or three amino acid substitutions, additions, deletions, or combinations thereof and/or wherein the $V_L$ framework comprises 0, 1, 2, 3, 4, 5, 6, 7, 8, 9, or 10 amino acid substitutions, additions, deletions, or combinations thereof. In particular embodiments, the host cell is a CHO or HEK-293 host cell.

The anti-ILT3 antibodies or antigen binding fragments thereof can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions.

In general, glycoproteins produced in a particular cell line or transgenic animal will have a glycosylation pattern that is characteristic for glycoproteins produced in the cell line or transgenic animal (See for example, Croset et al., J. Biotechnol. 161: 336-348 (2012)). Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have.

The following examples are intended to promote a further understanding of the present invention.

General Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif.). Standard methods also appear in Ausbel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, Mo.; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Monoclonal, polyclonal, and humanized antibodies can be prepared (see, e.g., Sheperd and Dean (eds.) (2000) Monoclonal Antibodies, Oxford Univ. Press, New York, N.Y.; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, N.Y., pp. 139-243; Carpenter, et al. (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272:10678-10684; Chothia et al. (1989) Nature 342:877-883; Foote and Winter (1992) J. Mol. Biol. 224:487-499; U.S. Pat. No. 6,329,511).

An alternative to humanization is to use human antibody libraries displayed on phage or human antibody libraries in transgenic mice (Vaughan et al. (1996) Nature Biotechnol. 14:309-314; Barbas (1995) Nature Medicine 1:837-839; Mendez et al. (1997) Nature Genetics 15:146-156; Hoogenboom and Chames (2000) Immunol. Today 21:371-377; Barbas et al. (2001) Phage Display: A Laboratory Manual, Cold Spring Harbor Laboratory Press, Cold Spring Harbor, N.Y.; Kay et al. (1996) Phage Display of Peptides and Proteins: A Laboratory Manual, Academic Press, San Diego, Calif.; de Bruin et al. (1999) Nature Biotechnol. 17:397-399).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) J. Immunol. 146:169-175; Gibellini et al. (1998) J. Immunol. 160:3891-3898; Hsing and Bishop (1999) J. Immunol. 162:2804-2811; Everts et al. (2002) J. Immunol. 168:883-889).

Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) Human Thymus: Histopathology and Pathology, Springer Verlag, New York, N.Y.; Hiatt, et al. (2000) Color Atlas of Histology, Lippincott, Williams, and Wilkins, Phila, PA; Louis, et al. (2002) Basic Histology: Text and Atlas, McGraw-Hill, New York, N.Y.).

Software packages and databases for determining, e.g., antigenic fragments, leader sequences, protein folding, functional domains, glycosylation sites, and sequence alignments, are available (see, e.g., GenBank, VECTOR NTI® Suite (Informax, Inc, Bethesda, Md.); GCG Wisconsin Package (Accelrys, Inc., San Diego, Calif.); DECYPHER® (TimeLogic Corp., Crystal Bay, Nev.); Menne, et al. (2000) Bioinformatics 16: 741-742; Menne, et al. (2000) Bioinformatics Applications Note 16:741-742; Wren, et al. (2002)

Comput. Methods Programs Biomed. 68:177-181; von Heijne (1983) Eur. J. Biochem. 133:17-21; von Heijne (1986) Nucleic Acids Res. 14:4683-4690).

Purity determinations: Size-exclusion ultra-high performance liquid chromatography (SE-UPLC) or (SEC) was carried out on an ACQUITY® UPLC® H-Class system. Column used was an ACQUITY® UPLC® Protein BEH SEC column (Part No. 186005225, 1.7 μm, 200 Å, 4.6 mm×150 mm) from Waters (Milford, Mass.). Column temperature used was 25C and 10 μl sample at 1 mg/mL was injected using a system flow rate of 0.5 ml/min. Mobile phase used was 100 mM sodium phosphate, 200 mM sodium chloride and 0.02% sodium azide, pH 7.0. Data was quantified at both 214 and 280 nm and analyzed using Empower 3 software. A BEH200 SEC Protein Standard Mix (Part No. 186006518) from Waters (Milford, Mass.) was utilized and injected at 10 ug and USP Resolution, Theoretical plates, and Tailing was measured.

NANO-DSF™ (tradename for modified differential scanning fluorimetry method to determine protein stability employing intrinsic tryptophan or tyrosin fluorescence): the temperature mid-point of a thermal unfolding curve, Tm, and mid-point of a thermal aggregation curve, Tagg, were determined by NANO-DSF® using a PROMETHEUS™ NT.48 Differential Scanning Fluorimeter (Nanotemper Technologies) controlled by PR THERMCONTROL™ v2.0.4 software. Excitation power was 40% and temperature was increased from 20° C. to 95° C. at a rate of 1 C/minute. Tm and Tagg were automatically measured. Samples were prepared by diluting to 1 mg/mL in 20 mM sodium acetate pH 5.5 buffer and drawn by capillary action into a PROMETHEUS™ glass capillary (PR-L002).

Capillary Isoelectric Focusing (cIEF): cIEF was conducted on a iCE3™ system from Protein Simple (San Jose, Calif.) using iCE CFR™ software 4.1.1 for instrument control and data analysis. cIEF Cartridge used was Fc-coated (Protein Simple, 101701) and prepared according to manufacturer's instruction. A 200 μL sample consisting of 40 μg of analyte and 1% v/v 3-10 PHARMALYTE®, 0.5% v/v 8-10.5 PHARMALYTE®, 0.5% v/v 5-8 PHARMALYTE® (GE Healthcare), 37.5% v/v 8.0 M Urea (Sigma-Aldrich), 35% v/v 1% methyl cellulose and 1 μL each of 5.85 and 9.22 pI markers (Protein Simple), was prepared. Samples were injected for 60 seconds. Isoelectric focusing parameters were 1500 V for 1 minute and 3000 V for 8 minutes. pI was automatically measured using the internal pI markers serving as a two-point calibration standard. Calibrated data was further analyzed and quantified by conversion to Empower format and analyzed using Empower 3.

Example 1

Hybridoma clone 52B8 was identified via standard mouse and rat immunization and hybridoma selections. In general, Balb/C mice or rats were immunized with human ILT3-HIS recombinant protein in a standard four week footpad immunization to generate a hyperimmune response. Electrofusion of bulk lymphocytes from draining lymph nodes with the P3 myeloma fusion partner produced immortalized hybridomas. Hybridoma supernatant fluid was screened in a primary cell-based ELISA binding assay on human CHO-human ILT3 cells. A secondary screen on CHO parental, CHO-ILT3 SNP, CHO-rhesus ILT3, CHO-ILT5, CHO-ILT8, and CHO-1LT11 cells was performed in a cell-based ELISA format (See Example 2). Subcloning by limited dilution was performed on the ILT3 specific and rhesus positive hybridoma cells. Subclones were expanded to generate purified protein to enable additional tests of Biacore analyses and functional screening. Table 5 shows 10 hybridoma clones that produced antibodies that binned together and had high affinity for human ILT3 as shown by CELISA and Biacore preformed as disclosed in Examples 2 and 4, respectively.

TABLE 5

| Clone | Parental species | cELISA - human ILT3 EC50 (ng/mL) | cELISA - rhesus ILT3 EC50 (ng/mL) | Biacore Kd (M) - ILT3_H | Biacore Kd (M) - ILT3_MM |
|---|---|---|---|---|---|
| LB181.52A8.1A1 | Mouse | 18.4 | 25 | $8.55 \times 10^{-10}$ | $1.3 \times 10^{-8}$ |
| LB181.52B8.1B1 | Mouse | 15.5 | 23.2 | $6.58 \times 10^{-10}$ | $2.44 \times 10^{-8}$ |
| LB182.11D1.1A1 | Mouse | 50.5 | No Binding | $1.41 \times 10^{-08}$ | No binding |
| LB182.1G12.1B1 | Mouse | 39.2 | No Binding | $1.69 \times 10^{-08}$ | No binding |
| LB184.16B1.1D2 | Rat | 64.9 | 67.9 | $9.57 \times 10^{-11}$ | $2.59 \times 10^{-10}$ |
| LB184.20E4.1E1.1D1 | Rat | 2 | 18 | $6.99 \times 10^{-9}$ | $1.8 \times 10^{-8}$ |
| LB184.24A4.1A1 | Rat | 21.4 | 23.1 | $2.05 \times 10^{-11}$ | $1.26 \times 10^{-10}$ |
| LB184.37C8.1A3.1B1 | Rat | 7.7 | 9.5 | $1.18. \times 10^{-11}$ | $1.5 \times 10^{-10}$ |
| LB184.40A6.1C1 | Rat | 17.9 | 25.9 | $1.79 \times 10^{-09}$ | $9.46 \times 10^{-10}$ |
| LB190.17H12.1A1 | Rat | 139.2 | No Binding | $5.92 \times 10^{-10}$ | No binding |

H = human
MM = rhesus monkey (*Macaca mulatta*)

Table 6 shows the amino acid sequences for the heavy chain and light chain variable domains for the mAbs obtained from the above clones.

TABLE 6

| | | SEQ ID NO: | |
|---|---|---|---|
| mAb No. | Description | Heavy Chain Variable domain | Light Chain Variable Domain |
| p52B8 | Mouse anti-ILT3 mAb 52B8 IgG2a/Kappa | 15 | 16 |
| p40A6 | Rat anti-ILT3 mAb 40A6 IgG2a/Kappa | 45 | 46 |
| p16B1 | Rat anti-ILT3 mAb 16B1 IgG2a/Kappa | 53 | 54 |

TABLE 6-continued

| mAb No. | Description | SEQ ID NO: Heavy Chain Variable domain | Light Chain Variable Domain |
|---|---|---|---|
| p49C6 | Mouse anti-ILT3 mAb 49C6 IgG2a/Kappa | Not sequenced | Not sequenced |
| p11D1 | Mouse anti-ILT3 mAb 11D1 IgG2b/Kappa | 61 | 62 |
| p17H12 | Rat anti-ILT3 mAb 17H12 IgG1/Kappa | 69 | 70 |
| p37C8 | Rat anti-ILT3 mAb 37C8 IgG2a/Kappa | 77 | 78 |
| p1G12 | Mouse anti-ILT3 mAb IG12 IgG2a/Kappa | 85 | 86 |
| p20E4 | Rat anti-ILT3 mAb 20E4 IgG2a/Kappa | 93 | 94 |
| p24A4 | Rat ant-ILT3 mAb 24A4 IgG2a/Kappa | 101 | 102 |

To ultimately guide the selection of a lead antibody, antibodies were further analyzed and re-evaluated in a set of bio-functional, biophysical, and physicochemical assays. Finally, antibodies were tested in an in vivo, proof of biology tumor regression study using human SKMEL5 melanoma-challenged humanized mice.

Example 2

Selectivity of various anti-ILT3 Antibodies Cell-based ELISA (cELISA) was used to show the selectivity of the various parental anti-ILT3 antibodies shown in Table 5 and humanized anti-ILT3 monoclonal antibody 9B11disclosed in U.S. Pat. No. 7,777,008 as having the amino acid sequences of SEQ ID NO: 33 (light chain) and SEQ ID NO: 34 (heavy chain).

Mouse anti-human ILT3 antibodies were tested for binding to human ILT3, and cross-reactivity to Rhesus monkey ILT3, human ILT5, human ILT7, human ILT8, and human ILT11 expressing CHO-K1 cells using a cell-based ELISA format. CHO-K1 cells were plated in 96-well tissue-culture plates in 50 µL of DMEM/F12, 10% BCS and gentamycin (CHO-K1 media). Cells were plated at either $2\times10^4$ cells/well two days prior to the assay or $4\times10^4$ cells/well one day prior to the assay. Media was removed from the wells prior to adding the test samples. Purified antibody was serially-diluted in CHO-K1 media and added to the CHO-K1 plates. The samples were incubated at room temperature for 30-60 minutes and plates were washed three times with PBS/05% Tween-20 using the cell wash program on the Biotek EL405x Select CW plate washer. Binding was detected using an HRP-conjugated goat anti-mouse IgG (Southern Biotech cat #1031-05) secondary antibody added at a 1:2000 dilution in CHO-K1 media and incubated at room temperature for 30-60 minutes. Assay plates were washed as above and developed with TMB and stopped with TMB stop solution (KPL cat #50-85-06). The absorbance at 450 nm-620 nm was determined. Mouse IgG1 (MIgG1) served as a control The results are shown in FIGS. 1A, 1B, 1C, 1D, and 1E. The figures show that representative antibodies from clones p40B5, p49C6, and p52B8 were specific for ILT3 and did not cross-react with or bind ILT5, ILT7, ILT8, and ILT11. Antibodies from clones p49C6 and p52B8 as were the antibodies from the other clones were capable of binding Rhesus monkey ILT3. The p52B8 clone was chosen for in vivo characterization based on (1) its high affinity to human ILT3, (2) lack of binding to other ILT family members, and (3) cross-reactivity to rhesus ILT3.

Example 3

Parental mouse 52B8 heavy chain (VH) and light chain (VL) variable domain sequences were compared to human germline sequences. Human framework sequences closely homologous to the framework of the mouse antibody were chosen.

The mouse $V_H$ domain of mouse anti-human ILT3 mAb 52B8 clone scored highly against human heavy chain germline 3-07 in subgroup III and JH4 for the J region. Based on structural considerations, two framework substitutions (R87K and A97G) were incorporated to maintain binding equivalent to the parental antibody. The mouse $V_L$ domain of the antibody clone scored highly against human light chain germline 1-O2 in kappa subgroup I. Mouse 52B8 CDRs were engineered onto the variable light chain sequence of 1-O2 and JK2 for the J region. Based on structural considerations, three framework substitutions (M4L, S64 Å, and G72R) were incorporated.

To generate humanized variants, the humanized $V_H$ sequence was cloned into a vector encoding human IgG4 S228P heavy chain constant domain and the humanized $V_L$ domain was cloned into a vector encoding for a kappa light chain constant domain. A total of two humanized $V_H$ (VH1 and VH2) and 8 humanized $V_L$ were designed. In silico sequence and structural analysis of mouse 52B8 revealed six potential "hot spots" on the molecule: two potential oxidation sites in VH-CDR2 (M64) and in VH-CDR3 (W101), one potential isomerization site in VH-CDR2 (D62), one potential deamidation site in VL-CDR1 (N34), two potential isomerization sites in VL-CDR1 (D30) and VL-CDR2 (D59). M64 was modified to V64 or L64, which maintained favorable physicochemical attributes and binding/functionality.

Figure 2B:
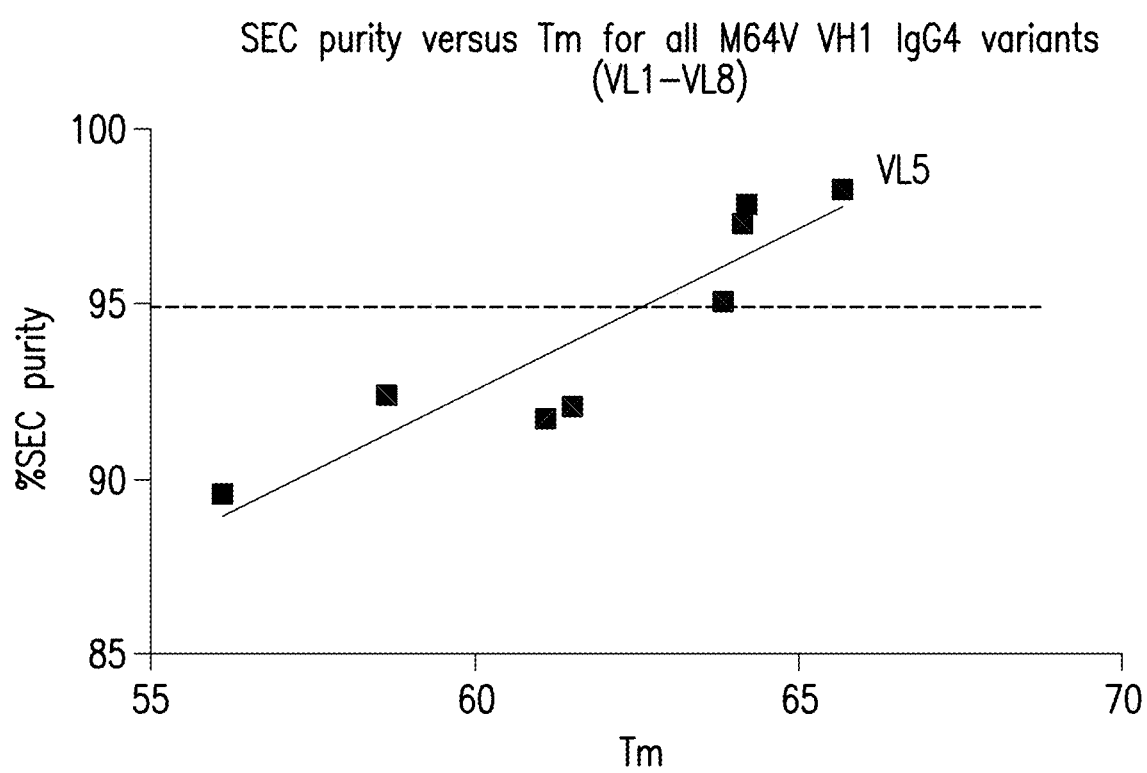
FIG. 2B shows the relationship of SEC purity and melting temperature of humanized light chain variants of mAb 10 (M64V VH1 IgG4). VL1-VL8 refer to variants having the amino acid sequence set forth in SEQ ID NOs: 126-133, respectively.

FIG. 2A provides a table showing data characteristics on binding affinity, isoelectric point, purity of monomer species, and thermal stability measurements for humanized variants that were designed. Biacore was used to measure binding affinity, cIEF was used to measure pI, purity was determined by SE-UPLC, Tm and Tgg was determined by NANO-DSF™. FIG. 2B shows the relationship of SEC purity and melting temperature of various humanized light chain variants. Data is plotted as values obtained from each of the eight humanized light chain variants demonstrating that VL5 has both the highest purity and thermal stability. Based on the data in FIG. 2A and FIG. 2B, VL5 was selected for the light chain.

Initial studies were performed on the humanized VH1 M64V/VL5 produced in transient CHO cells. Forced deamidation conditions employing both 50° C. incubation and high pH stress performed on unformulated humanized 52B8 VH1 M64V/VL5 revealed deamidation of LC N34 in VL-CDR1 (4.0 and 7.2%, respectively) and W101 oxidation in HC-CDR3 with 1× light stress exposure was 15.4%. Substitution of N34 to Q34 maintained binding affinity to human and rhesus ILT3 assessed by a Biacore SPR assay and functional activity assessed by a DC TNFα production assay; however, substitution of the W101 residue resulted in significant loss in binding as determined by a Biacore SPR assay.

In summary, the humanized 52B8 was anti-ILT3 mAb (52B8 VH1 M64V/VL5 N34Q IgG4 S228P/Kappa), contains one framework substitution in $V_L$ (M4L) and one framework substitution in $V_H$ (A97G).

Example 4

Binding Kinetics and Affinities for the Anti-Human ILT3 Antibodies to Recombinant Human or Rhesus ILT3

The binding kinetics and affinities of anti-human ILT3 clones for human or rhesus ILT3-His tagged recombinant protein were measured by surface plasmon resonance using a Biacore T200 system (GE Healthcare, Piscataway, N.J.). HBS-EP+ buffer (BR-1006-69) was used as the running buffer. Anti-human Fc antibody (Human Fc Capture Kit, BR100839, GE Healthcare) was immobilized via amine coupling chemistry in all four flow cells on a Series S CMS sensor chip (BR100530 or 29149603, GE Healthcare) following manufacturer instructions. Flow cell 1 was used as reference for background subtraction and was not used for capture. Anti-human ILT3 antibodies listed above (diluted to 1 μg/mL in HBS-EP+ buffer) were injected over the anti-human Fc capture surfaces in flow cells 2, 3 and 4 at 10 μL/mL for 10 seconds which resulted in antibody capture levels in the range of 60-70 RU Six-point, two-fold dilution series of human or rhesus ILT3-His protein ranging from 20 nM to 0.31 nM and two zeros (HBS-EP+) were injected at 50 μL/mL over the reference and captured antibody surfaces for 180 seconds of association followed by 600 seconds of dissociation. Following each injection cycle, all four flow cells were regenerated using 30 second injection of 3M $MgCl_2$ solution at a flow rate of 10 μL/minute. Reference subtracted sensorgrams were fit to a 1:1 Langmuir Binding Model in the Biacore T200 Evaluation Software (Version 2.0) to determine the association (ka) and dissociation (kd) rate constants and the equilibrium dissociation constant KD (=kd/ka).

Table 7 summarizes the binding kinetics and affinities for the anti-human ILT3 antibodies to recombinant human or rhesus ILT3.

TABLE 7

| mAb No. | Description | cELISA (human ILT3-CHO) EC50 (μg/mL) | cELISA (rhesus ILT3-CHO) EC50 (μg/mL) | Biacore KD (human ILT3-His) (nM) | Biacore KD (rhesus ILT3-His) (nM) | Purity by SEC (% main peak) | pI |
|---|---|---|---|---|---|---|---|
| 63 | Chimeric anti-ILT3 52B8 mouse VH/human IgG4 (S228P):mouse VL/human Kappa | 0.064 | 0.091 | 0.46 | 9.5 | 95.9 | n.d. |
| 64 | Chimeric anti-ILT3 52B8 mouse VH M64V/human IgG4 (S228P):mouse VL/human Kappa | 0.075 | 0.096 | 0.44 | 9.2 | 95.3 | n.d. |
| 65 | Chimeric anti-ILT3 52B8 mouse VH M64L/human IgG4 (S228P):mouse VL/human Kappa | 0.086 | 0.137 | 0.41 | 9.3 | 93.5 | n.d. |
| 1 | Humanized anti-ILT3 mAb (52B8 VH1/VL1) IgG4 S228P/Kappa | n.d. | n.d. | 0.99 | 25 | 93.1 | n.d. |
| 2 | Humanized anti-ILT3 mAb (52B8 VH1/VL2) IgG4 S228P/Kappa | 0.7 | 0.109 | 1.1 | 20 | 96.2 | n.d. |
| 3 | Humanized anti-ILT3 mAb (52B8 VH1/VL3) IgG4 S228P/Kappa | n.d. | n.d. | 1.1 | 26 | 90 | n.d. |
| 4 | Humanized anti-ILT3 mAb (52B8 VH1/VL4) IgG4 S228P/Kappa | n.d. | n.d. | 1.4 | 29 | 93.3 | n.d. |
| 5 | Humanized anti-ILT3 mAb (52B8 | n.d. | n.d. | 0.94 | 25 | 93.1 | n.d. |

TABLE 7-continued

| mAb No. | Description | cELISA (human ILT3-CHO) EC50 (μg/mL) | cELISA (rhesus ILT3-CHO) EC50 (μg/mL) | Biacore KD (human ILT3-His) (nM) | Biacore KD (rhesus ILT3-His) (nM) | Purity by SEC (% main peak) | pI |
|---|---|---|---|---|---|---|---|
| | VH2/VL1) IgG4 S228P/Kappa | | | | | | |
| 6 | Humanized anti-ILT3 mAb (52B8 VH2/VL2) IgG4 S228P/Kappa | 0.1 | 0.118 | 1.1 | 21 | 96.6 | n.d. |
| 7 | Humanized anti-ILT3 mAb (52B8 VH2/VL3) IgG4 S228P/Kappa | n.d. | n.d. | 0.96 | 26 | 89.6 | 6.33 |
| 8 | Humanized anti-ILT3 mAb (52B8 VH2/VL4) IgG4 S228P/Kappa | n.d. | n.d. | 1.3 | 27 | 92.8 | n.d. |
| 9 | Humanized anti-ILT3 mAb (52B8 VH1 M64V/VL1) IgG4 S228P/Kappa | n.d. | n.d. | 0.94 | 26 | 92.1 | n.d. |
| 10 | Humanized anti-ILT3 mAb (52B8 VH1 M64V/VL2) IgG4 S228P/Kappa | 0.085 | 0.148 | 1.1 | 22 | 95.1 | n.d. |
| 11 | Humanized anti-ILT3 mAb (52B8 VH1 M64V/VL3) IgG4 S228P/Kappa | n.d. | n.d. | 1.1 | 27 | 89.6 | n.d. |
| 12 | Humanized anti-ILT3 mAb (52B8 VH1 M64V/VL4) IgG4 S228P/Kappa | n.d. | n.d. | 1.5 | 29 | 92.4 | n.d. |
| 13 | Humanized anti-ILT3 mAb (52B8 VH2 M64V/VL1) IgG4 S228P/Kappa | n.d. | n.d. | 0.94 | 25 | 85.9 | n.d. |
| 14 | Humanized anti-ILT3 mAb (52B8 VH2 M64V/VL2) IgG4 S228P/Kappa | 0.077 | 0.126 | 1 | 22 | 92.8 | n.d. |
| 15 | Humanized anti-ILT3 mAb (52B8 VH2 M64V/VL3) IgG4 S228P/Kappa | n.d. | n.d. | 1 | 26 | 88.7 | n.d. |
| 16 | Humanized anti-ILT3 mAb (52B8 VH2 M64V/VL4) IgG4 S228P/Kappa | n.d. | n.d. | 1.4 | 29 | 93 | n.d. |
| 17 | Humanized anti-ILT3 mAb (52B8 VH1 M64L/VL1) IgG4 S228P/Kappa | n.d. | n.d. | 0.87 | 24 | 90.2 | n.d. |
| 18 | Humanized anti-ILT3 mAb (52B8 VH1 M64L/VL2) IgG4 S228P/Kappa | 0.079 | 0.137 | 1 | 22 | 92.2 | n.d. |
| 19 | Humanized anti-ILT3 mAb (52B8 VH1 M64L/VL3) IgG4 S228P/Kappa | n.d. | n.d. | 0.99 | 26 | 87.4 | n.d. |

TABLE 7-continued

| mAb No. | Description | cELISA (human ILT3-CHO) EC50 (µg/mL) | cELISA (rhesus ILT3-CHO) EC50 (µg/mL) | Biacore KD (human ILT3-His) (nM) | Biacore KD (rhesus ILT3-His) (nM) | Purity by SEC (% main peak) | pI |
|---|---|---|---|---|---|---|---|
| 20 | Humanized anti-ILT3 mAb (52B8 VH1 M64L/VL4) IgG4 S228P/Kappa | n.d. | n.d. | 1.3 | 29 | 90.8 | n.d. |
| 21 | Humanized anti-ILT3 mAb (52B8 VH2 M64L/VL1) IgG4 S228P/Kappa | 0.079 | 0.112 | 0.88 | 27 | 91.2 | n.d. |
| 22 | Humanized anti-ILT3 mAb (52B8 VH2 M64L/VL2) IgG4 S228P/Kappa | 0.057 | 0.081 | 0.97 | 21 | 96.8 | n.d. |
| 23 | Humanized anti-ILT3 mAb (52B8 VH2 M64L/VL3) IgG4 S228P/Kappa | n.d. | n.d. | 0.96 | 24 | 88.5 | n.d. |
| 24 | Humanized anti-ILT3 mAb (52B8 VH2 M64L/VL4) IgG4 S228P/Kappa | n.d. | n.d. | 1.2 | 27 | 91.9 | n.d. |
| 25 | Humanized anti-ILT3 mAb ((52B8 VH1 M64V/VL2) L234A L235A D265S) IgG1/Kappa | n.d. | n.d. | 0.74 | 8.7 | 94.9 | 7.76 |
| 26 | Humanized anti-ILT3 mAb ((52B8 VH1 M64V/VL5) L234A L235A D265S) IgG1/Kappa | n.d. | n.d. | 0.61 | 4.9 | 96.05 | 8.62 |
| 27 | Humanized anti-ILT3 mAb ((52B8 VH1 M64V/VL6) L234A L235A D265S) IgG1/Kappa | n.d. | n.d. | 0.92 | 10 | 90.17 | 8.84 |
| 28 | Humanized anti-ILT3 mAb ((52B8 VH1 M64V/VL7) L234A L235A D265S) IgG1/Kappa | n.d. | n.d. | 0.57 | 5.6 | 94.4 | 8.8 |
| 29 | Humanized anti-ILT3 mAb ((52B8 VH1 M64V/VL8) L234A L235A D265S) IgG1/Kappa | n.d. | n.d. | 0.56 | 5.7 | 94.14 | 8.85 |
| 30 | Humanized anti-ILT3 mAb (52B8 VH1 M64V/VL5) IgG4 S228P/Kappa | n.d. | n.d. | 0.60 | 4.8 | 98.22 | 7.21 |
| 31 | Humanized anti-ILT3 mAb (52B8 VH1 M64V/VL6) IgG4 S228P/Kappa | n.d. | n.d. | 0.88 | 10 | 91.74 | 7.45 |
| 32 | Humanized anti-ILT3 mAb (52B8 VH1 M64V/ | n.d. | n.d. | 0.53 | 5.6 | 97.79 | 7.45 |

TABLE 7-continued

| mAb No. | Description | cELISA (human ILT3-CHO) EC50 (µg/mL) | cELISA (rhesus ILT3-CHO) EC50 (µg/mL) | Biacore KD (human ILT3-His) (nM) | Biacore KD (rhesus ILT3-His) (nM) | Purity by SEC (% main peak) | pI |
|---|---|---|---|---|---|---|---|
| | VL7) IgG4 S228P/Kappa | | | | | | |
| 33 | Humanized anti-ILT3 mAb (52B8 VH1 M64V/VL8) IgG4 S228P/Kappa | n.d. | n.d. | 0.54 | 5.6 | 97.29 | 7.45 |
| 34 | Humanized anti-ILT3 mAb (52B8 VH1 M64V W101F/VL2) IgG4 S228P/Kappa | n.d. | n.d. | n.d. | n.d. | n.d. | n.d. |
| 35 | Humanized anti-ILT3 mAb (52B8 VH1 M64V W101Y/VL2) IgG4 S228P/Kappa | n.d. | n.d. | n.d. | n.d. | n.d. | n.d. |
| 36 | Humanized anti-ILT3 mAb (52B8 VH1 M64V W101Q/VL2) IgG4 S228P/Kappa | n.d. | n.d. | n.d. | n.d. | n.d. | n.d. |
| 37 | Humanized anti-ILT3 mAb ((52B8 VH1 M64V W101F/VL2) L234A L235A D265S) IgG1/Kappa | n.d. | n.d. | n.d. | n.d. | n.d. | n.d. |
| 38 | Humanized anti-ILT3 mAb ((52B8 VH1 M64V W101Y/VL2) L234A L235A D265S) IgG1/Kappa | n.d. | n.d. | n.d. | n.d. | n.d. | n.d. |
| 39 | Humanized anti-ILT3 mAb ((52B8 VH1 M64V W101Q/VL2) L234A L235A D265S) IgG1/Kappa | n.d. | n.d. | n.d. | n.d. | n.d. | n.d. |
| 40 | Humanized anti-ILT3 mAb (52B8 VH1 M64V/VL2 S35A) IgG4 S228P/Kappa | n.d. | n.d. | n.d. | n.d. | n.d. | n.d. |
| 41 | Humanized anti-ILT3 mAb (52B8 VH1 M64V/VL2 S35N) IgG4 S228P/Kappa | n.d. | n.d. | n.d. | n.d. | n.d. | n.d. |
| 42 | Humanized anti-ILT3 mAb (52B8 VH1 M64V/VL2 N34Q) IgG4 S228P/Kappa | n.d. | n.d. | n.d. | n.d. | n.d. | n.d. |
| 43 | Humanized anti-ILT3 mAb (52B8 VH1 M64V/VL2 N34D) IgG4 S228P/Kappa | n.d. | n.d. | n.d. | n.d. | n.d. | n.d. |
| 44 | Humanized anti-ILT3 mAb (52B8 VH1 M64V/VL5 S35A) IgG4 S228P/Kappa | n.d. | n.d. | 2.6 | 34 | n.d. | n.d. |

TABLE 7-continued

| mAb No. | Description | cELISA (human ILT3-CHO) EC50 (μg/mL) | cELISA (rhesus ILT3-CHO) EC50 (μg/mL) | Biacore KD (human ILT3-His) (nM) | Biacore KD (rhesus ILT3-His) (nM) | Purity by SEC (% main peak) | pI |
|---|---|---|---|---|---|---|---|
| 45 | Humanized anti-ILT3 mAb (52B8 VH1 M64V/ VL5 S35N) IgG4 S228P/Kappa | n.d. | n.d. | 4.7 | NB (No Binding) | n.d. | n.d. |
| 46 | Humanized anti-ILT3 mAb (52B8 VH1 M64V/ VL5 N34Q) IgG4 S228P/ Kappa | 0.088 | 0.12 | 0.77 | 15 | 97.9 | 7.1 |
| 47 | Humanized anti-ILT3 mAb (52B8 VH1 M64V/ VL5 N34D) IgG4 S228P/ Kappa | n.d. | n.d. | 3.8 | 115 | n.d. | n.d. |
| 48 | Humanized anti-ILT3 mAb (52B8 VH1 M64V W101F/VL5) IgG4 S228P/ Kappa | n.d. | n.d. | n.d. | n.d. | n.d. | n.d. |
| 49 | Humanized anti-ILT3 mAb (52B8 VH1 M64V W101Y/VL5) IgG4 S228P/ Kappa | n.d. | n.d. | n.d. | n.d. | n.d. | n.d. |
| 50 | Humanized anti-ILT3 mAb (52B8 VH1 M64V W101Q/VL5) IgG4 S228P/ Kappa | n.d. | n.d. | n.d. | n.d. | n.d. | n.d. |
| 51 | Humanized anti-ILT3 mAb (52B8 VH1 M64V W101F/VL5 S35A) IgG4 S228P/Kappa | n.d. | n.d. | NB (No Binding) | NB (No Binding) | n.d. | n.d. |
| 52 | Humanized anti-ILT3 mAb (52B8 VH1 M64V W101F/VL5 S35N) IgG4 S228P/Kappa | n.d. | n.d. | NB (No Binding) | NB (No Binding) | n.d. | n.d. |
| 53 | Humanized anti-ILT3 mAb (52B8 VH1 M64V W101F/VL5 N34Q) IgG4 S228P/Kappa | n.d. | n.d. | 35 | NB (No Binding) | n.d. | n.d. |
| 54 | Humanized anti-ILT3 mAb (52B8 VH1 M64V W101F/VL5 N34D) IgG4 S228P/Kappa | n.d. | n.d. | NB (No Binding) | NB (No Binding) | n.d. | n.d. |
| 55 | Humanized anti-ILT3 mAb (52B8 VH1 M64V W101Y/VL5 S35A) IgG4 S228P/Kappa | n.d. | n.d. | NB (No Binding) | NB (No Binding) | n.d. | n.d. |
| 56 | Humanized anti-ILT3 mAb (52B8 VH1 M64V W101Y/VL5 S35N) IgG4 S228P/Kappa | n.d. | n.d. | NB (No Binding) | NB (No Binding) | n.d. | n.d. |
| 57 | Humanized anti-ILT3 mAb (52B8 | n.d. | n.d. | NB (No | NB (No | | |

TABLE 7-continued

| mAb No. | Description | cELISA (human ILT3-CHO) EC50 (μg/mL) | cELISA (rhesus ILT3-CHO) EC50 (μg/mL) | Biacore KD (human ILT3-His) (nM) | Biacore KD (rhesus ILT3-His) (nM) | Purity by SEC (% main peak) | pI |
|---|---|---|---|---|---|---|---|
| | VH1 M64V W101Y/VL5 N34Q) IgG4 S228P/Kappa | | | Binding) | Binding) | | |
| 58 | Humanized anti-ILT3 mAb (52B8 VH1 M64V W101Y/VL5 N34D) IgG4 S228P/Kappa | n.d. | n.d. | NB (No Binding) | NB (No Binding) | n.d. | n.d. |
| 59 | Humanized anti-ILT3 mAb (52B8 VH1 M64V W101Q/VL5 S35A) IgG4 S228P/Kappa | n.d. | n.d. | NB (No Binding) | NB (No Binding) | n.d. | n.d. |
| 60 | Humanized anti-ILT3 mAb (52B8 VH1 M64V W101Q/VL5 S35N) IgG4 S228P/Kappa | n.d. | n.d. | NB (No Binding) | NB (No Binding) | n.d. | n.d. |
| 61 | Humanized anti-ILT3 mAb (52B8 VH1 M64V W101Q/VL5 N34Q) IgG4 S228P/Kappa | n.d. | n.d. | NB (No Binding) | NB (No Binding) | n.d. | n.d. |
| 62 | Humanized anti-ILT3 mAb (52B8 VH1 M64V W101Q/VL5 N34D) IgG4 S228P/Kappa | n.d. | n.d. | NB (No Binding) | NB (No Binding) | n.d. | n.d. |
| p52B8 | Clone 52B8 Hybridoma extract | 15.5 | 23.2 | 0.658 | 24.4 | 98 | n.d. |
| p40A6 | Clone 40A6 Hybridoma extract | 17.9 | 25.9 | 0.713 | 0.995 | n.d. | n.d. |
| p16B1 | Clone 16B1 Hybridoma extract | n.d. | n.d. | 0.096 | 0.259 | 98.1 | n.d. |
| p49C6 | Clone 49C6 Hybridoma extract (not sequenced) | 13.8 | 19.8 | n.d. | n.d. | n.d. | n.d. |
| p11D1 | Clone 11D1 Hybridoma extract | 50.46 | 2028 | n.d. | n.d. | n.d. | n.d. |
| p17H12 | Clone 17H12 Hybridoma extract | 139.2 | NB | n.d. | n.d. | 95.7 | n.d. |
| p37C8 | Clone 37C8 Hybridoma extract | 7.719 | 9.478 | 0.012 | 0.145 | 98.4 | n.d. |
| p1G12 | Clone 1G12 Hybridoma extract | 39.2 | NB | n.d. | n.d. | n.d. | n.d. |
| p20E4 | Clone 20E4 Hybridoma extract | 1.992 | 18.04 | 6.99 | 18.2 | 98.5 | n.d. |
| p24A4 | Clone 24A4 Hybridoma extract | 21.4 | 21.3 | 0.021 | 0.126 | n.d. | n.d. |

Example 5

Epitope Mapping of a Chimeric Anti-ILT3 52B8 Mouse VH/Human IgG4 (S228P):Mouse VL/Human Kappa ("c58B8"; mAb 73) Binding to Human ILT3 by Hydrogen Deuterium Exchange (HDX) Mass Spectrometry Contact areas of the antibody to human ILT3 extracellular domain were determined by use of hydrogen deuterium exchange mass spectrometry (HDX-MS) analysis. HDX-MS measures the incorporation of deuterium into the amide backbone of the protein and changes in this incorporation are influenced by the hydrogen's solvent exposure. A comparison of the deuterium exchange levels in antigen-alone samples and antibody-bound samples was done to identify regions on the ILT3 extracellular domain that may be in contact with the antibody. Human ILT3 extracellular domain with a C-terminal His tag (human ILT3-His) has the amino acid sequence shown in SEQ ID NO: 1.

His-tagged human ILT3-His extracellular domain was pre-incubated with antibody c58B8 (mAb 73), a chimeric anti-ILT3 52B8 mouse VH M64V/human IgG4 (S228P):mouse VL/human Kappa comprising a HC having the amino acid sequence of SEQ ID NO: 113 and a LC having the amino acid sequence shown in SEQ ID NO: 116, before incubation in a deuterium buffer. Human ILT3-His and the antibody were buffer exchanged to PBS pH 7.4 using 3 k MWCO spin columns. Human ILT3-His (80 pmol/µL) was mixed with an equal volume of the antibody (40 pmol/µL) or, as the unbound control, PBS pH 7.4. The antibody bound samples and the unbound control were incubated at room temperature for one hour before beginning the labeling experiment.

To deuterium label the samples, 2 µL of sample was mixed with 25 µL of PBS in deuterium oxide pH 7.6. Labeling time points were 30, 300, 3000, 6000 or 12000 seconds. After the set time, 25 µL of the labeling mixture was added to 30 µL of cold quench buffer (8M Urea, 150 mM TCEP). The quenched sample was incubated at 1.5° C. for 2 minutes. 53 µL, was then injected into the column cooling chamber where the sample was passed over the pepsin/protease XIII column and the resulting peptides loaded onto the trapping column. After three minutes, the analytical gradient and the mass spectrometer were started. A fully deuterated sample was generated by incubating 2 µL of human ILT3-His with 108 µL of deuterated denaturing buffer (4M Urea, 150 mM TCEP in 99.5% deuterium oxide). The sample was incubated at 37° C. overnight. Then 55 µL was directly injected into the column chamber and the data acquired.

LC-MS/MS data was acquired of an unlabeled sample and searched before deuterium labeling to verify successful digestion of the proteins and to generate a list of peptides. Data was database searched using Proteome Discoverer 1.4 and the SEQUEST HT search algorithm (ThermoFisher Scientific). The protein database used was the human ILT3-His sequence concatenated to the yeast *Saccharomycese cerevisiae* database.

Following labeling, 55 µL sample aliquotes were applied to a NovaBioAssays Pepsin/Protease XIII column followed by chromatography on Waters CSH C18 Guard column and Waters CSH C18 1×50 mm Analytical column in a loading buffer containing 2% Acetonitrile, 0.1% TFA. Deuterium incorporation into the human ILT3-His extracellular domain was measured by mass spectrometry. Quench: 8M Urea, 150 mM TCEP; Labeling buffer: PBS, pH 7.6; Blank buffer: PBS, pH 7.4. The mass spectrometer was a Thermo Scientific ORBITRAP-ELITE™. For the measurement of deuterium labeled samples, the mass spectrometer was set to acquire one full scan MS data in the orbitrap at 120,000 resolving power, a target ion count of 1E6 and a maximum ion injection time of 500 millisecond. For the acquisition of MS/MS data for peptide identifications, the mass spectrometer was set to acquire one full scan spectrum at 120,000 resolving power followed by ten data-dependent MS/MS spectra in the ion trap.

The liquid chromatography system used was a Waters NANOACQUITY® for the analytical column gradient and a Waters 515 isocratic pump for the sample digestion and loading. For sample digestion and loading, the buffer used was 2% acetonitrile and 0.1% trifluoroacetic acid at a flow rate of 100 µL/min For the analytical gradient, the buffers were Buffer A) 0.1% formic acid in water and Buffer B) 0.1% formic acid in acetonitrile. The gradient was at 40 µL/min from 2% B to 36% B in 10 minutes, followed by a wash of 80% B for 1.5 minute and a re-equilibration at 2% B for 3 minutes. The column was then washed by cycling the gradient between 2% and 80% B, three times with 1 minute at each step, followed by a final equilibration at 2% B for 5 minutes. The trapping column was a Waters VANGUARD™ C18 BEH 1.7 µm Guard Column and the analytical column was a Waters C18 BEH300, 1.7 µm 1×50 mm column.

Sample handling for the deuterium labeling was done by a Leaptec H/D-X PAL™ system. The labeling sample tray was set to a temperature of 25° C., the quenching tray was set to 1.5 C and the trap and analytical column chamber was set to 1.5° C. The immobilized pepsin column (Pepsin/Protease XIII column NBA2014002, 2.1×30 mm, NovaBioAssay) was kept outside the column chamber at room temperature.

Figure 3A:
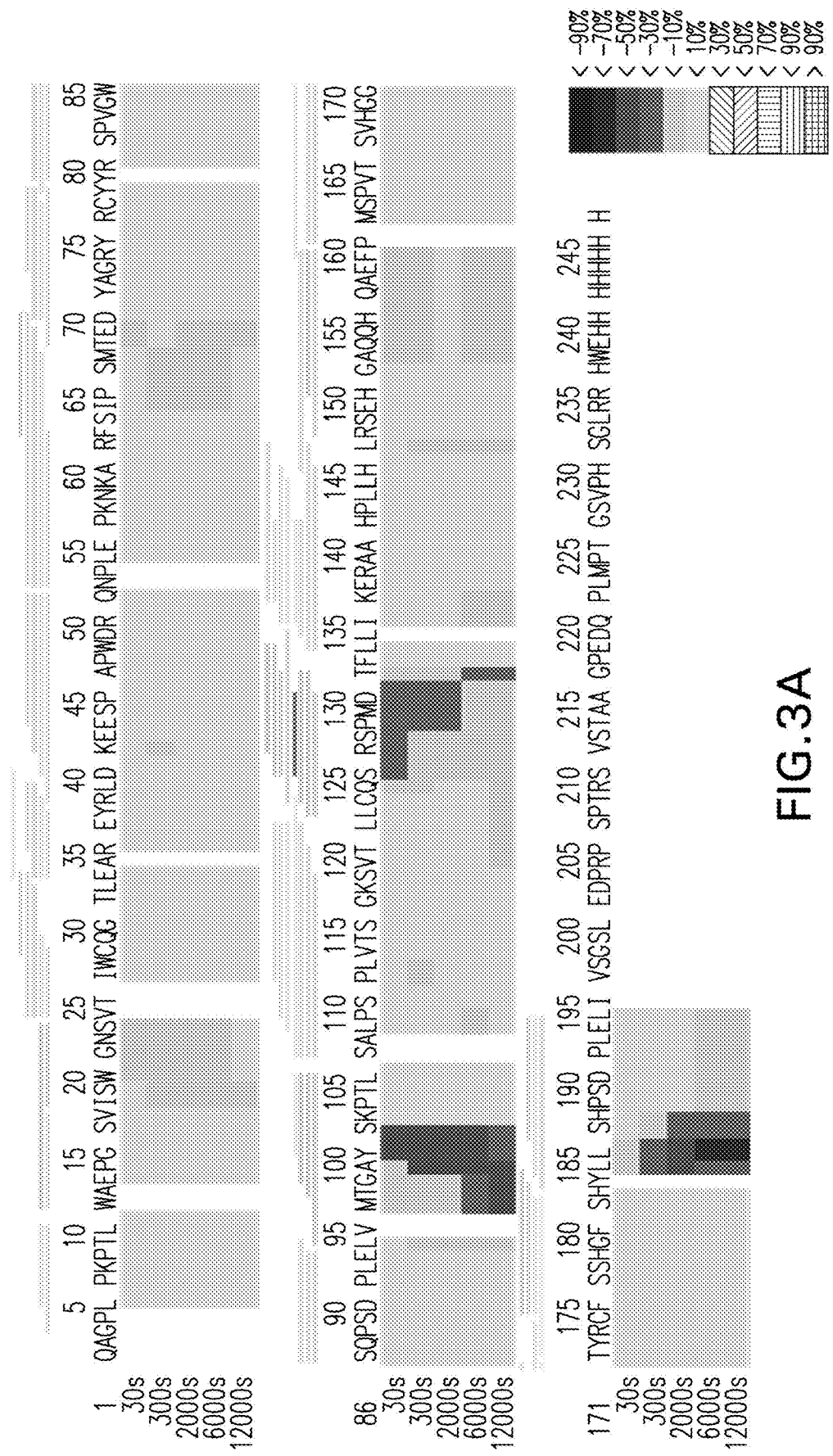
FIG. 3A shows a deuterium labeling difference heatmap of the human ILT3 extracellular domain amino acid residues that are bound by Chimeric Anti-ILT3 52B8 mouse 52B8 VH parental/human IgG4 (S228P): mouse 52B8 parental VL/human Kappa antibody ("c58B2"; mAb 73). These six peptide domains, which comprise the epitope bound by the antibody(residues 18-23 (ISWGNS; SEQ ID NO: 3), residues 64-69 (IPSMTE; SEQ ID NO: 4), residues 96-101 (MTGAYS; SEQ ID NO: 5), residues 124-131 (QSRSPMDT; SEQ ID NO: 6), residues 152-159 (AQQHQAEF; SEQ ID NO: 7) and residues 184-187 (LLSH; SEQ ID NO: 8)), are located near the border of the D1 and D2 domains of the ILT3 extracellular domain. The amino acid sequence of human extracellular domain with C-terminal His Tag is set forth in SEQ ID NO: 1.
Figure 3B:
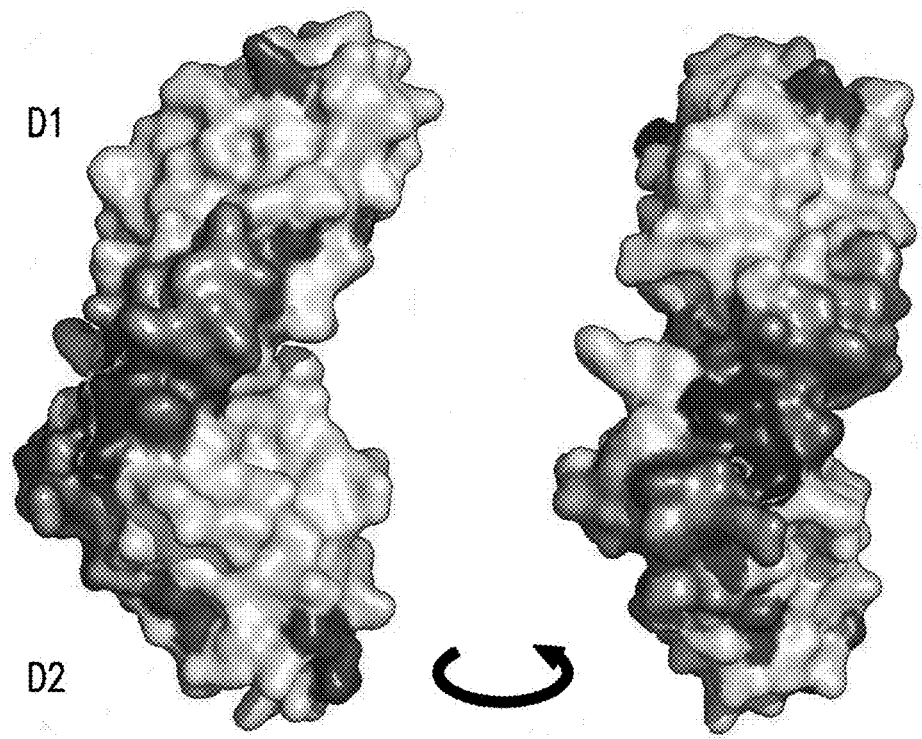
FIG. 3B shows a first view and a second view of a surface structure model of the extracellular domain of human ILT3. The dark region of the model shows the location of the six peptide domains comprising the human ILT3-His epitope bound by c58B8 (mAb 73).
Figure 3C:
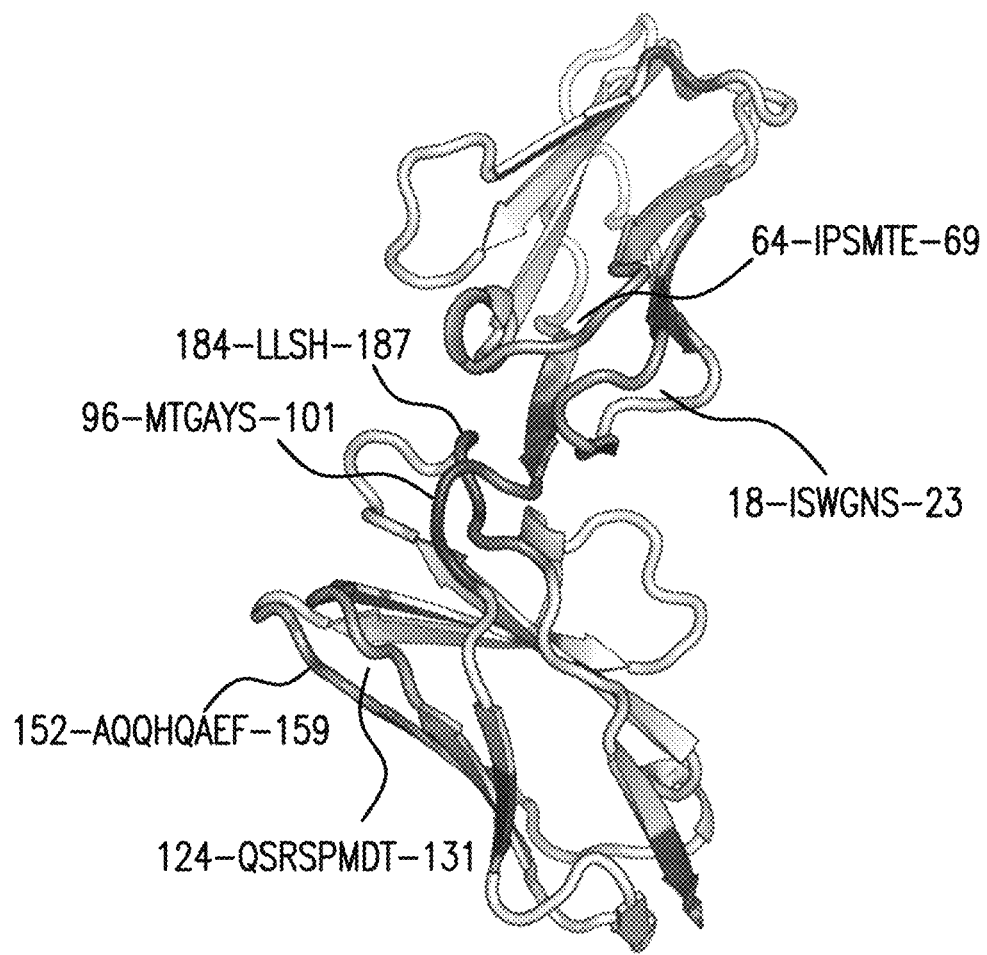
FIG. 3C is a ribbon diagram showing the placement of the epitope on the ILT3 extracellular domain: ISWGNS (SEQ ID NO: 3), IPSMTE (SEQ ID NO: 4), MTGAYS (SEQ ID NO: 5), QSRSPMDT (SEQ ID NO: 6), AQQHQAEF (SEQ ID NO: 7) and LLSH (SEQ ID NO: 8).
Figure 3D:
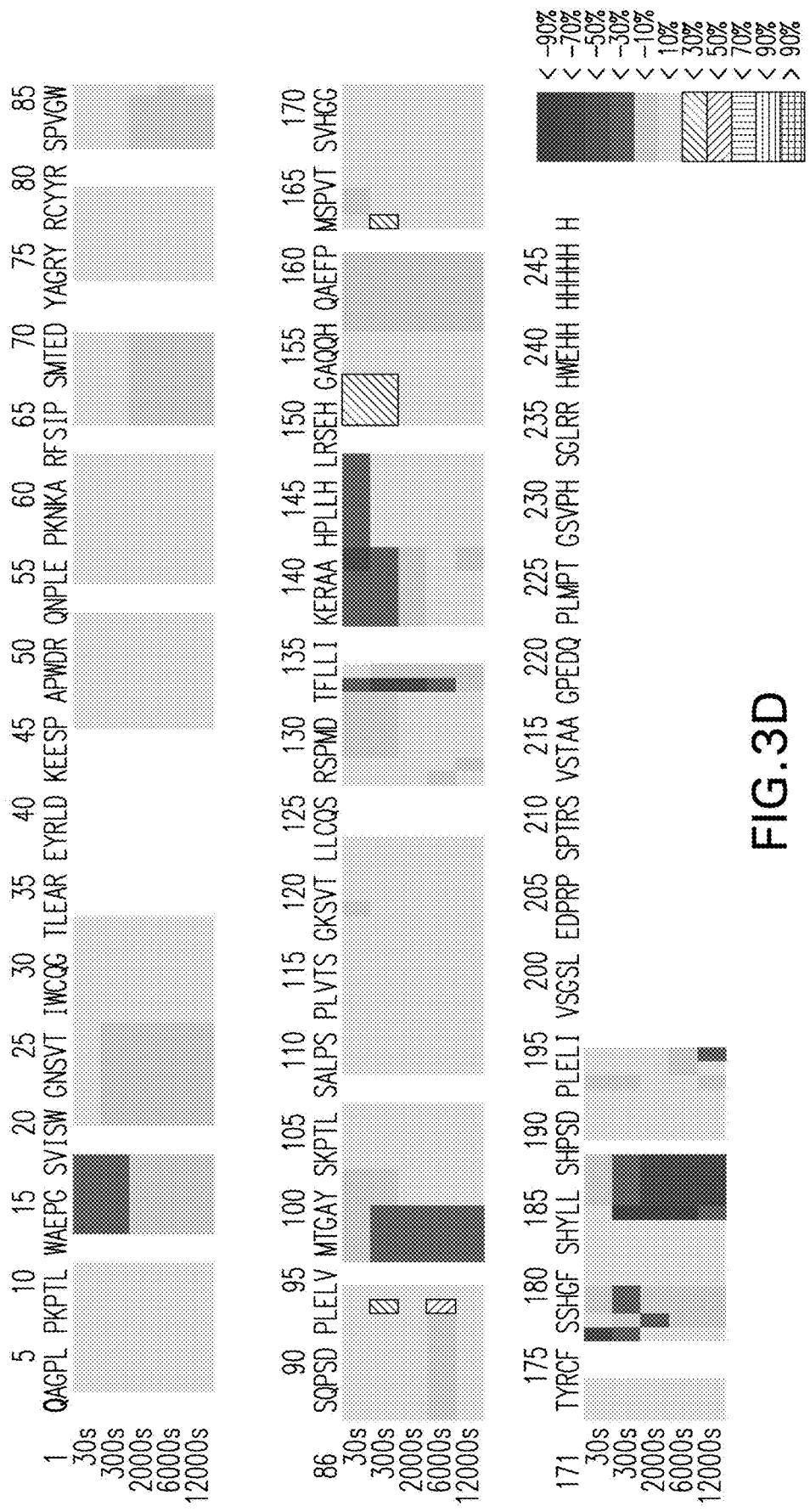
FIG. 3D shows a deuterium labeling difference heatmap of the human ILT3 extracellular domain amino acid residues that are bound by antibody ZM4.1.
Figure 3E:
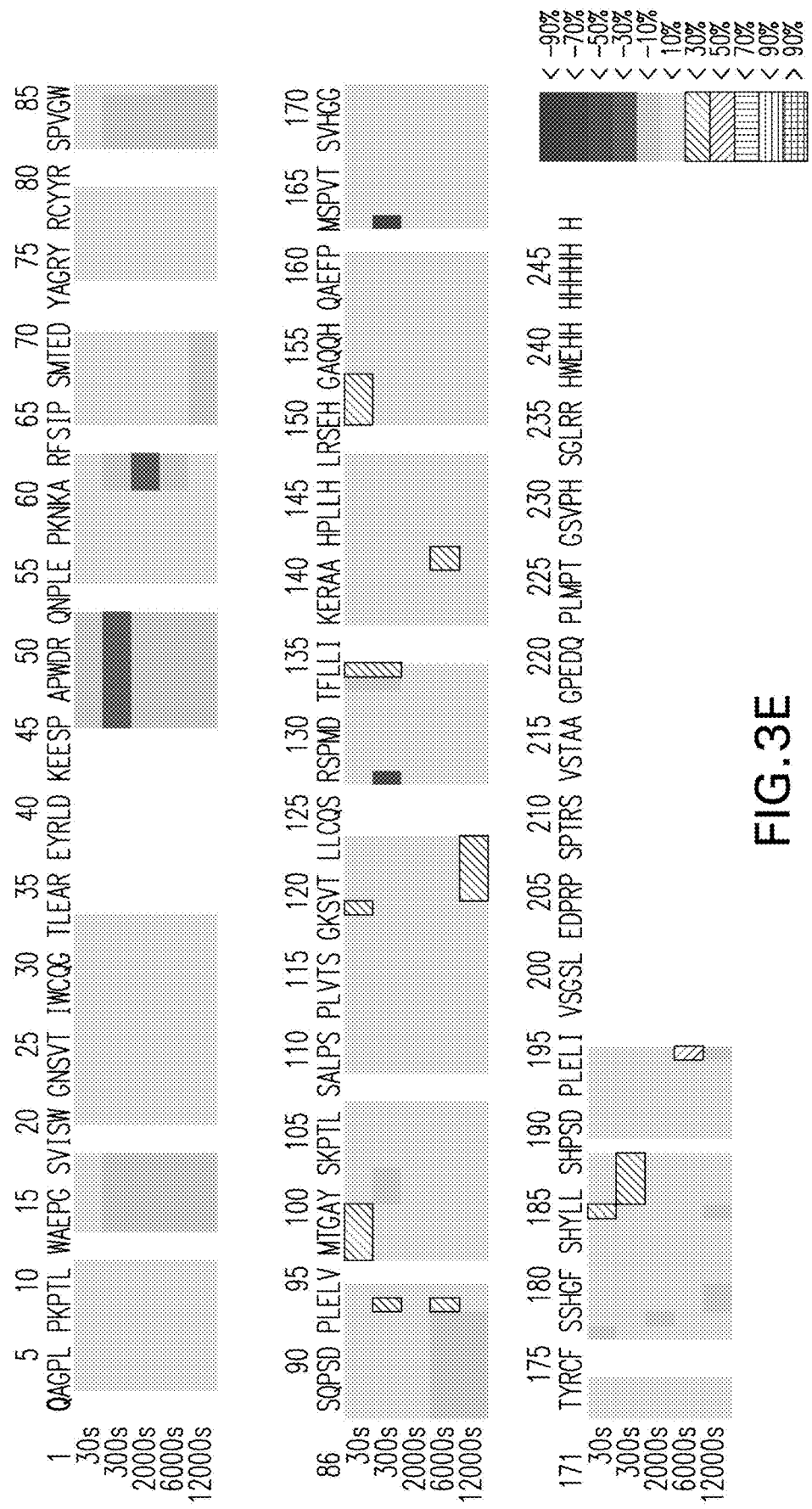
FIG. 3E shows a deuterium labeling difference heatmap of the human ILT3 extracellular domain amino acid residues that are bound by antibody DX446
Figure 3F:
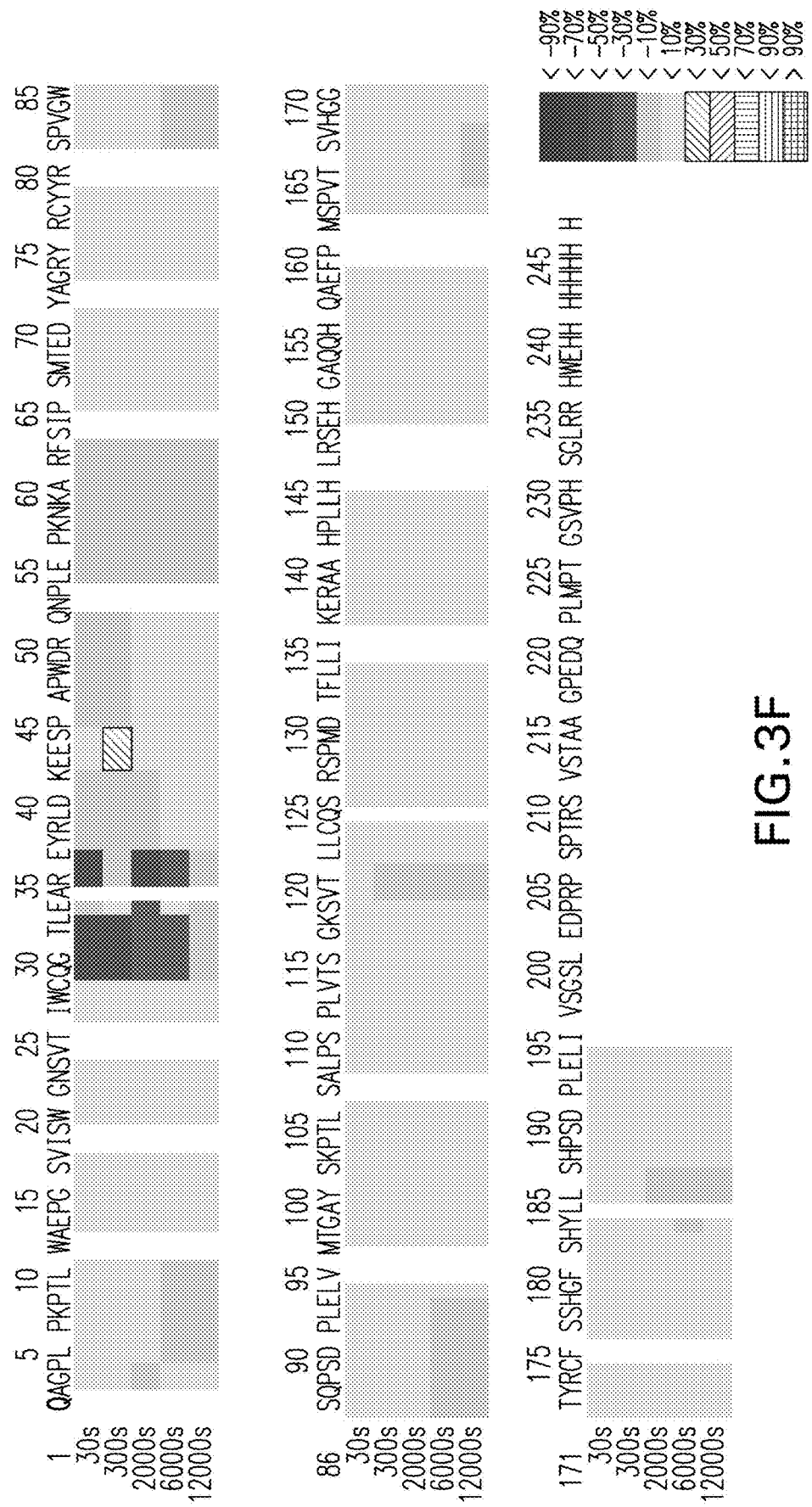
FIG. 3F shows a deuterium labeling difference heatmap of the human ILT3 extracellular domain amino acid residues that are bound by antibody DX439.
Figure 3G:
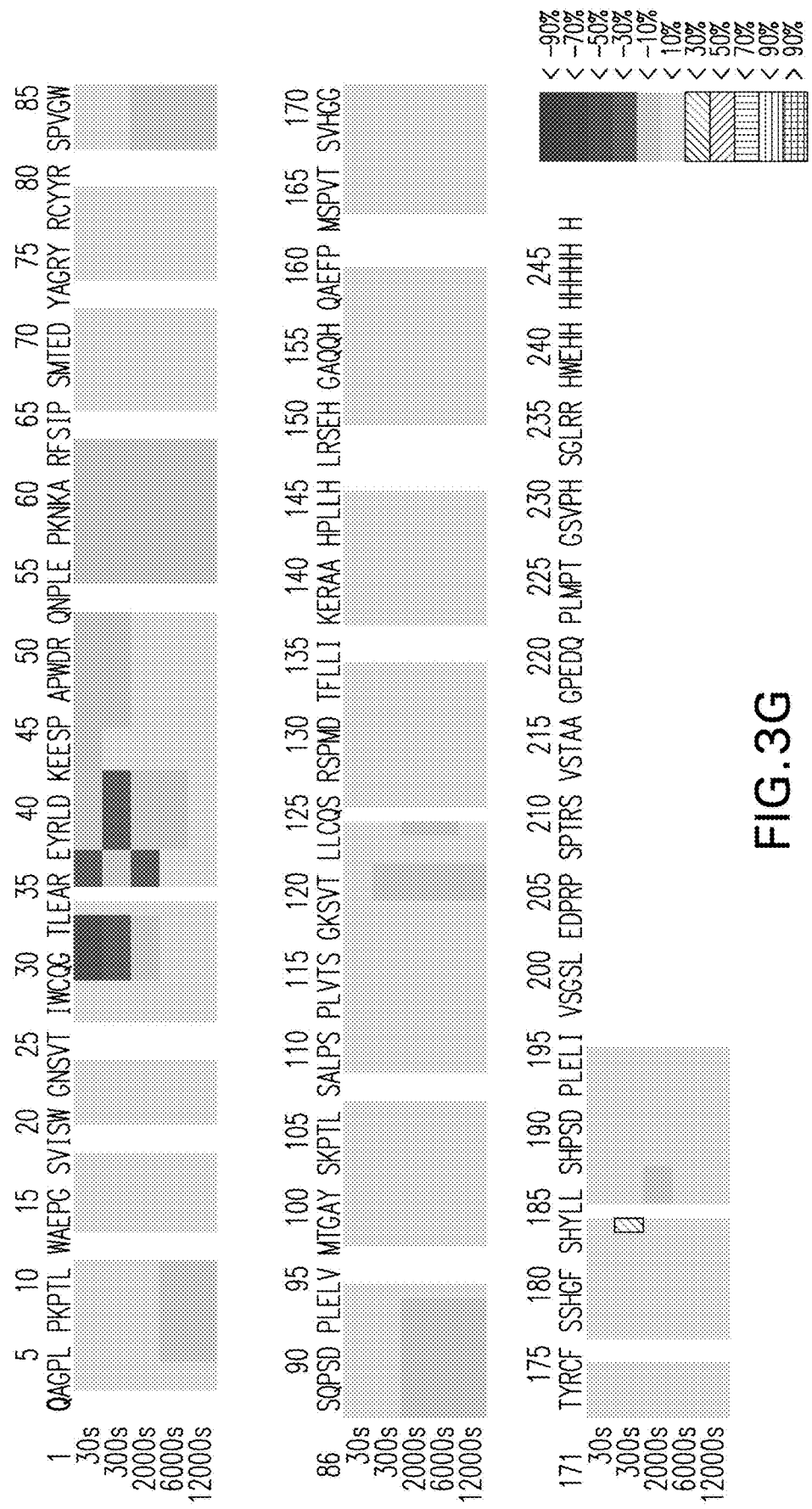
FIG. 3G shows a deuterium labeling difference heatmap of the human ILT3 extracellular domain amino acid residues that are bound by antibody 9B11.

A deuterium labeling difference heatmap of the human ILT3-His amino acid residues bound by the antibody is shown in FIG. 3A. The HDX mass spectrometry shows that the antibody and the other antibody families disclosed herein that cross-compete with the antibody bind an epitope comprising or consisting of at least one amino acid in one or more of amino acid residues 18-23 (ISWGNS; SEQ ID NO: 3), 64-69 (IPSMTE; SEQ ID NO: 4), 96-101 (MTGAYS; SEQ ID NO: 5), 124-131 (QSRSPMDT; SEQ ID NO: 6), 152-159 (AQQHQAEF; SEQ ID NO: 7) and 184-187 (LLSH; SEQ ID NO: 8) of ILT3. FIG. 3B shows a first-view and a second view of a three-dimensional surface structure model of the human ILT3 extracellular domain with the protected amino acid residues shown. These protected amino acid residues comprise a split or non-contiguous epitope that spans the border between the D1 and D2 domains of the extracellular domain. FIG. 3C is a ribbon diagram showing the placement of the epitope on the human ILT3 extracellular domain. Residues in black were protected from labeling by the antibody. Residues in white showed no changes in labeling and residues in dark gray did not have data acquired for them. The deuterium labeling difference for each residue was averaged and mapped onto a crystal structure of ILT3 (Cheng et al., "Crystal structure of leukocyte Ig-like receptor LILRB4 (ILT3/LIR-5/CD85 k): a myeloid inhibitory receptor involved in immune tolerance." J Biol Chem 286:18013-25 (2011)).

Similar HDX mapping experiments were preformed using antibodies ZM4.1, DX439, DX446, and 9B11. Antibody ZM4.1 is commercially available from ThermoFisher Scientific, Carlsbad, Calif. or BioLegend, San Diego, Calif. Antibodies DX439 and DX446 have been disclosed in WO2018089300 and Antibody 9B11 has been disclosed in U.S. Pat. No. 7,777,008. Of these antibodies, only antibody ZM4.1 was observed to bind an epitope that partially overlapped with the epitope bound by the antibodies of the present invention; however, binning studies showed that antibody ZM4.1 did not cross block binding of the antibodies of the present invention. FIGS. 3D, 3E, 3F, and 3G show heatmaps of the binding of antibodies ZM4.1, DX439, DX446, and 9B11 to human ILT3.

Example 6

Pharmacokinetics of Chimeric Anti-ILT3 52B8 Mouse VH/Human IGg4 (S228P):Mouse VL/Human Kappa ("C58B8"; mAb 73) in NSG Mice The pharmacokinetics of chimeric anti-ILT3 52B8 mouse VH/human IgG4 (S228P):mouse VL/human Kappa (c85B8, mAb 73) was evaluated in Panc08.13 human-NSG mice model and SK-MEL-5 human CD34+-NSG mice model.

SK-MEL-5 is a human melanoma-derived line that can grow as a subcutaneous tumor. Panc 08.13 is a human pancreatic carcinoma-derived tumor line. Panc 08.13 human-NSG model has been shown to be sensitive to pembrolizumab and ipilimumab treatment. SK-MEL-5 model has a robust and diverse myeloid infiltrate in the tumor compared to Panc 08.13 model. Both models show increased ILT3 expression on human CD14+ myeloid cells in the tumor and spleen.

An ECL-based target capture immunoassay was used to quantify the antibody in humanized mice plasma. The assay was established with biotinylated recombinant ILT3 as capture reagent, and sulfoTAG labeled mouse anti-huIgG (Fc specific) from Southern Biotech (cat #9190-01) for detection reagent. Both calibrators and QCs were prepared in neat C57BL/6 plasma and diluted 100 times when testing in plate. This assay has been qualified and the LLOQ of the assay was determined to be 40 ng/mL with an MRD of 100.

In Panc08.13 hu-NSG mice model, 20 mg/kg of antibody was administered with and without pembrolizumab (5 mg/kg) via IP weekly for the first three doses and two weeks after the 3rd dose for the 4th dose. Blood samples were collected before the third dose (Ctrough) and 24 hours after the third dose (Cmax). Terminal blood samples on day 5 and 6 after the fourth dose were also collected. In SK-MEL-5 huCD34+NSG mice model, the antibody was administered at 2 and 20 mg/kg via IP weekly. Blood samples were collected before the third dose (Ctrough) and 24 h after the third dose (Cmax). Terminal blood samples on day 3 and 7 after the third dose were also collected. The free (unbound) antibody concentrations were determined by an antigen-capture assay.

Pharmacokinetic parameters are generated from historical IgG4 antibody data (IV bolus administration of 1, 3, 10, 30 mg/kg of humanized IgG4 antibody in C57BL/6J mice) with Phoenix NLME. PK profiles at the studied dose of the antibody were simulated based on the generated pharmacokinetic parameters.

Figure 4:
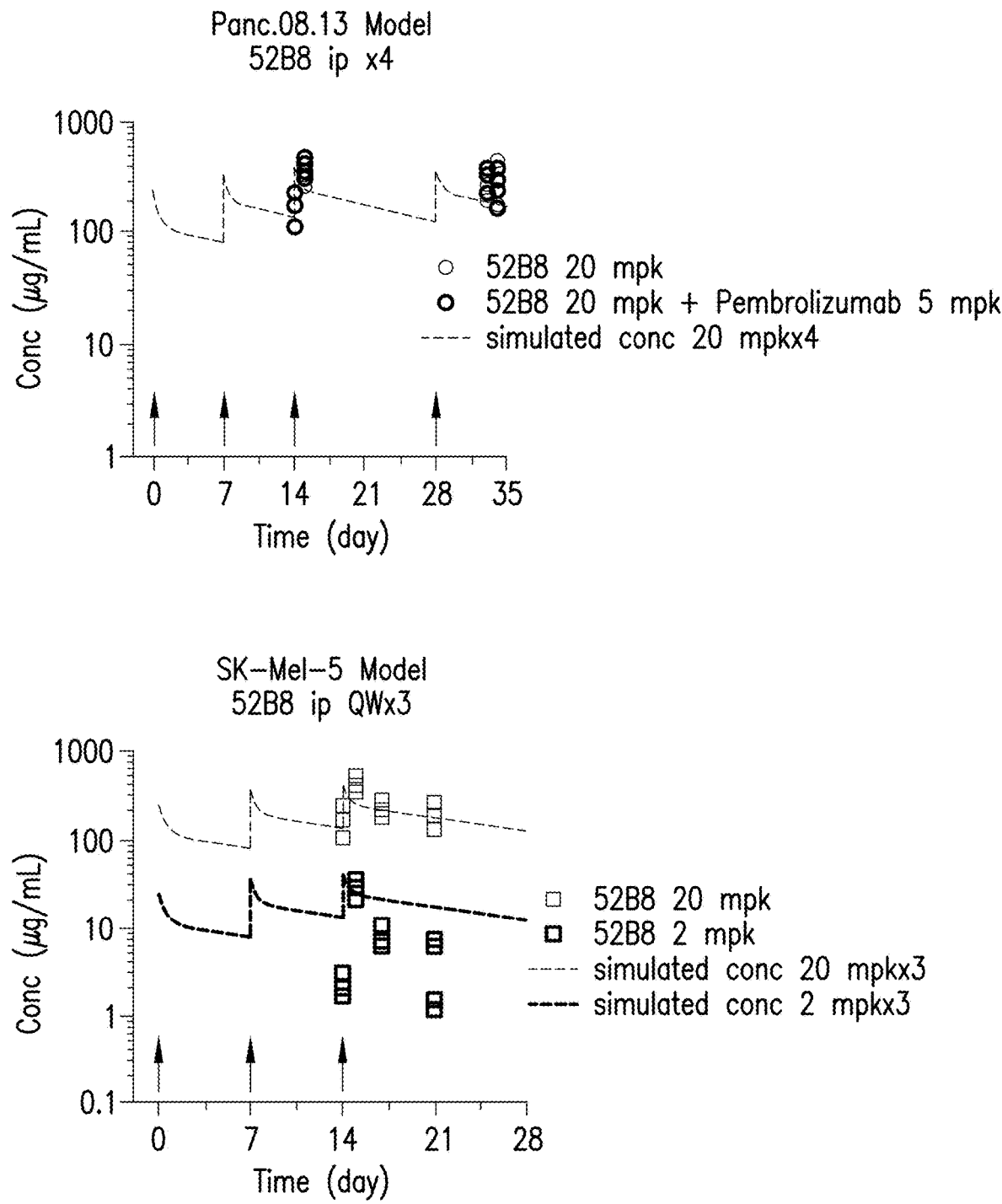
FIG. 4 shows free c52B8 (mAb 73) concentrations in blood after multiple doses in humanized tumor models (Panc08.13 and SK-MEL-5). Free c52B8 concentrations are expressed by circles and squares. Dashed lines indicate simulated historical antibody levels after IV bolus administration of 1, 3, 10, or 30 mg/kg of humanized IgG4 in C57BL/6J mice.

PK analysis of historical IgG4 antibody data showed a linear relationship between AUC and studied dose (See FIG. 4). With the assumptions including linear PK across different tested doses of c52B8, no PK difference among different mouse strains, rapid absorption and 100% bioavailable after IP administration of the antibody, PK profiles at the studied dose of c52B8 were simulated based on historical IgG4 antibody data. The results showed that the simulated profile at 20 mg/kg in both Panc08.13 human-NSG model and SK-MEL-5 huCD34+-NSG model follow the observed c52B8 concentrations.

Example 7

Anti-ILT3 Monoclonal Antibodies Activate Dendritic Cells and Reduces Suppressive Capacity of Myeloid-Derived Suppressor Cells (MDSCs)

Human PBMCs isolated from fresh leukopacs were frozen, thawed and CD14+ monocytes were purified by negative selection. The purified cells were cultured for 5 days with GM-CSF (1000 U/mL) and IL4 (1000 U/mL). These immature DCs were then further cultured for 42 hours with addition of IL-10 (50 ng/mL) and LPS (1 ug/mL) with or without anti-ILT3 antibody. TNFα is measured in the culture supernatant.

Figure 5A:
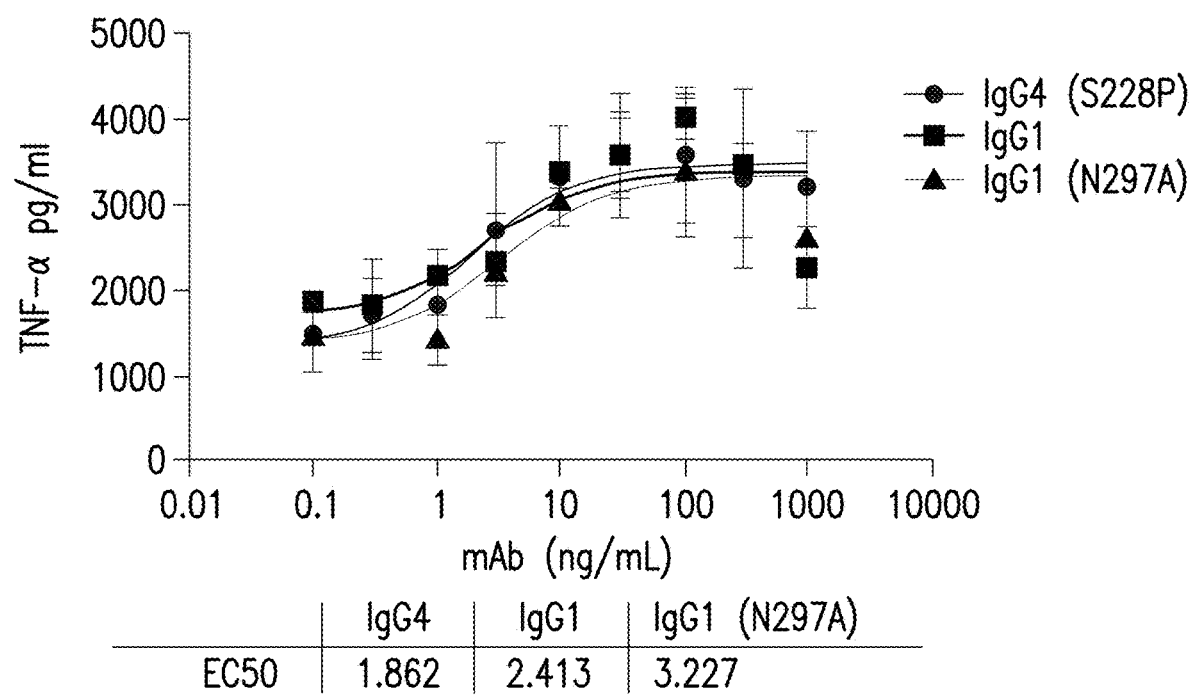
FIG. 5A shows a human dendritic cell (DC) functional assay demonstrating anti-ILT3 antibody chimeric antibodies in which the $V_H$ and $V_L$ from p52B8 fused to IgG4 Fc (c52B8; mAb 73), IgG1 Fc (mAb 78), or IgG1 (N297A) Fc (mAb 76) had comparable ability to activate dendritic cells (DCs). Human immature DCs were prepared and differentiated into CD11c+ dendritic cells with GM-CSF (1000 U/mL) and IL-4 (1000 U/mL) over 5 days. These cells were treated with IL-10, LPS (a grain negative bacterial cell wall component and a TLR4 ligand (Raetz et al. Ann. Rev. Biochem 71: 635-700 (2002)), and varying concentrations of the indicated antibodies for 42 hours. The data shown are mean and s.d of two technical replicates. This experiment is representative of four independent studies. Control IgGs had no effect (not shown).

Titration experiments showed that c52B8 caused a dose-dependent increase in TNFα secretion in the culture medium when added during the polarization step, whereas a control IgG4 did not (the control is an variant of a commercial antibody against RSV, trade name Synagis) (FIG. 5A). The concentration of antibody required to produce half of the maximal increase in TNFα levels (EC50) was approximately 1.9 ng/mL. This was not different for chimeric variants in which $V_H$ and $V_L$ of p58B8 were fused to Fc with a human IgG1 framework (mAb 78) or a N297A mutated human IgG1 framework (mAb 76). These data indicate that in this assay Fc receptor binding does not play any role in the functional activity. The independence from Fc receptor binding controls for the possibility that the mechanism of activation in this assay is DCs becoming activated through recognition of other DCs in the culture being decorated with antibody which would be a mechanism unrelated to ILT3.

Figure 5B:
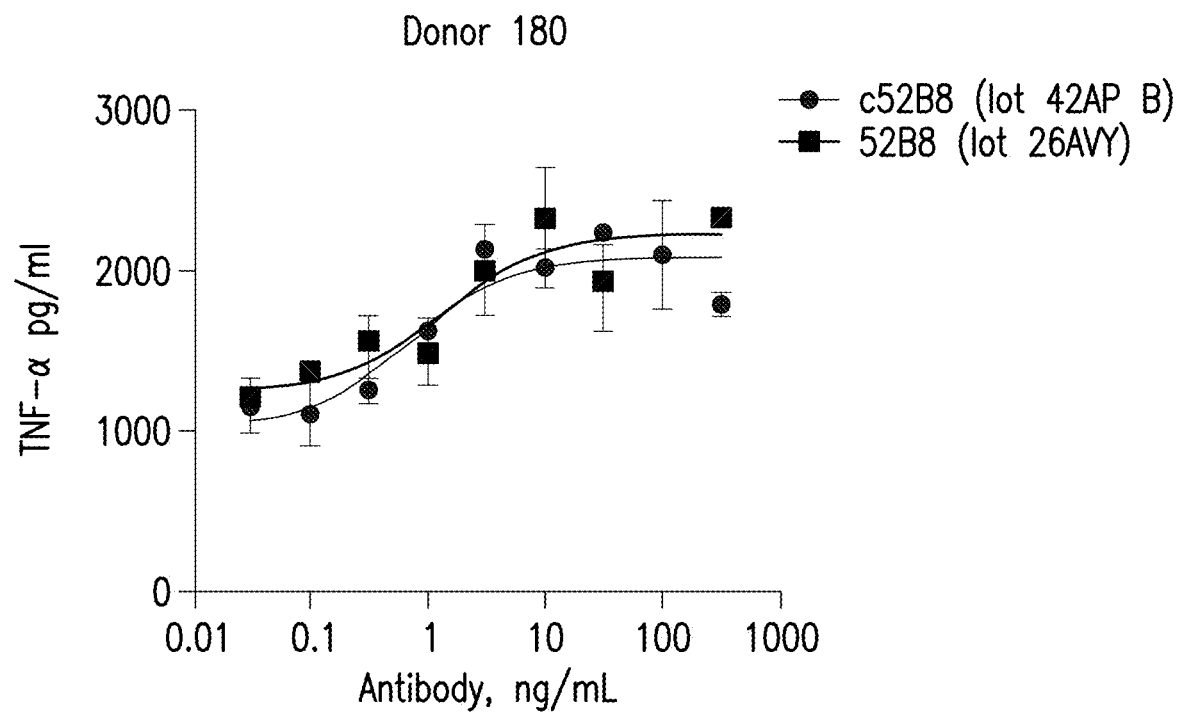
FIG. 5B and FIG. 5C show that humanized 52B8 (lot 26AVY; mAb 46) is indistinguishable from c52B8 (mAb 73) in the human DC functional assay using DCs from two different healthy human donors. The data shown are mean and s.d. of two technical replicates. The data shown are representative of three independent studies using these two donors.
Figure 5C:
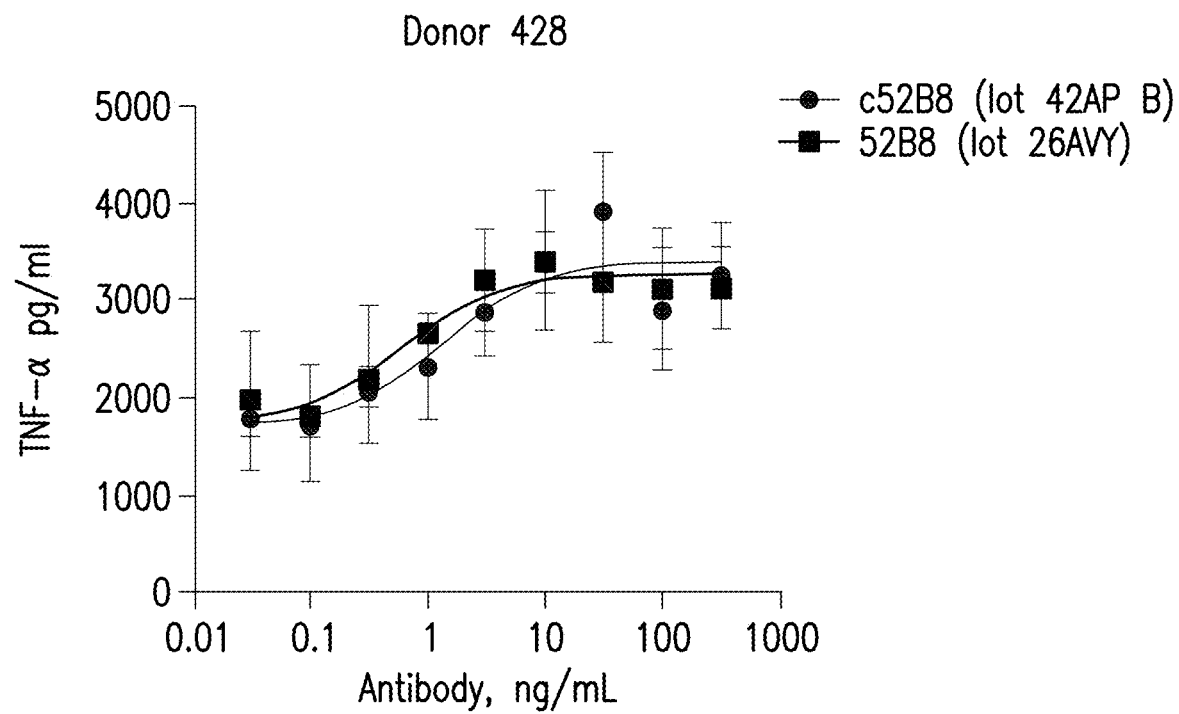

FIGS. 5B and 5C show there was no significant difference in functional activity between c52B8 (mAb 73) and humanized anti-ILT3 mAb 52B8 VH1 M64V/VL5 N34Q) IgG4 S228P/Kappa (mAb 46) in two donors. As shown, with antibody c52B8 added during polarization of the DCs, but not during T cell priming, DCs were better able to activate T cells to proliferate, similar to DCs not tolerized with IL10. When antibody c52B8 was added during T cell priming but not during DC polarization, T cells were better able to respond to subsequent re-stimulation. Following humanization, variants that retained binding comparable to the chimera were tested in this same assay and found to be active, with no meaningful differences in potency among them. These data indicate that data generated with c52B8 is representative of what the data would be if humanized mAb 46 had been used.

Example 8

Anti-ILT3 Antibodies Reduce Suppressive Capacity of Myeloid-Derived Suppressor Cells (MDSCs)

Without ascribing to any particular theory or hypothesis, we hypothesize that a productive T cell response to tumor can be limited in some cases by the presence of immature and suppressive myeloid cells. These cells express ILT3 and we hypothesize that ILT3 functions as an inhibitory manner to maintain an immature state characterized by low HLA-DR expression, IL-10 production, and effective suppression of T cell activation and proliferation. Establishment of a model based on co-culture of human PBMCs with SKMEL5 tumor cells in vitro, followed by purification of MDSCs and testing of their ability to suppress proliferation of autologous CD8+ T cells enabled exploration of this aspect of ILT3 biology. This example shows that c52B8 and humanized 52B8 (mAb 46) are able to impair the acquisition (or maintenance) of a T cell-suppressive phenotype.

To generate MDSCs, healthy human PBMCs were cultured with SKMEL5 cells and 20 ng/mL GM-CSF for 7 days. CD33+ cells were collected by positive antibody-based magnetic bead selection and then co-cultured at the indicated ratios with purified autologous CD8+ T cells for 3 days in the presence of a polyclonal stimulus. Cultures included c52B8 (mAb 73), humanized 52B8 (mAb 46), or isotype control antibody (1 µg/mL) in both the co-culture and T cell suppression steps. The T cell suppression assay was conducted with a T cell to MDSC ratio of 4:1 and measuring the amount of interferon gamma (INFγ) produced.

Figure 6A:
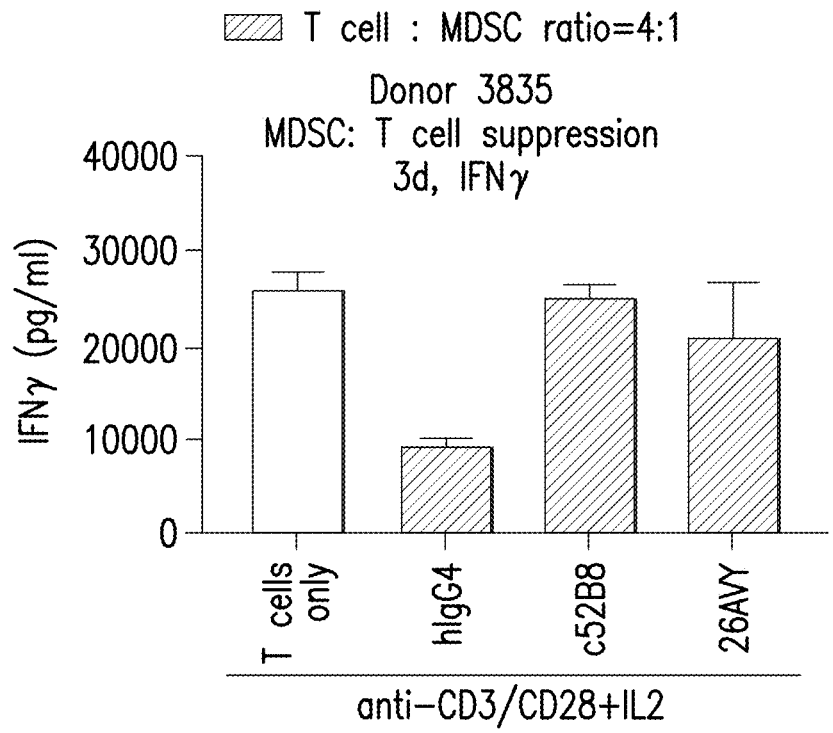
FIG. 6A and FIG. 6B show that anti-ILT3 antibody c52B8 (mAb 73) and humanized anti-ILT3 antibody 52B8 (mAb 46; lot 26AVY) reduce suppressive capacity of myeloid-derived suppressor cells (MDSCs). The T cell suppression assay was conducted with a T cell to MDSC ratio of 4:1. The data shown are means and s.d. of three technical replicates at the level of the T cell assay step. The experiment shown is representative of two independent studies using PBMCs from the same two donors with qualitatively similar results.
Figure 6B:
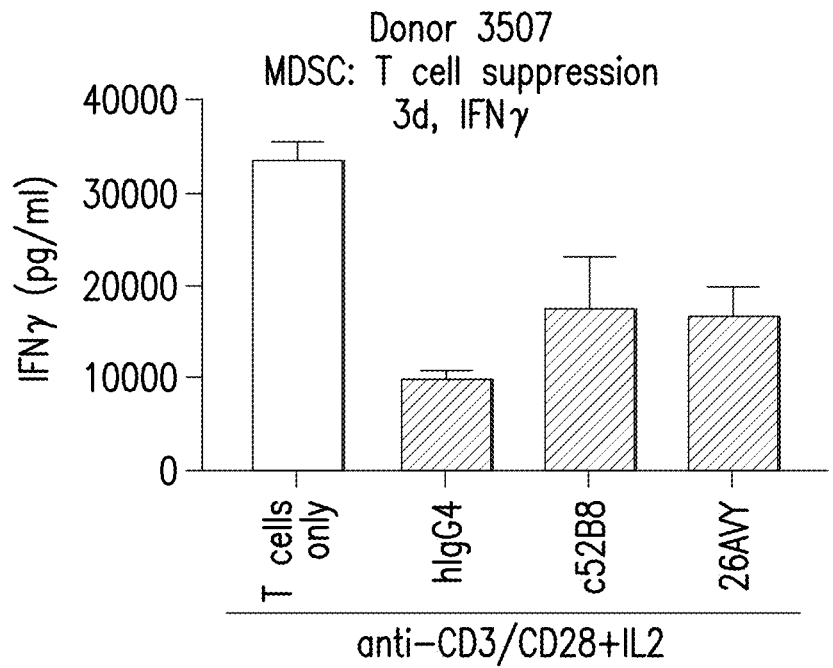

FIG. 6A and FIG. 6B exemplifies the activity of both humanized 52B8 and c52B8 in the MDSC model at a ratio of T cells to MDSCs where the effect of these antibodies was most evident show that the antibodies reduce the suppressive capacity of MDSCs in a comparable manner. These data further indicate that data generated with c52B8 is representative of what would be found with humanized mAb 46.

Example 9

Figure 7:
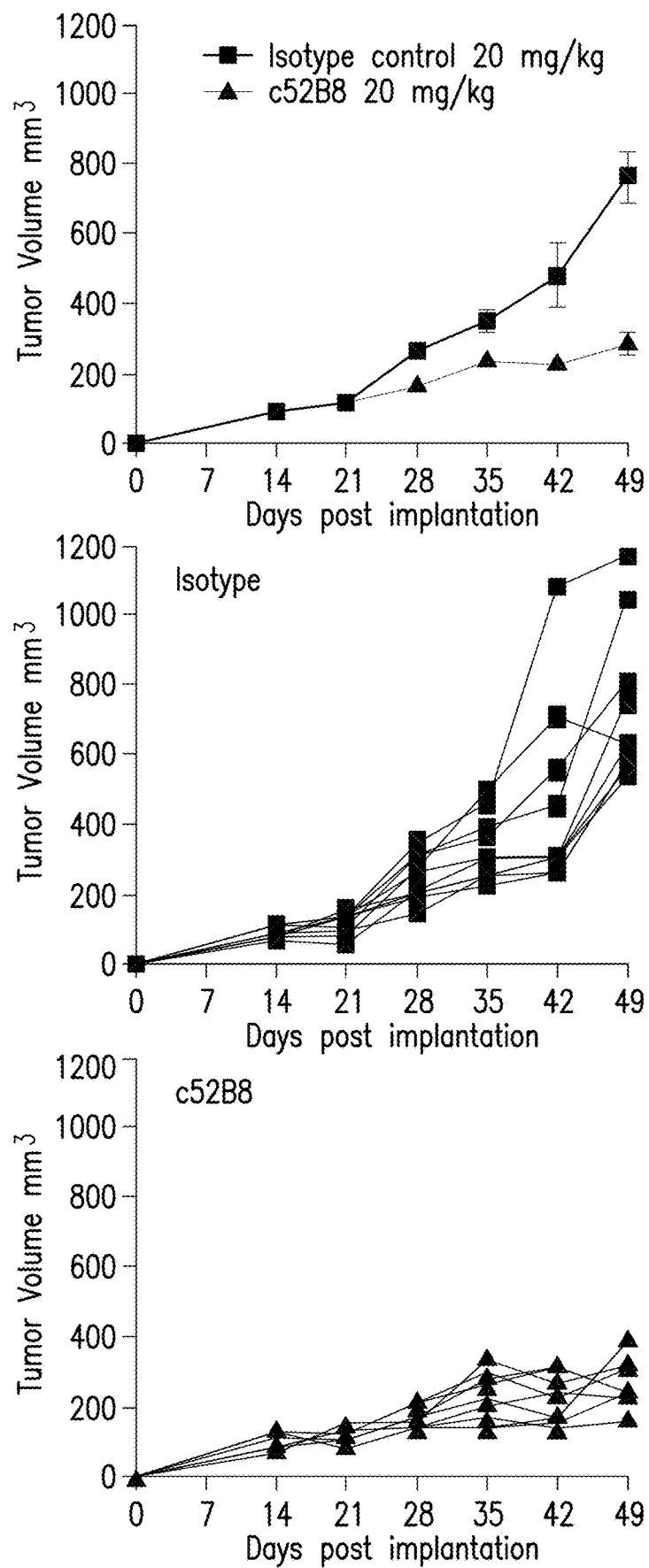
FIG. 7 shows c52B8 inhibits growth of SK-MEL-5 tumors in SK-MEL-5 human-NSG mice bearing SK-MEL-5 subcutaneous tumors. Animals were randomized to treatment on the basis of tumor volume on day 21 post-implantation and dosed s.c. with 20 mg/kg of c52B8 or isotype control once weekly beginning on day 21. Data shown in the top panel are means and std. error (nine per group). Individual animal tumor growth curves are shown in the middle and bottom panels. Body weight decreased to a similar degree in both control and 52B8 groups. This study is representative of three independent studies.

Anti-ILT3 Antibody cC52B8 Inhibits Growth of SK-MEL-5 Tumors in SK-MEL-5 Hu-NSG Mice Bearing SK-MEL-5 Subcutaneous Tumors Systemic administration of c52B8 once weekly to mice bearing established subcutaneous tumors afforded inhibition of tumor growth (FIG. 7). Animals were randomized to treatment on the basis of tumor volume on day 21 post-implantation and dosed s.c. with 20 mg/kg of c52B8 (mAb 73) or isotype control once weekly beginning on day 21. Data shown in the left panel are means and std. error (nine per group). Individual animal tumor growth curves are shown at right. Body weight decreased to a similar degree in both control and 52B8 groups. This study is representative of three independent studies.

The degree of inhibition of tumor growth was consistent and similar in three separate studies and was very similar to the effect of anti-ILT4. None of the other mechanisms tested to date (e.g. anti-PD-1, anti-ILT4, anti-CD27, anti-GITR) have afforded regressions leading us to speculate that tumor stasis may represent a floor for this model. This is clearly different from the mouse syngenic models commonly used for preclinical efficacy assays.

Example 10

Immune Activation in SK-MEL-5 Hu-NSG after c52B8 Treatment

Figure 8A:
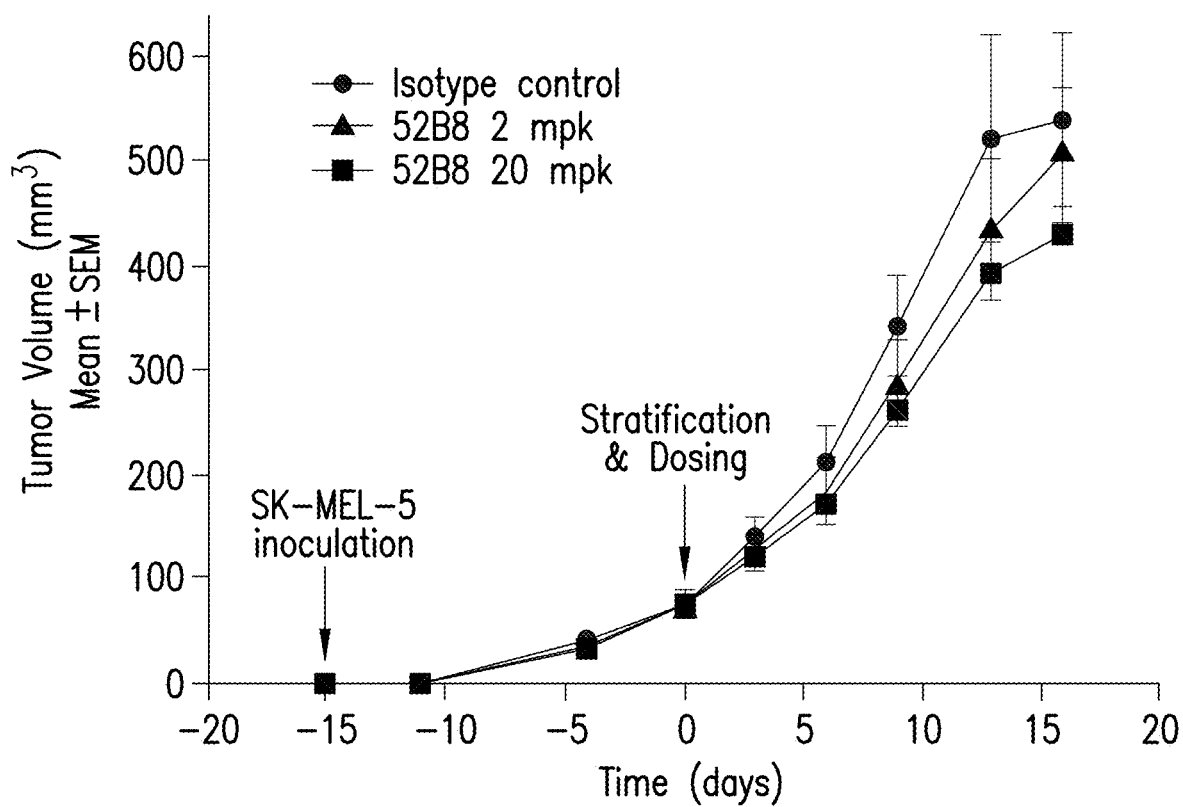
Figure 8B:
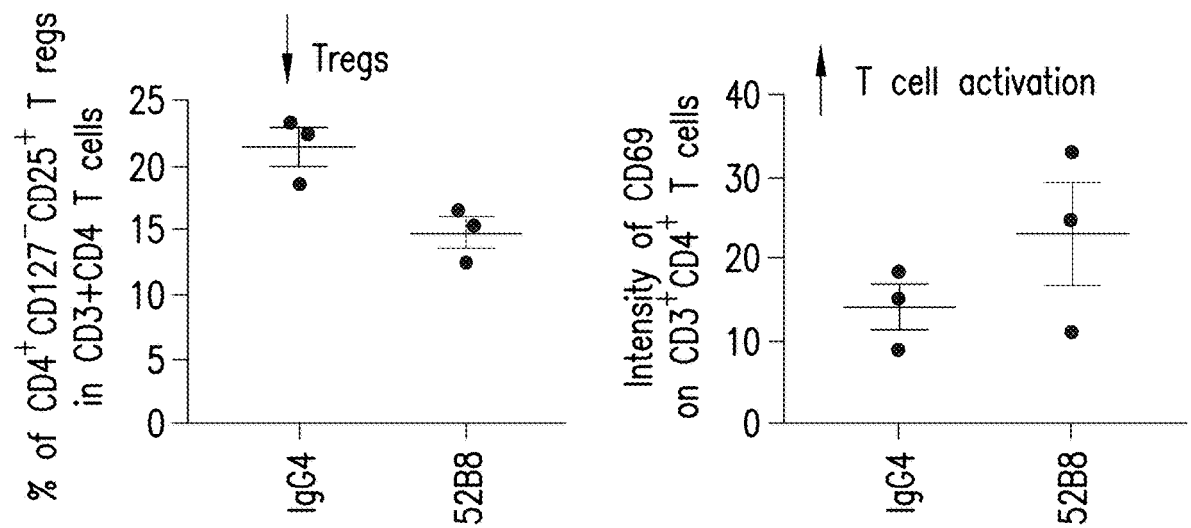
Figure 8C:
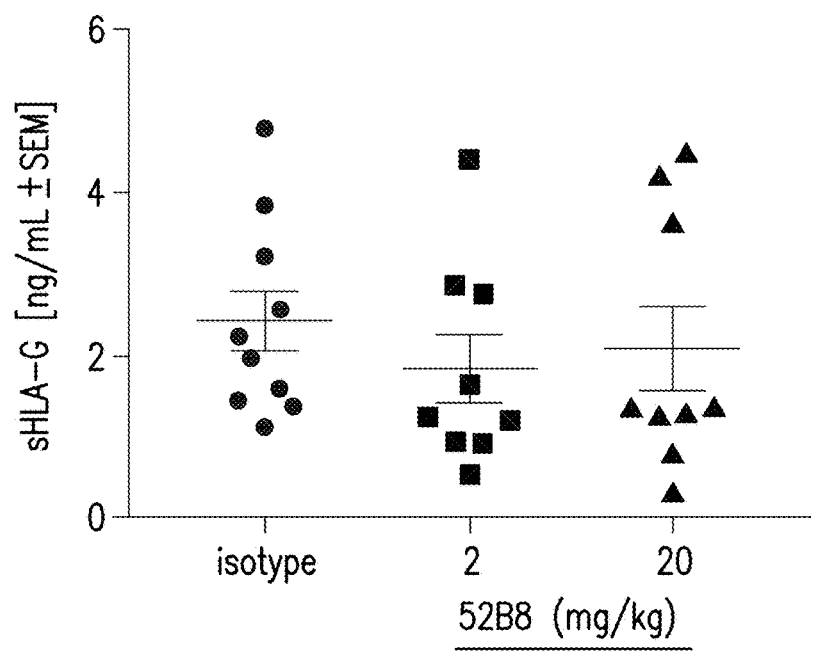
Figure 9A:
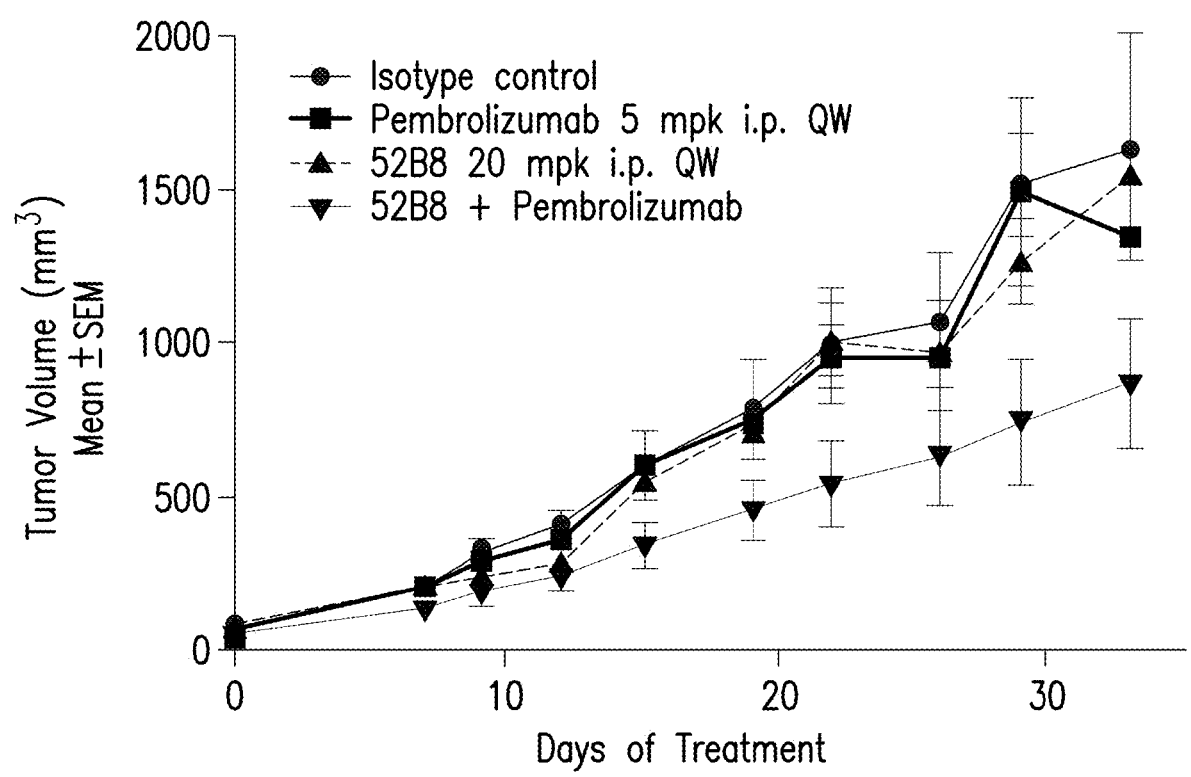
FIG. 9A, FIG. 9B, FIG. 9C, and FIG. 9D show the effect of a c52B8 and pembrolizumab combination in Panc 08.13 human-NSG mice.
Figure 9B:
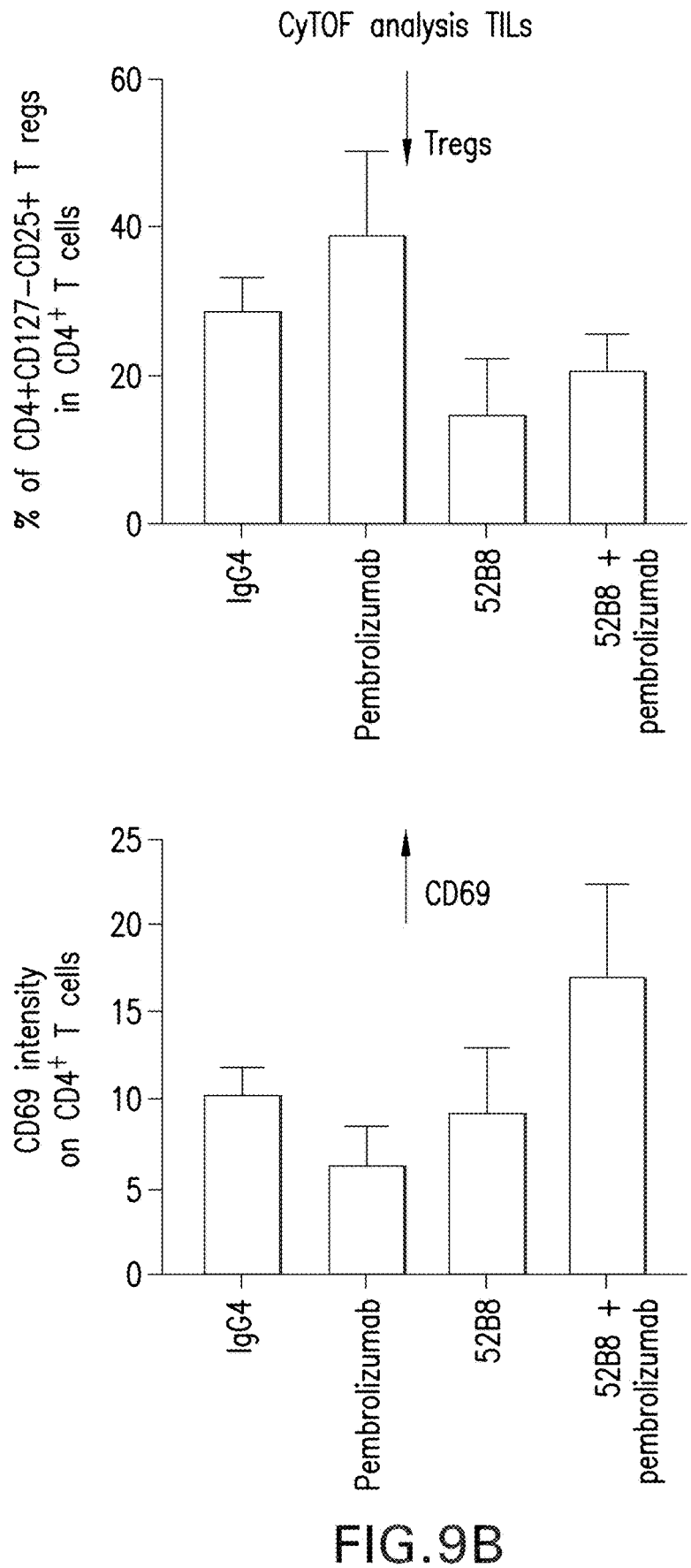
Figure 9C:
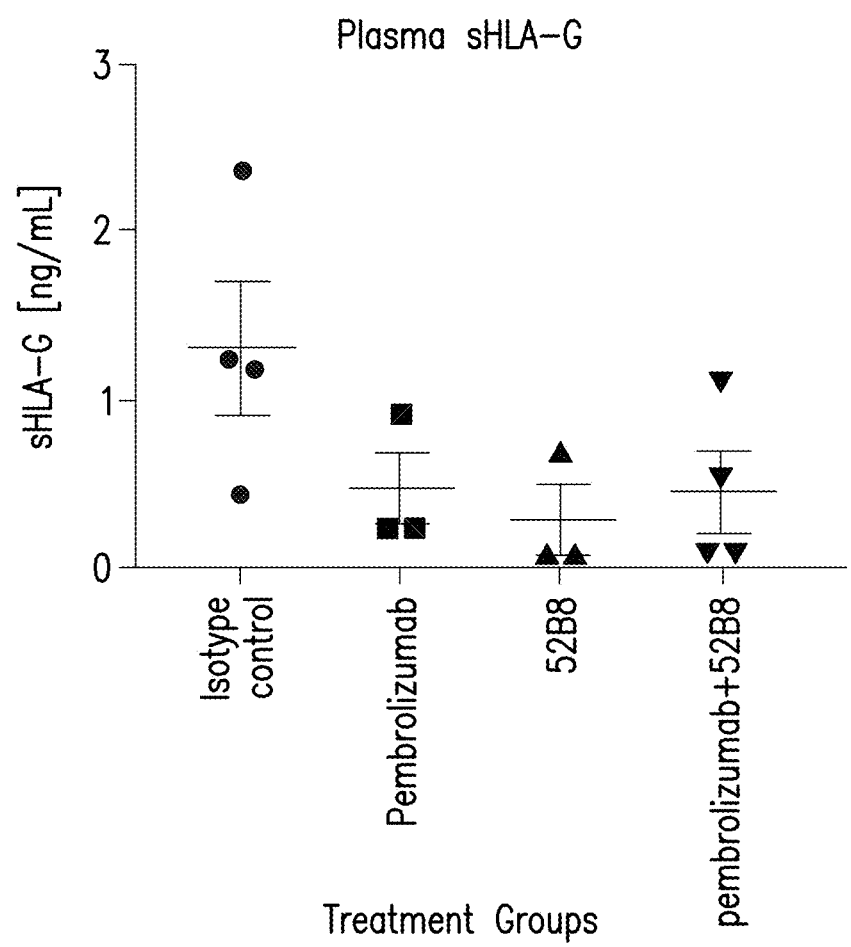
Figure 9D:
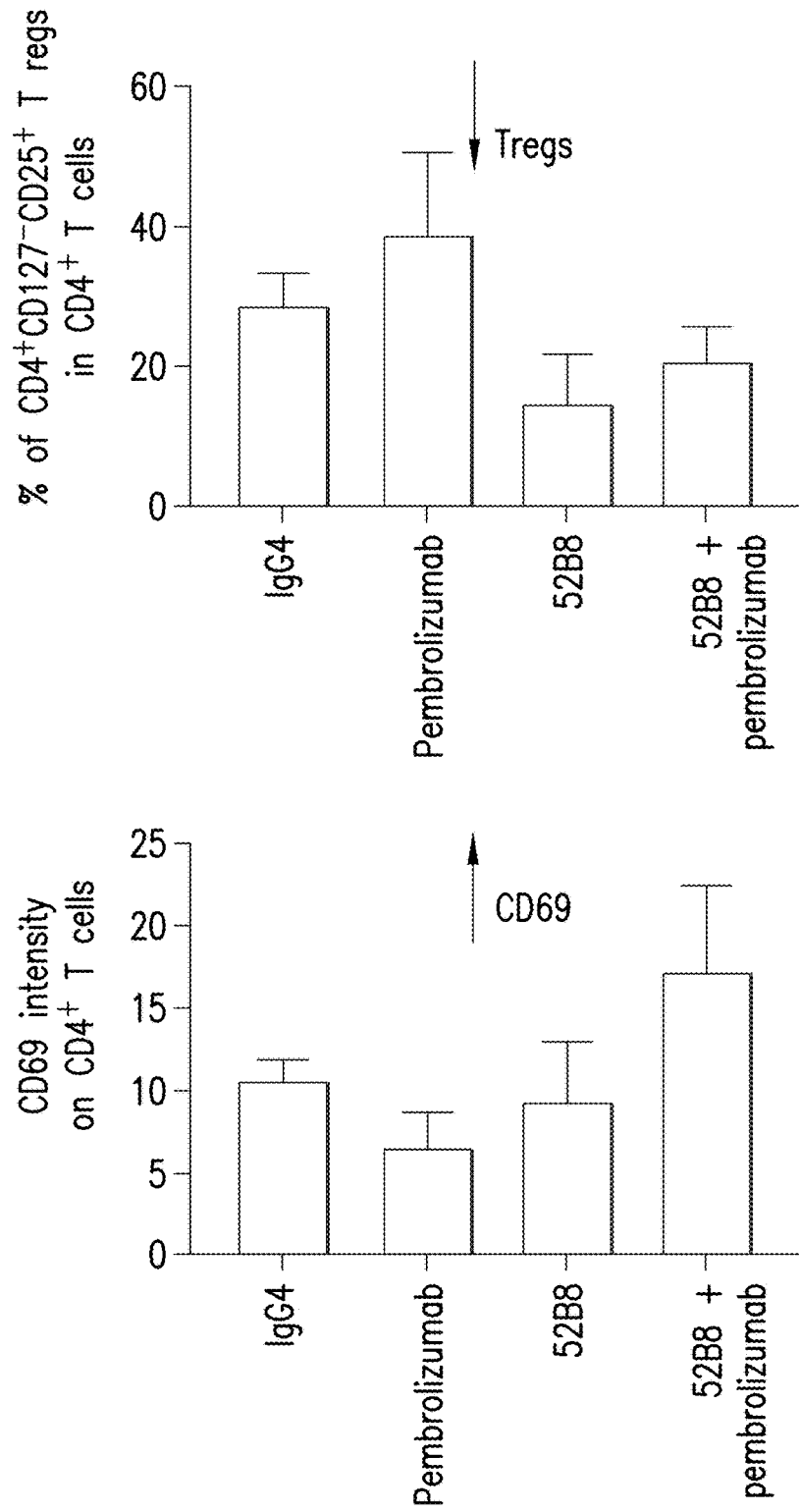

To understand immune mechanism that mediates the tumor efficacy, tumor infiltrating immune cells were profiled and measured sHLA-G levels were measured in the blood. Mice were treated with c52B8 (2 and 20 mg/kg i.p. QW). Antibody doses were selected based on $C_{max}$ and $C_{trough}$ levels detected in a mini-PK and simulations using historical studies. Blood samples were collected for PK, sHLA-G, and cytokine analyses. TILs profiling was performed using CyTOF to detect 36 markers simultaneously. Terminal tumor samples were fixed and used for human CD3+ T cell IHC analysis. Thirty percent tumor growth inhibition was observed in mice treated with 20 mpk 52B8. However, no statistical significant difference was detected due to big variability associated with the humanized tumor model. 52B8 modest tumor efficacy was associated with a modest decrease in tumor CD4+CD127-CD25+T suppressor cells (21% vs. 14%) and blood sHLA-G levels and an increase in activation of T cells (CD69 intensity, 14 vs. 23) in the tumor. No cytokine change was detected with c52B8 treatment as seen in FIG. 8.

Example 11

Effect of Anti-ILT3 Antibody c52B8 in Combination with Pembrolizumab in Panc 08.13 Hu-NSG Model: Tumor Efficacy and Immune Activation Anti-ILT3 antibody c52B8 was evaluated in Panc 08.13 hu-NSG model. 52B8 used as a single agent showed minimum effect on tumor growth inhibition. When 52B8 was used in combination with pembrolizumab, one in five cohorts (five different human donors) of humanized mice had 50% tumor growth inhibition (TGI) and the TGI was associated with increased T cell activation and IFNγ production and decreased blood sHLA-G level as seen in FIG. 9A, FIG. 9B, FIG. 9C, and FIG. 9D.

Example 12

Effect of Anti-ILT3 Antibody 52B8 in Combination with Pembrolizumab in an MDSC/T Cell Suppression Assay Humanized anti-ILT3 antibody 52B8 (mAb 46) with and without pembrolizumab effected an increase T-Cell activity in MDSC/T-cell suppression assays. The effect was additive when mAb 46 was used in combination with pembrolizumab.

To generate MDSCs, healthy human PBMCs from a particular donor were cultured with SKMEL5 cells and 20 ng/mL GM-CSF for seven days. Cultures were treated with 52B8 (1 µg/mL) or isotype control antibody (1 µg/mL). CD33+ cells were collected anti-CD33 magnetic microbeads and LS column separation (Miltenyi Biotec, Germany) and then co-cultured at the indicated ratios with purified autologous CD8+ T cells for 3 days in the presence of a polyclonal stimulus. Autologous CD8+ T cells were isolated from healthy human PBMCs using negative antibody-based magnetic bead selection (Stem Cell Technologies, Canada) then co-cultured in 96 well plates with CD33+ myeloid cells at the ratio of 8:1 (Tcell:MDSC) for 2 days. Cultures included humanized 52B8 (mAb 46) or isotype control antibody (IgG4) (1 µg/mL) alone or in combination with pembrolizumab (2 µg/mL) in both the co-culture and T cell suppression steps. Total antibody concentration in each treatment is adjusted to 3 ug/mL with isotype control antibody. T cell proliferation was induced by a polyclonal stimulus anti-CD3/CD28 beads and IL2. IFNγ levels were determined in culture supernatants using MSD ELISA (Mesoscale Discovery, MD). The T cell suppression assay was conducted with a T cell to MDSC ratio of 4:1 or 8:1 and measuring the amount of interferon gamma (INFγ) produced. The results are shown in FIGS. 10-14.

Figure 10:
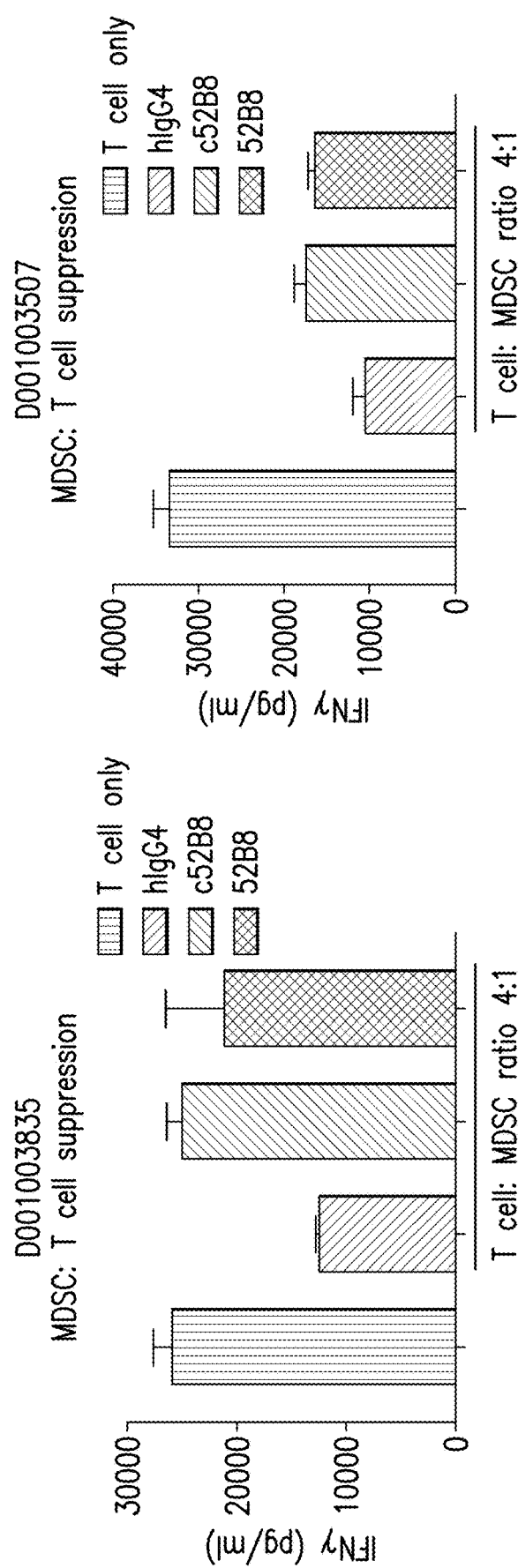

FIG. 10 shows that humanized anti-ILT3 antibody 52B8 (mAb 46) reduces the suppressive capacity of MDSCs to an extent comparable to chimeric anti-ILT3 antibody c52B8 (mAb 73; lot 26AVY) in MDSC/T-cell suppression assays using MDSCs obtained from PBMCs from two different human donors (D00100385 and D001003507, respectively).

Figure 11:
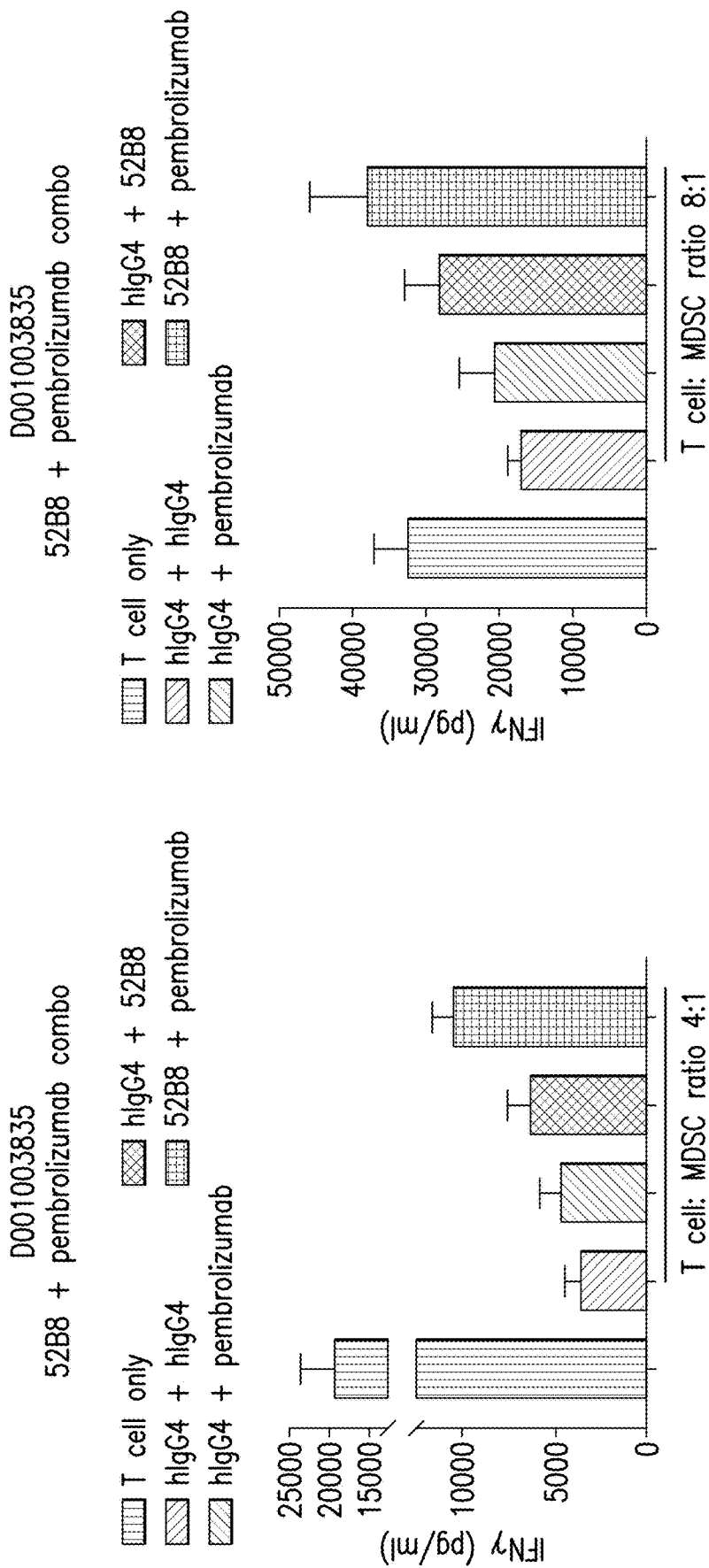
FIG. 11 shows the effect of the humanized anti-ILT3 antibody 52B8 (mAb 46) and pembrolizumab combination in an MDSC/T cell suppression assay at either a 4:1 or 8:1 ratio of T cell to MDSC using MDSC cells obtained from human donor D001003835.
Figure 12:
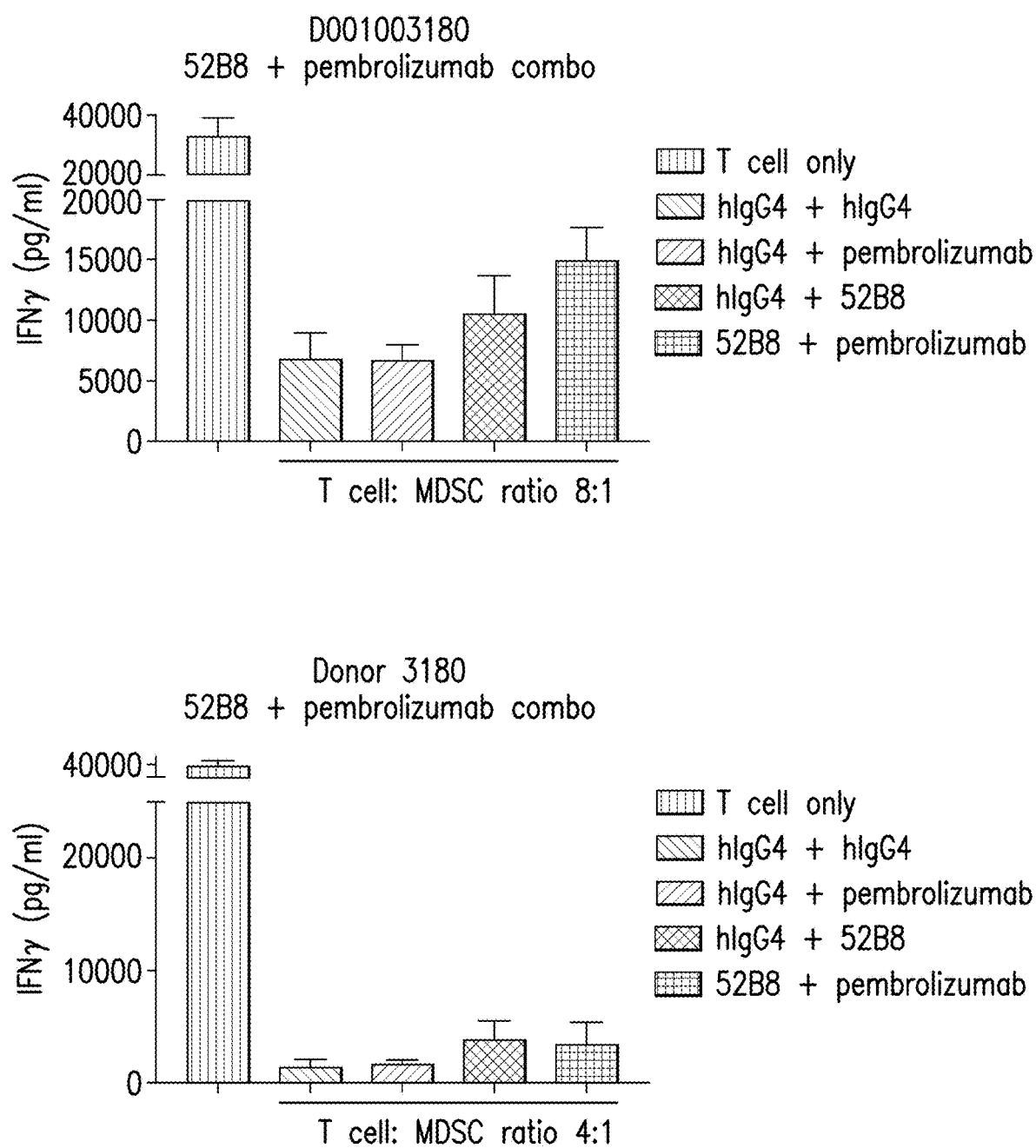
FIG. 12 shows the effect of the humanized anti-ILT3 antibody 52B8 (mAb 46) and pembrolizumab combination in an MDSC/T cell suppression assay at an 8:1 ratio of T cell to MDSC using MDSC cells obtained from human donor D001003180.
Figure 13:
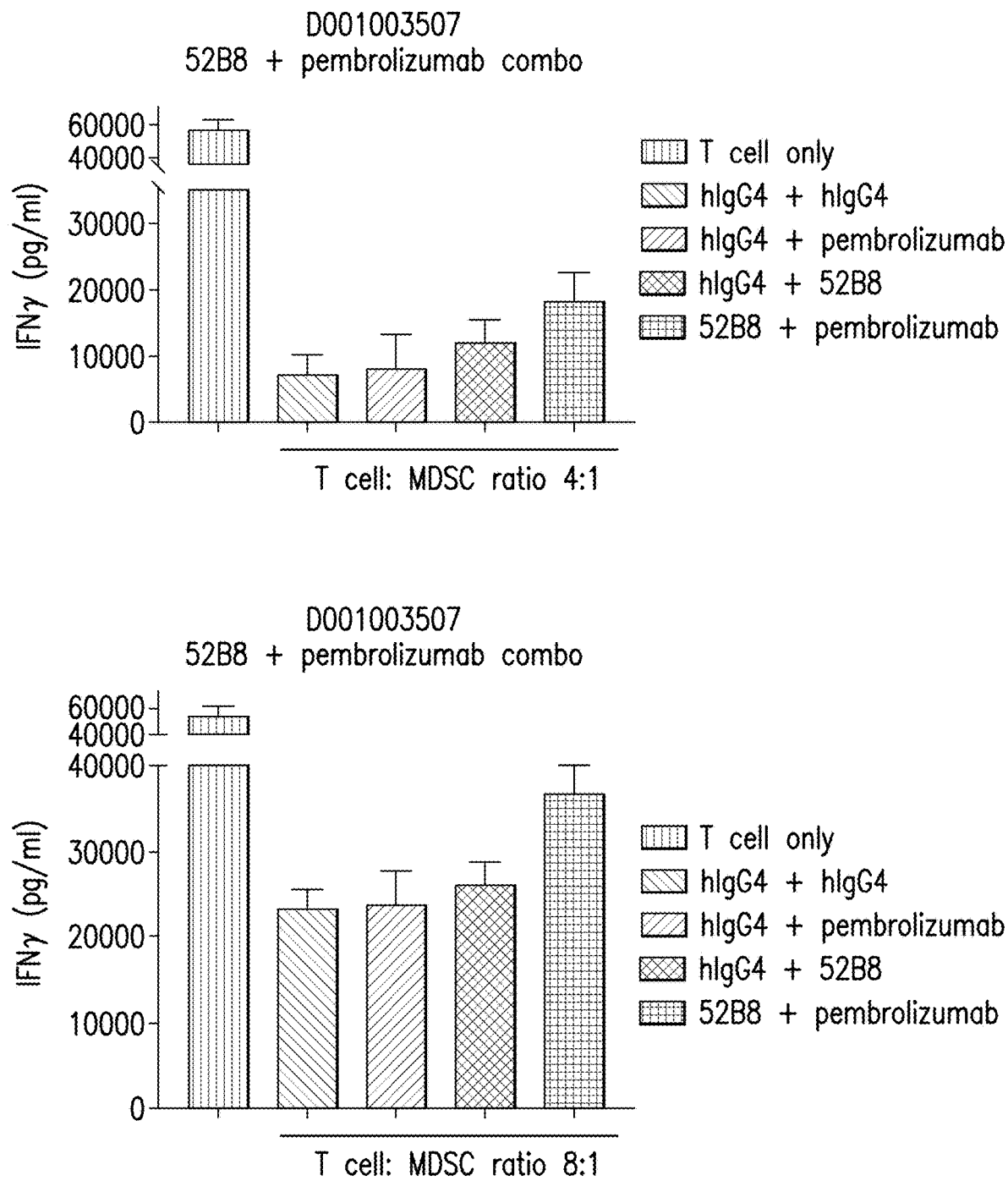
FIG. 13 shows the effect of the humanized anti-ILT3 antibody 52B8 (mAb 46) and pembrolizumab combination in an MDSC/T cell suppression assay at an 4:1 ratio of T cell to MDSC using MDSC cells obtained from human donor D001003507.
Figure 14:
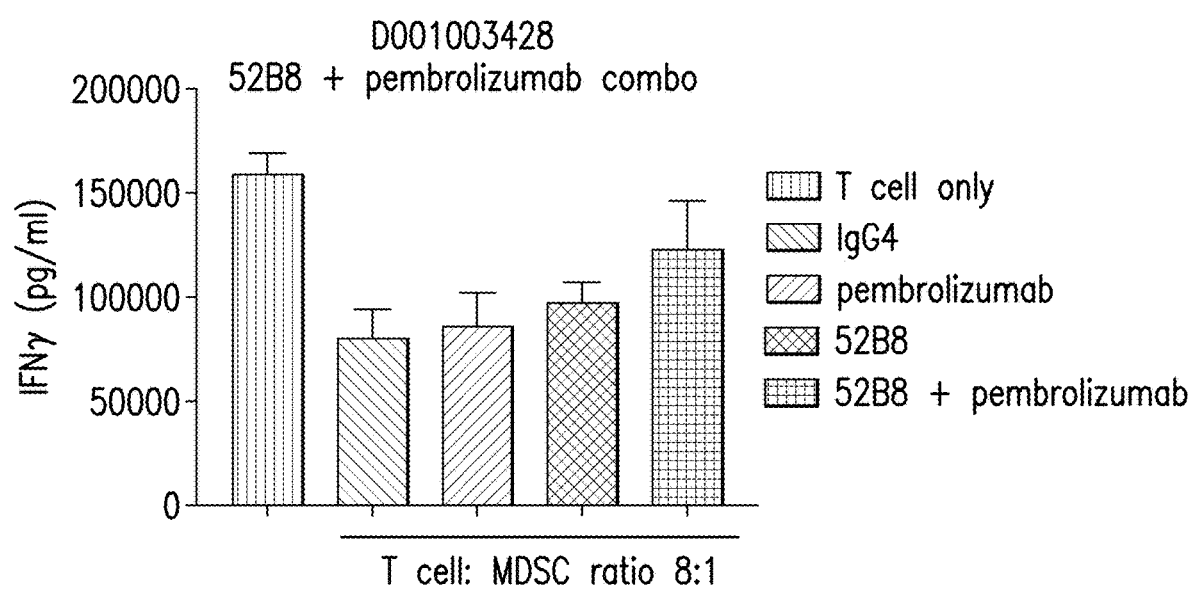
FIG. 14 shows the effect of the humnized anti-ILT3 antibody 52B8 (mAb 46) and pembrolizumab combination in an MDSC/T cell suppression assay at an 8:1 ratio of T cell to MDSC using MDSC cells obtained from human donor D001003428.

As shown in FIGS. 11-14 humanized anti-ILT3 antibody 52B8 (mAb 46) in combination with pembrolizumab reduced MDSC inhibition of T cell activation at a higher level compared to either alone in an MDSC/T cell suppression assay (a) at either a 4:1 or 8:1 ratio of T cell to MDSC using MDSCs obtained from PBMCs from human donor D001003835 (FIG. 11); (b) at either a 4:1 or 8:1 ratio of MDSC to T cell using MDSCs obtained from PBMCs from human donor D001003180 (FIG. 12); (c) at a 4:1 or 8:1 ratio of ratio of T cell to MDSC using MDSCs obtained from PBMCs from human donor D001003507 (FIG. 13); and an 8:1 ratio of ratio of T cell to MDSC using MDSCs obtained from PBMCs from human donor (FIG. 14). The results are summarized in Tables 8 and 9. As shown in FIGS. 10-13 and Tables 8 and 9, combining an anti-ILT3 antibody 52B8 with pembrolizumab resulted in an additive effect of increasing the activation of T cells over that achievable using pembrolizumab or 52B8 alone. As shown, increases in IFNγ for the combination relative to the other treatments ranged from 41% to 74%. These results indicate that the combination of pembrolizumab with 52B8 does not result in an excessive or uncontrolled escalation of T cell activation.

Example 13

Effect of Anti-ILT3 Antibody 52B8 in Combination with Pembrolizumab in Mixed Lymphocyte Reaction of Polarized IL-10 DCs and Allogenic CD8+ T Cells In this example, a mixed lymphocyte reaction of IL-10-polarized human monocyte-derived dendritic cells and allogenic CD8+ T cells, incubated for four days followed by measurement of interferon gamma (IFNγ) in the culture supernatant as a read out of T cell activation. In this experiment, the activities of pembrolizumab, 52B8, or the combination of the two were compared to isotype control antibody (IgG4 in both cases), in nine allogenic donor pairs.

Monocyte derived dendritic cells (DCs) —IL10 DCs from three CD14+ monocyte donors were differentiated for seven days (Granulocyte-macrophage colony-stimulating factor (GMCSF) and IL4 for five days and then two days with IL10, with and without IgG4 (lot 92ASJ), with and without 52B8 (Lot 41BAB) at 1 μg/mL) to produce DC129, DC226, and DC196. CD8+ cells from three donors were isolated and mixed leukocyte reactions (MLR) were established at 1:5 DC:T cell ratio from the three donors in a 96 well format (30 k DC vs 150 k CD8+ T cells) where cells were treated with and without IgG4 (lot 92 ASJ); with and without Pembrolizumab (lot 42ASN) at 2 μg/mL. IgG4 or 52B8 was also added back in the MLR at 1 μg/mL. Wound up with nine MLR pairs of IL10 DCs:CD8+ T cells:

DC129 vs T30, T3788 and T3259
DC226 vs T30, T3788 and T3259
DC196 vs T30, T3788 and T3259

IFNγ supernatant was collected at day four and quantified using Meso Scale Discovery (MSD). Additional supernatant fraction was collected at day five and cells were collected and stained for PD1 and PDL1 expression. Dendritic Cell Staining on Day seven of differentiation (just prior to MLR setup). T cell Staining of CD8+ T cells at day five of MLR assay.

Figure 15:
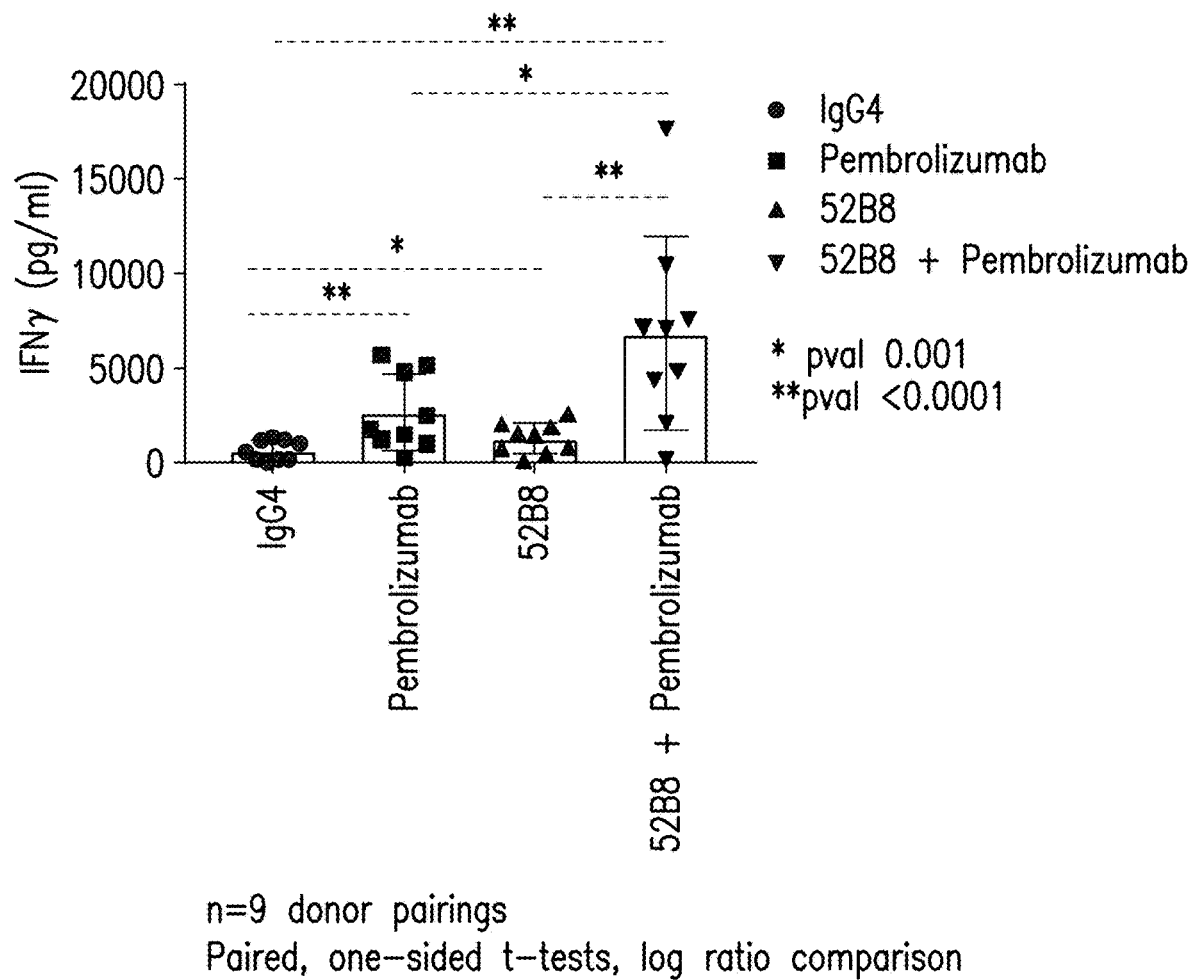
FIG. 15 shows the effect humanized anti-ILT3 antibody 52B8 (mAb 46) and pembrolizumab combination in a mixed lymphocyte reaction of IL-10-polarized human monocyte-derived dendritic cells and allogenic CD8+ T cells, incubated for four days followed by measurement of interferon gamma (IFNγ) in the culture supernatant as a read out of T cell activation.

FIG. 15 shows the results for all donor pairs combined into one figure (each mark is a donor pairing). As shown, 52B8 in combination with pembrolizumab effected a reverse of T cell tolerization, resulting in a statistically significant increase in activation of CD8+ T cells.

TABLE 8

Summary of the humanized anti-ILT3 antibody 52B8 and pembrolizumab combination data

| | | | Mean Avg ± SD | | | |
|---|---|---|---|---|---|---|
| | | | | T cell + MDSC | | |
| Donor | T Cell:MDSC ratio | T cell only | hIgG4 + hIgG4 | hIgG4 + Pembrolizumab | hIgG4 + 52B8 | 52B8 + Pembrolizumab |
| D001003835 | 4:1 | 19439 ± 4191 | 3667 ± 795 | 4676 ± 1162 | 6380 ± 1187 | 10438 ± 1132 |
| | 8:1 | 32644 ± 4146 | 17386 ± 1628 | 20556 ± 5028 | 28280 ± 4643 | 38163 ± 7817 |
| D001003180 | 4:1 | 38166 ± 7574 | 1482 ± 646 | 1781 ± 295 | 3983 ± 1528 | 3606 ± 1864 |
| | 8:1 | 33250 ± 6021 | 6823 ± 2170 | 6768 ± 1287 | 9532 ± 3025 | 14896 ± 2932 |
| D001003507 | 4:1 | 56836 ± 5777 | 7364 ± 2977 | 8111 ± 5220 | 12202 ± 3221 | 18422 ± 4135 |
| | 8:1 | 55376 ± 6310 | 23417 ± 8640 | 23981 ± 3135 | 26204 ± 3075 | 36992 ± 1856 |
| D001003428 | 8:1 | 159127 ± 10552 | 81071 ± 13458 | 87413 ± 15061 | 98902 ± 9884 | 123920 ± 22448 |

TABLE 9

52B8 Antibody + Pembrolizumab Combination - T cell:MDSC ratio (8:1)

| Condition | Ratios of GM | 95% CI | P-value |
|---|---|---|---|
| (52B8 + pembrolizumab)/ IgG4 | 1.84 | 1.35, 2.53 | 0.0043 |
| (52B8 + pembrolizumab)/ pembrolizumab | 1.73 | 1.26, 2.36 | 0.0057 |
| (52B8 + pembrolizumab)/ 52B8 | 1.39 | 1.20, 1.61 | 0.0028 |

The p-values are from one-sided paired t-tests comparing the 52B8 + pembrolizumab combination to each of the other groups, using logs of IFNγ values.
GM = geometric mean

TABLE OF SEQUENCES

| SEQ ID NO: | Description | Sequence |
|---|---|---|
| 1 | Human ILT3 (LILRB4) extracellular domain with C-terminal His Tag; epitope domains identified by bold-face type | QAGPLPKPTLWAEPGSVISWGNSVTIWCQGTLEAREYRLDK EESPAPWDRQNPLEPKNKARFSIPSMTEDYAGRYRCYYRSP VGWSQPSDPLELVMTGAYSKPTLSALPSPLVTSGKSVTLLC QSRSPMDTFLLIKERAAHPLLHLRSEHGAQQHQAEFPMSPV TSVHGGTYRCFSSHGFSHYLLSHPSDPLELIVSGSLEDPRPSP TRSVSTAAGPEDQPLMPTGSVPHSGLRRHWEHHHHHHHH |
| 2 | *Macaca mulatta* (Rhesus) ILT3 (LILRB4) extracellular domain (sequence obtained from GenBank NP_001035766) | QAGPLPKPTIWAEPGSVISWGSPVTIWCQGTLDAQEYYLDKE GSPAPWDTQNPLEPRNKAKFSIPSMTQHYAGRYRCYYHSHP DWSEDSDPLDLVMTGAYSKPILSVLPSPLVTSGESVTLLCQS QSPMDTFLLFKEGAAHPLPRLRSQHGAQLHWAEFPMGPVTS VHGGTYRCISSRSFSHYLLSRPSDPVELTVLGSLESPSPSPTRSI SAAGPEDQSLMPTGSDPQSGLRRHWE |
| 3 | Human ILT3 peptide A | ISWGNS |
| 4 | Human ILT3 peptide B | IPSMTE |
| 5 | Human ILT3 peptide C | MTGAYS |
| 6 | Human ILT3 peptide D | QSRSPMDT |
| 7 | Human ILT3 peptide E | AQQHQAEF |
| 8 | Human ILT3 peptide F | LLSH |
| 9 | Human IgG4 HC Constant domain (S228P; shown in bold-face type) | *ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCPPCPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLGK* |
| 10 | Human IgG4 HC Constant domain (S228P; shown in bold-face type) (lacks C-terminal K (herein referred to as "K-")) | *ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCPPCPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLG* |
| 11 | Human IgG1 HC constant domain | *ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTL MISRTPEVTCVVVDVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK* |
| 12 | Human IgG1 HC Constant domain (L234A, L235A, D265S; shown in bold-face type) | *ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREE QYNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK* |
| 13 | Human IgG1 HC Constant domain (K-) (L234A, L235A, D265S; | *ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREEQ* |

TABLE OF SEQUENCES-continued

| SEQ ID NO: | Description | Sequence |
|---|---|---|
| | shown in bold-face type) | YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPG |
| 14 | Human LC Kappa Constant domain | RTVAAPSVFIFPPSDEQLKSGTASVVCLLNNFYPREAKVQWKVD NALQSGNSQESVTEQDSKDSTYSLSSTLTLSKADYEKHKVYACEV THQGLSSPVTKSFNRGEC |
| 15 | Anti-ILT3 52B8 parental HC variable domain | EVQLVESGGDLVKPGGSLKLSCAASGFTFS<u>NYGMS</u>WVRQTP DRRLEWVA<u>TISGGGDYTNYPDSMRG</u>RFTISRDNAKNTLYLQ MSSLKSEDTAMYYCGR<u>RLWFRSLYYAMDY</u>WGQGTSVTVSS |
| 16 | Anti-ILT3 52B8 parental LC variable domain | NIVLTQSPASLAVSLGQRATISC<u>RASEKVDSFGNSFMH</u>WYQQ KPGQPPKLLIY<u>LTSNLDS</u>GVPARFSGSGSRTDFALTIDPVEAD DAATYYC<u>QQNNEDPYT</u>FGGGTKLEIK |
| 17 | 52B8 HC-CDR1 | NYGMS |
| 18 | 52B8 HC-CDR2 (Wherein Xaa15 is M, V, or L) | TISGGGDYTNYPDSXRG |
| 19 | 52B8 HC-CDR2 M | TISGGGDYTNYPDSMRG |
| 20 | 52B8 HC-CDR2 V | TISGGGDYTNYPDSVRG |
| 21 | 52B8 HC-CDR2 L | TISGGGDYTNYPDSLRG |
| 22 | 52B8 HC-CDR3 (Wherein Xaa3 is W, Y, Q, or F) | RLXFRSLYYAMDY |
| 23 | 52B8 HC-CDR3 | RLWFRSLYYAMDY |
| 24 | 52B8 HC-CDR3 | RLYFRSLYYAMDY |
| 25 | 52B8 HC-CDR3 | RLQFRSLYYAMDY |
| 26 | 52B8 HC-CDR3 | RLFFRSLYYAMDY |
| 27 | 52B8 LC-CDR1 (Wherein Xaa11 is N, D, or Q and Xaa12 is S, N, or A) | RASEKVDSFGXXFMH |
| 28 | 52B8 LC-CDR1 N (WhereinXaa12 is S, N, or A) | RASEKVDSFGNXFMH |
| 29 | 52B8 LC-CDR1 D (WhereinXaa12 is S, N, or A) | RASEKVDSFGDXFMH |
| 30 | 52B8 LC-CDR1 Q (WhereinXaa12 is S, N, or A) | RASEKVDSFGQXFMH |
| 31 | 52B8 LC-CDR1 S (Wherein Xaa11 is N, D, or Q) | RASEKVDSFGXSFMH |
| 32 | 52B8 LC-CDR1 N (Wherein Xaa11 is N, D, or Q) | RASEKVDSFGXNFMH |
| 33 | 52B8 LC-CDR1 A (Wherein Xaa11 is N, D, or Q) | RASEKVDSFGXAFMH |
| 34 | 52B8 LC-CDR1 (NN) | RASEKVDSFGNNFMH |
| 35 | 52B8 LC-CDR1 (DN) | RASEKVDSFGDNFMH |

TABLE OF SEQUENCES-continued

| SEQ ID NO: | Description | Sequence |
|---|---|---|
| 36 | 52B8 LC-CDR1 (QN) | RASEKVDSFGQNFMH |
| 37 | 52B8 LC-CDR1 (NS) | RASEKVDSFGNSFMH |
| 38 | 52B8 LC-CDR1 (DS) | RASEKVDSFGDSFMH |
| 39 | 52B8 LC-CDR1 (NA) | RASEKVDSFGNAFMH |
| 40 | 52B8 LC-CDR1 (DA) | RASEKVDSFGDAFMH |
| 41 | 52B8 LC-CDR1 (QS) | RASEKVDSFGQSFMH |
| 42 | 52B8 LC-CDR1 (AF) | RASEKVDSFGQAFMH |
| 43 | 52B8 LC-CDR2 | LTSNLDS |
| 44 | 52B8 LC-CDR3 | QQNNEDPYT |
| 45 | Anti-ILT3 40A6 parental HC variable domain | QVQLKESGPGLVQASETLSLTCTVSGFSLTSYSINWVRQSSG KGPEWMGRFWYDEGIAYNLTLESRLSISGDTSKNQVFLKMN SLRTGDTGTYYCTRDRDTVGITGWFAYWGQGTLVTVSS |
| 46 | Anti-ILT3 40A6 parental LC variable domain | ETVMTQSPTSLSASIGERVTLNCKASQSVGVNVDWYQQTPG QSPKLLIYGSANRHTGVPDRFTGSGFGSDFTLTISDVEPEDLG VYYCLQYGSVPYTFGAGTKLELK |
| 47 | 40A6 HC-CDR1 | SYSIN |
| 48 | 40A6 HC-CDR2 | RFWYDEGIAYNLTLES |
| 49 | 40A6 HC-CDR3 | DRDTVGITGWFAY |
| 50 | 40A6 LC-CDR1 | KASQSVGVNVD |
| 51 | 40A6 LC-CDR2 | GSANRHT |
| 52 | 40A6 LC-CDR3 | LQYGSVPYT |
| 53 | Anti-ILT3 16B1 parental HC variable domain | QVQLKESGPGLVQASETLSLTCTVSGFSLTNYCVNWVRQPS GKGPEWLGRFWFDEGKAYNLTLESRLSISGDTSKNQVFLRM NSLRADDTGTYYCTRDRDTVGITGWFAYWGQGTLVTVSS |
| 54 | Anti-ILT3 16B1 parental LC variable domain | ETVMTQSPTSLSASIGERVTLNCKASQSVGINVDWYQQTPGQ SPKLLIYGSANRHTGVPDRFTGSGFGSDFTLTISNVEPEDLGV YYCLQYGSVPYTFGPGTKLELK |
| 55 | 16B1 HC-CDR1 | NYCVN |
| 56 | 16B1 HC-CDR2 | RFWFDEGKAYNLTLES |
| 57 | 16B1 HC-CDR3 | DRDTVGITGWFAY |
| 58 | 16B1 LC-CDR1 | KASQSVGINVD |
| 59 | 16B1 LC-CDR2 | GSANRHT |
| 60 | 16B1 LC-CDR3 | LQYGSVPYT |
| 61 | Anti-ILT3 11D1 parental HC variable domain | QVQLQQSGAELMKPGASVKISCKATGYTFRTYWIEWVKQRP GHGLEWIGEILPGNGNTHFNENFKDKATFTADTSSNAAYMQ LSSLTSEDSAVYYCVRRLGRGPFDFWGQGTTLTVSS |
| 62 | Anti-ILT3 11D1 parental LC variable domain | DIQMTQSPSSLSVSLGGKVTITCKASQDINEYIGWYQRKPGK GPRLLIHYTSTLQSGIPSRFSGSGSGRDYSLSISNLEPEDIATYY CLQYANPLPTFGGGTKLEIK |
| 63 | 11D1 HC-CDR1 | TYWIE |

TABLE OF SEQUENCES-continued

| SEQ ID NO: | Description | Sequence |
|---|---|---|
| 64 | 11D1 HC-CDR2 | EILPGNGNTHFNENFKD |
| 65 | 11D1 HC-CDR3 | RRLGRGPFDF |
| 66 | 11D1 LC-CDR1 | KASQDINEYIG |
| 67 | 11D1 LC-CDR2 | YTSTLQS |
| 68 | 11D1 LC-CDR3 | LQYANPLPT |
| 69 | Anti-ILT3 17H12 parental HC variable domain | EVQLVESGGGLVQPGRSMKLSCAASGFTFS<u>NFDMA</u>WVRQA PTRGLEWVS<u>SITYDGGSTSYRDSVKG</u>RFTISRDNAKGTLYLQ MDSLRSEDTATYYCTT<u>VESIATISTYFDY</u>WGQGVMVTVSS |
| 70 | Anti-ILT3 17H12 parental LC variable domain | DIVLTQSPALAVSLGQRATISC<u>RASQSVSMSRYDLIH</u>WYQQK PGQQPKLLIF<u>RASDLAS</u>GIPARFSGSGSGTDFTLTINPVQADDI ATYYC<u>QQTRKSPPT</u>FGGGTRLELK |
| 71 | 17H12 HC-CDR1 | NFDMA |
| 72 | 17H12 HC-CDR2 | SITYDGGSTSYRDSVKG |
| 73 | 17H12 HC-CDR3 | VESIATISTYFDY |
| 74 | 17H12 LC-CDR1 | RASQSVSMSRYDLIH |
| 75 | 17H12 LC-CDR2 | RASDLAS |
| 76 | 17H12 LC-CDR3 | QQTRKSPPT |
| 77 | Anti-ILT3 37C8 parental HC variable domain | QVQLKESGPGLVQASETLSLTCTVSGFSLT<u>SYCVN</u>WVRQPSG KGPEWLG<u>RFWYDEGKVYNLTLES</u>RLSISGDTSKNQVFLKMN RLRTDDTGTYYCTR<u>DRDTMGITGWFAY</u>WGQGTLVTVSS |
| 78 | Anti-ILT3 37C8 parental LC variable domain | ETVMTQSPTSLSASIGERVTLNC<u>KASQSVGINVD</u>WYQQTPGQ SPKLLIY<u>GSANRHT</u>GVPDRFTGSGFGSGFTLTISNVEPEDLGV YYC<u>LQYGSVPYT</u>FGPGTKLELK |
| 79 | 37C8 HC-CDR1 | SYCVN |
| 80 | 37C8 HC-CDR2 | RFWYDEGKVYNLTLES |
| 81 | 37C8 HC-CDR3 | DRDTMGITGWFAY |
| 82 | 37C8 LC-CDR1 | KASQSVGINVD |
| 83 | 37C8 LC-CDR2 | GSANRHT |
| 84 | 37C8 LC-CDR3 | LQYGSVPYT |
| 85 | Anti-ILT3 1G12 parental HC variable domain | QVQMQQSGTELMKPGASMKISCKATGYTFS<u>TYWIQ</u>WIKQRP GHGLEWIG<u>EILPGSGTTNYNENFKG</u>KATFSADTSSNTAYIHLS SLTSEDSAVFYCAR<u>RLGRGPFDY</u>VVGQGTTLTVSS |
| 86 | Anti-ILT3 1G12 parental LC variable domain | DIQMTQSPSSLSASLGGKVTITC<u>EASQDINKHID</u>WYQHQPGR GPSLLIH<u>YASILQP</u>GIPSRFSGSGSGRDYSFSITSLEPEDIATYY C<u>LQYDNLLPT</u>FGGGTKLEIK |
| 87 | 1G12 HC-CDR1 | TYWIQ |
| 88 | 1G12 HC-CDR2 | EILPGSGTTNYNENFKG |
| 89 | 1G12 HC-CDR3 | RLGRGPFDY |
| 90 | 1G12 LC-CDR1 | EASQDINKHID |
| 91 | 1G12 LC-CDR2 | YASILQP |
| 92 | 1G12 LC-CDR3 | LQYDNLLPT |
| 93 | Anti-ILT3 20E4 parental HC variable domain | QVQLKESGPGLVQASETLSLTCTVSGFSLT<u>SYSVN</u>WVRQPSG KGLEWMG<u>RFWYDGGTAYNSTLES</u>RLSISGDTSKNQVFLKM NSLQTDDTGTYYCTR<u>DRDTMGITGWFAY</u>WGQGTLVTVSP |

TABLE OF SEQUENCES-continued

| SEQ ID NO: | Description | Sequence |
|---|---|---|
| 94 | Anti-ILT3 20E4 parental LC variable domain | ETVMTQSPTSLSASIGERVTLNC<u>KASQSVGVNVD</u>WYQQTPG QSPKLLIY<u>GSANRHT</u>GVPDRFTGSGFGSDFTLTISNVEPEDLG VYYC<u>LQYGSVPYT</u>FGAGTKLELK |
| 95 | 20E4 HC-CDR1 | SYSVN |
| 96 | 20E4 HC-CDR2 | RFWYDGGTAYNSTLES |
| 97 | 20E4 HC-CDR3 | DRDTMGITGWFAY |
| 98 | 20E4 LC-CDR1 | KASQSVGVNVD |
| 99 | 20E4 LC-CDR2 | GSANRHT |
| 100 | 20E4 LC-CDR3 | LQYGSVPYT |
| 101 | Anti-ILT3 24A4 parental HC variable domain | QVQLKESGPGLVQASETLSLTCTVSGFSLT<u>SYCVN</u>WVRQPSG KGPEWLG<u>RFWYDEGKVYNLTLES</u>RLSISGDTSKNQVFLKMN RLRTDDTGTYYCTR<u>DRDTLGITGWFAY</u>WGQGTLVTVSS |
| 102 | Anti-ILT3 24A4 parental LC variable domain | ETVMTQSPTSLSASIGERVTLNC<u>KASQSVGINVD</u>WYQQTPGQ SPKLLIY<u>GSANRHT</u>GVPDRFTGSGFGSGFTLTISNVEPEDLGV YYC<u>LQYGSVPYT</u>FGPGTKLELK |
| 103 | 24A4 HC-CDR1 | SYCVN |
| 104 | 24A4 HC-CDR2 | RFWYDEGKVYNLTLES |
| 105 | 24A4 HC-CDR3 | DRDTLGITGWFAY |
| 106 | 24A4 LC-CDR1 | KASQSVGINVD |
| 107 | 24A4 LC-CDR2 | GSANRHT |
| 108 | 24A4 LC-CDR3 | LQYGSVPYT |
| 109 | Leader sequence A | MEWSWVFLFFLSVTTGVHS |
| 110 | Leader sequence B | MSVPTQVLGLLLLWLTDARC |
| 111 | Mouse Anti-ILT3 p52B8 parental HC: Murine IgG2a heavy chain | EVQLVESGGDLVKPGGSLKLSCAASGFTFSNYGMSWVRQTP DRRLEWVATISGGGDYTNYPDSMRGRFTISRDNAKNTLYLQ MSSLKSEDTAMYYCGRRLWFRSLYYAMDYWGQGTSVTVSS AKTTAPSVYPLAPVCGDTTGSSVTLGCLVKGYFPEPVTLTW NSGSLSSGVHTFPAVLQSDLYTLSSSVTVTSSTWPSQSITCNV AHPASSTKVDKKIEPRGPTIKPCPPCKCPAPNLLGGPSVFIFPP KIKDVLMISLSPIVTCVVVDVSEDDPDVQISWFVNNVEVHTA QTQTHREDYNSTLRVVSALPIQHQDWMSGKEFKCKVNNKD LPAPIERTISKPKGSVRAPQVYVLPPPEEEMTKKQVTLTCMV TDFMPEDIYVEWTNNGKTELNYKNTEPVLDSDGSYFMYSKL RVEKKNWVERNSYSCSVVHEGLHNHHTTKSFSRTPGK |
| 112 | Mouse Anti-ILT3 p52B8 parental LC: murine Kappa light chain | NIVLTQSPASLAVSLGQRATISCRASEKVDSFGNSFMHWYQQ KPGQPPKLLIYLTSNLDSGVPARFSGSGSRTDFALTIDPVEAD DAATYYCQQNNEDPYTFGGGTKLEIKRADAAPTVSIFPPSSE QLTSGGASVVCFLNNFYPKDINVKWKIDGSERQNGVLNSWT DQDSKDSTYSMSSTLTLTKDEYERHNSYTCEATHKTSTSPIV KSFNREC |
| 113 | Chimeric Anti-ILT3 mouse 52B8 VH parental/human IgG4 (S228P) | EVQLVESGGDLVKPGGSLKLSCAASGFTFS<u>NYGMS</u>WVRQTP DRRLEWVA<u>TISGGGDYTNYPDSMRG</u>RFTISRDNAKNTLYLQ MSSLKSEDTAMYYCGR<u>RLWFRSLYYAMDY</u>WGQGTSVTVSS *ASTKGPSVFPLAPCSRSTSESTAALGCLVKDYFPEPVTSWNSGA LTSGVHTFPAVLQSSGLYSLSSVVTVPSSSLGTKTYTCNVDHKPSN TKVDKRVESKYGPPCPPCPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLGK* |
| 114 | Chimeric Anti-ILT3 mouse 52B8 VH M64V/human IgG4 (S228P) | EVQLVESGGDLVKPGGSLKLSCAASGFTFS<u>NYGMS</u>WVRQTP DRRLEWVA<u>TISGGGDYTNYPDSVRG</u>RFTISRDNAKNTLYLQ MSSLKSEDTAMYYCGR<u>RLWFRSLYYAMDY</u>WGQGTSVTVSS *ASTKGPSVFPLAPCSRSTSESTAALGCLVKDYFPEPVTSWNSGA* |

TABLE OF SEQUENCES-continued

| SEQ ID NO: | Description | Sequence |
|---|---|---|
| | | LTSGVHTFPAVLQSSGLYSLSSVVTVPSSSLGTKTYTCNVDHKPSN TKVDKRVESKYGPPCPPCPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDLIAVEWESNGQP ENNYKTTPPVLDSDGSFFLYSRLTVDKSRWQEGNVFSCSVMHEA LHNHYTQKSLSLSLGK |
| 115 | Mouse Anti-ILT3 52B8 VH M64L/human IgG4 (S228P) | EVQLVESGGDLVKPGGSLKLSCAASGFTFS<u>NYGMS</u>WVRQTP DRRLEWVA<u>TISGGGDYTNYPDSLR</u>GRFTISRDNAKNTLYLQ MSSLKSEDTAMYYCGR<u>RLWFRSLYYAMDY</u>WGQGTSVTVSS ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCPPCPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDLIAVEWESNGQP ENNYKTTPPVLDSDGSFFLYSRLTVDKSRWQEGNVFSCSVMHEA LHNHYTQKSLSLSLGK |
| 116 | Chimeric Anti-ILT3 mouse 52B8 parental VL / human Kappa | NIVLTQSPASLAVSLGQRATISC<u>RASEKVDSFGNSFMH</u>WYQQ KPGQPPKLLIY<u>LTSNLDS</u>GVPARFSGSGSRTDFALTIDPVEAD DAATYYC<u>QQNNEDPYT</u>FGGGTKLEIKRTVAAPSVFIFPPSDEQ LKSGTASVVCLLNNFYPREAKVQWKVDNALQSGNSQESVTEQDS KDSTYSLSSTLTLSKADYEKHKVYACEVTHQGLSSPVTKSFNRGE C |
| 117 | Humanized 52B8 HC variable domain VH1 | EVQLVESGGGLVQPGGSLRLSCAASGFTFS<u>NYGMS</u>WVRQAP GKGLEWVA<u>TISGGGDYTNYPDSMR</u>GRFTISRDNAKNSLYLQ MNSLRAEDTAVYYCGR<u>RLWFRSLYYAMDY</u>WGQGTLVTVS S |
| 118 | Humanized 52B8 HC variable domain VH1 (M64V) | EVQLVESGGGLVQPGGSLRLSCAASGFTFS<u>NYGMS</u>WVRQAP GKGLEWVA<u>TISGGGDYTNYPDSVR</u>GRFTISRDNAKNSLYLQ MNSLRAEDTAVYYCGR<u>RLWFRSLYYAMDY</u>WGQGTLVTVS S |
| 119 | Humanized 52B8 HC variable domain VH1 (M64L) | EVQLVESGGGLVQPGGSLRLSCAASGFTFS<u>NYGMS</u>WVRQAP GKGLEWVA<u>TISGGGDYTNYPDSLR</u>GRFTISRDNAKNSLYLQ MNSLRAEDTAVYYCGR<u>RLWFRSLYYAMDY</u>WGQGTLVTVS S |
| 120 | Humanized 52B8 HC variable domain VH1 (M64V, W101F) | EVQLVESGGGLVQPGGSLRLSCAASGFTFS<u>NYGMS</u>WVRQAP GKGLEWVA<u>TISGGGDYTNYPDSVR</u>GRFTISRDNAKNSLYLQ MNSLRAEDTAVYYCGR<u>RLFFRSLYYAMDY</u>WGQGTLVTVSS |
| 121 | Humanized 52B8 HC variable domain VH1 (M64V, W101Y) | EVQLVESGGGLVQPGGSLRLSCAASGFTFS<u>NYGMS</u>WVRQAP GKGLEWVA<u>TISGGGDYTNYPDSVR</u>GRFTISRDNAKNSLYLQ MNSLRAEDTAVYYCGR<u>RLYFRSLYYAMDY</u>WGQGTLVTVSS |
| 122 | Humanized 52B8 HC variable domain VH1 (M64V, W101Q) | EVQLVESGGGLVQPGGSLRLSCAASGFTFS<u>NYGMS</u>WVRQAP GKGLEWVA<u>TISGGGDYTNYPDSVR</u>GRFTISRDNAKNSLYLQ MNSLRAEDTAVYYCGR<u>RLQFRSLYYAMDY</u>WGQGTLVTVSS |
| 123 | Humanized 52B8 HC variable domain VH2 | EVQLVESGGGLVQPGGSLRLSCAASGFTFS<u>NYGMS</u>WVRQAP GKGLEWVA<u>TISGGGDYTNYPDSMR</u>GRFTISRDNAKNSLYLQ MNSLKAEDTAVYYCGR<u>RLWFRSLYYAMDY</u>WGQGTLVTVS S |
| 124 | Humanized 52B8 HC variable domain VH2 (M64V) | EVQLVESGGGLVQPGGSLRLSCAASGFTFS<u>NYGMS</u>WVRQAP GKGLEWVA<u>TISGGGDYTNYPDSVR</u>GRFTISRDNAKNSLYLQ MNSLKAEDTAVYYCGR<u>RLWFRSLYYAMDY</u>WGQGTLVTVS S |
| 125 | Humanized 52B8 HC variable domain VH2 (M64L) | EVQLVESGGGLVQPGGSLRLSCAASGFTFS<u>NYGMS</u>WVRQAP GKGLEWVA<u>TISGGGDYTNYPDSLR</u>GRFTISRDNAKNSLYLQ MNSLKAEDTAVYYCGR<u>RLWFRSLYYAMDY</u>WGQGTLVTVS S |
| 126 | Humanized 52B8 LC variable domain VL1 | DIVLTQSPDSLAVSLGERATINC<u>RASEKVDSFGNSFMH</u>WYQQ KPGQPPKLLIY<u>LTSNLDS</u>GVPDRFSGSGSRTDFTLTISSLQAED VAVYYC<u>QQNNEDPYT</u>FGQGTKLEIK |

TABLE OF SEQUENCES-continued

| SEQ ID NO: | Description | Sequence |
|---|---|---|
| 127 | Humanized 52B8 LC variable domain VL2 | DIVLTQSPDSLAVSLGERATINC<u>RASEKVDSFGNSFMH</u>WYQQ KPGQPPKLLIY<u>LTSNLDS</u>GVPDRFSGSGSGTDFTLTISSLQAED VAVYYC<u>QQNNEDPYT</u>FGQGTKLEIK |
| 128 | Humanized 52B8 LC variable domain VL3 | EIVLTQSPATLSLSPGERATLSC<u>RASEKVDSFGNSFMH</u>WYQQ KPGQAPRLLIY<u>LTSNLDS</u>GVPARFSGSGSRTDFTLTISSLEPED FAVYYC<u>QQNNEDPYT</u>FGQGTKLEIK |
| 129 | Humanized 52B8 LC variable domain VL4 | EIVLTQSPATLSLSPGERATLSC<u>RASEKVDSFGNSFMH</u>WYQQ KPGQAPRLLIY<u>LTSNLDS</u>GIPARFSGSGSGTDFTLTISSLEPEDF AVYYC<u>QQNNEDPYT</u>FGQGTKLEIK |
| 130 | Humanized 52B8 LC variable domain VL5 | DIQLTQSPSSLSASVGDRVTITC<u>RASEKVDSFGNSFMH</u>WYQQ KPGKAPKLLIY<u>LTSNLDS</u>GVPSRFSGSGSGTDFTLTISSLQPED FATYYC<u>QQNNEDPYT</u>FGQGTKLEIK |
| 131 | Humanized 52B8 LC variable domain VL6 | DIQMTQSPSSLSASVGDRVTITC<u>RASEKVDSFGNSFMH</u>WYQQ KPGKAPKLLIY<u>LTSNLDS</u>GVPSRFSGSGSRTDFTLTISSLQPED FATYYC<u>QQNNEDPYT</u>FGQGTKLEIK |
| 132 | Humanized 52B8 LC variable domain VL7 | DIQLTQSPSSLSASVGDRVTITC<u>RASEKVDSFGNSFMH</u>WYQQ KPGKAPKLLIY<u>LTSNLDS</u>GVPSRFSGSGSRTDFTLTISSLQPED FATYYC<u>QQNNEDPYT</u>FGQGTKLEIK |
| 133 | Humanized 52B8 LC variable domain VL8 | DIQLTQSPSSLSASVGDRVTITC<u>RASEKVDSFGNSFMH</u>WYQQ KPGKAPKLLIY<u>LTSNLDS</u>GVPARFSGSGSRTDFTLTISSLQPED FATYYC<u>QQNNEDPYT</u>FGQGTKLEIK |
| 134 | Humanized 52B8 LC variable domain VL2, (S35A) | DIVLTQSPDSLAVSLGERATINC<u>RASEKVDSFGNAFMH</u>WYQ QKPGQPPKLLIY<u>LTSNLDS</u>GVPDRFSGSGSGTDFTLTISSLQAE DVAVYYC<u>QQNNEDPYT</u>FGQGTKLEIK |
| 135 | Humanized 52B8 LC variable domain VL2, (S35N) | DIVLTQSPDSLAVSLGERATINC<u>RASEKVDSFGNNFMH</u>WYQ QKPGQPPKLLIY<u>LTSNLDS</u>GVPDRFSGSGSGTDFTLTISSLQAE DVAVYYC<u>QQNNEDPYT</u>FGQGTKLEIK |
| 136 | Humanized 52B8 LC variable domain VL2, (N34Q) | DIVLTQSPDSLAVSLGERATINC<u>RASEKVDSFGQSFMH</u>WYQQ KPGQPPKLLIY<u>LTSNLDS</u>GVPDRFSGSGSGTDFTLTISSLQAED VAVYYC<u>QQNNEDPYT</u>FGQGTKLEIK |
| 137 | Humanized 52B8 LC variable domain VL2, (N34D) | DIVLTQSPDSLAVSLGERATINC<u>RASEKVDSFGDSFMH</u>WYQQ KPGQPPKLLIY<u>LTSNLDS</u>GVPDRFSGSGSGTDFTLTISSLQAED VAVYYC<u>QQNNEDPYT</u>FGQGTKLEIK |
| 138 | Humanized 52B8 LC variable domain VL5, (S35A) | DIQLTQSPSSLSASVGDRVTITC<u>RASEKVDSFGNAFMH</u>WYQQ KPGKAPKLLIY<u>LTSNLDS</u>GVPSRFSGSGSGTDFTLTISSLQPED FATYYC<u>QQNNEDPYT</u>FGQGTKLEIK |
| 139 | Humanized 52B8 LC variable domain VL5, (S35N) | DIQLTQSPSSLSASVGDRVTITC<u>RASEKVDSFGNNFMH</u>WYQQ KPGKAPKLLIY<u>LTSNLDS</u>GVPSRFSGSGSGTDFTLTISSLQPED FATYYC<u>QQNNEDPYT</u>FGQGTKLEIK |
| 140 | Humanized 52B8 LC variable domain VL5 (N34Q) | DIQLTQSPSSLSASVGDRVTITC<u>RASEKVDSFGQSFMH</u>WYQQ KPGKAPKLLIY<u>LTSNLDS</u>GVPSRFSGSGSGTDFTLTISSLQPED FATYYC<u>QQNNEDPYT</u>FGQGTKLEIK |
| 141 | Humanized 52B8 LC variable domain VL5, (N34D) | DIQLTQSPSSLSASVGDRVTITC<u>RASEKVDSFGDSFMH</u>WYQQ KPGKAPKLLIY<u>LTSNLDS</u>GVPSRFSGSGSGTDFTLTISSLQPED FATYYC<u>QQNNEDPYT</u>FGQGTKLEIK |
| 142 | Humanized 52B8 HC variable domain VH1/Human IgG4 (S228P) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLRAEDTAVYYCGR<u>RLWFRSLYYAMD</u>YWGQGTLVTVS *SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCPPCPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ* |

| SEQ ID NO: | Description | Sequence |
|---|---|---|
| | | PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLGK |
| 143 | Humanized 52B8 HC variable domain VH1 (M64V)/Human IgG4 (S228P) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGRR<u>LWFRSLYYAMDY</u>WGQGTLVTVS *SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLGK* |
| 144 | Humanized 52B8 HC variable domain VH1 (M64L)/Human IgG4 (S228P) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLRAEDTAVYYCGRR<u>LWFRSLYYAMDY</u>WGQGTLVTVS *SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLGK* |
| 145 | Humanized 52B8 HC variable domain VH1 (M64V, W101F)/Human IgG4 (S228P) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGRR<u>LFFRSLYYAMDY</u>WGQGTLVTVSS *ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCP CPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLGK* |
| 146 | Humanized 52B8 HC variable domain VH1 (M64V, W101Y)/Human IgG4 (S228P) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGRR<u>LYFRSLYYAMDY</u>WGQGTLVTVSS *ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCP CPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLGK* |
| 147 | Humanized 52B8 HC variable domain VH1 (M64V, W101Q)/Human IgG4 (S228P) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGRR<u>LQFRSLYYAMDY</u>WGQGTLVTVSS *ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCP CPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLGK* |
| 148 | Humanized 52B8 HC variable domain VH2/Human IgG4 (S228P) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLKAEDTAVYYCGRR<u>LWFRSLYYAMDY</u>WGQGTLVTVS *SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLGK* |

TABLE OF SEQUENCES-continued

| SEQ ID NO: | Description | Sequence |
|---|---|---|
| 149 | Humanized 52B8 HC variable domain VH2 (M64V)/Human IgG4 (S228P) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLKAEDTAVYYCGR<u>RLWFRSLYYAMDY</u>WGQGTLVTVS *SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP*CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLGK* |
| 150 | Humanized 52B8 HC variable domain VH2 (M64L)/Human IgG4 (S228P) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLKAEDTAVYYCGR<u>RLWFRSLYYAMDY</u>WGQGTLVTVS *SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP*CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLGK* |
| 151 | Humanized 52B8 LC variable domain VL1/kappa constant domain | DIVLTQSPDSLAVSLGERATINC<u>RASEKVDSFGNSFMH</u>WYQQ KPGQPPKLLIY<u>LTSNLDS</u>GVPDRFSGSGSRTDFTLTISSLQAED VAVYYCQQNNEDPYTFGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 152 | Humanized 52B8 LC variable domain VL2/kappa constant domain | DIVLTQSPDSLAVSLGERATINC<u>RASEKVDSFGNSFMH</u>WYQQ KPGQPPKLLIY<u>LTSNLDS</u>GVPDRFSGSGSGTDFTLTISSLQAED VAVYYC<u>QQNNEDPYT</u>FGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 153 | Humanized 52B8 LC variable domain VL3/kappa constant domain | EIVLTQSPATLSLSPGERATLSC<u>RASEKVDSFGNSFMH</u>WYQQ KPGQAPRLLIY<u>LTSNLDS</u>GVPARFSGSGSGTDFTLTISSLEPED FAVYYC<u>QQNNEDPYT</u>FGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 154 | Humanized 52B8 LC variable domain VL4/kappa constant domain | EIVLTQSPATLSLSPGERATLSC<u>RASEKVDSFGNSFMH</u>WYQQ KPGQAPRLLIY<u>LTSNLDS</u>GIPARFSGSGSGTDFTLTISSLEPEDF AVYYC<u>QQNNEDPYT</u>FGQGTKLEIKR*TVAAPSVFIFPPSDEQLK SGTASVVCLLNNFYPREAKVQWKVDNALQSGNSQESVTEQDSKD STYSLSSTLTLSKADYEKHKVYACEVTHQGLSSPVTKSFNRGEC* |
| 155 | Humanized 52B8 LC variable domain VL5/kappa constant domain | DIQLTQSPSSLSASVGDRVTITC<u>RASEKVDSFGNSFMH</u>WYQQ KPGKAPKLLIY<u>LTSNLDS</u>GVPSRFSGSGSGTDFTLTISSLQPED FATYYC<u>QQNNEDPYT</u>FGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 156 | Humanized 52B8 LC variable domain VL6/kappa constant domain | DIQMTQSPSSLSASVGDRVTITC<u>RASEKVDSFGNSFMH</u>WYQQ KPGKAPKLLIY<u>LTSNLDS</u>GVPSRFSGSGSRTDFTLTISSLQPED FATYYC<u>QQNNEDPYT</u>FGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 157 | Humanized 52B8 LC variable domain VL7/kappa constant domain | DIQLTQSPSSLSASVGDRVTITCRASEKVDSFGNSFMHWYQQ KPGKAPKLLIY<u>LTSNLDS</u>GVPSRFSGSGSRTDFTLTISSLQPED FATYYC<u>QQNNEDPYT</u>FGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 158 | Humanized 52B8 LC variable domain VL8/kappa constant domain | DIQLTQSPSSLSASVGDRVTITC<u>RASEKVDSFGNSFMH</u>WYQQ KPGKAPKLLIY<u>LTSNLDS</u>GVPARFSGSGSRTDFTLTISSLQPED FATYYC<u>QQNNEDPYT</u>FGQGTKLEIKR*TVAAPSVFIFPPSDEQL KSGTASVVCLLNNFYPREAKVQWKVDNALQSGNSQESVTEQDSK DSTYSLSSTLTLSKADYEKHKVYACEVTHQGLSSPVTKSFNRGEC* |
| 159 | Humanized 52B8 LC variable domain VL2 (S35A)/kappa | DIVLTQSPDSLAVSLGERATINC<u>RASEKVDSFGNAFMH</u>WYQ QKPGQPPKLLIY<u>LTSNLDS</u>GVPDRFSGSGSGTDFTLTISSLQAE DVAVYYC<u>QQNNEDPYT</u>FGQGTKLEIKR*TVAAPSVFIFPPSDEQ LKSGTASVVCLLNNFYPREAKVQWKVDNALQSGNSQESVTEQDS* |

TABLE OF SEQUENCES-continued

| SEQ ID NO: | Description | Sequence |
|---|---|---|
| | constant domain | KDSTYSLSSTLTLSKADYEKHKVYACEVTHQGLSSPVTKSFNRGEC |
| 160 | Humanized 52B8 LC variable domain VL2 (S35N)/kappa constant domain | DIVLTQSPDSLAVSLGERATINCRASEKVDSFGNNFMHWYQQKPGQPPKLLIYLTSNLDSGVPDRFSGSGSGTDFTLTISSLQAEDVAVYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 161 | Humanized 52B8 LC variable domain VL2 (N34Q)/kappa constant domain | DIVLTQSPDSLAVSLGERATINCRASEKVDSFGQSFMHWYQQKPGQPPKLLIYLTSNLDSGVPDRFSGSGSGTDFTLTISSLQAEDVAVYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 162 | Humanized 52B8 LC variable domain VL2 (N34D)/kappa constant domain | DIVLTQSPDSLAVSLGERATINCRASEKVDSFGDSFMHWYQQKPGQPPKLLIYLTSNLDSGVPDRFSGSGSGTDFTLTISSLQAEDVAVYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 163 | Humanized 52B8 LC variable domain VL5 (S35A)/kappa constant domain | DIQLTQSPSSLSASVGDRVTITCRASEKVDSFGNAFMHWYQQKPGKAPKLLIYLTSNLDSGVPSRFSGSGSGTDFTLTISSLQPEDFATYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 164 | Humanized 52B8 LC variable domain VL5 (S35N)/kappa constant domain | DIQLTQSPSSLSASVGDRVTITCRASEKVDSFGNNFMHWYQQKPGKAPKLLIYLTSNLDSGVPSRFSGSGSGTDFTLTISSLQPEDFATYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 165 | Humanized 52B8 LC variable domain VL5 (N34Q)/kappa constant domain | DIQLTQSPSSLSASVGDRVTITCRASEKVDSFGQSFMHWYQQKPGKAPKLLIYLTSNLDSGVPSRFSGSGSGTDFTLTISSLQPEDFATYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 166 | Humanized 52B8 LC variable domain VL5 (N34D)/kappa constant domain | DIQLTQSPSSLSASVGDRVTITCRASEKVDSFGDSFMHWYQQKPGKAPKLLIYLTSNLDSGVPSRFSGSGSGTDFTLTISSLQPEDFATYYCQQNNEDPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 167 | Humanized 52B8 HC variable domain VH1/ Human IgG1 HC (L234A L235A D265S) constant domain | EVQLVESGGGLVQPGGSLRLSCAASGFTFSNYGMSWVRQAPGKGLEWVATISGGGDYTNYPDSMRGRFTISRDNAKNSLYLQMNSLRAEDTAVYYCGRRLWFRSLYYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGPSVFLFPPKPKDTLMISRTPEVTCVVVSVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 168 | Humanized 52B8 HC variable domain VH1 (M64V)/ Human IgG1 HC (L234A, L235A, D265S) constant domain | EVQLVESGGGLVQPGGSLRLSCAASGFTFSNYGMSWVRQAPGKGLEWVATISGGGDYTNYPDSVRGRFTISRDNAKNSLYLQMNSLRAEDTAVYYCGRRLWFRSLYYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGPSVFLFPPKPKDTLMISRTPEVTCVVVSVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 169 | Humanized 52B8 HC variable domain VH1 (M64L)/ Human IgG1 HC (L234A, L235A, | EVQLVESGGGLVQPGGSLRLSCAASGFTFSNYGMSWVRQAPGKGLEWVATISGGGDYTNYPDSLRGRFTISRDNAKNSLYLQMNSLRAEDTAVYYCGRRLWFRSLYYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGPSVFLFPPKPKDT |

TABLE OF SEQUENCES-continued

| SEQ ID NO: | Description | Sequence |
|---|---|---|
| | D265S) constant domain | LMISRTPEVTCVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| 170 | Humanized 52B8 HC variable domain VH1 (M64V, W101 F)/ Human IgG1 HC (L234A, L235A, D265S) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLFFRSLYYAMDY</u>WGQGTLVTVSS ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREEQ YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 171 | Humanized 52B8 HC variable domain VH1 (M64V, W101Y)/ Human IgG1 HC (L234A, L235A, D265S) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLYFRSLYYAMDY</u>WGQGTLVTVSS ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLEPPKPKDTL MISRTPEVTCVVVSVSHEDPEVKFNWYVDGVEVHNAKTKPREEQ YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 172 | Humanized 52B8 HC variable domain VH1 (M64V, W101Q)/ Human IgG1 HC (L234A, L235A, D265S) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLQFRSLYYAMDY</u>WGQGTLVTVSS ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREEQ YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 173 | Humanized 52B8 HC variable domain VH2/ Human IgG1 HC (L234A, L235A, D265S) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLKAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| 174 | Humanized 52B8 HC variable domain VH2 (M64V)/ Human IgG1 HC (L234A, L235A, D265S) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLKAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| 175 | Humanized 52B8 HC variable domain VH2 (M64L)/ Human IgG1 HC (L234A, L235A, D265S) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLKAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES |

TABLE OF SEQUENCES-continued

| SEQ ID NO: | Description | Sequence |
|---|---|---|
| | | NGQPENNYKTTPPVLDSDGSFFLYSKLTVDKSRWQQGNVFSCSV MHEALHNHYTQKSLSLSPGK |
| 176 | Humanized 52B8 HC variable domain VH1/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLRAEDTAVYYCGR<u>RLWFRSLYYAMDY</u>WGQGTLVTVS SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP<b>P</b>CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLG |
| 177 | Humanized 52B8 HC variable domain VH1 (M64V)/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLWFRSLYYAMDY</u>WGQGTLVTVS SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP<b>P</b>CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLG |
| 178 | Humanized 52B8 HC variable domain VH1 (M64L)/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLRAEDTAVYYCGR<u>RLWFRSLYYAMDY</u>WGQGTLVTVS SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCP<b>P</b>CPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLG |
| 179 | Humanized 52B8 HC variable domain VH1 (M64V), W101F/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLFFRSLYYAMDY</u>WGQGTLVTVS ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCP<b>P</b>CPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLG |
| 180 | Humanized 52B8 HC variable domain VH1 (M64V, W101Y)/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLYFRSLYYAMDY</u>WGQGTLVTVSS ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCP<b>P</b>CPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLG |
| 181 | Humanized 52B8 HC variable domain VH1 (M64V, 101Q)/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLQFRSLYYAMDY</u>WGQGTLVTVSS ASTKGPSVFPLAPCSRSTSESTAALGCLVKDYFPEPVTVSWNSGA LTSGVHTFPAVLQSSGLYSLSSVVTVPSSSLGTKTYTCNVDHKPSN TKVDKRVESKYGPPCP<b>P</b>CPAPEFLGGPSVFLFPPKPKDTLMISR TPEVTCVVVDVSQEDPEVQFNWYVDGVEVHNAKTKPREEQFNS TYRVVSVLTVLHQDWLNGKEYKCKVSNKGLPSSIEKTISKAKGQP REPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLG |

TABLE OF SEQUENCES-continued

| SEQ ID NO: | Description | Sequence |
|---|---|---|
| 182 | Humanized 52B8 HC variable domain VH2/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLKAEDTAVYYCGR<u>RLWFRSLYYAMDY</u>WGQGTLVTVS SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCPPCPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLG |
| 183 | Humanized 52B8 HC variable domain VH2 (M64V)/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLKAEDTAVYYCGR<u>RLWFRSLYYAMDY</u>WGQGTLVTVS SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCPPCPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLG |
| 184 | Humanized 52B8 HC variable domain VH2 (M64L)/Human IgG4 (S228P)(K-) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLKAEDTAVYYCGR<u>RLWFRSLYYAMDY</u>WGQGTLVTVS SASTKGPSVFPLAPCSRSTSESTAALGCLVKDYFPEPVTVSWNSG ALTSGVHTFPAVLQSSGLYSLSSVVTVPSSSLGTKTYTCNVDHKPS NTKVDKRVESKYGPPCPPCPAPEFLGGPSVFLFPPKPKDTLMIS RTPEVTCVVVDVSQEDPEVQFNWYVDGVEVHNAKTKPREEQFN STYRVVSVLTVLHQDWLNGKEYKCKVSNKGLPSSIEKTISKAKGQ PREPQVYTLPPSQEEMTKNQVSLTCLVKGFYPSDIAVEWESNGQ PENNYKTTPPVLDSDGSFFLYSRLTVDKSRWQEGNVFSCSVMHE ALHNHYTQKSLSLSLG |
| 185 | Humanized 52B8 HC variable domain VH1/Human IgG1 HC (L234A, L235A, D265S)(K-) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLRAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| 186 | Humanized 52B8 HC variable domain VH1 (M64V)/ Human IgG1 HC (L234A, L235A, D265S)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| 187 | Humanized 52B8 HC variable domain VH1 (M64L)/ Human IgG1 HC (L234A, L235A, D265S)(K-) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLRAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| 188 | Humanized 52B8 HC variable domain VH1 | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLFFRSLYYAMDY</u>WGQGTLVTVSS |

TABLE OF SEQUENCES-continued

| SEQ ID NO: | Description | Sequence |
|---|---|---|
| | (M64V, W101F)/ Human IgG1 HC (L234A, L235A, D265S)(K-) constant domain | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREEQ YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPG |
| 189 | Humanized 52B8 HC variable domain VH1 (M64V, W101Y)/ Human IgG1 HC (L234A, L235A, D265S)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLYFRSLYYAMDY</u>WGQGTLVTVSS ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREEQ YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPG |
| 190 | Humanized 52B8 HC variable domain VH1 (M64V, W101Q)/ Human IgG1 HC (L234A, L235A, D265S)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLRAEDTAVYYCGR<u>RLQFRSLYYAMDY</u>WGQGTLVTVSS ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPEAAGGPSVFLFPPKPKDTL MISRTPEVTCVVVSVSHEDPEVKFNWYVDGVEVHNAKTKPREEQ YNSTYRVVSVLTVLHQDWLNGKEYKCKVSNKALPAPIEKTISKAK GQPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPG |
| 191 | Humanized 52B8 HC variable domain VH2/ Human IgG1 HC (L234A, L235A, D265S)(K-) constant domain | EVQLVESGGGLVQPGGSLRLSCAASGFTFS<u>NYGMS</u>WVRQAP GKGLEWVA<u>TISGGGDYTNYPDSMRG</u>RFTISRDNAKNSLYLQ MNSLKAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| 192 | Humanized 52B8 HC variable domain VH2 M64V/ Human IgG1 HC (L234A, L235A, D265s)(K-) constant domain | EVQLVESGGGLVQPGGSLRLSCAASGFTFS<u>NYGMS</u>WVRQAP GKGLEWVA<u>TISGGGDYTNYPDSVRG</u>RFTISRDNAKNSLYLQ MNSLKAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| 193 | Humanized 52B 8 HC variable domain VH2 M64L/ Human IgG1 HC (L234A, L235A, D265 S) (K-) constant domain | EVQLVESGGGLVQPGGSLRLSCAASGFTFS<u>NYGMS</u>WVRQAP GKGLEWVA<u>TISGGGDYTNYPDSLRG</u>RFTISRDNAKNSLYLQ MNSLKAEDTAVYYCGR<u>RLWFRSLYYAMDY</u>WGQGTLVTVS SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPEAAGGPSVFLFPPKPKDT LMISRTPEVTCVVVSVSHEDPEVKFNWYVDGVEVHNAKTKPREE QYNSTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPG |
| 194 | Chimeric Anti-ILT3 rat 40A6 parental HC variable domain/human IgG4 (S228P) constant domain | QVQLKESGPGLVQASETLSLTCTVSGFSLT<u>SYSIN</u>WVRQSSG KGPEWMG<u>RFWYDEGIAYNLTLESRLSISGD</u>TSKNQVFLKMN SLRTGDTYYCTR<u>DRDTVGITGWFAY</u>WGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPEAAGGPSVFLFPPKPKDTLMISR TPEVTCVVVSVSHEDPEVKFNWYVDGVEVHNAKTKPREEQYNST |

TABLE OF SEQUENCES-continued

| SEQ ID NO: | Description | Sequence |
|---|---|---|
| | | YRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 195 | Chimeric Anti-ILT3 rat 40A6 parental LC variable domain/human kappa | ETVMTQSPTSLSASIGERVTLNC<u>KASQSVGVNVD</u>WYQQTPG QSPKLLIY<u>GSANRHT</u>GVPDRFTGSGFGSDFTLTISDVEPEDLG VYYC<u>LQYGSVPYT</u>FGAGTKLELKRTVAAPSVFIFPPSDEQLKS GTASVVCLLNNFYPREAKVQWKVDNALQSGNSQESVTEQDSKDS TYSLSSTLTLSKADYEKHKVYACEVTHQGLSSPVTKSFNRGEC |
| 196 | Chimeric Anti-ILT3 rat 16B1 parental HC variable domain/human IgG4 (S228P) constant domain | QVQLKESGPGLVQASETLSLTCTVSGFSLT<u>NYCVN</u>WVRQPS GKGPEWLG<u>RFWFDEGKAYNLTLES</u>RLSISGDTSKNQVFLRM NSLRADDTGTYYCTR<u>DRDTVGITGWFAY</u>WGQGTLVTVSSAS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKKVEPKSCDKTHTCPPCPAPEAAGGPSVFLFPPKPKDTLMIS RTPEVTCVVVSVSHEDPEVKFNWYVDGVEVHNAKTKPREEQYNS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 197 | Chimeric Anti-ILT3 rat 16B1 parental LC variable domain/human kappa | ETVMTQSPTSLSASIGERVTLNC<u>KASQSVGINVD</u>WYQQTPGQ SPKLLIY<u>GSANRHT</u>GVPDRFTGSGFGSDFTLTISNVEPEDLGV YYC<u>LQYGSVPYT</u>FGPGTKLELKRTVAAPSVFIFPPSDEQLKSGT ASVVCLLNNFYPREAKVQWKVDNALQSGNSQESVTEQDSKDSTY SLSSTLTLSKADYEKHKVYACEVTHQGLSSPVTKSFNRGEC |
| 198 | Chimeric Anti-ILT3 mouse 11D1 parental HC variable domain/human IgG4 (S228P) constant domain | QVQLQQSGAELMKPGASVKISCKATGYTFR<u>TYWIE</u>WVKQRP GHGLEWIG<u>EILPGNGNTHFNENFKD</u>KATFTADTSSNAAYMQ LSSLTSEDSAVYYCV<u>RRLGRGPFDF</u>WGQGTTLTVSSASTKGP SVFPLAPSSKSTSGGTAALGCLVKDYFPEPVTVSWNSGALTSGVH TFPAVLQSSGLYSLSSVVTVPSSSLGTQTYICNVNHKPSNTKVDKK VEPKSCDKTHTCPPCPAPEAAGGPSVFLFPPKPKDTLMISRTPE VTCVVVSVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLTCLVKGFYPSDIAVEWESNGQPENN YKTTPPVLDSDGSFFLYSKLTVDKSRWQQGNVFSCSVMHEALHN HYTQKSLSLSPGK |
| 199 | Chimeric Anti-ILT3 mouse 11D1 parental LC variable domain/human kappa | DIQMTQSPSSLSVSLGGKVTITC<u>KASQDINEYIG</u>WYQRKPGK GPRLLIH<u>YTSTLQS</u>GIPSRFSGSGSGRDYSLSISNLEPEDIATYY CL<u>QYANPLPT</u>FGGGTKLEIKRTVAAPSVFIFPPSDEQLKSGTAS VVCLLNNFYPREAKVQWKVDNALQSGNSQESVTEQDSKDSTYSL SSTLTLSKADYEKHKVYACEVTHQGLSSPVTKSFNRGEC |
| 200 | Chimeric Anti-ILT3 rat 17H12 parental HC variable domain/human IgG4 (S228P) constant domain | EVQLVESGGGLVQPGRSMKLSCAASGFTFS<u>NFDMA</u>WVRQA PTRGLEWVS<u>SITYDGGSTSYRDSVKG</u>RFTISRDNAKGTLYLQ MDSLRSEDTATYYCTT<u>VESIATISTYFDY</u>WGQGVMVTVSSAS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKKVEPKSCDKTHTCPPCPAPEAAGGPSVFLFPPKPKDTLMIS RTPEVTCVVVSVSHEDPEVKFNWYVDGVEVHNAKTKPREEQYNS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 201 | Chimeric Anti-ILT3 rat 17H12 parental LC variable domain/human kappa | DIVLTQSPALAVSLGQRATISC<u>RASQSVSMSRYDLIH</u>WYQQK PGQQPKLLIF<u>RASDLAS</u>GIPARFSGSGSGTDFTLTINPVQADDI ATYYC<u>QQTRKSPPT</u>FGGGTRLELKRTVAAPSVFIFPPSDEQLKS GTASVVCLLNNFYPREAKVQWKVDNALQSGNSQESVTEQDSKDS TYSLSSTLTLSKADYEKHKVYACEVTHQGLSSPVTKSFNRGEC |
| 202 | Chimeric Anti-ILT3 rat 37C8 parental HC variable domain/human IgG4 (S228P) constant domain | QVQLKESGPGLVQASETLSLTCTVSGFSLT<u>SYCVN</u>WVRQPSG KGPEWLG<u>RFWYDEGKVYNLTLES</u>RLSISGDTSKNQVFLKMN RLRTDDTGTYYCTR<u>DRDTMGITGWFAY</u>WGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPEAAGGPSVFLFPPKPKDTLMISR TPEVTCVVVSVSHEDPEVKFNWYVDGVEVHNAKTKPREEQYNST |

TABLE OF SEQUENCES-continued

| SEQ ID NO: | Description | Sequence |
|---|---|---|
| | | YRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 203 | Chimeric Anti-ILT3 rat 37C8 parental LC variable domain/human kappa | ETVMTQSPTSLSASIGERVTLNC<u>KASQSVGINVD</u>WYQQTPGQ SPKLLIY<u>GSANRHT</u>GVPDRFTGSGFGSGFTLTISNVEPEDLGV YYC<u>LQYGSVPYT</u>FGPGTKLELKRT*VAAPSVFIFPPSDEQLKSGT ASVVCLLNNFYPREAKVQWKVDNALQSGNSQESVTEQDSKDSTY SLSSTLTLSKADYEKHKVYACEVTHQGLSSPVTKSFNRGEC* |
| 204 | Chimeric Anti-ILT3 mouse 1G12 parental HC variable domain/human IgG4 (S228P) constant domain | QVQMQQSGTELMKPGASMKISCKATGYTF<u>STYWIQ</u>WIKQRP GHGLEWI<u>GEILPGSGTTNYNENFKG</u>KATFSADTSSNTAYIHLS SLTSEDSAVFYCARR<u>LGRGPFDY</u>WGQGTTLTVSS*ASTKGPSV FPLAPSSKSTSGGTAALGCLVKDYFPEPVTVSWNSGALTSGVHTF PAVLQSSGLYSLSSVVTVPSSSLGTQTYICNVNHKPSNTKVDKKVE PKSCDKTHTCPPCPAPEAAGGPSVFLFPPKPKDTLMISRTPEVT CVVVSVSHEDPEVKFNWYVDGVEVHNAKTKPREEQYNSTYRVVS VLTVLHQDWLNGKEYKCKVSNKALPAPIEKTISKAKGQPREPQV YTLPPSRDELTKNQVSLTCLVKGFYPSDIAVEWESNGQPENNYKT TPPVLDSDGSFFLYSKLTVDKSRWQQGNVFSCSVMHEALHNHYT QKSLSLSPGK* |
| 205 | Chimeric Anti-ILT3 mouse 1G12 parental LC variable domain/human kappa | DIQMTQSPSSLSASLGGKVTITC<u>EASQDINKHID</u>WYQHQPGR GPSLLIH<u>YASILQP</u>GIPSRFSGSGSGRDYSFSITSLEPEDIATYY C<u>LQYDNLLPT</u>FGGGTKLEIKRT*VAAPSVFIFPPSDEQLKSGTAS VVCLLNNFYPREAKVQWKVDNALQSGNSQESVTEQDSKDSTYSL SSTLTLSKADYEKHKVYACEVTHQGLSSPVTKSFNRGEC* |
| 206 | Chimeric Anti-ILT3 rat 20E4 parental HC variable domain/human IgG4 (S228P) constant domain | QVQLKESGPGLVQASETLSLTCTVSGFSLT<u>SYSVN</u>WVRQPSG KGLEWMG<u>RFWYDGGTAYNSTLESR</u>LSISGDTSKNQVFLKM NSLQTDDTGTYYCTR<u>DRDTMGITGWFAY</u>WGQGTLVTVSP*AS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKKVEPKSCDKTHTCPPCPAPEAAGGPSVFLFPPKPKDTLMIS RTPEVTCVVVSVSHEDPEVKFNWYVDGVEVHNAKTKPREEQYNS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK* |
| 207 | Chimeric Anti-ILT3 rat 20E4 parental LC variable domain/human kappa | ETVMTQSPTSLSASIGERVTLNC<u>KASQSVGINVD</u>WYQQTPG QSPKLLIY<u>GSANRHT</u>GVPDRFTGSGFGSDFTLTISNVEPEDLG VYYC<u>LQYGSVPYT</u>FGAGTKLELKRT*VAAPSVFIFPPSDEQLKS GTASVVCLLNNFYPREAKVQWKVDNALQSGNSQESVTEQDSKDS TYSLSSTLTLSKADYEKHKVYACEVTHQGLSSPVTKSFNRGEC* |
| 208 | Chimeric Anti-ILT3 rat 24A4 parental HC variable domain/human IgG4 (S228P) constant domain | QVQLKESGPGLVQASETLSLTCTVSGFSLT<u>SYCVN</u>WVRQPSG KGPEWLG<u>RFWYDEGKVYNLTLESR</u>LSISGDTSKNQVFLKMN RLRTDDTGTYYCTR<u>DRDTLGITGWFAY</u>WGQGTLVTVSS*AST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPEAAGGPSVFLFPPKPKDTLMISR TPEVTCVVVSVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK* |
| 209 | Chimeric Anti-ILT3 rat 24A4 parental LC variable domain/human kappa | ETVMTQSPTSLSASIGERVTLNC<u>KASQSVGINVD</u>WYQQTPGQ SPKLLIY<u>GSANRHT</u>GVPDRFTGSGFGSGFTLTISNVEPEDLGV YYC<u>LQYGSVPYT</u>FGPGTKLELKRT*VAAPSVFIFPPSDEQLKSGT ASVVCLLNNFYPREAKVQWKVDNALQSGNSQESVTEQDSKDSTY SLSSTLTLSKADYEKHKVYACEVTHQGLSSPVTKSFNRGEC* |
| 210 | Humanized 52B8 HC variable domain VH1 (M64V)/ Human IgG1 HC (N297A) constant domain | EVQLVESGGGLVQPGGSLRLSCAASGFTF<u>SNYGMS</u>WVRQAP GKGLEWVA<u>TISGGGDYTNYPDSVRG</u>RFTISRDNAKNSLYLQ MNSLRAEDTAVYYCGR<u>RLWFRSLYYAMDY</u>WGQGTLVTVS *SASTKGPSVFPLAPSSKSTSGGTAALGCLVKDYFPEPVTVSWNSG ALTSGVHTFPAVLQSSGLYSLSSVVTVPSSSLGTQTYICNVNHKPS NTKVDKKVEPKSCDKTHTCPPCPAPELLGGPSVFLFPPKPKDTL MISRTPEVTCVVVDVSHEDPEVKFNWYVDGVEVHNAKTKPREE* |

TABLE OF SEQUENCES-continued

| SEQ ID NO: | Description | Sequence |
|---|---|---|
| | | QYASTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| 211 | Human IgG1 HC constant domain (N297A; shown in bold-face type) | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTL MISRTPEVTCVVVDVSHEDPEVKFNWYVDGVEVHNAKTKPREE QY STYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK |
| 212 | Chimeric anti-ILT3 40A6 rat VH/ human IgG1 (N297A) | QVQLKESGPGLVQASETLSLTCTVSGFSLT<u>SYSIN</u>WVRQSSG KGPEWMG<u>RFWYDEGIAYNLTLES</u>RLSISGDTSKNQVFLKMN SLRTGDTGTYYCTR<u>DRDTVGITGWFAY</u>WGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYAS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 213 | Chimeric anti-ILT3 16B1 rat VH/ human IgG1 (N297A) | QVQLKESGPGLVQASETLSLTCTVSGFSLT<u>NYCVN</u>WVRQPS GKGPEWLG<u>RFWFDEGKAYNLTLES</u>RLSISGDTSKNQVFLRM NSLRADDTGTYYCTR<u>DRDTVGITGWFAY</u>WGQGTLVTVSSAS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQYA STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 214 | Chimeric anti-ILT3 11D1 mouse VH/ human IgG1 (N297A) | QVQLQQSGAELMKPGASVKISCKATGYTFR<u>TYWIE</u>WVKQRP GHGLEWIG<u>EILPGNGNTHFNENFKD</u>KATFTADTSSNAAYMQ LSSLTSEDSAVYYCV<u>RRLGRGPFDF</u>WGQGTTLTVSSASTKGP SVFPLAPSSKSTSGGTAALGCLVKDYFPEPVTVSWNSGALTSGVH TFPAVLQSSGLYSLSSVVTVPSSSLGTQTYICNVNHKPSNTKVDKK VEPKSCDKTHTCPPCPAPELLGGPSVFLFPPKPKDTLMISRTPE VTCVVVDVSHEDPEVKFNWYVDGVEVHNAKTKPREEQYASTYR VVSVLTVLHQDWLNGKEYKCKVSNKALPAPIEKTISKAKGQPRE PQVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGK |
| 215 | Chimeric anti-ILT3 17H12 rat VH/ human IgG1 (N297A) | EVQLVESGGGLVQPGRSMKLSCAASGFTFS<u>NFDMA</u>WVRQA PTRGLEWVS<u>SITYDGGSTSYRDSVKG</u>RFTISRDNAKGTLYLQ MDSLRSEDTATYYCTT<u>VESIATISTYFDY</u>WGQGVMVTVSSAS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQYA STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 216 | Chimeric anti-ILT3 37C8 rat VH/ human IgG1 (N297A) | QVQLKESGPGLVQASETLSLTCTVSGFSLT<u>SYCVN</u>WVRQPSG KGPEWLG<u>RFWYDEGKVYNLTLES</u>RLSISGDTSKNQVFLKMN RLRTDDTGTYYCTR<u>DRDTMGITGWFAY</u>WGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYAS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 217 | Chimeric anti-ILT3 1G12 mouse VH/ | QVQMQQSGTELMKPGASMKISCKATGYTFS<u>TYWIQ</u>WIKQRP GHGLEWIG<u>EILPGSGTTNYNENFKG</u>KATFSADTSSNTAYIHLS |

TABLE OF SEQUENCES-continued

| SEQ ID NO: | Description | Sequence |
|---|---|---|
| | human IgG1 (N297A) | SLTSEDSAVFYCARRLGRGPFDYWGQGTTLTVSSASTKGPSV FPLAPSSKSTSGGTAALGCLVKDYFPEPVTVSWNSGALTSGVHTF PAVLQSSGLYSLSSVVTVPSSSLGTQTYICNVNHKPSNTKVDKKVE PKSCDKTHTCPPCPAPELLGGPSVFLFPPKPKDTLMISRTPEVT CVVVDVSHEDPEVKFNWYVDGVEVHNAKTKPREEQYASTYRVV SVLTVLHQDWLNGKEYKCKVSNKALPAPIEKTISKAKGQPREPQ VYTLPPSRDELTKNQVSLTCLVKGFYPSDIAVEWESNGQPENNYK TTPPVLDSDGSFFLYSKLTVDKSRWQQGNVFSCSVMHEALHNHY TQKSLSLSPGK |
| 218 | Chimeric anti-ILT3 20E4 rat VH/ human IgG1 (N297A) | QVQLKESGPGLVQASETLSLTCTVSGFSLTSYSVNWVRQPSG KGLEWMGRFWYDGGTAYNSTLESRLSISGDTSKNQVFLKM NSLQTDDTGTYYCTRDRDTMGITGWFAYWGQGTLVTVSPAS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQYA STYRVVSVLTVLHQDWLNGKEYKCKVSNKALPAPIEKTISKAKGQ PREPQVYTLPPSRDELTKNQVSLTCLVKGFYPSDIAVEWESNGQP ENNYKTTPPVLDSDGSFFLYSKLTVDKSRWQQGNVFSCSVMHEA LHNHYTQKSLSLSPGK |
| 219 | Chimeric anti-ILT3 24A4 rat VH/ human IgG1 (N297A) | QVQLKESGPGLVQASETLSLTCTVSGFSLTSYCVNWVRQPSG KGPEWLGRFWYDEGKVYNLTLESRLSISGDTSKNQVFLKMN RLRTDDTGTYYCTRDRDTLGITGWFAYWGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYAS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 220 | Chimeric anti-ILT3 40A6 rat VH/ human IgG1 (N297A) | QVQLKESGPGLVQASETLSLTCTVSGFSLTSYSINWVRQSSG KGPEWMGRFWYDEGIAYNLTLESRLSISGDTSKNQVFLKMN SLRTGDTGTYYCTRDRDTVGITGWFAYWGQGTLVTVSSAST KGPSVFPLAPSSKSTSGGTAALGCLVKDYFPEPVTVSWNSGALTS GVHTFPAVLQSSGLYSLSSVVTVPSSSLGTQTYICNVNHKPSNTKV DKKVEPKSCDKTHTCPPCPAPELLGGPSVFLFPPKPKDTLMISR TPEVTCVVVDVSHEDPEVKFNWYVDGVEVHNAKTKPREEQYAS TYRVVSVLTVLHQDWLNGKEYKCKVSNKALPAPIEKTISKAKGQP REPQVYTLPPSRDELTKNQVSLTCLVKGFYPSDIAVEWESNGQPE NNYKTTPPVLDSDGSFFLYSKLTVDKSRWQQGNVFSCSVMHEAL HNHYTQKSLSLSPGK |
| 221 | Residues after LC-CDR3 Xaa is any amino acid | FGXG |
| 222 | Residues before HC-CDR1 Xaa is any amino acid | CXXX |
| 223 | Residues before HC-CDR1 | LEWIG |
| 224 | Residues after HC-CDR3 Xaa is any residue | WGXG |
| 225 | Pembrolizumab Heavy Chain | QVQLVQSGVEVKKPGASVKVSCKASGYTFTNYYMYWVRQ APGQGLEWMGGINPSNGGTNFNEKFKNRVTLTTDSSTTTAY MELKSLQFDDTAVYYCARRDYRFDMGFDYWGQGTTVTVSS ASTKGPSVFPLAPCSRSTSESTAALGCLVKDYFPEPVTVSWN SGALTSGVHTFPAVLQSSGLYSLSSVVTVPSSSLGTKTYTCN VDHKPSNTKVDKRVESKYGPPCPPCPAPEFLGGPSVFLFPPKP KDTLMISRTPEVTCVVVDVSQEDPEVQFNWYVDGVEHNA KTKPREEQFNSTYRVVSVLTVLHQDWLNGKEYKCKVSNKG LPSSIEKTISKAKGQPREPQVYTLPPSQEEMTKNQVSLTCLVK GFYPSDIAVEWESNGQPENNYKTTPPVLDSDGSFFLYSRLTV DKSRWQEGNVFSCSVMHEALHNHYTQKSLSLSLGK |

TABLE OF SEQUENCES-continued

| SEQ ID NO: | Description | Sequence |
|---|---|---|
| 226 | Pembrolizumab Light Chain | EIVLTQSPATLSLSPGERATLSCRASKGVSTSGYSYLHWYQQ KPGQAPRLLIYLASYLESGVPARFSGSGSGTDFTLTISSLEPED FAVYYCQHSRDLPLTFGGGTKVEIKRTVAAPSVFIFPPSDEQL KSGTASVVCLLNNFYPREAKVQWKVDNALQSGNSQESVTE QDSKDSTYSLSSTLTLSKADYEKHKVYACEVTHQGLSSPVTK SFNRGEC |
| 227 | Human IgG1 HC constant domain (N297A, D265A; shown in bold-face type) | *ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTL MISRTPEVTCVVVAVSHEDPEVKFNWYVDGVEVHNAKTKPREE QYASTYRVVSVLTVLHQDWLNGKEYKCKVSNKALPAPIEKTISKA KGQPREPQVYTLPPSRDELTKNQVSLTCLVKGFYPSDIAVEWES NGQPENNYKTTPPVLDSDGSFFLYSKLTVDKSRWQQGNVFSCSV MHEALHNHYTQKSLSLSPGK* |

Constant regions are shown in italics.
Amino acid sequences underlined are CDRs.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. An antibody or antigen binding fragment that binds the extracellular domain of human immunoglobulin-like transcript 3 (ILT3) having amino acids 1-238 of SEQ ID NO: 1, wherein the antibody or antigen binding fragment comprises
   (a) a heavy chain complementarity determining region 1 (HC-CDR1), wherein the HC-CDR1 has the amino acid sequence set forth in SEQ ID NO: 17; an HC-CDR2, wherein the HC-CDR2 has the amino acid sequence set forth in SEQ ID NO: 19, 20, or 21; an HC-CDR3, wherein the HC-CDR3 has the amino acid sequence set forth in SEQ ID NO: 23; and
   (b) a light chain complementarity determining region 1 (LC-CDR1), wherein the LC-CDR1 has the amino acid sequence set forth in SEQ ID NO: 34, 35, 36, 37, 38, 39, 40, 41, or 42; an LC-CDR2, wherein the LC-CDR2 has the amino acid sequence set forth in SEQ ID NO: 43; and an LC-CDR3, wherein the LC-CDR3 has the amino acid sequence set forth in SEQ ID NO: 44.

2. The antibody or antigen binding fragment of claim 1, wherein
   (a) the HC-CDR1 has the amino acid sequence set forth in SEQ ID NO: 17; the HC-CDR2 has the amino acid sequence set forth in SEQ ID NO:20; and the HC-CDR3 has the amino acid sequence set forth in SEQ ID NO: 23; and
   (b) the LC-CDR1 has the amino acid sequence set forth in SEQ ID NO: 41; the LC-CDR2 has the amino acid sequence set forth in SEQ ID NO:43; and, the LC-CDR3 has the amino acid sequence set forth in SEQ ID NO: 44.

3. The antibody or antigen binding fragment of claim 2, wherein the antibody comprises:
   (i) a $V_H$ having a framework selected from the group consisting of human $V_H1$, $V_H2$, $V_H3$, $V_H4$, $V_H5$, and $V_H6$ and a human IgG1 or IgG4 HC constant domain or variant thereof comprising 1, 2, 3, 4, 5, 6, 7, 8, 9, or 10 amino acid substitutions, additions, deletions, or combinations thereof compared to the amino acid sequence of the native IgG1 or IgG4 isotype HC constant domain; and,
   (ii) a $V_L$ having a framework selected from the group consisting of human $V_\kappa1$, $V_\kappa2$, $V_\kappa3$, $V_\kappa4$, $V_\kappa5$, $V_\kappa6$, $V_\lambda1$, $V_\lambda2$, $V_\lambda3$, $V_\lambda4$, $V_\lambda5$, $V_\lambda6$, $V_\lambda7$, $V_\lambda8$, $V_\lambda9$, and $V_\lambda10$ and a human kappa or lambda LC constant domain or variant thereof comprising 1, 2, 3, 4, 5, 6, 7, 8, 9, or 10 amino acid substitutions, additions, deletions, or combinations thereof compared to the amino acid sequence of the native human kappa or lambda LC constant domain.

4. The antibody or antigen binding fragment of claim 3, wherein the antibody comprises a heavy chain (HC) constant domain comprising the amino acid sequence set forth in SEQ ID NO: 9, 10, 11, 12, or 13.

5. The antibody or antigen binding fragment of claim 3, wherein the antibody comprises a light chain (LC) constant domain comprising the amino acid sequence set forth in SEQ ID NO: 14.

6. The antibody or antigen binding fragment of claim 3, wherein the antibody comprises a heavy chain (HC) comprising the amino acid sequence set forth in SEQ ID NO: 142, 143, 144, 148, 149, 150, 167, 168, 169, 170, 174, 175, 176, 177, 178, 182, 183, 184, 185, 186, 187, 191, 192, or 193.

7. The antibody or antigen binding fragment of claim 3, wherein the antibody comprises a light chain (LC) comprising the amino acid sequence set forth in SEQ ID NO: 151, 152, 153, 154, 155, 156, 157, 158, 159, 160, 161, 162, 163, 164, 165, or 166.

8. The antibody or antigen binding fragment of claim 3, wherein the antibody comprises a heavy chain (HC) comprising the amino acid sequence set forth in SEQ ID NO: 143 and a light chain (LC) comprising the amino acid sequence set forth in SEQ ID NO: 165, and variants thereof wherein the HC lacks a C-terminal Lysine residue or a C-terminal glycine-lysine.

9. The antibody or antigen binding fragment of claim 1, wherein the $V_H$ comprises a framework selected from the group consisting of human $V_H1$, $V_H2$, $V_H3$, $V_H4$, $V_H5$, and $V_H6$, and variants thereof having 1, 2, 3, 4, 5, 6, 7, 8, 9, or 10 amino acid substitutions, additions, deletions, or combinations thereof; and, the $V_L$ comprises a framework selected from the group consisting of human $V_\kappa1$, $V_\kappa2$, $V_\kappa3$, $V_\kappa4$, $V_\kappa5$, $V_\kappa6$, $V_\lambda1$, $V_\lambda2$, $V_\lambda3$, $V_\lambda4$, $V_\lambda5$, $V_\lambda6$, $V_\lambda7$, $V_\lambda8$, $V_\lambda9$, and $V_\lambda10$, and variants thereof having 1, 2, 3, 4, 5, 6, 7, 8, 9, or 10 amino acid substitutions, additions, deletions, or combinations thereof.

10. The antibody or antigen binding fragment of claim 9, wherein the antibody or antigen binding fragment comprises a $V_H$ and a $V_L$ having the amino acid sequences set forth in SEQ ID NO: 15 and SEQ ID NO: 16, respectively; SEQ ID NO:45 and SEQ ID NO: 46, respectively; SEQ ID NO: 53 and SEQ ID NO: 54, respectively; SEQ ID NO: 61 and SEQ ID NO: 62, respectively; SEQ ID NO: 69 and SEQ ID NO: 70, respectively; SEQ ID NO: 77 and SEQ ID NO: 78, respectively; SEQ ID NO: 85 and SEQ ID NO: 86, respectively; SEQ ID NO: 93 and SEQ ID NO: 94, respectively; or SEQ ID NO:101 and SEQ ID NO: 102, respectively.

11. The antibody or antigen binding fragment of claim 9, wherein the antibody or antigen binding fragment comprises a $V_H$ having the amino acid sequence set forth in SEQ ID NO: 117, 118, 119, 123, 124, or 125 and a $V_L$ having the amino acid sequence set forth in SEQ ID NO: 126, 127, 128, 129, 130, 131, 132, 133, 134, 135, 136, 137, 138, 139, 140, or 141.

12. The antibody or antigen binding fragment of claim 11, wherein the antibody or antigen binding fragment comprises a $V_H$ having the amino acid sequence set forth in SEQ ID NO: 118 and a $V_L$ having the amino acid sequence set forth in SEQ ID NO: 140.

13. The antibody or antigen binding fragment of claim 1, wherein the antibody comprises an HC having a human IgG1, IgG2, IgG3, or IgG4 HC constant domain or variant thereof having 1, 2, 3, 4, 5, 6, 7, 8, 9, or 10 amino acid substitutions, additions, deletions, or combinations thereof compared to the amino acid sequence of the native IgG1, IgG2, IgG3, or IgG4 isotype constant domain.

14. The antibody or antigen binding fragment of claim 13, wherein the antibody comprises an LC having a human kappa or lambda LC constant domain or variant thereof comprising 1, 2, 3, 4, 5, 6, 7, 8, 9, or 10 amino acid substitutions, additions, deletions, or combinations thereof compared to the amino acid sequence of the native human kappa or lambda light chain constant domain.

15. A composition comprising:
an antibody or antigen binding fragment of claim 1 and a pharmaceutically acceptable carrier.

16. An antibody or antigen binding fragment that binds the extracellular domain of human immunoglobulin-like transcript 3 (ILT3) having amino acids 1-238 of SEQ ID NO: 1, wherein the antibody or antigen binding fragment comprises
 (a) a heavy chain complementarity determining region 1 (HC-CDR1), wherein the HC-CDR1 has the amino acid sequence set forth in SEQ ID NO: 17; an HC-CDR2, wherein the HC-CDR2 has the amino acid sequence set forth in SEQ ID NO: 20; an HC-CDR3, wherein the HC-CDR3 has the amino acid sequence set forth in SEQ ID NO: 23; and
 (b) a light chain complementarity determining region 1 (LC-CDR1), wherein the LC-CDR1 has the amino acid sequence set forth in SEQ ID NO: 41; an LC-CDR2, wherein the LC-CDR2 has the amino acid sequence set forth in SEQ ID NO: 43; and an LC-CDR3, wherein the LC-CDR3 has the amino acid sequence set forth in SEQ ID NO: 44.

17. The antibody or antigen binding fragment of claim 16, wherein the antibody or antigen binding fragment comprises a $V_H$ and a $V_L$ having the amino acid sequences set forth in SEQ ID NO: 118 and SEQ ID NO: 140, respectively.

18. The antibody or antigen binding fragment of claim 17, wherein the antibody comprises a heavy chain (HC) comprising the amino acid sequence set forth in SEQ ID NO: 143 and a light chain (LC) comprising the amino acid sequence set forth in SEQ ID NO: 165, and variants thereof wherein the HC lacks a C-terminal Lysine residue or a C-terminal glycine-lysine.

19. A composition comprising:
an antibody or antigen binding fragment of claim 16 and a pharmaceutically acceptable carrier.

20. A composition comprising:
an antibody or antigen binding fragment of claim 17 and a pharmaceutically acceptable carrier.

21. A composition comprising:
an antibody or antigen binding fragment of claim 18 and a pharmaceutically acceptable carrier.

* * * * *